(12) United States Patent
Yu et al.

(10) Patent No.: US 9,676,714 B2
(45) Date of Patent: Jun. 13, 2017

(54) SULFONYLINDOLE DERIVATIVES AND METHOD FOR PREPARING THE SAME

(71) Applicant: Daewoong Pharmaceutical Co., Ltd., Gyeonggi-do (KR)

(72) Inventors: Kyung A Yu, Gyeonggi-do (KR); Ji Sung Yoon, Gyeonggi-do (KR); Deok Ki Eom, Gyeonggi-do (KR); Yeon Im Lee, Gyeonggi-do (KR); Hye Ryun Shin, Gyeonggi-do (KR); Jun Hee Lee, Seoul (KR); Ha Nee Seo, Gyeonggi-do (KR); Ji Duck Kim, Gyeonggi-do (KR); Sang Ho Lee, Gyeonggi-do (KR); Chun Ho Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/026,471

(22) PCT Filed: Oct. 2, 2014

(86) PCT No.: PCT/KR2014/009353
§ 371 (c)(1),
(2) Date: Mar. 31, 2016

(87) PCT Pub. No.: WO2015/050412
PCT Pub. Date: Apr. 9, 2015

(65) Prior Publication Data
US 2016/0221946 A1 Aug. 4, 2016

(30) Foreign Application Priority Data

Oct. 2, 2013 (KR) .................. 10-2013-0118189

(51) Int. Cl.
| C07D 209/30 | (2006.01) |
| C07D 403/12 | (2006.01) |
| C07D 401/14 | (2006.01) |
| C07D 401/06 | (2006.01) |
| C07D 401/12 | (2006.01) |
| C07D 403/04 | (2006.01) |
| C07D 471/04 | (2006.01) |
| C07D 209/14 | (2006.01) |
| C07D 405/14 | (2006.01) |

(52) U.S. Cl.
CPC ......... *C07D 209/30* (2013.01); *C07D 209/14* (2013.01); *C07D 401/06* (2013.01); *C07D 401/12* (2013.01); *C07D 401/14* (2013.01); *C07D 403/04* (2013.01); *C07D 403/12* (2013.01); *C07D 405/14* (2013.01); *C07D 471/04* (2013.01)

(58) Field of Classification Search
CPC .. C07D 209/30; C07D 209/14; C07D 401/06; C07D 401/12; C07D 401/14; C07D 403/04; C07D 403/12; C07D 405/14; C07D 471/04
USPC .......................................... 514/274
See application file for complete search history.

(56) References Cited

U.S. PATENT DOCUMENTS 5,654,305 A  8/1997  Sheppard et al.

FOREIGN PATENT DOCUMENTS

| JP | 52-97970 A | 8/1977 |
| JP | 11-503758 A | 3/1999 |
| JP | 2007-516203 A | 6/2007 |
| JP | 2008-511621 A | 4/2008 |
| JP | 2009-520017 A | 5/2009 |
| WO | WO-2004/099189 A1 | 11/2004 |
| WO | WO-2005/009958 A1 | 2/2005 |
| WO | WO-2006/025716 A1 | 3/2006 |
| WO | WO-2007/026916 A1 | 3/2007 |
| WO | WO-2007/072146 A1 | 6/2007 |
| WO | WO-2007/149557 A1 | 12/2007 |

OTHER PUBLICATIONS

Jiang et al., "Sulfonation and Trifluoromethylation of Enol Acetates with Sulfonyl Chlorides Using Visible-Light Photoredox Catalysis", Eur. J. Org. Chem. 2013, pp. 5485-5492, 8 pages.
Berge et al., "Pharmaceutical Salts", Journal of Pharmaceutical Sciences, vol. 66, No. 1, Jan. 1977, 20 pages.
Search Report and Written Opinion in International Application No. PCT/KR2014/009353 dated Jan. 9, 2015, 13 pages.

*Primary Examiner* — Yevegeny Valenrod
(74) *Attorney, Agent, or Firm* — Marshall, Gerstein & Borun LLP

(57) ABSTRACT

Disclosed are a sulfonylindole derivative useful for the prevention or treatment of peptic ulcer, gastritis or reflux esophagitis, a method of preparing the same, and a pharmaceutical composition containing the same.

19 Claims, No Drawings

SULFONYLINDOLE DERIVATIVES AND METHOD FOR PREPARING THE SAME

TECHNICAL FIELD

The present invention relates to a sulfonylindole derivative useful for the prevention or treatment of peptic ulcer, gastritis or reflux esophagitis, a method of preparing the same, and a pharmaceutical composition containing the same.

BACKGROUND ART

Therapeutic agents for treating peptic ulcer have been developed based on two main modes of action—i.e., regulation of aggressive factors and enhancement of defensive factors. Development has been particularly focused on the regulation of aggressive factors. Development on the regulation of aggressive factors has evolved from the use of antacids to anti-cholinergic drugs and $H_2$ receptor antagonists, and recently to proton pump inhibitors (PPI), which are the leading products in the current market.

Since the discovery of highly concentrated HCl secretion in mucosal membranes by Prout in 1884, the mechanism of acid secretion has been actively studied for almost a century. Initially, Belladonna, the first antiulcer drug, was used, followed by anti-cholinergic drugs. In 1920, it was found that antacid secretion is stimulated by histamine. In 1977, Cimetidine (Tagamet®) was developed as the first histamine $H_2$ receptor antagonist which inhibits the action of histamine, a strong gastric acid-secreting hormone, at $H_2$ receptor. Since then, various drugs which antagonize receptors for several stimulants of acid secretion have been developed, and histamine $H_2$ receptor antagonists, such as Ranitidine (Zantac®(developed in 1981) and Famotidine (Gaster®/Pepcid®)(developed in 1985) now occupy most of the global peptic ulcer drugs market. Additionally, since the first isolation of *Helicobacter pylori* as a pathogen causing gastritis and gastric ulcer in 1983, combination therapies consisting of proton pump inhibitors or $H_2$ receptor antagonists and chemotherapeutics for eradication of *Helicobacter pylori* have been developed.

Recently, there has been a growing need for the development of a proton pump inhibitor with a reversible inhibition mechanism, and global pharmaceutical firms are actively involved in the research. To be distinguishable from conventional PPI drugs, represented by Omeprazole, the reversible proton pump inhibitors are called as potassium competitive acid blockers (P-CAB) or acid pump antagonists (APA).

Meanwhile, the $H^+$ secretion pathway in the gastric parietal cells was not identified for a long time until it was recently discovered that $H^+$ secretion in the gastrointestinal tract involves an action of $H^+/K^+$-ATPase in the microsomal fraction from the gastric parietal cells for the exchange of $H^+$ and $K^+$, and $H^+/K^+$-ATPase was then termed a "proton pump". $H^+/K^+$-ATPase uses the energy obtained by the decomposition of ATP, abundant in mitochondria, to secrete $H^+$ derived from $H_2O$ decomposition into the gastric cavity in vivo. Here, the exchange between $K^+$ and $H^+$ occurs at a ratio of 1:1, and it was confirmed that $H^+/K^+$-ATPase is present in many $H^+$-secreting animals as well as in humans.

In other words, various acid-secretion stimulants (histamine, acetylcholine, gastrin, etc.) bind to receptors present in the cell membrane of the gastric parietal cells and thereby cause a series of reactions for gastric acid secretion, and in its final step, $H^+/K^+$-ATPase, a proton pump, operates to release $H^+$ and absorb $K^+$ in the gastric parietal cells. Accordingly, compounds which can prevent gastric acid secretion by inhibiting the proton pump in the final step of gastric acid secretion have no anti-cholinergic action or $H_2$ receptor antagonistic action. In particular, they are absorbed into the body in the form of an inactive pro-drug and are densely distributed within the secretory canaliculi of parietal cells in gastric mucosa, i.e., the unique acidic compartments in the human body, and are then activated to inhibit the proton pump in the final step of gastric acid production, thereby inhibiting gastric acid secretion in a unique and selective manner.

Examples of the representative drugs developed for the purpose of inhibiting the proton pump include Omeprazole, Lansoprazole, Pantoprazole, Esomeprazole, etc. These drugs have stronger and more sustained inhibition activity against gastric acid secretion than conventional drugs and are thus widely used as therapeutics for the treatment of peptic ulcer. Additionally, Omeprazole-based compounds exhibit a dual characteristic of both aggressive and defensive actions with strong inhibition of gastric acid secretion and gastric membrane protection activity (cytoprotective activity) at the same time. As compared with $H_2$ receptor antagonists, these compounds exhibit a stronger acid inhibition during daytime as well as at night, and also have a low recurrence rate of peptic ulcer.

However, a proton pump inhibitor with an irreversible action mechanism, due to its long-term inhibition of gastric acid secretion in the stomach, can cause gastric bacteria proliferation, promotion of proton pump expression, and tumorigenesis induced by increased gastrin levels. Accordingly, in order to overcome the above problems, research has been focused on the development of a reversible proton pump inhibitor capable of inhibiting the secretion of gastric acid only for a particular period of time from administration of a drug. So far, revaprazan (Revanex®) released by Yuhan Corp. (Korea) on January 2007 is the only drug, but more novel drugs are expected to enter the market because major global pharmaceutical firms have been conducting research efforts to develop anti-peptic ulcer drugs which are capable of functioning as reversible proton pump inhibitors.

Examples of representative proton pump inhibitors include a pyrrole derivative disclosed in International Publication No. WO2007/026916 (Takeda Pharmaceutical Co. Ltd.), a pyrrolo[2,3-c]pyridine derivative disclosed in International Publication No. WO2006/025716 (Yuhan Corp.), and a benzimidazole derivative disclosed in International Publication No. WO2007/072146 (Pfizer Inc., Japan; Raqualia Pharma Inc.).

DISCLOSURE

Technical Problem

The inventors of the present invention, while endeavoring to develop a novel compound having a proton pump inhibitory effect, have found that a sulfonylindole derivative has a reversible proton pump inhibition effect and thus can be used for the treatment or prevention of peptic ulcer, gastritis or reflux esophagitis, thereby completing the present invention.

Technical Solution

An objective of the present invention is to provide a sulfonylindole derivative or a pharmaceutically acceptable salt thereof useful for the prevention or treatment of peptic ulcer, gastritis or reflux esophagitis, and a method of preparing the same.

Another objective of the present invention is to provide a pharmaceutical composition comprising a sulfonylindole derivative or a pharmaceutically acceptable salt thereof according to the present invention.

A further objective of the present invention is to provide a pharmaceutical composition for the prevention or treatment of peptic ulcer, gastritis or reflux esophagitis, comprising a sulfonylindole derivative or a pharmaceutically acceptable salt thereof according to the present invention as an active ingredient.

A still further objective of the present invention is to provide a method for the prevention or treatment of peptic ulcer, gastritis or reflux esophagitis in a subject in need thereof, comprising administering an effective amount of a compound or a pharmaceutically acceptable salt thereof according to the present invention to the subject.

A yet further objective of the present invention is to provide an intermediate useful for the preparation of a sulfonylindole derivative according to the present invention.

Advantageous Effects

The sulfonylindole derivative of the present invention has a reversible proton pump inhibitory effect as an acid pump antagonist (APA), and therefore it can be useful for the treatment or prevention of peptic ulcer, gastritis or reflux esophagitis.

BEST MODE

In order to achieve the above objectives, the present invention provides a compound represented by Chemical Formula 1 below or a pharmaceutically acceptable salt thereof:

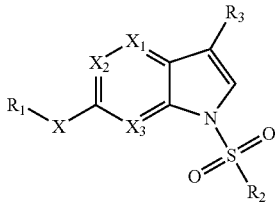

[Chemical Formula 1]

wherein,

X is a bond, —$CH_2$—, —O—, —NH—, —N($CH_3$)—, or —N(CHO)—, $X_1$, $X_2$ and $X_3$ are each independently CH or N, $R_1$ is phenyl, pyrazolyl, pyridinyl, pyrimidinyl, quinolinyl, or phenyl fused with a 6-membered-heterocycloalkyl including one or two nitrogen or oxygen atoms, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), $R_2$ is naphthyl, phenyl, or pyridinyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl, $R_3$ is —$CH_2NR_4R_5$, —$CONR_4R_5$, —$COOR_4$ or —$NR_4R_5$, wherein the $R_4$ and $R_5$ are each independently hydrogen or $C_{1-4}$ alkyl, or the $R_4$ and $R_5$ together with the nitrogen atom to which $R_4$ and $R_5$ are attached form a 5-membered or 6-membered nitrogen-containing heterocyclyl.

Preferably, $R_1$ is phenyl, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl).

Preferably, $R_1$ is pyridinyl, wherein the $R_1$ is unsubstituted or substituted with one to three substituents independently selected from the group consisting of $C_{1-6}$ alkyl, $C_{1-4}$ alkoxy, $C_{1-4}$ haloalkyl and halogen.

Preferably, $R_1$ is pyrimidinyl, wherein the $R_1$ is unsubstituted or substituted with a $C_{1-4}$ alkoxy or halogen.

Preferably, $R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, $R_2$ is pyridinyl, wherein the $R_2$ is unsubstituted or substituted with a $C_{1-4}$ alkoxy or halogen.

Preferably, $R_3$ is —$CH_2NHCH_3$, —$CH_2NHCH_2CH_3$, —$CH_2N(CH_3)_2$, —$CH2$(pyrrolidin-1-yl), —$CONHCH_3$, —$CON(CH_3)_2$, —$COOCH_3$ or —$NHCH_3$.

Preferably, $R_1$ is phenyl, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), and $R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, $R_1$ is phenyl, wherein the $R_1$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, and halogen, and $R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, $R_1$ is phenyl, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), and $R_2$ is pyridinyl, wherein the $R_2$ is unsubstituted or substituted with a $C_{1-4}$ alkoxy or halogen.

Preferably, $R_1$ is pyridinyl, wherein the $R_1$ is unsubstituted or substituted with one to three substituents independently selected from the group consisting of $C_{1-6}$ alkyl, $C_{1-4}$ alkoxy, $C_{1-4}$ haloalkyl and halogen, and $R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, $R_1$ is pyridinyl, wherein the $R_1$ is unsubstituted or substituted with a $C_{1-4}$ alkoxy or halogen, and $R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, $R_1$ is pyridinyl, wherein the $R_1$ is unsubstituted or substituted with one to three substituents independently selected from the group consisting of $C_{1-6}$ alkyl, $C_{1-4}$ alkoxy, $C_{1-4}$ haloalkyl and halogen, and $R_2$ is pyridinyl, wherein the $R_2$ is unsubstituted or substituted with a $C_{1-4}$ alkoxy or halogen.

Preferably, $R_1$ is pyridinyl, wherein the $R_1$ is unsubstituted or substituted with a $C_{1-4}$ alkoxy or halogen, and $R_2$ is pyridinyl, wherein the $R_2$ is unsubstituted or substituted with a $C_{1-4}$ alkoxy or halogen.

Preferably, the phenyl fused with a 6-membered-heterocycloalkyl containing one or two nitrogen or oxygen atoms is 1,2,3,4-tetrahydroquinolinyl or 2,3-dihydrobenzo[b][1,4]dioxinyl.

Preferably, the $X_1$, $X_2$ and $X_3$ are all CH.

Preferably, one of the $X_1$, $X_2$ and $X_3$ is N, and the others are both CH.

Preferably, the $X_1$, $X_2$ and $X_3$ are all CH, and X is —NH—,
$R_1$ is phenyl, wherein the $R_1$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy and halogen, and
$R_2$ is phenyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl.

Preferably, the $X_1$, $X_2$ and $X_3$ are all CH, and X is —NH—,
$R_1$ is phenyl, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), and
$R_2$ is pyridinyl, wherein the $R_2$ is unsubstituted or substituted with a $C_{1-4}$ alkoxy or halogen.

Preferably, the $X_1$, $X_2$ and $X_3$ are all CH, and X is —NH—,
$R_1$ is pyridinyl, wherein the $R_1$ is unsubstituted or substituted with one or two substituents independently selected from the group consisting of $C_{1-6}$ alkyl, $C_{1-4}$ alkoxy, $C_{1-4}$ haloalkyl and halogen, and
$R_2$ is phenyl, wherein the $R_2$ is unsubstituted or substituted with one or two substituents independently selected from the group consisting of $C_{1-6}$ alkyl, $C_{1-4}$ alkoxy, $C_{1-4}$ haloalkyl, $C_{1-4}$ haloalkoxy and halogen.

Preferably, the $X_1$, $X_2$ and $X_3$ are all CH, and X is —NH—,
$R_1$ is pyridinyl, wherein the $R_1$ is unsubstituted or substituted with one to three substituents independently selected from the group consisting of $C_{1-6}$ alkyl, $C_{1-4}$ alkoxy, $C_{1-4}$ haloalkyl and halogen, and
$R_2$ is pyridinyl, wherein the $R_2$ is unsubstituted or substituted with a $C_{1-4}$ alkoxy or halogen.

Examples of the compound represented by Chemical Formula 1 above or a pharmaceutically acceptable salt thereof according to the present invention are as follows:
1) N-(2-fluoro-4-methylphenyl)-3-((methylamino)methyl)-1-(pyridin-3-ylsulfonyl)-1H-indol-6-amine hydrochloride,
2) 3-((methylamino)methyl)-N-phenyl-1-(pyridin-3-ylsulfonyl)-1H-indol-6-amine hydrochloride,
3) N-(2-fluorophenyl)-3-((methylamino)methyl)-1-(pyridin-3-ylsulfonyl)-1H-indol-6-amine hydrochloride,
4) N-(2-chlorophenyl)-3-((methylamino)methyl)-1-(pyridin-3-ylsulfonyl)-1H-indol-6-amine hydrochloride,
5) N-(3-bromophenyl)-3-((methylamino)methyl)-1-(pyridin-3-ylsulfonyl)-1H-indol-6-amine hydrochloride,
6) N-(3-fluorophenyl)-3-((methylamino)methyl)-1-(pyridin-3-ylsulfonyl)-1H-indol-6-amine hydrochloride,
7) N-(3-chlorophenyl)-3-((methylamino)methyl)-1-(pyridin-3-ylsulfonyl)-1H-indol-6-amine hydrochloride,
8) N-(3-ethylphenyl)-3-((methylamino)methyl)-1-(pyridin-3-ylsulfonyl)-1H-indol-6-amine hydrochloride,
9) N-(4-fluorophenyl)-3-((methylamino)methyl)-1-(pyridin-3-ylsulfonyl)-1H-indol-6-amine hydrochloride,
10) 3-((methylamino)methyl)-1-(pyridin-3-ylsulfonyl)-N-(p-tolyl)-1H-indol-6-amine hydrochloride,
11) N-(4-chlorophenyl)-3-((methylamino)methyl)-1-(pyridin-3-ylsulfonyl)-1H-indol-6-amine hydrochloride,
12) N-(4-methoxyphenyl)-3-((methylamino)methyl)-1-(pyridin-3-ylsulfonyl)-1H-indol-6-amine hydrochloride,
13) 3-((methylamino)methyl)-1-(pyridin-3-ylsulfonyl)-N-(4-(trifluoromethyl)phenyl)-1H-indol-6-amine hydrochloride,
14) N-(4-(tert-butyl)phenyl)-3-((methylamino)methyl)-1-(pyridin-3-ylsulfonyl)-1H-indol-6-amine hydrochloride,
15) N-(3'-methoxy-[1,1'-biphenyl]-4-yl)-3-((methylamino)methyl)-1-(pyridin-3-ylsulfonyl)-1H-indol-6-amine hydrochloride,
16) N-(4-methyl-[1,1'-biphenyl]-3-yl)-3-((methylamino)methyl)-1-(pyridin-3-ylsulfonyl)-1H-indol-6-amine hydrochloride,
17) 3-((methylamino)methyl)-N-(4-phenoxyphenyl)-1-(pyridin-3-ylsulfonyl)-1H-indol-6-amine hydrochloride,
18) N-(4-(4-fluorophenoxy)phenyl)-3-((methylamino)methyl)-1-(pyridin-3-ylsulfonyl)-1H-indol-6-amine hydrochloride,
19) N-(4-(4-chlorophenoxy)phenyl)-3-((methylamino)methyl)-1-(pyridin-3-ylsulfonyl)-1H-indol-6-amine hydrochloride,
20) N-(2-fluoro-3-methylphenyl)-3-((methylamino)methyl)-1-(pyridin-3-ylsulfonyl)-1H-indol-6-amine hydrochloride,
21) N-(2,4-dimethylphenyl)-3-((methylamino)methyl)-1-(pyridin-3-ylsulfonyl)-1H-indol-6-amine hydrochloride,
22) N-(2-chloro-4-methylphenyl)-3-((methylamino)methyl)-1-(pyridin-3-ylsulfonyl)-1H-indol-6-amine,
23) N-(4-fluoro-2-methylphenyl)-3-((methylamino)methyl)-1-(pyridin-3-ylsulfonyl)-1H-indol-6-amine hydrochloride,
24) N-(2,4-difluorophenyl)-3-((methylamino)methyl)-1-(pyridin-3-ylsulfonyl)-1H-indol-6-amine hydrochloride,
25) N-(2-chloro-4-fluorophenyl)-3-((methylamino)methyl)-1-(pyridin-3-ylsulfonyl)-1H-indol-6-amine hydrochloride,
26) N-(4-fluoro-2-(trifluoromethyl)phenyl)-3-((methylamino)methyl)-1-(pyridin-3-ylsulfonyl)-1H-indol-6-amine hydrochloride,
27) N-(4-chloro-2-methylphenyl)-3-((methylamino)methyl)-1-(pyridin-3-ylsulfonyl)-1H-indol-6-amine hydrochloride,
28) N-(4-chloro-2-fluorophenyl)-3-((methylamino)methyl)-1-(pyridin-3-ylsulfonyl)-1H-indol-6-amine hydrochloride,
29) N-(2,4-dichlorophenyl)-3-((methylamino)methyl)-1-(pyridin-3-ylsulfonyl)-1H-indol-6-amine hydrochloride,
30) 5-chloro-2-((3-((methylamino)methyl)-1-(pyridin-3-ylsulfonyl)-1H-indol-6-yl)amino)benzonitrile hydrochloride,
31) N-(4-chloro-2-(trifluoromethyl)phenyl)-3-((methylamino)methyl)-1-(pyridin-3-ylsulfonyl)-1H-indol-6-amine hydrochloride, 32) N-(2-methyl-4-(trifluoromethyl)phenyl)-3-((methylamino)methyl)-1-(pyridin-3-ylsulfonyl)-1H-indol-6-amine hydrochloride,
33) N-(2-fluoro-4-(trifluoromethyl)phenyl)-3-((methylamino)methyl)-1-(pyridin-3-ylsulfonyl)-1H-indol-6-amine hydrochloride,
34) N-(2-chloro-4-(trifluoromethyl)phenyl)-3-((methylamino)methyl)-1-(pyridin-3-ylsulfonyl)-1H-indol-6-amine hydrochloride,
35) N-(2,4-Bis(trifluoromethyl)phenyl)-3-((methylamino)methyl)-1-(pyridin-3-ylsulfonyl)-1H-indol-6-amine hydrochloride,
36) 3-methyl-4-((3-((methylamino)methyl)-1-(pyridin-3-ylsulfonyl)-1H-indol-6-yl)amino)benzonitrile hydrochloride,
37) 3-ethyl-4-((3-((methylamino)methyl)-1-(pyridin-3-ylsulfonyl)-1H-indol-6-yl)amino)benzonitrile hydrochloride,
38) 3-fluoro-4-((3-((methylamino)methyl)-1-(pyridin-3-ylsulfonyl)-1H-indol-6-yl)amino)benzonitrile hydrochloride,
39) 3-chloro-4-((3-((methylamino)methyl)-1-(pyridin-3-ylsulfonyl)-1H-indol-6-yl)amino)benzonitrile hydrochloride,
40) 4-((3-((methylamino)methyl)-1-(pyridin-3-ylsulfonyl)-1H-indol-6-yl)amino)-3-(trifluoromethyl)benzonitrile hydrochloride,
41) N-(2-chloro-4-nitrophenyl)-3-((methylamino)methyl)-1-(pyridin-3-ylsulfonyl)-1H-indol-6-amine hydrochloride,
42) N-(2-methyl-4-nitrophenyl)-3-((methylamino)methyl)-1-(pyridin-3-ylsulfonyl)-1H-indol-6-amine hydrochloride,
43) N-(4-bromo-2-ethylphenyl)-3-((methylamino)methyl)-1-(pyridin-3-ylsulfonyl)-1H-indol-6-amine hydrochloride,
44) N-(4-bromo-2-chlorophenyl)-3-((methylamino)methyl)-1-(pyridin-3-ylsulfonyl)-1H-indol-6-amine hydrochloride,
45) N-(4-bromo-2-(trifluoromethyl)phenyl)-3-((methylamino)methyl)-1-(pyridin-3-ylsulfonyl)-1H-indol-6-amine hydrochloride,
46) N-(4-bromo-2-(trifluoromethoxy)phenyl)-3-((methylamino)methyl)-1-(pyridin-3-ylsulfonyl)-1H-indol-6-amine hydrochloride,
47) 3-methyl-4-((3-((methylamino)methyl)-1-(pyridin-3-ylsulfonyl)-1H-indol-6-yl)amino)phenol hydrochloride,
48) N-(4-methoxy-2-methylphenyl)-3-((methylamino)methyl)-1-(pyridin-3-ylsulfonyl)-1H-indol-6-amine hydrochloride,
49) N-(2-fluoro-4-methoxyphenyl)-3-((methylamino)methyl)-1-(pyridin-3-ylsulfonyl)-1H-indol-6-amine hydrochloride,
50) N-(4-methoxy-2-(trifluoromethoxy)phenyl)-3-((methylamino)methyl)-1-(pyridin-3-ylsulfonyl)-1H-indol-6-amine hydrochloride,
51) N-(4-methoxy-2-(trifluoromethyl)phenyl)-3-((methylamino)methyl)-1-(pyridin-3-ylsulfonyl)-1H-indol-6-amine hydrochloride,
52) N-(4-methoxy-2-nitrophenyl)-3-((methylamino)methyl)-1-(pyridin-3-ylsulfonyl)-1H-indol-6-amine hydrochloride,
53) N-(2-methyl-4-(trifluoromethoxy)phenyl)-3-((methylamino)methyl)-1-(pyridin-3-ylsulfonyl)-1H-indol-6-amine hydrochloride,
54) N-(2-fluoro-4-(trifluoromethoxy)phenyl)-3-((methylamino)methyl)-1-(pyridin-3-ylsulfonyl)-1H-indol-6-amine hydrochloride,
55) N-(2-chloro-4-(trifluoromethoxy)phenyl)-3-((methylamino)methyl)-1-(pyridin-3-ylsulfonyl)-1H-indol-6-amine hydrochloride,
56) N-(2-methoxy-4-(trifluoromethoxy)phenyl)-3-((methylamino)methyl)-1-(pyridin-3-ylsulfonyl)-1H-indol-6-amine hydrochloride,
57) methyl 3-chloro-4-((3-((methylamino)methyl)-1-(pyridin-3-ylsulfonyl)-1H-indol-6-yl)amino)benzoate hydrochloride,
58) N-(2,5-difluorophenyl)-3-((methylamino)methyl)-1-(pyridin-3-ylsulfonyl)-1H-indol-6-amine hydrochloride,
59) N-(2-fluoro-5-methylphenyl)-3-((methylamino)methyl)-1-(pyridin-3-ylsulfonyl)-1H-indol-6-amine hydrochloride,
60) N-(2,6-difluorophenyl)-3-((methylamino)methyl)-1-(pyridin-3-ylsulfonyl)-1H-indol-6-amine hydrochloride,
61) N-(2-chloro-6-methylphenyl)-3-((methylamino)methyl)-1-(pyridin-3-ylsulfonyl)-1H-indol-6-amine hydrochloride,
62) N-(3,4-difluorophenyl)-3-((methylamino)methyl)-1-(pyridin-3-ylsulfonyl)-1H-indol-6-amine hydrochloride,
63) N-(3,5-dimethoxyphenyl)-3-((methylamino)methyl)-1-(pyridin-3-ylsulfonyl)-1H-indol-6-amine hydrochloride,
64) N-(3,5-dichlorophenyl)-3-((methylamino)methyl)-1-(pyridin-3-ylsulfonyl)-1H-indol-6-amine hydrochloride,
65) N-(2,3-difluoro-4-methylphenyl)-3-((methylamino)methyl)-1-(pyridin-3-ylsulfonyl)-1H-indol-6-amine hydrochloride,
66) N-(4-fluoro-2,3-dimethylphenyl)-3-((methylamino)methyl)-1-(pyridin-3-ylsulfonyl)-1H-indol-6-amine hydrochloride,
67) 3-((methylamino)methyl)-1-(pyridin-3-ylsulfonyl)-N-(2,3,4-trifluorophenyl)-1H-indol-6-amine hydrochloride,
68) N-(2,4-difluoro-3-methoxyphenyl)-3-((methylamino)methyl)-1-(pyridin-3-ylsulfonyl)-1H-indol-6-amine hydrochloride,
69) N-(3-ethoxy-2,4-difluorophenyl)-3-((methylamino)methyl)-1-(pyridin-3-ylsulfonyl)-1H-indol-6-amine hydrochloride,
70) N-(2,3-difluoro-4-methoxyphenyl)-3-((methylamino)methyl)-1-(pyridin-3-ylsulfonyl)-1H-indol-6-amine hydrochloride,
71) N-(4-ethoxy-2,3-difluorophenyl)-3-((methylamino)methyl)-1-(pyridin-3-ylsulfonyl)-1H-indol-6-amine hydrochloride,
72) N-(2,5-difluoro-4-methylphenyl)-3-((methylamino)methyl)-1-(pyridin-3-ylsulfonyl)-1H-indol-6-amine hydrochloride,
73) N-(4,5-difluoro-2-methylphenyl)-3-((methylamino)methyl)-1-(pyridin-3-ylsulfonyl)-1H-indol-6-amine hydrochloride,
74) 3-((methylamino)methyl)-1-(pyridin-3-ylsulfonyl)-N-(2,4,5-trifluorophenyl)-1H-indol-6-amine hydrochloride,
75) N-(4-chloro-2,5-dimethylphenyl)-3-((methylamino)methyl)-1-(pyridin-3-ylsulfonyl)-1H-indol-6-amine hydrochloride,
76) 3-((methylamino)methyl)-1-(pyridin-3-ylsulfonyl)-N-(2,4,5-trichlorophenyl)-1H-indol-6-amine hydrochloride,
77) N-(2,4-dichloro-5-methoxyphenyl)-3-((methylamino)methyl)-1-(pyridin-3-ylsulfonyl)-1H-indol-6-amine hydrochloride,
78) N-(2,5-difluoro-4-(trifluoromethyl)phenyl)-3-((methylamino)methyl)-1-(pyridin-3-ylsulfonyl)-1H-indol-6-amine hydrochloride, 79) N-(4-bromo-2,5-difluorophenyl)-3-((methylamino)methyl)-1-(pyridin-3-ylsulfonyl)-1H-indol-6-amine hydrochloride,
80) N-mesityl-3-((methylamino)methyl)-1-(pyridin-3-ylsulfonyl)-1H-indol-6-amine hydrochloride,
81) N-(4-fluoro-2,6-dimethylphenyl)-3-((methylamino)methyl)-1-(pyridin-3-ylsulfonyl)-1H-indol-6-amine hydrochloride,
82) 3-((methylamino)methyl)-1-(pyridin-3-ylsulfonyl)-N-(2,4,6-trifluorophenyl)-1H-indol-6-amine hydrochloride,
83) N-(2-chloro-4,6-difluorophenyl)-3-((methylamino)methyl)-1-(pyridin-3-ylsulfonyl)-1H-indol-6-amine hydrochloride,
84) N-(2,6-dichloro-4-fluorophenyl)-3-((methylamino)methyl)-1-(pyridin-3-ylsulfonyl)-1H-indol-6-amine hydrochloride,
85) N-(4-chloro-2,6-dimethylphenyl)-3-((methylamino)methyl)-1-(pyridin-3-ylsulfonyl)-1H-indol-6-amine hydrochloride,
86) N-(4-chloro-2,6-difluorophenyl)-3-((methylamino)methyl)-1-(pyridin-3-ylsulfonyl)-1H-indol-6-amine hydrochloride,
87) 3-((methylamino)methyl)-1-(pyridin-3-ylsulfonyl)-N-(2,4,6-trichlorophenyl)-1H-indol-6-amine hydrochloride,
88) N-(2,6-difluoro-4-methoxyphenyl)-3-((methylamino)methyl)-1-(pyridin-3-ylsulfonyl)-1H-indol-6-amine hydrochloride,
89) N-(4-ethoxy-2,6-difluorophenyl)-3-((methylamino)methyl)-1-(pyridin-3-ylsulfonyl)-1H-indol-6-amine hydrochloride,
90) N-(4-bromo-2,6-dimethylphenyl)-3-((methylamino)methyl)-1-(pyridin-3-ylsulfonyl)-1H-indol-6-amine hydrochloride,
91) N-(2-bromo-4,6-difluorophenyl)-3-((methylamino)methyl)-1-(pyridin-3-ylsulfonyl)-1H-indol-6-amine hydrochloride,
92) N-(4-bromo-2,6-difluorophenyl)-3-((methylamino)methyl)-1-(pyridin-3-ylsulfonyl)-1H-indol-6-amine hydrochloride,
93) N-(2,4-dibromo-6-fluorophenyl)-3-((methylamino)methyl)-1-(pyridin-3-ylsulfonyl)-1H-indol-6-amine hydrochloride,
94) N-(4-chloro-2-methyl-6-nitrophenyl)-3-((methylamino)methyl)-1-(pyridin-3-ylsulfonyl)-1H-indol-6-amine hydrochloride,
95) 3-((methylamino)methyl)-1-(pyridin-3-ylsulfonyl)-N-(2,3,5,6-tetrafluorophenyl)-1H-indol-6-amine hydrochloride,
96) 3-((methylamino)methyl)-1-(pyridin-3-ylsulfonyl)-N-(2,3,5,6-tetrafluoro-4-(trifluoromethyl)phenyl)-1H-indol-6-amine hydrochloride,
97) N-(2,3-dihydrobenzo[b][1,4]dioxin-6-yl)-3-((methylamino)methyl)-1-(pyridin-3-ylsulfonyl)-1H-indol-6-amine hydrochloride,
98) 3-((methylamino)methyl)-N-(3-methylpyridin-2-yl)-1-(pyridin-3-ylsulfonyl)-1H-indol-6-amine hydrochloride,
99) N-(3-fluoropyridin-2-yl)-3-((methylamino)methyl)-1-(pyridin-3-ylsulfonyl)-1H-indol-6-amine hydrochloride,
100) N-(3-chloropyridin-2-yl)-3-((methylamino)methyl)-1-(pyridin-3-ylsulfonyl)-1H-indol-6-amine hydrochloride,
101) 3-((methylamino)methyl)-1-(pyridin-3-ylsulfonyl)-N-(3-(trifluoromethyl)pyridin-2-yl)-1H-indol-6-amine hydrochloride,
102) N-(3-bromopyridin-2-yl)-3-((methylamino)methyl)-1-(pyridin-3-ylsulfonyl)-1H-indol-6-amine hydrochloride,
103) N-(5-chloro-4-methylpyridin-2-yl)-3-((methylamino)methyl)-1-(pyridin-3-ylsulfonyl)-1H-indol-6-amine hydrochloride,
104) N-(5-chloro-6-methylpyridin-2-yl)-3-((methylamino)methyl)-1-(pyridin-3-ylsulfonyl)-1H-indol-6-amine hydrochloride,
105) 3-((methylamino)methyl)-N-(2-methylpyridin-3-yl)-1-(pyridin-3-ylsulfonyl)-1H-indol-6-amine hydrochloride,
106) N-(2-fluoropyridin-3-yl)-3-((methylamino)methyl)-1-(pyridin-3-ylsulfonyl)-1H-indol-6-amine hydrochloride,
107) N-(2-chloropyridin-3-yl)-3-((methylamino)methyl)-1-(pyridin-3-ylsulfonyl)-1H-indol-6-amine hydrochloride,
108) N-(2-methoxypyridin-3-yl)-3-((methylamino)methyl)-1-(pyridin-3-ylsulfonyl)-1H-indol-6-amine hydrochloride,
109) 3-((methylamino)methyl)-1-(pyridin-3-ylsulfonyl)-N-(2-(trifluoromethyl)pyridin-3-yl)-1H-indol-6-amine hydrochloride,
110) N-(5-bromopyridin-3-yl)-3-((methylamino)methyl)-1-(pyridin-3-ylsulfonyl)-1H-indol-6-amine hydrochloride,
111) N-(2,6-dimethylpyridin-3-yl)-3-((methylamino)methyl)-1-(pyridin-3-ylsulfonyl)-1H-indol-6-amine hydrochloride,
112) N-(2-fluoro-6-methylpyridin-3-yl)-3-((methylamino)methyl)-1-(pyridin-3-ylsulfonyl)-1H-indol-6-amine hydrochloride,
113) N-(2-chloro-6-methylpyridin-3-yl)-3-((methylamino)methyl)-1-(pyridin-3-ylsulfonyl)-1H-indol-6-amine hydrochloride,
114) N-(2-methoxy-6-methylpyridin-3-yl)-3-((methylamino)methyl)-1-(pyridin-3-ylsulfonyl)-1H-indol-6-amine hydrochloride,
115) N-(6-methyl-2-(trifluoromethyl)pyridin-3-yl)-3-((methylamino)methyl)-1-(pyridin-3-ylsulfonyl)-1H-indol-6-amine hydrochloride,
116) N-(6-fluoro-2-methylpyridin-3-yl)-3-((methylamino)methyl)-1-(pyridin-3-ylsulfonyl)-1H-indol-6-amine hydrochloride,
117) N-(2-bromo-6-fluoropyridin-3-yl)-3-((methylamino)methyl)-1-(pyridin-3-ylsulfonyl)-1H-indol-6-amine hydrochloride,
118) N-(6-chloro-2-methylpyridin-3-yl)-3-((methylamino)methyl)-1-(pyridin-3-ylsulfonyl)-1H-indol-6-amine hydrochloride,
119) N-(2,6-dichloropyridin-3-yl)-3-((methylamino)methyl)-1-(pyridin-3-ylsulfonyl)-1H-indol-6-amine hydrochloride,
120) N-(6-chloro-2-methoxypyridin-3-yl)-3-((methylamino)methyl)-1-(pyridin-3-ylsulfonyl)-1H-indol-6-amine hydrochloride,
121) N-(6-chloro-2-(trifluoromethyl)pyridin-3-yl)-3-((methylamino)methyl)-1-(pyridin-3-ylsulfonyl)-1H-indol-6-amine hydrochloride,
122) N-(6-methoxy-2-methylpyridin-3-yl)-3-((methylamino)methyl)-1-(pyridin-3-ylsulfonyl)-1H-indol-6-amine hydrochloride,
123) N-(2-chloro-6-methoxypyridin-3-yl)-3-((methylamino)methyl)-1-(pyridin-3-ylsulfonyl)-1H-indol-6-amine hydrochloride,
124) N-(2-methyl-6-(trifluoromethyl)pyridin-3-yl)-3-((methylamino)methyl)-1-(pyridin-3-ylsulfonyl)-1H-indol-6-amine hydrochloride,
125) N-(2-chloro-6-(trifluoromethyl)pyridin-3-yl)-3-((methylamino)methyl)-1-(pyridin-3-ylsulfonyl)-1H-indol-6-amine hydrochloride, 126) N-(5-chloro-2-methylpyridin-3-yl)-3-((methylamino)methyl)-1-(pyridin-3-ylsulfonyl)-1H-indol-6-amine hydrochloride,
127) N-(2-chloro-4-methylpyridin-3-yl)-3-((methylamino)methyl)-1-(pyridin-3-ylsulfonyl)-1H-indol-6-amine hydrochloride,
128) N-(3-chloropyridin-4-yl)-3-((methylamino)methyl)-1-(pyridin-3-ylsulfonyl)-1H-indol-6-amine hydrochloride,
129) 3-((methylamino)methyl)-1-(pyridin-3-ylsulfonyl)-N-(3-(trifluoromethyl)pyridin-4-yl)-1H-indol-6-amine hydrochloride,
130) N-(3-chloro-2-methoxypyridin-4-yl)-3-((methylamino)methyl)-1-(pyridin-3-ylsulfonyl)-1H-indol-6-amine hydrochloride,
131) N-(3-bromo-2-methoxypyridin-4-yl)-3-((methylamino)methyl)-1-(pyridin-3-ylsulfonyl)-1H-indol-6-amine hydrochloride,
132) N-(2,3-dichloropyridin-4-yl)-3-((methylamino)methyl)-1-(pyridin-3-ylsulfonyl)-1H-indol-6-amine hydrochloride,
133) N-(3-bromo-2-chloropyridin-4-yl)-3-((methylamino)methyl)-1-(pyridin-3-ylsulfonyl)-1H-indol-6-amine hydrochloride,
134) 3-((methylamino)methyl)-1-(pyridin-3-ylsulfonyl)-N-(2,3,5-trifluoropyridin-4-yl)-1H-indol-6-amine hydrochloride,
135) N-3-((methylamino)methyl)-1-(pyridin-3-ylsulfonyl)-1H-indol-6-yl)quinolin-6-amine hydrochloride,
136) N-(2-fluoro-4-methylphenyl)-1-((3-fluorophenyl)sulfonyl)-3-((methylamino)methyl)-1H-indol-6-amine hydrochloride,
137) N-(2-chloro-4-methylphenyl)-1-((3-fluorophenyl)sulfonyl)-3-((methylamino)methyl)-1H-indol-6-amine hydrochloride,
138) N-(4-fluoro-2-methylphenyl)-1-((3-fluorophenyl)sulfonyl)-3-((methylamino)methyl)-1H-indol-6-amine hydrochloride,
139) N-(2-fluoro-4-methoxyphenyl)-1-((3-fluorophenyl)sulfonyl)-3-((methylamino)methyl)-1H-indol-6-amine hydrochloride,
140) 1-((3-fluorophenyl)sulfonyl)-N-(2-methyl-4-(trifluoromethoxy)phenyl)-3-((methylamino)methyl)-1H-indol-6-amine hydrochloride,
141) N-(6-chloro-2-methoxypyridin-3-yl)-1-((3-fluorophenyl)sulfonyl)-3-((methylamino)methyl)-1H-indol-6-amine hydrochloride,
142) N-(2,6-dichloropyridin-3-yl)-1-((3-fluorophenyl)sulfonyl)-3-((methylamino)methyl)-1H-indol-6-amine hydrochloride,
143) N-(6-chloro-2-(trifluoromethyl)pyridin-3-yl)-1-((3-fluorophenyl)sulfonyl)-3-((methylamino)methyl)-1H-indol-6-amine hydrochloride,
144) N-(2-chloro-6-methoxypyridin-3-yl)-1-((3-fluorophenyl)sulfonyl)-3-((methylamino)methyl)-1H-indol-6-amine hydrochloride,
145) N-(2-chloro-6-(trifluoromethyl)pyridin-3-yl)-1-((3-fluorophenyl)sulfonyl)-3-((methylamino)methyl)-1H-indol-6-amine hydrochloride,
146) 1-((3-chlorophenyl)sulfonyl)-N-(2-fluoro-4-methylphenyl)-3-((methylamino)methyl)-1H-indol-6-amine hydrochloride,
147) N-(2-chloro-4-methylphenyl)-1-((3-chlorophenyl)sulfonyl)-3-((methylamino)methyl)-1H-indol-6-amine hydrochloride,
148) 1-((3-chlorophenyl)sulfonyl)-N-(4-methyl-2-(trifluoromethoxy)phenyl)-3-((methylamino)methyl)-1H-indol-6-amine hydrochloride,
149) N-(2-chloro-4-fluorophenyl)-1-((3-chlorophenyl)sulfonyl)-3-((methylamino)methyl)-1H-indol-6-amine hydrochloride,
150) N-(4-chloro-2-fluorophenyl)-1-((3-chlorophenyl)sulfonyl)-3-((methylamino)methyl)-1H-indol-6-amine hydrochloride,
151) N-(4-chloro-2-(trifluoromethyl)phenyl)-1-((3-chlorophenyl)sulfonyl)-3-((methylamino)methyl)-1H-indol-6-amine hydrochloride,
152) N-(2-chloro-4-(trifluoromethyl)phenyl)-1-((3-chlorophenyl)sulfonyl)-3-((methylamino)methyl)-1H-indol-6-amine hydrochloride,
153) 1-((3-chlorophenyl)sulfonyl)-N-(2-fluoro-4-methoxyphenyl)-3-((methylamino)methyl)-1H-indol-6-amine hydrochloride,
154) 1-((3-chlorophenyl)sulfonyl)-N-(2-methyl-4-(trifluoromethoxy)phenyl)-3-((methylamino)methyl)-1H-indol-6-amine hydrochloride,
155) 1-((3-chlorophenyl)sulfonyl)-N-(2-fluoro-4-(trifluoromethoxy)phenyl)-3-((methylamino)methyl)-1H-indol-6-amine hydrochloride,
156) 1-((3-chlorophenyl)sulfonyl)-N-(2,3-difluoro-4-methylphenyl)-3-((methylamino)methyl)-1H-indol-6-amine hydrochloride,
157) 1-((3-chlorophenyl)sulfonyl)-N-(2-methoxypyridin-3-yl)-3-((methylamino)methyl)-1H-indol-6-amine hydrochloride,
158) 1-((3-chlorophenyl)sulfonyl)-N-(2-fluoro-6-methylpyridin-3-yl)-3-((methylamino)methyl)-1H-indol-6-amine hydrochloride,
159) 1-((3-chlorophenyl)sulfonyl)-N-(2,6-dichloropyridin-3-yl)-3-((methylamino)methyl)-1H-indol-6-amine hydrochloride,
160) N-(2-chloro-6-methoxypyridin-3-yl)-1-((3-chlorophenyl)sulfonyl)-3-((methylamino)methyl)-1H-indol-6-amine hydrochloride,
161) N-(2-chloro-6-(trifluoromethyl)pyridin-3-yl)-1-((3-chlorophenyl)sulfonyl)-3-((methylamino)methyl)-1H-indol-6-amine hydrochloride,
162) N-(2-fluoro-4-methylphenyl)-1-((3-methoxyphenyl)sulfonyl)-3-((methylamino)methyl)-1H-indol-6-amine hydrochloride,
163) N-(2-chloro-4-methylphenyl)-1-((3-methoxyphenyl)sulfonyl)-3-((methylamino)methyl)-1H-indol-6-amine hydrochloride,
164) N-(4-chloro-2-fluorophenyl)-1-((3-methoxyphenyl)sulfonyl)-3-((methylamino)methyl)-1H-indol-6-amine hydrochloride,
165) N-(4-chloro-2-(trifluoromethyl)phenyl)-1-((3-methoxyphenyl)sulfonyl)-3-((methylamino)methyl)-1H-indol-6-amine hydrochloride,
166) N-(2-chloro-4-(trifluoromethyl)phenyl)-1-((3-methoxyphenyl)sulfonyl)-3-((methylamino)methyl)-1H-indol-6-amine hydrochloride,
167) N-(2-fluoro-4-methoxyphenyl)-1-((3-methoxyphenyl)sulfonyl)-3-((methylamino)methyl)-1H-indol-6-amine hydrochloride,
168) 1-((3-methoxyphenyl)sulfonyl)-N-(2-methyl-4-(trifluoromethoxy)phenyl)-3-((methylamino)methyl)-1H-indol-6-amine hydrochloride,
169) N-(2-chloro-4-(trifluoromethoxy)phenyl)-1-((3-methoxyphenyl)sulfonyl)-3-((methylamino)methyl)-1H-indol-6-amine hydrochloride,
170) N-(2,3-difluoro-4-methylphenyl)-1-((3-methoxyphenyl)sulfonyl)-3-((methylamino)methyl)-1H-indol-6-amine hydrochloride, 171) N-(2-fluoro-6-methylpyridin-3-yl)-1-((3-methoxyphenyl)sulfonyl)-3-((methylamino)methyl)-1H-indol-6-amine hydrochloride,
172) N-(2-chloro-6-methylpyridin-3-yl)-1-((3-methoxyphenyl)sulfonyl)-3-((methylamino)methyl)-1H-indol-6-amine hydrochloride,
173) N-(2-chloro-6-methoxypyridin-3-yl)-1-((3-methoxyphenyl)sulfonyl)-3-((methylamino)methyl)-1H-indol-6-amine hydrochloride,
174) 1-((3-(difluoromethoxy)phenyl)sulfonyl)-N-(2-fluoro-4-methylphenyl)-3-((methylamino)methyl)-1H-indol-6-amine hydrochloride,
175) N-(2-chloro-4-methylphenyl)-1-((3-(difluoromethoxy)phenyl)sulfonyl)-3-((methylamino)methyl)-1H-indol-6-amine hydrochloride,
176) N-(4-chloro-2-fluorophenyl)-1-((3-(difluoromethoxy)phenyl)sulfonyl)-3-((methylamino)methyl)-1H-indol-6-amine hydrochloride,
177) N-(4-chloro-2-(trifluoromethyl)phenyl)-1-((3-(difluoromethoxy)phenyl)sulfonyl)-3-((methylamino)methyl)-1H-indol-6-amine hydrochloride,
178) 1-((3-(difluoromethoxy)phenyl)sulfonyl)-N-(2-fluoro-4-methoxyphenyl)-3-((methylamino)methyl)-1H-indol-6-amine hydrochloride,
179) 1-((3-(difluoromethoxy)phenyl)sulfonyl)-N-(2-methyl-4-(trifluoromethoxy)phenyl)-3-((methylamino)methyl)-1H-indol-6-amine hydrochloride,
180) N-(2,3-difluoro-4-methylphenyl)-1-((3-(difluoromethoxy)phenyl)sulfonyl)-3-((methylamino)methyl)-1H-indol-6-amine hydrochloride,
181) 1-((3-(difluoromethoxy)phenyl)sulfonyl)-N-(2-fluoro-6-methylpyridin-3-yl)-3-((methylamino)methyl)-1H-indol-6-amine hydrochloride,
182) N-(2-chloro-6-methoxypyridin-3-yl)-1-((3-(difluoromethoxy)phenyl)sulfonyl)-3-((methylamino)methyl)-1H-indol-6-amine hydrochloride,
183) N-(2-fluoro-4-methylphenyl)-3-((methylamino)methyl)-1-((3-(trifluoromethyl)phenyl)sulfonyl)-1H-indol-6-amine hydrochloride,
184) N-(2-chloro-4-methylphenyl)-3-((methylamino)methyl)-1-((3-(trifluoromethyl)phenyl)sulfonyl)-1H-indol-6-amine hydrochloride,
185) N-(4-chloro-2-fluorophenyl)-3-((methylamino)methyl)-1-((3-(trifluoromethyl)phenyl)sulfonyl)-1H-indol-6-amine hydrochloride,
186) N-(4-chloro-2-(trifluoromethyl)phenyl)-3-((methylamino)methyl)-1-((3-(trifluoromethyl)phenyl)sulfonyl)-1H-indol-6-amine hydrochloride,
187) N-(2-chloro-4-(trifluoromethyl)phenyl)-3-((methylamino)methyl)-1-((3-(trifluoromethyl)phenyl)sulfonyl)-1H-indol-6-amine hydrochloride,
188) N-(2-fluoro-4-methoxyphenyl)-3-((methylamino)methyl)-1-((3-(trifluoromethyl)phenyl)sulfonyl)-1H-indol-6-amine hydrochloride,
189) N-(2-methyl-4-(trifluoromethoxy)phenyl)-3-((methylamino)methyl)-1-((3-(trifluoromethyl)phenyl)sulfonyl)-1H-indol-6-amine hydrochloride,
190) N-(2-methoxy-4-(trifluoromethoxy)phenyl)-3-((methylamino)methyl)-1-((3-(trifluoromethyl)phenyl)sulfonyl)-1H-indol-6-amine hydrochloride,
191) N-(2,3-difluoro-4-methylphenyl)-3-((methylamino)methyl)-1-((3-(trifluoromethyl)phenyl)sulfonyl)-1H-indol-6-amine hydrochloride,
192) N-(2-chloro-6-methylpyridin-3-yl)-3-((methylamino)methyl)-1-((3-(trifluoromethyl)phenyl)sulfonyl)-1H-indol-6-amine hydrochloride,
193) N-(2,6-dichloropyridin-3-yl)-3-((methylamino)methyl)-1-((3-(trifluoromethyl)phenyl)sulfonyl)-1H-indol-6-amine hydrochloride,
194) N-(2-chloro-6-methoxypyridin-3-yl)-3-((methylamino)methyl)-1-((3-(trifluoromethyl)phenyl)sulfonyl)-1H-indol-6-amine hydrochloride,
195) N-(2-chloro-6-(trifluoromethyl)pyridin-3-yl)-3-((methylamino)methyl)-1-((3-(trifluoromethyl)phenyl)sulfonyl)-1H-indol-6-amine hydrochloride,
196) N-(2-chloro-4-methylphenyl)-3-((methylamino)methyl)-1-((3-(trifluoromethoxy)phenyl)sulfonyl)-1H-indol-6-amine hydrochloride,
197) N-(4-chloro-2-fluorophenyl)-3-((methylamino)methyl)-1-((3-(trifluoromethoxy)phenyl)sulfonyl)-1H-indol-6-amine hydrochloride,
198) N-(2-chloro-4-(trifluoromethyl)phenyl)-3-((methylamino)methyl)-1-((3-(trifluoromethoxy)phenyl)sulfonyl)-1H-indol-6-amine hydrochloride,
199) N-(2-fluoro-4-methoxyphenyl)-3-(methylamino)methyl)-1-((3-(trifluoromethoxy)phenyl)sulfonyl)-1H-indol-6-amine hydrochloride,
200) N-(2-methyl-4-(trifluoromethoxy)phenyl)-3-((methylamino)methyl)-1-((3-(trifluoromethoxy)phenyl)sulfonyl)-1H-indol-6-amine hydrochloride,
201) N-(2-chloro-4-(trifluoromethoxy)phenyl)-3-((methylamino)methyl)-1-((3-(trifluoromethoxy)phenyl)sulfonyl)-1H-indol-6-amine hydrochloride,
202) N-(2-methoxy-4-(trifluoromethoxy)phenyl)-3-((methylamino)methyl)-1-((3-(trifluoromethoxy)phenyl)sulfonyl)-1H-indol-6-amine hydrochloride,
203) N-(2,3-difluoro-4-methylphenyl)-3-((methylamino)methyl)-1-((3-(trifluoromethoxy)phenyl)sulfonyl)-1H-indol-6-amine hydrochloride,
204) N-(2-fluoro-6-methylpyridin-3-yl)-3-((methylamino)methyl)-1-((3-(trifluoromethoxy)phenyl)sulfonyl)-1H-indol-6-amine hydrochloride,
205) N-(2-chloro-6-methylpyridin-3-yl)-3-((methylamino)methyl)-1-((3-(trifluoromethoxy)phenyl)sulfonyl)-1H-indol-6-amine hydrochloride,
206) N-(2-fluoro-4-methylphenyl)-3-((methylamino)methyl)-1-((4-(trifluoromethoxy)phenyl)sulfonyl)-1H-indol-6-amine hydrochloride,
207) N-(2-chloro-4-methylphenyl)-3-((methylamino)methyl)-1-((4-(trifluoromethoxy)phenyl)sulfonyl)-1H-indol-6-amine hydrochloride,
208) N-(2-chloro-4-(trifluoromethyl)phenyl)-3-((methylamino)methyl)-1-((4-(trifluoromethoxy)phenyl)sulfonyl)-1H-indol-6-amine hydrochloride,
209) N-(2-methyl-4-(trifluoromethoxy)phenyl)-3-((methylamino)methyl)-1-((4-(trifluoromethoxy)phenyl)sulfonyl)-1H-indol-6-amine hydrochloride,
210) N-(2-fluoro-4-methylphenyl)-1-((5-fluoropyridin-3-yl)sulfonyl)-3-((methylamino)methyl)-1H-indol-6-amine hydrochloride,
211) N-(2-chloro-4-methylphenyl)-1-((5-fluoropyridin-3-yl)sulfonyl)-3-((methylamino)methyl)-1H-indol-6-amine hydrochloride,
212) N-(4-fluoro-2-methylphenyl)-1-((5-fluoropyridin-3-yl)sulfonyl)-3-((methylamino)methyl)-1H-indol-6-amine hydrochloride,
213) N-(2-chloro-4-fluorophenyl)-1-((5-fluoropyridin-3-yl)sulfonyl)-3-((methylamino)methyl)-1H-indol-6-amine hydrochloride,
214) 1-((5-fluoropyridin-3-yl)sulfonyl)-N-(4-methoxy-2-(trifluoromethoxy)phenyl)-3-((methylamino)methyl)-1H-indol-6-amine hydrochloride, 215) N-(2-chloro-4-(trifluoromethoxy)phenyl)-1-((5-fluoropyridin-3-yl)sulfonyl)-3-((methylamino)methyl)-1H-indol-6-amine hydrochloride,
216) 1-((5-fluoropyridin-3-yl)sulfonyl)-N-(2-methoxy-4-(trifluoromethoxy)phenyl)-3-((methylamino)methyl)-1H-indol-6-amine hydrochloride,
217) N-(2-chloro-6-methoxypyridin-3-yl)-1-((5-fluoropyridin-3-yl)sulfonyl)-3-((methylamino)methyl)-1H-indol-6-amine hydrochloride,
218) N-(2-chloro-6-(trifluoromethyl)pyridin-3-yl)-1-((5-fluoropyridin-3-yl)sulfonyl)-3-((methylamino)methyl)-1H-indol-6-amine hydrochloride,
219) N-(2-chloro-4-methylphenyl)-1-((4-methoxyphenyl)sulfonyl)-3-((methylamino)methyl)-1H-indol-6-amine hydrochloride,
220) N-(2-chloro-4-methylphenyl)-1-((4-(difluoromethoxy)phenyl)sulfonyl)-3-((methylamino)methyl)-1H-indol-6-amine hydrochloride,
221) N-(2-chloro-4-methylphenyl)-3-((methylamino)methyl)-1-((4-(trifluoromethyl)phenyl)sulfonyl)-1H-indol-6-amine hydrochloride,
222) N-(2-fluoro-4-methylphenyl)-3-((methylamino)methyl)-1-(phenylsulfonyl)-1H-indol-6-amine hydrochloride,
223) N-(2-fluoro-4-methylphenyl)-3-((methylamino)methyl)-1-(o-tolylsulfonyl)-1H-indol-6-amine hydrochloride,
224) N-(2-fluoro-4-methylphenyl)-1-((2-fluorophenyl)sulfonyl)-3-((methylamino)methyl)-1H-indol-6-amine hydrochloride,
225) 1-((2-chlorophenyl)sulfonyl)-N-(2-fluoro-4-methylphenyl)-3-((methylamino)methyl)-1H-indol-6-amine hydrochloride,
226) N-(2-fluoro-4-methylphenyl)-3-((methylamino)methyl)-1-(m-tolylsulfonyl)-1H-indol-6-amine hydrochloride,
227) 3-((6-((2-fluoro-4-methylphenyl)amino)-3-((methylamino)methyl)-1H-indol-1-yl)sulfonyl)benzonitrile hydrochloride,
228) 1-((3-bromophenyl)sulfonyl)-N-(2-fluoro-4-methylphenyl)-3-((methylamino)methyl)-1H-indol-6-amine hydrochloride,
229) N-(2-fluoro-4-methylphenyl)-3-((methylamino)methyl)-1-tosyl-1H-indol-6-amine hydrochloride,
230) 1-((4-chlorophenyl)sulfonyl)-N-(2-fluoro-4-methylphenyl)-3-((methylamino)methyl)-1H-indol-6-amine hydrochloride,
231) 1-((4-(tert-butyl)phenyl)sulfonyl)-N-(2-fluoro-4-methylphenyl)-3-((methylamino)methyl)-1H-indol-6-amine hydrochloride,
232) 1-([1,1'-biphenyl]-4-ylsulfonyl)-N-(2-fluoro-4-methylphenyl)-3-((methylamino)methyl)-1H-indol-6-amine hydrochloride,
233) N-(2-fluoro-4-methylphenyl)-3-((methylamino)methyl)-1-(naphthalen-1-ylsulfonyl)-1H-indol-6-amine hydrochloride,
234) 1-((2,3-dichlorophenyl)sulfonyl)-N-(2-fluoro-4-methylphenyl)-3-((methylamino)methyl)-1H-indol-6-amine hydrochloride,
235) 1-((2,4-dichlorophenyl)sulfonyl)-N-(2-fluoro-4-methylphenyl)-3-((methylamino)methyl)-1H-indol-6-amine hydrochloride,
236) 1-((2,5-dimethylphenyl)sulfonyl)-N-(2-fluoro-4-methylphenyl)-3-((methylamino)methyl)-1H-indol-6-amine hydrochloride,
237) 1-((3,4-difluorophenyl)sulfonyl)-N-(2-fluoro-4-methylphenyl)-3-((methylamino)methyl)-1H-indol-6-amine hydrochloride,
238) 1-((3,4-dichlorophenyl)sulfonyl)-N-(2-fluoro-4-methylphenyl)-3-((methylamino)methyl)-1H-indol-6-amine hydrochloride,
239) 1-((3,5-dimethylphenyl)sulfonyl)-N-(2-fluoro-4-methylphenyl)-3-((methylamino)methyl)-1H-indol-6-amine hydrochloride,
240) N-(2-fluoro-4-methylphenyl)-3-((methylamino)methyl)-1-((2,3,4-trichlorophenyl)sulfonyl)-1H-indol-6-amine hydrochloride,
241) 1-((5-bromopyridin-3-yl)sulfonyl)-N-(2-fluoro-4-methylphenyl)-3-((methylamino)methyl)-1H-indol-6-amine hydrochloride,
242) N-(2-fluoro-4-methylphenyl)-1-((6-methoxypyridin-3-yl)sulfonyl)-3-((methylamino)methyl)-1H-indol-6-amine hydrochloride,
243) N-methyl-1-(6-phenyl-1-(pyridin-3-ylsulfonyl)-1H-indol-3-yl)-methanamine,
244) 1-(6-(3-chlorophenyl)-1-(pyridin-3-ylsulfonyl)-1H-indol-3-yl)-N-methylmethanamine,
245) N-(3-(3-((methylamino)methyl)-1-(pyridin-3-ylsulfonyl)-1H-indol-6-yl)phenyl)acetamide,
246) 4-(3-((methylamino)methyl)-1-(pyridin-3-ylsulfonyl)-1H-indol-6-yl)aniline,
247) 1-(6-([1,1'-biphenyl]-4-yl)-1-(pyridin-3-ylsulfonyl)-1H-indol-3-yl)-N-methylmethanamine,
248) 1-(6-(6-methoxypyridin-3-yl)-1-(pyridin-3-ylsulfonyl)-1H-indol-3-yl)-N-methylmethanamine,
249) N-methyl-1-(6-(1-methyl-1H-pyrazol-4-yl)-1-(pyridin-3-ylsulfonyl)-1H-indol-3-yl)methanamine,
250) N-methyl-1-(6-(1-methyl-1H-pyrazol-5-yl)-1-(pyridin-3-ylsulfonyl)-1H-indol-3-yl)methanamine,
251) 1-(6-(4-methoxyphenyl)-1-(pyridin-3-ylsulfonyl)-1H-indol-3-yl)-N-methylmethanamine hydrochloride,
252) 1-(6-(2-fluoro-4-methylphenyl)-1-(pyridin-3-ylsulfonyl)-1H-indol-3-yl)-N-methylmethanamine hydrochloride,
253) 1-(6-(2-chloro-4-methylphenyl)-1-(pyridin-3-ylsulfonyl)-1H-indol-3-yl)-N-methylmethanamine hydrochloride,
254) N-methyl-1-(1-(pyridin-3-ylsulfonyl)-6-(2-(trifluoromethyl)pyridin-3-yl)-1H-indol-3-yl)methanamine hydrochloride,
255) 1-(6-(6-fluoropyridin-3-yl)-1-(pyridin-3-ylsulfonyl)-1H-indol-3-yl)-N-methylmethanamine hydrochloride,
256) 1-(6-(2-fluoropyridin-4-yl)-1-(pyridin-3-ylsulfonyl)-1H-indol-3-yl)-N-methylmethanamine hydrochloride,
257) 1-(6-(6-fluoro-5-methylpyridin-3-yl)-1-(pyridin-3-ylsulfonyl)-1H-indol-3-yl)-N-methylmethanamine hydrochloride,
258) N-methyl-1-(1-(pyridin-3-ylsulfonyl)-6-(pyrimidin-5-yl)-1H-indol-3-yl)methanamine hydrochloride,
259) 1-(6-(2-methoxypyrimidin-5-yl)-1-(pyridin-3-ylsulfonyl)-1H-indol-3-yl)-N-methylmethanamine hydrochloride,
260) N-methyl-1-(6-(6-methyl-3,4-dihydroquinolin-1(2H)-yl)-1-(pyridin-3-ylsulfonyl)-1H-indol-3-yl)methanamine hydrochloride,
261) 1-(1-((3-(difluoromethoxy)phenyl)sulfonyl)-6-(2-(trifluoromethyl)pyridin-3-yl)-1H-indol-3-yl)-N-methylmethanamine hydrochloride,
262) 1-(1-((3-(difluoromethoxy)phenyl)sulfonyl)-6-(2-fluoropyridin-4-yl)-1H-indol-3-yl)-N-methylmethanamine hydrochloride, 263) 1-(1-((3-(difluoromethoxy)phenyl)sulfonyl)-6-(6-fluoro-5-methylpyridin-3-yl)-1H-indol-3-yl)-N-methylmethanamine hydrochloride,
264) 1-(1-((3-(difluoromethoxy)phenyl)sulfonyl)-6-(pyrimidin-5-yl)-1H-indol-3-yl)-N-methylmethanamine hydrochloride,
265) 1-(1-((4-(difluoromethoxy)phenyl)sulfonyl)-6-(pyrimidin-5-yl)-1H-indol-3-yl)-N-methylmethanamine hydrochloride,
266) 1-(1-((3-(difluoromethoxy)phenyl)sulfonyl)-6-(2-methoxypyrimidin-5-yl)-1H-indol-3-yl)-N-methylmethanamine hydrochloride,
267) 1-(6-(2-chloro-4-methylbenzyl)-1-(pyridin-3-ylsulfonyl)-1H-indol-3-yl)-N-methylmethanamine hydrochloride,
268) 1-(6-benzyl-1-(pyridin-3-ylsulfonyl)-1H-indol-3-yl)-N-methylmethanamine hydrochloride,
269) 1-(6-(2-fluorobenzyl)-1-(pyridin-3-ylsulfonyl)-1H-indol-3-yl)-N-methylmethanamine hydrochloride,
270) N-methyl-1-(6-(4-methylbenzyl)-1-(pyridin-3-ylsulfonyl)-1H-indol-3-yl)methanamine hydrochloride,
271) N-methyl-1-(1-(pyridin-3-ylsulfonyl)-6-(4-(trifluoromethoxy)benzyl)-1H-indol-3-yl)methanamine hydrochloride,
272) 1-(6-(2-fluoro-4-methylbenzyl)-1-(pyridin-3-ylsulfonyl)-1H-indol-3-yl)-N-methylmethanamine hydrochloride,
273) 1-(6-(2-chloro-4-fluorobenzyl)-1-(pyridin-3-ylsulfonyl)-1H-indol-3-yl)-N-methylmethanamine hydrochloride,
274) 1-(6-(4-chloro-2-fluorobenzyl)-1-(pyridin-3-ylsulfonyl)-1H-indol-3-yl)-N-methylmethanamine hydrochloride,
275) 1-(6-(4-chloro-2-(trifluoromethyl)benzyl)-1-(pyridin-3-ylsulfonyl)-1H-indol-3-yl)-N-methylmethanamine hydrochloride,
276) 1-(6-(2-chloro-4-(trifluoromethyl)benzyl)-1-(pyridin-3-ylsulfonyl)-1H-indol-3-yl)-N-methylmethanamine hydrochloride,
277) 1-(6-(2-fluoro-4-methoxybenzyl)-1-(pyridin-3-ylsulfonyl)-1H-indol-3-yl)-N-methylmethanamine hydrochloride,
278) N-methyl-1-(6-(2-methyl-4-(trifluoromethoxy)benzyl)-1-(pyridin-3-ylsulfonyl)-1H-indol-3-yl)methanamine hydrochloride,
279) 1-(6-(2-fluoro-4-(trifluoromethoxy)benzyl)-1-(pyridin-3-ylsulfonyl)-1H-indol-3-yl)-N-methylmethanamine hydrochloride,
280) 1-(6-(2-chloro-4-(trifluoromethoxy)benzyl)-1-(pyridin-3-ylsulfonyl)-1H-indol-3-yl)-N-methylmethanamine hydrochloride,
281) 1-(6-(2-methoxy-4-(trifluoromethoxy)benzyl)-1-(pyridin-3-ylsulfonyl)-1H-indol-3-yl)-N-methylmethanamine hydrochloride,
282) 1-(6-((2-methoxypyridin-3-yl)methyl)-1-(pyridin-3-ylsulfonyl)-1H-indol-3-yl)-N-methylmethanamine hydrochloride,
283) 1-(6-((2-fluoro-6-methylpyridin-3-yl)methyl)-1-(pyridin-3-ylsulfonyl)-1H-indol-3-yl)-N-methylmethanamine hydrochloride,
284) 1-(6-((2-chloro-6-methylpyridin-3-yl)methyl)-1-(pyridin-3-ylsulfonyl)-1H-indol-3-yl)-N-methylmethanamine hydrochloride,
285) 1-(6-((2,6-dichloropyridin-3-yl)methyl)-1-(pyridin-3-ylsulfonyl)-1H-indol-3-yl)-N-methylmethanamine hydrochloride,
286) 1-(6-(2,3-difluoro-4-methylbenzyl)-1-(pyridin-3-ylsulfonyl)-1H-indol-3-yl)-N-methylmethanamine hydrochloride,
287) 1-(6-(2,3-difluoro-4-methylbenzyl)-1-((3-fluorophenyl)sulfonyl)-1H-indol-3-yl)-N-methylmethanamine,
288) 1-(6-(2,3-difluoro-4-methylbenzyl)-1-((3-(trifluoromethyl)phenyl)sulfonyl)-1H-indol-3-yl)-N-methylmethanamine,
289) 1-(6-(2,3-difluoro-4-methylbenzyl)-1-((3-methoxyphenyl)sulfonyl)-1H-indol-3-yl)-N-methylmethanamine,
290) 1-(6-(2,3-difluoro-4-methylbenzyl)-1-((3-(difluoromethoxy)phenyl)sulfonyl)-1H-indol-3-yl)-N-methylmethanamine,
291) 1-(6-((2-chloro-6-methoxypyridin-3-yl)methyl)-1-(pyridin-3-ylsulfonyl)-1H-indol-3-yl)-N-methylmethanamine hydrochloride,
292) 1-(6-((2-chloro-6-methoxypyridin-3-yl)methyl)-1-((3-fluorophenyl)sulfonyl)-1H-indol-3-yl)-N-methylmethanamine hydrochloride,
293) 1-(6-((2-chloro-6-methoxypyridin-3-yl)methyl)-1-((3-chlorophenyl)sulfonyl)-1H-indol-3-yl)-N-methylmethanamine,
294) 1-(6-((2-chloro-6-methoxypyridin-3-yl)methyl)-1-((3-(trifluoromethyl)phenyl)sulfonyl)-1H-indol-3-yl)-N-methylmethanamine hydrochloride,
295) 1-(6-((2-chloro-6-methoxypyridin-3-yl)methyl)-1-((3-methoxyphenyl)sulfonyl)-1H-indol-3-yl)-N-methylmethanamine,
296) 1-(6-((2-chloro-6-methoxypyridin-3-yl)methyl)-1-((3-(difluoromethoxy)phenyl)sulfonyl)-1H-indol-3-yl)-N-methylmethanamine,
297) 1-(6-((2-chloro-6-methoxypyridin-3-yl)methyl)-1-((3-(trifluoromethoxy)phenyl)sulfonyl)-1H-indol-3-yl)-N-methylmethanamine,
298) 1-(6-((2-chloro-6-methoxypyridin-3-yl)methyl)-1-((4-(difluoromethoxy)phenyl)sulfonyl)-1H-indol-3-yl)-N-methylmethanamine,
299) 1-(6-(2-chloro-4-methylbenzyl)-1-((3-fluorophenyl)sulfonyl)-1H-indol-3-yl)-N-methylmethanamine,
300) 1-(6-(2-chloro-4-methylbenzyl)-1-((2-fluorophenyl)sulfonyl)-1H-indol-3-yl)-N-methylmethanamine,
301) 1-(6-(2-chloro-4-methylbenzyl)-1-((3-chlorophenyl)sulfonyl)-1H-indol-3-yl)-N-methylmethanamine,
302) 1-(6-(2-chloro-4-methylbenzyl)-1-((3-(trifluoromethyl)phenyl)sulfonyl)-1H-indol-3-yl)-N-methylmethanamine,
303) 1-(6-(2-chloro-4-methylbenzyl)-1-((3-methoxyphenyl)sulfonyl)-1H-indol-3-yl)-N-methylmethanamine,
304) 1-(6-(2-chloro-4-methylbenzyl)-1-((3-(difluoromethoxy)phenyl)sulfonyl)-1H-indol-3-yl)-N-methylmethanamine,
305) 1-(6-(2-chloro-4-methylbenzyl)-1-((3-(trifluoromethoxy)phenyl)sulfonyl)-1H-indol-3-yl)-N-methylmethanamine,
306) 1-(6-(2-chloro-4-methylbenzyl))-1-((4-fluorophenyl)sulfonyl)-1H-indol-3-yl)-N-methylmethanamine,
307) 1-(6-(2-chloro-4-methylbenzyl)-1-((4-methoxyphenyl)sulfonyl)-1H-indol-3-yl)-N-methylmethanamine,
308) 1-(6-(2-chloro-4-methylbenzyl)-1-((4-(difluoromethoxy)phenyl)sulfonyl)-1H-indol-3-yl)-N-methylmethanamine,
309) 1-(6-(5-chloro-nitrophenoxy)-1-(pyridin-3-ylsulfonyl)-1H-indol-3-yl)-N-methylmethanamine hydrochloride,
310) N-methyl-1-(6-(2-nitrophenoxy)-1-(pyridin-3-ylsulfonyl)-1H-indol-3-yl)methanamine hydrochloride, 311) 1-(6-(2-chloro-4-(trifluoromethyl)phenoxy)-1-(pyridin-3-ylsulfonyl)-1H-indol-3-yl)-N-methylmethanamine hydrochloride,
312) 1-(6-((3-chloro-5-(trifluoromethyl)pyridin-2-yl)oxy)-1-(pyridin-3-ylsulfonyl)-1H-indol-3-yl)-N-methylmethanamine hydrochloride,
313) 1-(6-((5-fluoropyrimidin-2-yl)oxy)-1-(pyridin-3-ylsulfonyl)-1H-indol-3-yl)-N-methylmethanamine hydrochloride,
314) 1-(6-((6-chloropyrimidin-4-yl)oxy)-1-(pyridin-3-ylsulfonyl)-1H-indol-3-yl)-N-methylmethanamine hydrochloride,
315) N-(2-chloro-6-methoxypyridin-3-yl)-N-methyl-3-((methylamino)methyl)-1-((3-(trifluoromethyl)phenyl)sulfonyl)-1H-indol-6-amine hydrochloride,
316) N-(2-methoxy-4-(trifluoromethoxy)phenyl)-N-(3-((methylamino)methyl)-1-(pyridin-3-ylsulfonyl)-1H-indol-6-yl)formamide,
317) N-(2-chloro-6-methoxypyridin-3-yl)-3-((ethylamino)methyl)-1-((3-(trifluoromethyl)phenyl)sulfonyl)-1H-indol-6-amine,
318) N-(2-chloro-6-methoxypyridin-3-yl)-3-(pyrrolidin-1-ylmethyl)-1-((3-(trifluoromethyl)phenyl)sulfonyl)-1H-indol-6-amine,
319) N-(2-chloro-6-methoxypyridin-3-yl)-3-((dimethylamino)methyl)-1-((3-(trifluoromethyl)phenyl)sulfonyl)-1H-indol-6-amine,
320) 6-((2-chloro-6-methoxypyridin-3-yl)amino)-N-methyl-1-((3-(trifluoromethyl)phenyl)sulfonyl)-1H-indol-3-carboxamide,
321) 6-((2-chloro-6-methoxypyridin-3-yl)amino)-N,N-dimethyl-1-((3-(trifluoromethyl)phenyl)sulfonyl)-1H-indol-3-carboxamide,
322) 6-((2-fluoro-4-methylphenyl)amino)-N,N-dimethyl-1-(pyridin-3-ylsulfonyl)-1H-indol-3-carboxamide,
323) 6-((2-chloro-4-methylphenyl)amino)-N,N-dimethyl-1-(pyridin-3-ylsulfonyl)-1H-indol-3-carboxamide,
324) 6-((2-fluoro-4-methoxyphenyl)amino)-N,N-dimethyl-1-(pyridin-3-ylsulfonyl)-1H-indol-3-carboxamide,
325) 6-((2-chloro-4-(trifluoromethyl)phenyl)amino)-N,N-dimethyl-1-(pyridin-3-ylsulfonyl)-1H-indol-3-carboxamide,
326) N,N-dimethyl-6-((2-methyl-4-(trifluoromethoxy)phenyl)amino)-1-(pyridin-3-ylsulfonyl)-1H-indol-3-carboxamide,
327) 6-((2-chloro-4-(trifluoromethoxy)phenyl)amino)-N,N-dimethyl-1-(pyridin-3-ylsulfonyl)-1H-indol-3-carboxamide,
328) 6-((2-methoxy-4-(trifluoromethoxy)phenyl)amino)-N,N-dimethyl-1-(pyridin-3-ylsulfonyl)-1H-indol-3-carboxamide,
329) 6-((2,3-difluoro-4-methylphenyl)amino)-N,N-dimethyl-1-(pyridin-3-ylsulfonyl)-1H-indol-3-carboxamide,
330) 6-((2-chloro-6-methylpyridin-3-yl)amino)-N,N-dimethyl-1-(pyridin-3-ylsulfonyl)-1H-indol-3-carboxamide,
331) 6-((2,6-dichloropyridin-3-yl)amino)-N,N-dimethyl-1-(pyridin-3-ylsulfonyl)-1H-indol-3-carboxamide,
332) 6-((2-chloro-6-methoxypyridin-3-yl)amino)-N,N-dimethyl-1-(pyridin-3-ylsulfonyl)-1H-indol-3-carboxamide,
333) $N^6$-(2-fluoro-4-methylphenyl)-N3-methyl-1-(pyridin-3ylsulfonyl)-1H-indol-3,6-diamine hydrochloride,
334) $N^6$-(2-chloro-4-methylphenyl)-N3-methyl-1-(pyridin-3ylsulfonyl)-1H-indol-3,6-diamine hydrochloride,
335) methyl 6-(4-methoxyphenyl)-1-(pyridin-3-ylsulfonyl)-1H-indol-3-carboxylate,
336) methyl 6-(6-fluoropyridin-3-yl)-1-(pyridin-3-ylsulfonyl)-1H-indol-3-carboxylate,
337) methyl 1-((6-chloropyridin-3-yl)sulfonyl)-6-(6-fluoropyridin-3-yl)-1H-indol-3-carboxylate,
338) methyl 6-(6-methoxypyridin-3-yl)-1-(pyridin-3-ylsulfonyl)-1H-indol-3-carboxylate,
339) N-(2-fluoro-4-methylphenyl)-1-((3-fluorophenyl)sulfonyl)-3-((methylamino)methyl)-1H-pyrrolo[3,2-b]pyridin-6-amine hydrochloride,
340) 1-((3-fluorophenyl)sulfonyl)-N-(4-methyl-2-(trifluoromethoxy)phenyl)-3-((methylamino)methyl)-1H-pyrrolo[3,2-b]pyridin-6-amine hydrochloride,
341) N-(4-chloro-2-methylphenyl)-1-((3-fluorophenyl)sulfonyl)-3-((methylamino)methyl)-1H-pyrrolo[3,2-b]pyridin-6-amine hydrochloride,
342) N-(2,4-dichlorophenyl)-1-((3-fluorophenyl)sulfonyl)-3-((methylamino)methyl)-1H-pyrrolo[3,2-b]pyridin-6-amine hydrochloride,
343) 1-((3-fluorophenyl)sulfonyl)-N-(2-methoxy-4-(trifluoromethoxy)phenyl)-3-((methylamino)methyl)-1H-pyrrolo[3,2-b]pyridin-6-amine hydrochloride,
344) N-(6-chloro-2-methylpyridin-3-yl)-1-((3-fluorophenyl)sulfonyl)-3-((methylamino)methyl)-1H-pyrrolo[3,2-b]pyridin-6-amine hydrochloride,
345) N-(2-chloro-4-methylphenyl)-3-((methylamino)methyl)-1-(pyridin-3-ylsulfonyl)-1H-pyrrolo[3,2-b]pyridin-6-amine hydrochloride,
346) N-(4-fluoro-2-methylphenyl)-3-((methylamino)methyl)-1-(pyridin-3-ylsulfonyl)-1H-pyrrolo[3,2-b]pyridin-6-amine hydrochloride,
347) N-(2-chloro-4-fluorophenyl)-3-((methylamino)methyl)-1-(pyridin-3-ylsulfonyl)-1H-pyrrolo[3,2-b]pyridin-6-amine hydrochloride,
348) N-(4-chloro-2-methylphenyl)-3-((methylamino)methyl)-1-(pyridin-3-ylsulfonyl)-1H-pyrrolo[3,2-b]pyridin-6-amine hydrochloride,
349) N-(2,4-dichlorophenyl)-3-((methylamino)methyl)-1-(pyridin-3-ylsulfonyl)-1H-pyrrolo[3,2-b]pyridin-6-amine hydrochloride,
350) N-(2-chloro-4-methylphenyl)-1-((5-fluoropyridin-3-yl)sulfonyl)-3-((methylamino)methyl)-1H-pyrrolo[3,2-b]pyridin-6-amine hydrochloride,
351) N-(4-fluoro-2-methylphenyl)-1-((5-fluoropyridin-3-yl)sulfonyl)-3-((methylamino)methyl)-1H-pyrrolo[3,2-b]pyridin-6-amine hydrochloride,
352) N-(2-chloro-4-fluorophenyl)-1-((5-fluoropyridin-3-yl)sulfonyl)-3-((methylamino)methyl)-1H-pyrrolo[3,2-b]pyridin-6-amine hydrochloride,
353) N-(2-chloro-4-methylphenyl)-1-((3-fluorophenyl)sulfonyl)-3-((methylamino)methyl)-1H-pyrrolo[3,2-c]pyridin-6-amine hydrochloride,
354) N-(4-fluoro-2-methylphenyl)-1-((3-fluorophenyl)sulfonyl)-3-((methylamino)methyl)-1H-pyrrolo[3,2-c]pyridin-6-amine hydrochloride,
355) N-(2-chloro-4-fluorophenyl)-1-((3-fluorophenyl)sulfonyl)-3-((methylamino)methyl)-1H-pyrrolo[3,2-c]pyridin-6-amine hydrochloride,
356) 1-((3-fluorophenyl)sulfonyl)-N-(2-methoxy-4-(trifluoromethoxy)phenyl)-3-((methylamino)methyl)-1H-pyrrolo[3,2-c]pyridin-6-amine hydrochloride,
357) N-(2,6-dichloropyridin-3-yl)-1-((3-fluorophenyl)sulfonyl)-3-((methylamino)methyl)-1H-pyrrolo[3,2-c]pyridin-6-amine hydrochloride,
358) N-(2-chloro-6-methylpyridin-3-yl)-1-((3-fluorophenyl)sulfonyl)-3-((methylamino)methyl)-1H-pyrrolo[3,2-c]pyridin-6-amine hydrochloride, and
359) N-(2,6-dichloropyridin-3-yl)-1-((3-fluorophenyl)sulfonyl)-3-((methylamino)methyl)-1H-pyrrolo[2,3-b]pyridin-6-amine hydrochloride.

Additionally, the present invention provides the following intermediates useful for the preparation of the compound represented by Chemical Formula 1 above, or a pharmaceutically acceptable salt thereof:
1) pyridin-3-sulfonyl chloride,
2) 6-bromo-1-(pyridin-3-ylsulfonyl)-1H-indol-3-carbaldehyde,
3) 1-(6-bromo-1-(pyridin-3-ylsulfonyl)-1H-indol-3-yl)-N-methylmethanamine,
4) tert-butyl ((6-bromo-1-(pyridin-3-ylsulfonyl)-1H-indol-3-yl)methyl)(methyl)carbamate,
5) tert-butyl ((6-((2-fluoro-4-methylphenyl)amino)-1-(pyridin-3-ylsulfonyl)-1H-indol-3-yl)methyl)(methyl)carbamate,
6) tert-butyl ((6-bromo-1H-indol-3-yl)methyl)(methyl)carbamate,
7) tert-butyl ((6-bromo-1-((3-fluorophenyl)sulfonyl)-1H-indol-3-yl)methyl)(methyl)carbamate,
8) tert-butyl ((6-((2-fluoro-4-methylphenyl)amino)-1-((3-fluorophenyl)sulfonyl)-1H-indol-3-yl)methyl)(methyl)carbamate,
9) tert-butyl ((6-((2-fluoro-4-methylphenyl)amino)-1H-indol-3-yl)methyl)(methyl)carbamate,
10) tert-butyl ((6-((2-fluoro-4-methylphenyl)amino)-1-(phenylsulfonyl)-1H-indol-3-yl)methyl)(methyl)carbamate,
11) tert-butyl ((6-(4-methoxyphenyl)-1-(pyridin-3-ylsulfonyl)-1H-indol-3-yl)methyl)(methyl)carbamate,
12) tert-butyl ((6-bromo-1-((3-(difluoromethoxy)phenyl)sulfonyl)-1H-indol-3-yl)methyl)(methyl)carbamate,
13) tert-butyl ((1-((3-(difluoromethoxy)phenyl)sulfonyl)-6-(2-(trifluoromethyl)pyridin-3-yl)-1H-indol-3-yl)methyl)(methyl)carbamate,
14) methyl 3-formyl-1-(pyridin-3-ylsulfonyl)-1H-indol-6-carboxylate,
15) methyl 3-((methylamino)methyl)-1-(pyridin-3-ylsulfonyl)-1H-indol-6-carboxylate,
16) methyl 3-(((tert-butoxycarbonyl)(methyl)amino)methyl)-1-(pyridin-3-ylsulfonyl)-1H-indol-6-carboxylate,
17) tert-butyl ((6-(hydroxymethyl)-1-(pyridin-3-ylsulfonyl)-1H-indol-3-yl)methyl)(methyl)carbamate,
18) tert-butyl ((6-(bromomethyl)-1-(pyridin-3-ylsulfonyl)-1H-indol-3-yl)methyl)(methyl)carbamate,
19) tert-butyl ((6-(2-chloro-4-methylbenzyl)-1-(pyridin-3-ylsulfonyl)-1H-indol-3-yl)methyl)(methyl)carbamate,
20) tert-butyl ((6-(2-chloro-4-methylbenzyl)-1H-indol-3-yl)methyl)(methyl)carbamate,
21) tert-butyl ((6-(2-chloro-4-methylbenzyl)-1-((3-fluorophenyl)sulfonyl)-1H-indol-3-yl)methyl)(methyl)carbamate,
22) tert-butyl methyl((1-(pyridin-3-ylsulfonyl)-6-(4,4,5,5-tetramethyl-1,3,2-dioxaborolan-2-yl)-1H-indol-3-yl)methyl)carbamate,
23) tert-butyl ((6-hydroxy-1-(pyridin-3-ylsulfonyl)-1H-indol-3-yl)methyl)(methyl)carbamate,
24) tert-butyl ((6-(5-chloro-2-nitrophenoxy)-1-(pyridin-3-ylsulfonyl)-1H-indol-3-yl)methyl)(methyl)carbamate,
25) tert-butyl ((6-bromo-1-((3-(trifluoromethyl)phenyl)sulfonyl)-1H-indol-3-yl)methyl)(methyl)carbamate,
26) tert-butyl ((6-((2-chloro-6-methoxypyridin-3-yl)amino)-1-((3-(trifluoromethyl)phenyl)sulfonyl)-1H-indol-3-yl)methyl)(methyl)carbamate,
27) tert-butyl (6-((2-chloro-6-methoxypyridin-3-yl)(methyl)amino)-1-((3-(trifluoromethyl)phenyl)sulfonyl)-1H-indol-3-yl)methyl)(methyl)carbamate,
28) tert-butyl ((6-((2-methoxy-4-(trifluoromethoxy)phenyl)amino)-1-(pyridin-3-ylsulfonyl)-1H-indol-3-yl)methyl)(methyl)carbamate,
29) 6-bromo-1-((3-(trifluoromethyl)phenyl)sulfonyl)-1H-indol-3-carbaldehyde,
30) 6-((2-chloro-6-methoxypyridin-3-yl)amino)-1-((3-(trifluoromethyl)phenyl)sulfonyl)-1H-indol-3-carbaldehyde,
31) 6-bromo-N-methyl-1H-indol-3-carboxamide,
32) 6-bromo-N-methyl-1-((3-(trifluoromethyl)phenyl)sulfonyl)-1H-indol-3-carboxamide,
33) tert-butyl (6-bromo-1-(pyridin-3-ylsulfonyl)-1H-indol-3-yl)(methyl)carbamate,
34) tert-butyl (6-((2-fluoro-4-methylphenyl)amino)-1-(pyridin-3-ylsulfonyl)-1H-indol-3-yl)(methyl)carbamate,
35) methyl 6-bromo-1-(pyridin-3-ylsulfonyl)-1H-indol-3-carboxylate,
36) 6-bromo-1-((3-fluorophenyl)sulfonyl)-1H-pyrrolo[3,2-b]pyridin-3-carbaldehyde,
37) 1-(6-bromo-1-((3-fluorophenyl)sulfonyl)-1H-pyrrolo[3,2-b]pyridin-3-yl)-N-methylmethanamine,
38) tert-butyl ((6-bromo-1-((3-fluorophenyl)sulfonyl)-1H-pyrrolo[3,2-b]pyridin-3-yl)methyl)(methyl)carbamate,
39) tert-butyl ((6-((2-fluoro-4-methylphenyl)amino)-1-((3-fluorophenyl)sulfonyl)-1H-pyrrolo[3,2-b]pyridin-3-yl)methyl)(methyl)carbamate,
40) 6-bromo-1-((3-fluorophenyl)sulfonyl)-1H-pyrrolo[3,2-c]pyridin-3-carbaldehyde,
41) 1-(6-bromo-1-((3-fluorophenyl)sulfonyl)-1H-pyrrolo[3,2-c]pyridin-3-yl)-N-methylmethanamine,
42) tert-butyl ((6-bromo-1-((3-fluorophenyl)sulfonyl)-1H-pyrrolo[3,2-c]pyridin-3-yl)methyl)(methyl)carbamate,
43) tert-butyl ((6-((2-chloro-4-methylphenyl)amino)-1-((3-fluorophenyl)sulfonyl)-1H-pyrrolo[3,2-c]pyridin-3-yl)methyl)(methyl)carbamate,
44) 6-bromo-1-((3-fluorophenyl)sulfonyl)-1H-pyrrolo[2,3-b]pyridin-3-carbaldehyde,
45) 1-(6-bromo-1-((3-fluorophenyl)sulfonyl)-1H-pyrrolo[2,3-b]pyridin-3-yl)-N-methylmethanamine,
46) tert-butyl ((6-bromo-1-((3-fluorophenyl)sulfonyl)-1H-pyrrolo[2,3-b]pyridin-3-yl)methyl)(methyl)carbamate, and
47) tert-butyl ((6-((2,6-dichloropyridin-3-yl)amino)-1-((3-fluorophenyl)sulfonyl)-1H-pyrrolo[2,3-b]pyridin-3-yl)methyl)(methyl)carbamate.

Additionally, the present invention provides a method for the preparation of the compound represented by Chemical Formula 1 above or a pharmaceutically acceptable salt thereof. For example, when $R_3$ is —$CH_2NHR_4$ (or —$CH_2NHR_5$), the compound represented by Chemical Formula 1 above or a pharmaceutically acceptable salt thereof can be prepared as shown in the Reaction Scheme below:

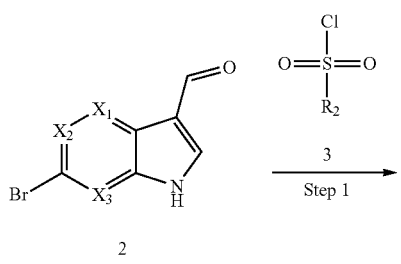

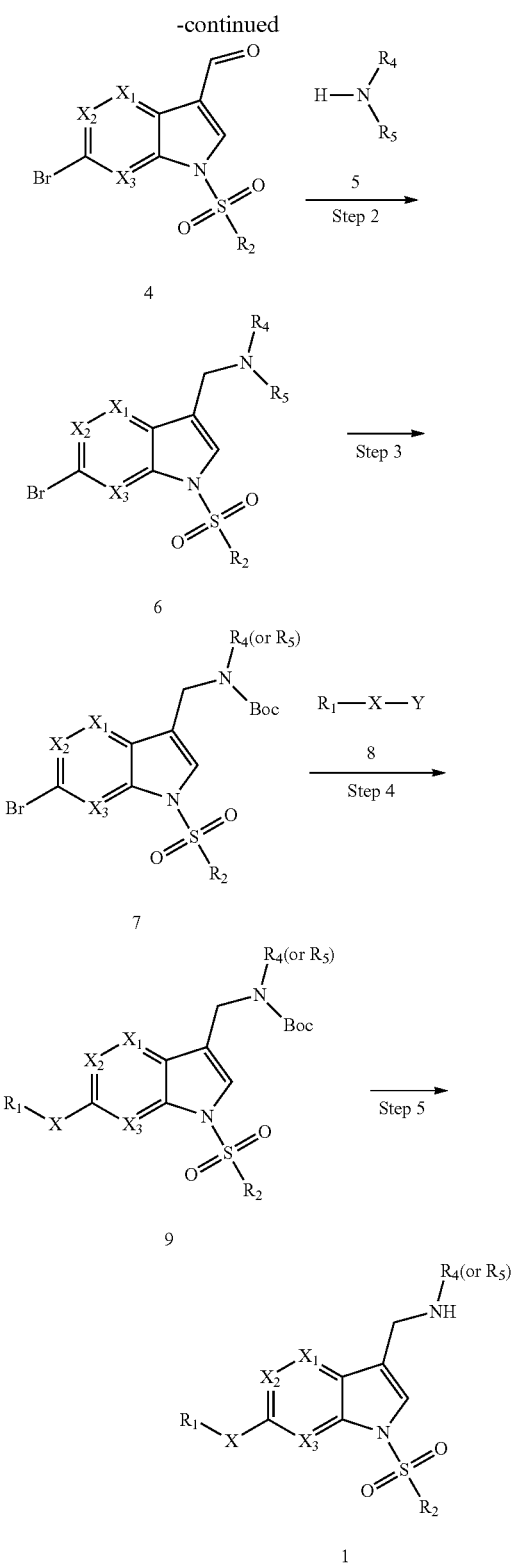

(wherein X, $X_1$, $X_2$, $X_3$, $R_1$, $R_2$, $R_4$ and $R_5$ are the same as defined above, and Y is hydrogen or —B(OH)$_2$).

In detail, the present invention provides a method for preparing a compound represented by Chemical Formula 1 above or a pharmaceutically acceptable salt thereof, comprising:

reacting a compound represented by Chemical Formula 2 above with a compound represented by Chemical Formula 3 above to obtain a compound represented by Chemical Formula 4 above (Step 1), reacting the compound represented by Chemical Formula 4 above with a compound represented by Chemical Formula 5 above to obtain a compound represented by Chemical Formula 6 above (Step 2), introducing a protection group into the compound represented by Chemical Formula 6 above to obtain a compound represented by Chemical Formula 7 above (Step 3), reacting the compound represented by Chemical Formula 7 above with a compound represented by Chemical Formula 8 above to obtain a compound represented by Chemical Formula 9 above (Step 4), and removing the protection group from the compound represented by Chemical Formula 9 above to obtain the compound represented by Chemical Formula 1 above (Step 5).

In Step 1, a reaction is carried out to introduce a —SO$_2$—R$_2$ substituent into a compound represented by Chemical Formula 2 above, and THF may be used as a solvent.

In Step 2, a reaction is carried out to introduce a R$_3$ substituent into a compound represented by Chemical Formula 4 above, and THF may be used as a solvent.

In Step 3, a reaction is carried out to introduce a protection group into a R$_3$ substituent in a compound represented by Chemical Formula 6 above. Preferably, the protection group is -Boc, and di-tert-butyl dicarbonate may be used to introduce the Boc group. As a solvent, dichloromethane may be used, and the reaction is preferably carried out in the presence of triethylamine.

In Step 4, a reaction is carried out to introduce —X—R$_1$ into a compound represented by Chemical Formula 7 above. Y may be appropriately selected as either hydrogen or —B(OH)$_2$ depending on the type of X, and toluene may be used as a solvent.

In Step 5, a compound represented by Chemical Formula 1 above according to the present invention is prepared by removing the protection group from a compound represented by Chemical Formula 9 above, and the protection group may be removed using an acidic solution (e.g., HCl).

Additionally, the compound represented by Chemical Formula 1 above according to the present invention or a pharmaceutically acceptable salt thereof may be prepared using a suitable reactant selected by a person skilled in the art based on the reaction schemes 1-18 described in Examples, in addition to the above reaction scheme.

The thus prepared compound represented by Chemical Formula 1 of the present invention may form salts, in particular pharmaceutically acceptable salts. Suitable pharmaceutically acceptable salts may not be particularly limited to those conventionally used in the art, such as acid addition salts (see J. Pharm. Sci., 66, 1(1977)). Preferred examples of pharmaceutically acceptable acid addition salts may include addition salts of inorganic acids such as hydrochloric acid, hydrobromic acid, phosphoric acid, orthophosphoric acid or sulfuric acid; or organic acids such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid or acetylsalicylic acid.

Additionally, a pharmaceutically acceptable metal salt may be prepared by a conventional method using a base. For example, the pharmaceutically acceptable metal salt may be obtained by dissolving the compound of Chemical Formula 1 above in the excess amount of alkali metal hydroxide or alkali earth metal hydroxide solution, filtering undissolved salt, and subjecting the filtrate to evaporation and drying. Preferably, the metal salt to be prepared is a sodium salt, a potassium salt, or a calcium salt, and these metal salts may be reacted with a suitable salt (e.g., nitrate).

Additionally, the compound of Chemical Formula 1 above may include not only its pharmaceutically acceptable salt thereof but also all possible solvates, hydrates, and stereoisomers which may be prepared from the same. The solvates, hydrates, and stereoisomers of Chemical Formula 1 above may be prepared from the compound of Chemical Formula 1 according to the present invention by the conventional methods.

Additionally, the compound of Chemical Formula 1 according to the present invention may be prepared in a crystalline or non-crystalline form. When the compound of Chemical Formula 1 is prepared in the crystalline form, it may be optionally hydrated or solvated. In the present invention, the compound of Chemical Formula 1 may include not only stoichiometric hydrates but also compounds containing various amounts of water. The solvates of the compound of Chemical Formula 1 according to the present invention may include both stoichiometric solvates and non-stoichiometric solvates.

Additionally, the present invention provides a pharmaceutical composition comprising a compound represented by Chemical Formula 1 above, or a pharmaceutically acceptable salt thereof.

Additionally, the present invention provides a pharmaceutical composition for the prevention or treatment of peptic ulcer, gastritis or reflux esophagitis comprising a compound represented by Chemical Formula 1 above or a pharmaceutically acceptable salt thereof as an active ingredient.

As used herein, the term "prevention" refers to all activities capable of inhibiting or delaying peptic ulcer, gastritis, or reflux esophagitis by administering a pharmaceutical composition comprising a compound of represented by Chemical Formula 1 above or a pharmaceutically acceptable salt thereof. Additionally, as used herein, the term "treatment" refers to all activities capable of alleviating or curing the symptoms of peptic ulcer, gastritis, or reflux esophagitis by administering a pharmaceutical composition comprising a compound represented by Chemical Formula 1 above or a pharmaceutically acceptable salt thereof.

The compound represented by Chemical Formula 1 above of the present invention or a pharmaceutically acceptable salt thereof has an inhibitory effect against the proton pump ($H^+/K^+$-ATPase) activity (Experimental Example), and an inhibitory activity against a basal gastric acid secretion in a pylorus-ligated rat (Experimental Example), and is thus useful for the for the treatment or prevention of peptic ulcer, gastritis or reflux esophagitis.

The pharmaceutical composition of the present invention may be prepared in orally or parenterally administrable formulations according to the standards in pharmaceutical practice. These formulations may contain additives such as a pharmaceutically acceptable carrier, adjuvant, or diluent in addition to the active ingredient. Examples of the suitable carrier may include a physiological saline solution, polyethylene glycol, ethanol, vegetable oils, and isopropyl myristate, and examples of the suitable diluent may include lactose, dextrose, sucrose, mannitol, sorbitol, cellulose and/or glycine, but are not limited thereto. Additionally, the compound of the present invention or a pharmaceutically acceptable salt thereof may be dissolved in oils conventionally used for the preparation of injection solutions, propylene glycol or other solvents. Additionally, the compound of the present invention or a pharmaceutically acceptable salt thereof may be prepared in an ointment or cream formulation for local effects.

A preferred dose of the compound of the present invention or a pharmaceutically acceptable salt thereof may vary depending on the health status, body weight, severity of disease(s) of a patient, drug types, administration routes and duration, but may be appropriately selected by a skilled person in the art. However, for desirable effects, the compound of the present invention should be administered daily in the amount of from 0.0001 to 100 mg/kg (body weight), preferably from 0.001 to 100 mg/kg (body weight). The administration may be performed once daily or in divided doses per day via an oral or parenteral route, and according to the administration method, the pharmaceutical composition of the present invention may contain from 0.001 wt % to 99 wt % of the compound of the present invention, preferably from 0.01 wt % to 60 wt %.

The pharmaceutical composition of the present invention may be administered to mammals including rats, mice, livestock, and humans via various routes. All administration routes may be predicted, e.g., orally or via rectal or intravenous, intramuscular, intradermal, intrauterine or intracerebroventricular injections.

Additionally, the present invention provides a method for the prevention or treatment of peptic ulcer, gastritis or reflux esophagitis in a subject need thereof, comprising administering an effective amount of a compound represented by Chemical Formula 1 of the present invention or a pharmaceutically acceptable salt thereof to the subject.

As used herein, the term "subject" refers to all animals including humans already having or suspected of having pepetic ulcer, gastritis or reflux esophagitis. The compound above may be administered in the form of a pharmaceutically acceptable composition, via oral or parenteral administration. Additionally, the effective dose of the compound of the present invention may vary depending on the health status, body weight, severity of disease(s) of a subject, drug types, administration routes and duration, but may be appropriately selected by a skilled person in the art.

The present invention will be explained in further details herein below with reference to Preparation Examples and Examples, however, they are disclosed for illustrative purposes and should not be construed as limiting the scope of the present invention.

Example 1: Preparation of N-(2-fluoro-4-methyl-phenyl)-3-((methylamino)methyl)-1-(pyridin-3-yl-sulfonyl)-1H-indol-6-amine hydrochloride The compound of Example 1 was prepared as shown in Reaction Scheme 1 below.

[Reaction Scheme 1]

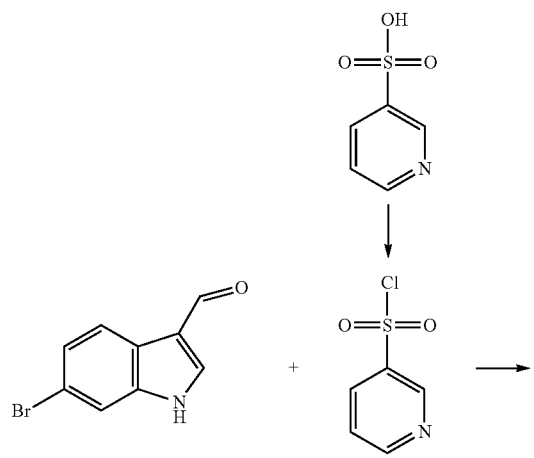

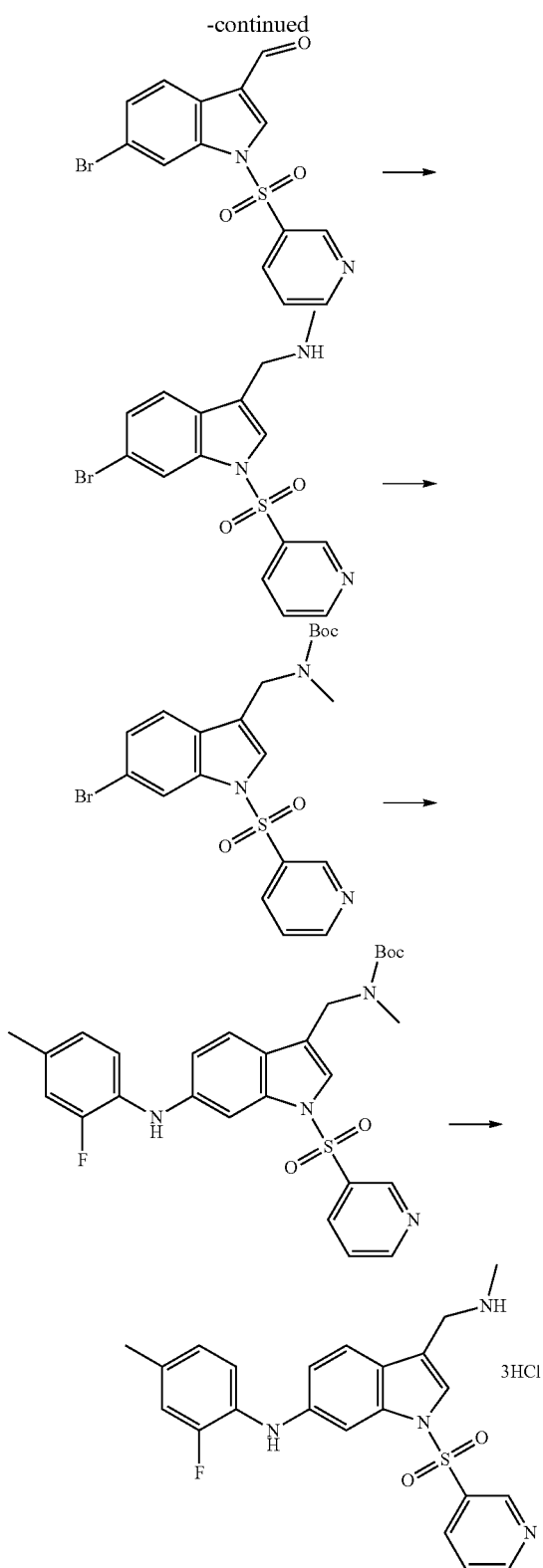

hours, and then the mixture was concentrated to remove phosphorous oxychloride. The reaction mixture was added with ice water and diethyl ether, stirred, and then extracted into the organic layer. The resulting separated organic layer was washed with a saturated sodium bicarbonate solution, and the organic layer was dried on anhydrous magnesium sulfate and concentrated under reduced pressure to obtain 4.1 g of a title compound (yield: 75%).

$^1$H NMR (500 MHz, CDCl$_3$): 8.91 (s, 1H), 8.84 (d, 1H), 8.43 (dd, 1H), 7.57 (t, 1H)

Step 2: Preparation of 6-bromo-1-(pyridin-3-ylsulfonyl)-1H-indol-3-carbaldehyde 6-bromo-1H-indol-3-carbaldehyde (100 mg, 0.4 mmole) was dissolved in tetrahydrofuran solution (5 ml), cooled to 0° C., and dropwisely added with sodium hydride (60% in oil)(26 mg, 0.6 mmol). The reaction mixture was stirred at 0° C. for 30 minutes, and then added with the compound prepared in Step 1 (119 mg, 0.6 mmol) and stirred at room temperature for 2 hours. The reaction mixture was added with an aqueous ammonium chloride solution and then extracted with ethyl acetate. The separated organic layer was washed with saturated brine, dried on anhydrous magnesium sulfate and concentrated under reduced pressure. The resulting residue was purified by silica gel column chromatography (ethyl acetate:n-hexane=1:1 (v/v)) to obtain 143 mg of a target compound (yield: 87.7%).

$^1$H NMR (500 MHz, CDCl$_3$): 9.73 (s, 1H), 8.89-8.91 (m, 2H), 8.73 (s, 1H), 8.43 (d, 1H), 8.32 (d, 1H), 7.58-7.69 (m, 3H)

Step 3: Preparation of 1-(6-bromo-1-(pyridin-3-ylsulfonyl)-1H-indol-3-yl)-N-methylmethanamine 6-bromo-1-(pyridin-3-ylsulfonyl)-1H-indol-3-carbaldehyde (50 mg, 0.1 mmole) prepared in Step 2, dissolved in 3 ml of methanol, was added with 2 M methylamine-tetrahydrofuran solution (1.3 ml, 2.7 mmole), and stirred at room temperature for 3 hours. The resultant was added with sodium borohydride (10 mg, 0.2 mmole), stirred at room temperature for 2 hours, and concentrated under reduced pressure. The resultant was added with a saturated sodium bicarbonate solution and the mixture was extracted with ethyl acetate. The extract was washed with saturated brine, dried on anhydrous magnesium sulfate and concentrated under reduced pressure. The resulting residue was purified by silica gel column chromatography (methanol:dichloromethane=1:30 (v/v)) to obtain 17 mg of a title compound (yield: 32.6%).

$^1$H NMR (300 MHz, CD$_3$OD): 9.15 (s, 1H), 8.82 (d, 1H), 8.42 (dd, 1H), 8.23 (s, 1H), 8.01 (s, 1H), 7.68 (d, 1H), 7.54-7.63 (m, 1H), 7.53 (d, 1H), 4.35 (s, 2H), 2.74 (s, 3H)

Step 4: Preparation of tert-butyl ((6-bromo-1-(pyridin-3-ylsulfonyl)-1H-indol-3-yl)methyl)(methyl)carbamate 1-(6-bromo-1-(pyridin-3-ylsulfonyl)-1H-indol-3-yl)-N-methylmethanamine (50 mg, 0.1 mmole) prepared in Step 3 was dissolved in 1.2 ml of dichloromethane, added with triethylamine (20 µl, 0.1 mmole) and di-tert-butyl dicarbonate (30 mg, 0.1 mmole), and stirred at room temperature for 2 hours. The reaction mixture was added with water, extracted with dichloromethane, and the resulting separated organic layer was washed with saturated brine, dried on anhydrous magnesium sulfate and concentrated under Step 1: Preparation of pyridin-3-sulfonyl chloride Pyridin-3-sulfonic acid (5.0 g, 31.4 mmol) was added with phosphorous pentachloride (9.8 g, 47.1 mmol) and phosphorous oxychloride (10 ml), stirred under reflux for 4 reduced pressure. The resulting residue was purified by silica gel column chromatography (ethyl acetate:n-hexane=1:3 (v/v)) to obtain 53 mg of a title compound (yield: 84%).

$^1$H NMR (500 MHz, CDCl$_3$): 9.13 (s, 1H), 8.80 (d, 1H), 8.39 (dd, 1H), 8.19 (s, 1H), 7.98 (s, 1H), 7.64 (d, 1H), 7.51-7.60 (m, 1H), 7.48 (d, 1H), 4.31 (s, 2H), 2.70 (s, 3H), 1.27 (s, 9H)

Step 5: Preparation of tert-butyl ((6-((2-fluoro-4-methylphenyl)amino)-1-(pyridin-3-ylsulfonyl)-1H-indol-3-yl)methyl)(methyl)carbamate Tert-butyl ((6-bromo-1-(pyridin-3-ylsulfonyl)-1H-indol-3-yl)methyl)(methyl)carbamate (100 mg, 0.2 mmole) prepared in Step 4; tris(dibenzylideneacetone)dipalladium(0) (12 mg, 0.02 mmole); tri-tert-butylphosphine, 50% solution in toluene (7.5 μl, 0.03 mmole); 4,5-Bis(diphenylphosphino)-9,9-dimethylxanthene (18 mg, 0.03 mmole); cesium carbonate (110 mg, 0.3 mmole); and 2-fluoro-4-methylaniline (9.3 mg, 0.07 mmole) were suspended in 1 ml of toluene, and stirred at 110° C. for 12 hours. The reaction mixture was filtrated with celite, and the filtrate was added with water and then extracted with ethyl acetate. The resulting extract was washed with saturated brine, dried on anhydrous magnesium sulfate and concentrated under reduced pressure. The resulting residue was purified by silica gel column chromatography (ethyl acetate:n-hexane=1:2 (v/v)) to obtain 60 mg of a title compound (yield: 55%).

$^1$H NMR (300 MHz, CDCl$_3$): 9.06 (d, 1H), 8.77 (dd, 1H), 8.08 (td, 1H), 7.62 (s, 1H), 7.38-7.48 (m, 2H), 7.31 (s, 1H), 7.16 (t, 1H), 6.89-6.97 (m, 3H), 4.46 (s, 2H), 2.73 (s, 3H), 2.32 (s, 3H), 1.48 (s, 9H)

Step 6: Preparation of N-(2-fluoro-4-methylphenyl)-3-((methylamino)methyl)-1-(pyridin-3-ylsulfonyl)-1H-indol-6-amine hydrochloride Tert-butyl ((6-((2-fluoro-4-methylphenyl)amino)-1-(pyridin-3-ylsulfonyl)-1H-indol-3-yl)methyl)(methyl)carbamate (30 mg, 0.05 mmole) prepared in Step 5 was added with 1 ml of 1.25 M HCl-methanol solution, and stirred at room temperature for 15 hours. The reaction mixture was concentrated under reduced pressure, and the resulting residue was recrystallized with diethyl ether to obtain 13 mg of a title compound (yield: 42.6%).

$^1$H NMR (300 MHz, CD$_3$OD): 9.05 (s, 1H), 8.80 (d, 1H), 8.30 (dd, 1H), 7.74 (s, 1H), 7.59-7.64 (m, 1H), 7.53 (s, 1H), 7.49 (d, 1H), 7.16 (t, 1H), 6.97-7.06 (m, 3H), 4.30 (s, 2H), 2.73 (s, 3H), 2.36 (s, 3H)

In Examples 2 through 135, compounds were prepared in the same manner as in Example 1 except that reactants were appropriately changed as necessary depending on the structures of the compounds to be prepared and in consideration of Reaction Scheme 1.

Example 2: Preparation of 3-((methylamino)methyl)-N-phenyl-1-(pyridin-3-ylsulfonyl)-1H-indol-6-amine hydrochloride

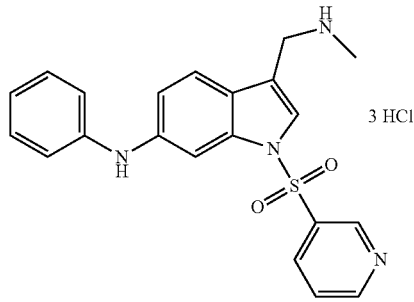 [SMILES: CNCc1cn(S(=O)(=O)c2cccnc2)c2cc(Nc3ccccc3)ccc12]

1H NMR (500 MHz, CD3OD): 9.15 (s, 1H), 8.84 (d, 1H), 8.40 (td, 1H), 7.81 (s, 1H), 7.65-7.70 (m, 3H), 7.60 (d, 1H), 7.26 (d, 2H), 7.10 (dd, 1H), 7.04 (d, 2H), 4.35 (s, 2H), 2.77 (s, 3H)

Example 3: Preparation of N-(2-fluorophenyl)-3-((methylamino)methyl)-1-(pyridin-3-ylsulfonyl)-1H-indol-6-amine hydrochloride

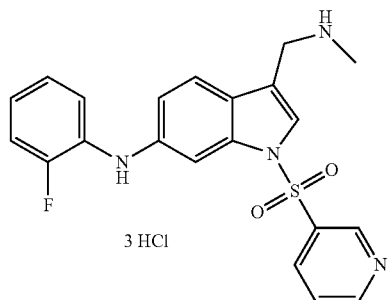 [SMILES: CNCc1cn(S(=O)(=O)c2cccnc2)c2cc(Nc3ccccc3F)ccc12]

1H NMR (500 MHz, CD3OD): 9.09 (s, 1H), 8.85 (s, 1H), 8.32 (d, 1H), 7.80 (s, 1H), 7.55-7.70 (m, 3H), 7.30 (t, 1H), 7.17-7.23 (m, 2H), 7.13 (d, 1H), 7.06-7.09 (m, 1H), 4.33 (s, 2H), 2.76 (s, 3H)

Example 4: Preparation of N-(2-chlorophenyl)-3-((methylamino)methyl)-1-(pyridin-3-ylsulfonyl)-1H-indol-6-amine hydrochloride

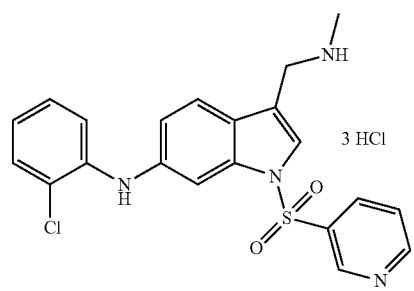 [SMILES: CNCc1cn(S(=O)(=O)c2cccnc2)c2cc(Nc3ccccc3Cl)ccc12]

¹H NMR (500 MHz, CD₃OD): 9.10 (s, 1H), 8.89 (s, 1H), 8.35 (d, 1H), 7.81 (s, 1H), 7.58-7.71 (m, 3H), 7.33 (t, 1H), 7.20-7.27 (m, 2H), 7.10 (d, 1H), 7.01-7.06 (m, 1H), 4.30 (s, 2H), 2.72 (s, 3H)

Example 5: Preparation of N-(3-bromophenyl)-3-((methylamino)methyl)-1-(pyridin-3-ylsulfonyl)-1H-indol-6-amine hydrochloride

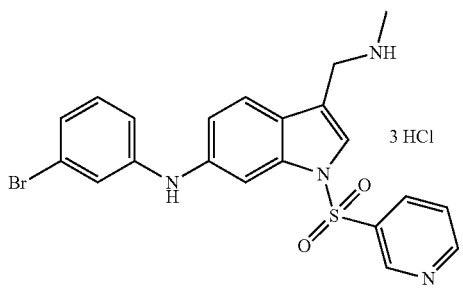 [SMILES: CNCc1cn(S(=O)(=O)c2cccnc2)c2cc(Nc3cccc(Br)c3)ccc12]

¹H NMR (500 MHz, CD₃OD): 9.08 (d, 1H), 8.81 (d, 1H), 8.35 (td, 1H), 7.83 (s, 1H), 7.74 (d, 1H), 7.58-7.62 (m, 2H), 7.25 (t, 1H), 7.14 (dd, 1H), 7.08 (t, 1H), 6.99 (dd, 1H), 6.87 (dd, 1H), 4.31 (s, 2H), 2.74 (s, 3H)

Example 6: Preparation of N-(3-fluorophenyl)-3-((methylamino)methyl)-1-(pyridin-3-ylsulfonyl)-1H-indol-6-amine hydrochloride

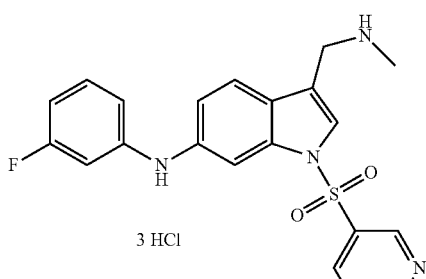

¹H NMR (500 MHz, CD₃OD): 9.10 (d, 1H), 8.84 (dd, 1H), 8.35 (td, 1H), 7.84 (s, 1H), 7.77 (d, 1H), 7.61-7.65 (m, 2H), 7.27-7.30 (m, 1H), 7.18 (dd, 1H), 6.89 (dd, 1H), 6.81 (d, 1H), 6.64 (td, 1H), 4.35 (s, 2H), 2.77 (s, 3H)

Example 7: Preparation of N-(3-chlorophenyl)-3-((methylamino)methyl)-1-(pyridin-3-ylsulfonyl)-1H-indol-6-amine hydrochloride

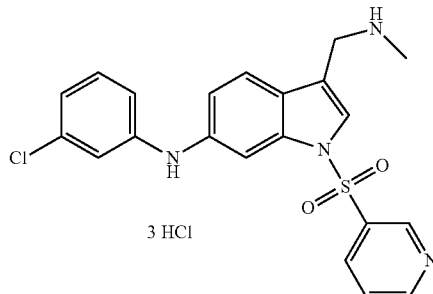

¹H NMR (500 MHz, CD₃OD): 9.12 (d, 1H), 8.84 (d, 1H), 8.37 (td, 1H), 7.85 (s, 1H), 7.77 (d, 1H), 7.62-7.66 (m, 2H), 7.27 (t, 1H), 7.16 (dd, 1H), 7.11 (t, 1H), 7.01 (dd, 1H), 6.91 (dd, 1H), 4.35 (s, 2H), 2.77 (s, 3H)

Example 8: Preparation of N-(3-ethylphenyl)-3-((methylamino)methyl)-1-(pyridin-3-ylsulfonyl)-1H-indol-6-amine hydrochloride

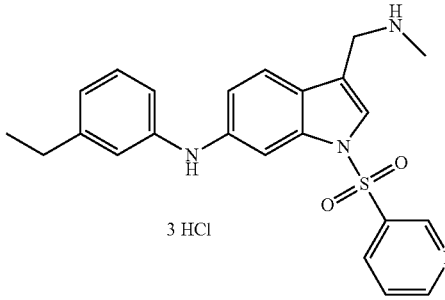

¹H NMR (500 MHz, CD₃OD): 9.19 (s, 1H), 8.83 (d, 1H), 8.33 (td, 1H), 7.78 (s, 1H), 7.75 (d, 1H), 7.63 (q, 1H), 7.56 (d, 1H), 7.24 (t, 1H), 7.11 (dd, 1H), 7.02 (s, 1H), 6.94 (dd, 1H), 6.82 (d, 1H), 4.33 (s, 2H), 2.76 (s, 3H), 2.66 (q, 2H), 1.28 (t, 3H)

Example 9: Preparation of N-(4-fluorophenyl)-3-((methylamino)methyl)-1-(pyridin-3-ylsulfonyl)-1H-indol-6-amine hydrochloride

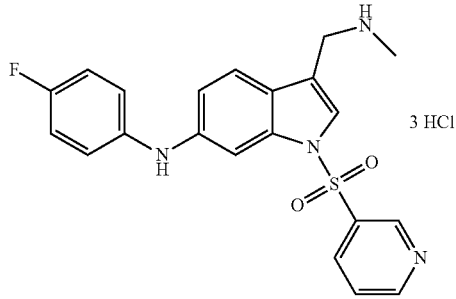 [SMILES: CNCc1cn(S(=O)(=O)c2cccnc2)c2cc(Nc3ccc(F)cc3)ccc12]

¹H NMR (500 MHz, CD₃OD): 9.07 (d, 1H), 8.83 (dd, 1H), 8.31 (td, 1H), 7.78 (s, 1H), 7.61-7.64 (m, 2H), 7.55 (d, 1H), 7.05-7.14 (m, 5H), 4.32 (s, 2H), 2.76 (s, 3H)

Example 10: Preparation of 3-((methylamino)methyl)-1-(pyridin-3-ylsulfonyl)-N-(p-tolyl)-1H-indol-6-amine hydrochloride

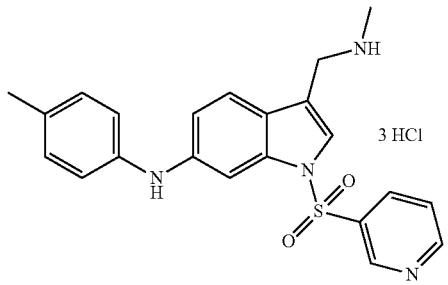 [SMILES: CNCc1cn(S(=O)(=O)c2cccnc2)c2cc(Nc3ccc(C)cc3)ccc12]

¹H NMR (500 MHz, CD₃OD): 9.10 (d, 1H), 8.86 (dd, 1H), 8.38 (td, 1H), 7.80 (s, 1H), 7.64-7.68 (m, 2H), 7.58 (d, 1H), 7.10-7.15 (m, 5H), 4.33 (s, 2H), 2.77 (s, 3H), 2.33 (s, 3H)

Example 11: Preparation of N-(4-chlorophenyl)-3-((methylamino)methyl)-1-(pyridin-3-ylsulfonyl)-1H-indol-6-amine hydrochloride

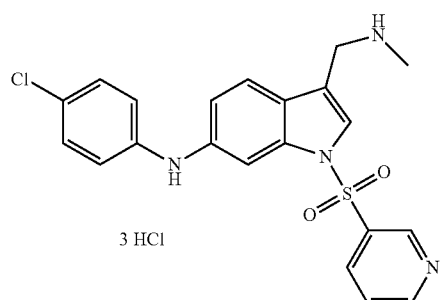

¹H NMR (500 MHz, CD₃OD): 9.16 (s, 1H), 8.87 (d, 1H), 8.42 (td, 1H), 7.84 (s, 1H), 7.69-7.72 (m, 2H), 7.61 (d, 1H), 7.30 (d, 2H), 7.13 (dd, 1H), 7.09 (d, 2H), 4.34 (s, 2H), 2.76 (s, 3H)

Example 12: Preparation of N-(4-methoxyphenyl)-3-((methylamino)methyl)-1-(pyridin-3-ylsulfonyl)-1H-indol-6-amine hydrochloride

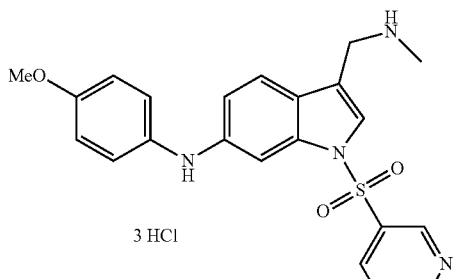

¹H NMR (500 MHz, CD₃OD): 9.10 (s, 1H), 8.87 (s, 1H), 8.31 (d, 1H), 7.74 (s, 1H), 7.66 (q, 1H), 7.50-7.53 (m, 2H), 7.11 (d, 2H), 6.98 (d, 3H), 4.31 (s, 2H), 3.84 (s, 3H), 2.75 (s, 3H)

Example 13: Preparation of 3-((methylamino)methyl)-1-(pyridin-3-ylsulfonyl)-N-(4-(trifluoromethyl)phenyl)-1H-indol-6-amine hydrochloride

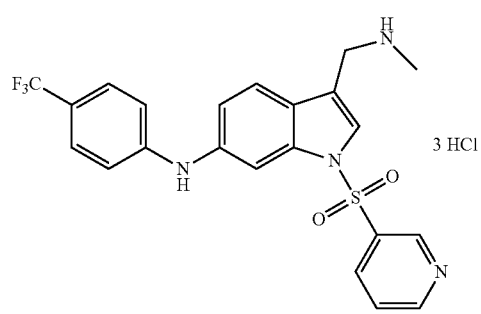 [SMILES: CNCc1cn(S(=O)(=O)c2cccnc2)c2cc(Nc3ccc(C(F)(F)F)cc3)ccc12]

¹H NMR (500 MHz, CD₃OD): 9.13 (s, 1H), 8.85 (d, 1H), 8.36 (td, 1H), 7.88 (s, 1H), 7.83 (d, 1H), 7.67 (d, 1H), 7.64 (q, 1H), 7.56 (d, 2H), 7.25 (dd, 1H), 7.18 (d, 2H), 4.36 (s, 2H), 2.77 (s, 3H)

Example 14: Preparation of N-(4-(tert-butyl)phenyl)-3-((methylamino)methyl)-1-(pyridin-3-ylsulfonyl)-1H-indol-6-amine hydrochloride

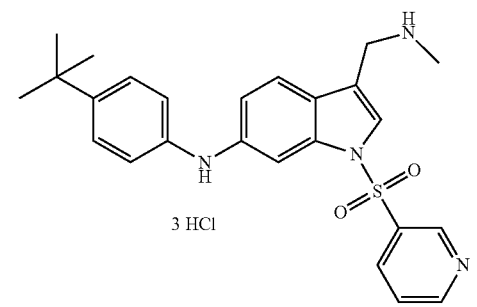 [SMILES: CNCc1cn(S(=O)(=O)c2cccnc2)c2cc(Nc3ccc(C(C)(C)C)cc3)ccc12]

¹H NMR (500 MHz, CD₃OD): 9.12 (d, 1H), 8.87 (dd, 1H), 8.40 (td, 1H), 7.81 (s, 1H), 7.65-7.68 (m, 2H), 7.61 (d, 1H), 7.15-7.20 (m, 5H), 4.34 (s, 2H), 2.76 (s, 3H), 1.27 (s, 9H)

Example 15: Preparation of N-(3'-methoxy-[1,1'-biphenyl]-4-yl)-3-((methylamino)methyl)-1-(pyridin-3-ylsulfonyl)-1H-indol-6-amine hydrochloride

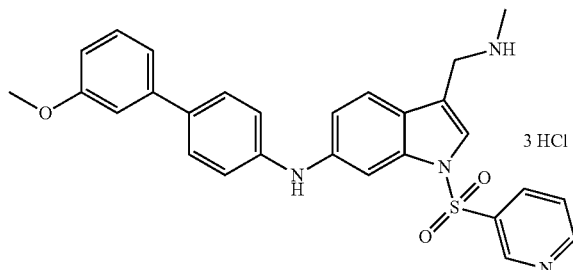

¹H NMR (500 MHz, CD₃OD): 9.10 (d, 1H), 8.84 (dd, 1H), 8.28 (td, 1H), 7.78 (s, 1H), 7.67 (q, 1H), 7.65 (d, 1H), 7.54 (d, 1H), 7.31-7.37 (m, 2H), 7.11-7.15 (m, 2H), 7.08 (dd, 2H), 6.97-7.00 (m, 3H), 4.34 (s, 2H), 4.00 (s, 3H), 2.77 (s, 3H)

Example 16: Preparation of N-(4-methyl-[1,1'-biphenyl]-3-yl)-3-((methylamino)methyl)-1-(pyridin-3-ylsulfonyl)-1H-indol-6-amine hydrochloride

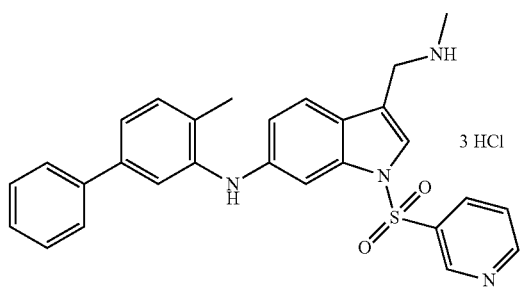 [SMILES: CNCc1cn(S(=O)(=O)c2cccnc2)c2cc(Nc3cc(-c4ccccc4)ccc3C)ccc12]

¹H NMR (500 MHz, CD₃OD): 8.99 (d, 1H), 8.78 (dd, 1H), 8.22 (td, 1H), 7.73 (s, 1H), 7.64 (q, 1H), 7.60 (d, 1H), 7.50 (d, 1H), 7.27-7.31 (m, 2H), 7.05-7.09 (m, 2H), 6.99 (dd, 2H), 6.87-6.97 (m, 3H), 4.31 (s, 2H), 2.75 (s, 3H), 2.30 (s, 3H)

Example 17: Preparation of 3-((methylamino)methyl)-N-(4-phenoxyphenyl)-1-(pyridin-3-ylsulfonyl)-1H-indol-6-amine hydrochloride

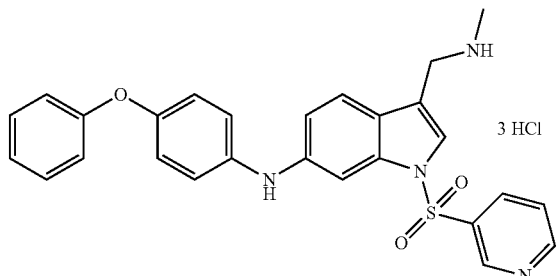

¹H NMR (300 MHz, CD₃OD): 9.14 (d, 1H), 8.86 (dd, 1H), 8.40 (td, 1H), 7.80 (s, 1H), 7.70 (q, 1H), 7.66 (d, 1H), 7.57 (d, 1H), 7.34-7.39 (m, 2H), 7.15-7.19 (m, 2H), 7.11 (dd, 2H), 7.00-7.06 (m, 4H), 4.34 (s, 2H), 2.77 (s, 3H)

Example 18: Preparation of N-(4-(4-fluorophenoxy)phenyl)-3-((methylamino)methyl)-1-(pyridin-3-ylsulfonyl)-1H-indol-6-amine hydrochloride

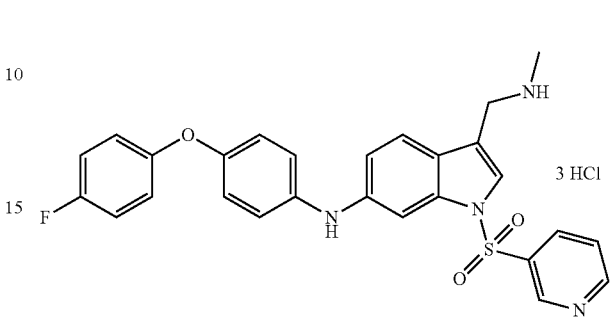

¹H NMR (300 MHz, CD₃OD): 9.16 (d, 1H), 8.87 (d, 1H), 8.45 (td, 1H), 7.81 (s, 1H), 7.72 (q, 1H), 7.66 (d, 1H), 7.58 (d, 1H), 7.14-7.18 (m, 2H), 7.07-7.13 (m, 3H), 6.93-7.05 (m, 4H), 4.34 (s, 2H), 2.77 (s, 3H)

Example 19: Preparation of N-(4-(4-chlorophenoxy)phenyl)-3-((methylamino)methyl)-1-(pyridin-3-ylsulfonyl)-1H-indol-6-amine hydrochloride

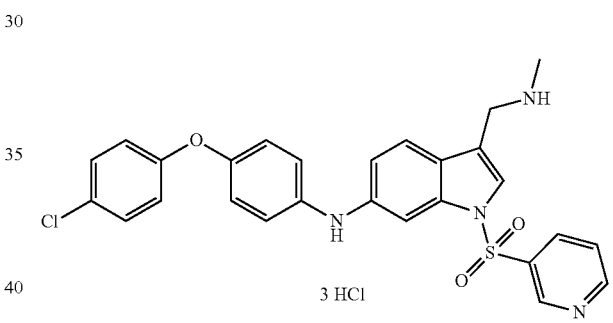

¹H NMR (500 MHz, CD₃OD): 9.12 (d, 1H), 8.85 (d, 1H), 8.40 (td, 1H), 7.80 (s, 1H), 7.71 (q, 1H), 7.64 (d, 1H), 7.55 (d, 1H), 7.10-7.13 (m, 2H), 7.05-7.09 (m, 3H), 6.90-7.01 (m, 4H), 4.32 (s, 2H), 2.75 (s, 3H)

Example 20: Preparation of N-(2-fluoro-3-methylphenyl)-3-((methylamino)methyl)-1-(pyridin-3-ylsulfonyl)-1H-indol-6-amine hydrochloride

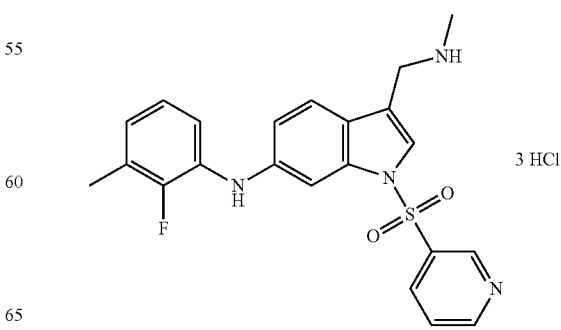

¹H NMR (500 MHz, CD₃OD): 9.00 (s, 1H), 8.76 (d, 1H), 8.21 (d, 1H), 7.68 (s, 1H), 7.61 (q, 1H), 7.42 (d, 1H), 7.15 (s, 1H), 7.10-7.15 (m, 1H), 7.01 (dd, 1H), 6.90-6.98 (m, 1H), 6.88 (dd, 1H), 4.24 (s, 2H), 2.70 (s, 3H), 2.14 (s, 3H)

Example 21: Preparation of N-(2,4-dimethylphenyl)-3-((methylamino)methyl)-1-(pyridin-3-ylsulfonyl)-1H-indol-6-amine hydrochloride

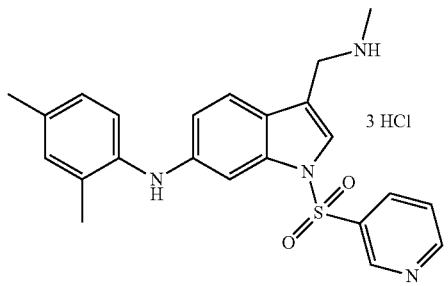 [SMILES: CNCc1cn(S(=O)(=O)c2cccnc2)c2cc(Nc3ccc(C)cc3C)ccc12]

¹H NMR (500 MHz, CD₃OD): 9.05 (s, 1H), 8.74 (d, 1H), 8.25 (d, 1H), 7.69 (s, 1H), 7.65 (q, 1H), 7.44 (d, 1H), 7.19 (s, 1H), 7.11-7.16 (m, 1H), 7.05 (dd, 1H), 6.99-7.01 (m, 1H), 6.91 (dd, 1H), 4.22 (s, 2H), 2.72 (s, 3H), 2.14 (s, 3H), 2.11 (s, 3H)

Example 22: Preparation of N-(2-chloro-4-methylphenyl)-3-((methylamino)methyl)-1-(pyridin-3-ylsulfonyl)-1H-indol-6-amine

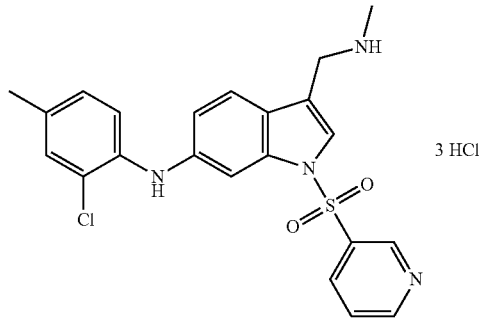 [SMILES: CNCc1cn(S(=O)(=O)c2cccnc2)c2cc(Nc3ccc(C)cc3Cl)ccc12]

¹H NMR (500 MHz, CD₃OD): 9.01 (s, 1H), 8.70 (d, 1H), 8.21 (d, 1H), 7.66 (s, 1H), 7.63 (q, 1H), 7.41 (d, 1H), 7.16 (s, 1H), 7.10-7.14 (m, 1H), 7.06 (dd, 1H), 6.98-7.02 (m, 1H), 6.94 (dd, 1H), 4.25 (s, 2H), 2.71 (s, 3H), 2.15 (s, 3H)

Example 23: Preparation of N-(4-fluoro-2-methylphenyl)-3-((methylamino)methyl)-1-(pyridin-3-ylsulfonyl)-1H-indol-6-amine hydrochloride

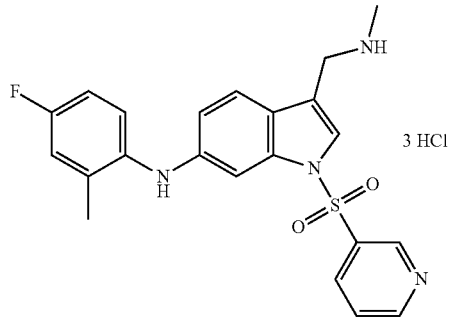 [SMILES: CNCc1cn(S(=O)(=O)c2cccnc2)c2cc(Nc3ccc(F)cc3C)ccc12]

¹H NMR (300 MHz, CD₃OD): 9.03 (s, 1H), 8.80 (d, 1H), 8.24 (d, 1H), 7.71 (s, 1H), 7.64 (q, 1H), 7.48 (d, 1H), 7.20 (s, 1H), 7.12-7.17 (m, 1H), 7.07 (dd, 1H), 6.95-7.01 (m, 1H), 6.94 (dd, 1H), 4.29 (s, 2H), 2.73 (s, 3H), 2.19 (s, 3H)

Example 24: Preparation of N-(2,4-difluorophenyl)-3-((methylamino)methyl)-1-(pyridin-3-ylsulfonyl)-1H-indol-6-amine hydrochloride

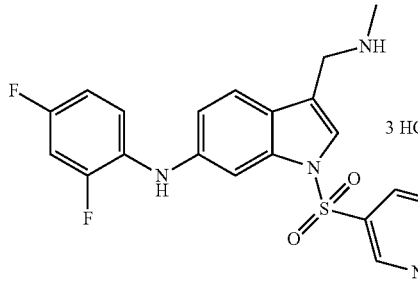

¹H NMR (500 MHz, CD₃OD): 9.06 (s, 1H), 8.81 (d, 1H), 8.35 (d, 1H), 7.86 (s, 1H), 7.69 (s, 1H), 7.60-7.66 (m, 2H), 7.56 (d, 1H), 7.27 (dd, 1H), 7.20 (d, 1H), 7.16 (dd, 1H), 4.33 (s, 2H), 2.75 (s, 3H)

Example 25: Preparation of N-(2-chloro-4-fluorophenyl)-3-((methylamino)methyl)-1-(pyridin-3-ylsulfonyl)-1H-indol-6-amine hydrochloride ¹H NMR (500 MHz, CD₃OD): 9.07 (s, 1H), 8.79 (d, 1H), 8.28 (d, 1H), 7.85 (s, 1H), 7.64 (s, 1H), 7.55-7.59 (m, 2H), 7.51 (d, 1H), 7.26 (dd, 1H), 7.21 (d, 1H), 7.16 (dd, 1H), 4.33 (s, 2H), 2.77 (s, 3H)

Example 26: Preparation of N-(4-fluoro-2-(trifluoromethyl)phenyl)-3-((methylamino)methyl)-1-(pyridin-3-ylsulfonyl)-1H-indol-6-amine hydrochloride

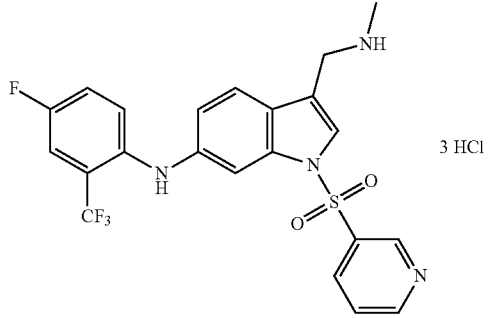 [SMILES: CNCc1cn(S(=O)(=O)c2cccnc2)c2cc(Nc3ccc(F)cc3C(F)(F)F)ccc12]

¹H NMR (500 MHz, CD₃OD): 9.08 (s, 1H), 8.79 (d, 1H), 8.32 (d, 1H), 7.83 (s, 1H), 7.66 (s, 1H), 7.57-7.61 (m, 2H), 7.43 (d, 1H), 7.26 (dd, 1H), 7.18 (d, 1H), 7.11 (dd, 1H), 4.28 (s, 2H), 2.72 (s, 3H)

Example 27: Preparation of N-(4-chloro-2-methylphenyl)-3-((methylamino)methyl)-1-(pyridin-3-ylsulfonyl)-1H-indol-6-amine hydrochloride

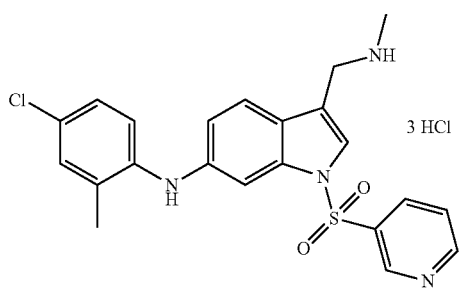 [SMILES: CNCc1cn(S(=O)(=O)c2cccnc2)c2cc(Nc3ccc(Cl)cc3C)ccc12]

¹H NMR (500 MHz, CD₃OD): 9.01 (s, 1H), 8.78 (d, 1H), 8.22 (d, 1H), 7.70 (s, 1H), 7.61 (q, 1H), 7.46 (d, 1H), 7.21 (s, 1H), 7.14-7.18 (m, 1H), 7.09 (dd, 1H), 6.98-7.02 (m, 1H), 6.93 (dd, 1H), 4.25 (s, 2H), 2.72 (s, 3H), 2.15 (s, 3H)

Example 28: Preparation of N-(4-chloro-2-fluorophenyl)-3-((methylamino)methyl)-1-(pyridin-3-ylsulfonyl)-1H-indol-6-amine hydrochloride

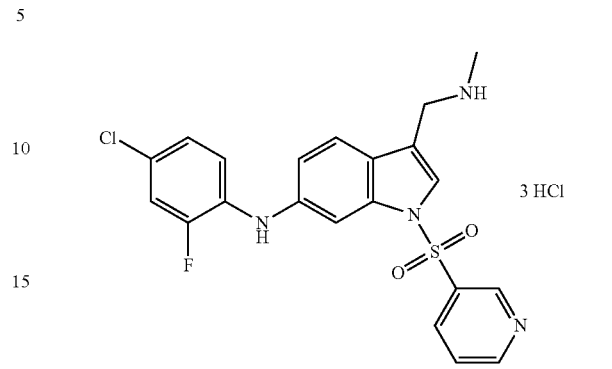

¹H NMR (500 MHz, CD₃OD): 9.06 (s, 1H), 8.78 (d, 1H), 8.25 (d, 1H), 7.86 (s, 1H), 7.62 (s, 1H), 7.54-7.59 (m, 2H), 7.48 (d, 1H), 7.25 (dd, 1H), 7.18 (d, 1H), 7.13 (dd, 1H), 4.31 (s, 2H), 2.74 (s, 3H)

Example 29: Preparation of N-(2,4-dichlorophenyl)-3-((methylamino)methyl)-1-(pyridin-3-ylsulfonyl)-1H-indol-6-amine hydrochloride

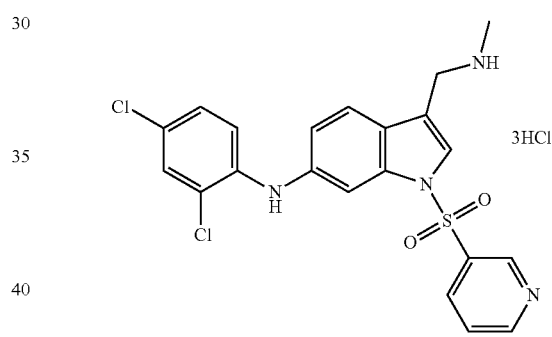

¹H NMR (500 MHz, CD₃OD): 9.08 (s, 1H), 8.80 (d, 1H), 8.33 (d, 1H), 7.84 (s, 1H), 7.67 (s, 1H), 7.59-7.62 (m, 2H), 7.47 (d, 1H), 7.24 (dd, 1H), 7.17 (d, 1H), 7.13 (dd, 1H), 4.32 (s, 2H), 2.74 (s, 3H)

Example 30: Preparation of 5-chloro-2-((3-((methylamino)methyl)-1-(pyridin-3-ylsulfonyl)-1H-indol-6-yl)amino)benzonitrile hydrochloride

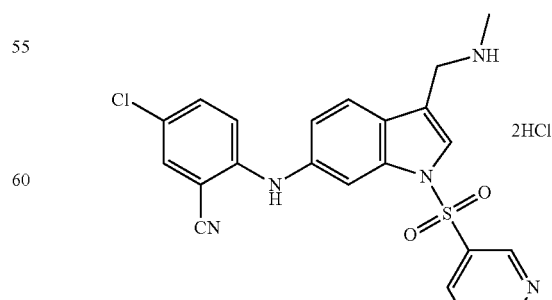

¹H NMR (500 MHz, CD₃OD): 9.17 (d, 1H), 8.84 (d, 2H), 8.45 (td, 1H), 8.25 (d, 1H), 8.04 (s, 1H), 7.68-7.73 (m, 2H), 7.62-7.65 (m, 2H), 7.56 (dd, 1H), 4.37 (s, 2H), 2.76 (s, 3H)

Example 31: Preparation of N-(4-chloro-2-(trifluoromethyl)phenyl)-3-((methylamino)methyl)-1-(pyridin-3-ylsulfonyl)-1H-indol-6-amine hydrochloride

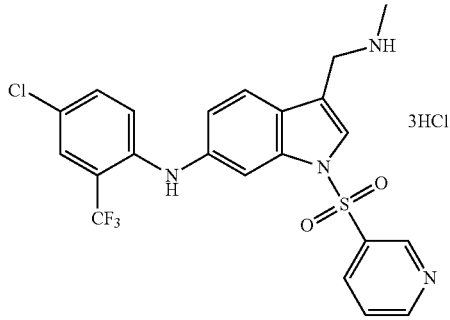 [SMILES: CNCc1cn(S(=O)(=O)c2cccnc2)c2cc(Nc3ccc(Cl)cc3C(F)(F)F)ccc12]

¹H NMR (500 MHz, CD³OD): 9.05 (s, 1H), 8.79 (d, 1H), 8.30 (d, 1H), 7.81 (s, 1H), 7.64 (s, 1H), 7.59-7.63 (m, 2H), 7.45 (d, 1H), 7.22 (dd, 1H), 7.15 (d, 1H), 7.08 (dd, 1H), 4.30 (s, 2H), 2.72 (s, 3H)

Example 32: Preparation of N-(2-methyl-4-(trifluoromethyl)phenyl)-3-((methylamino)methyl)-1-(pyridin-3-ylsulfonyl)-1H-indol-6-amine hydrochloride

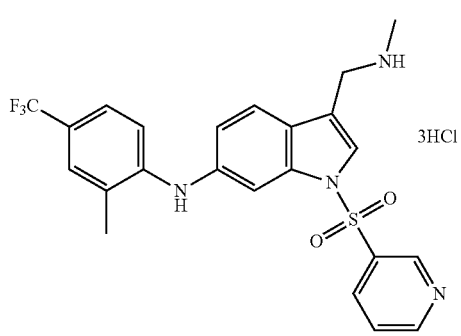 [SMILES: CNCc1cn(S(=O)(=O)c2cccnc2)c2cc(Nc3ccc(C(F)(F)F)cc3C)ccc12]

¹H NMR (500 MHz, CD₃OD): 9.11 (d, 1H), 8.84 (d, 1H), 8.36 (td, 1H), 7.88 (s, 1H), 7.72-7.74 (m, 1H), 7.62-7.66 (m, 2H), 7.50 (s, 1H), 7.42 (d, 1H), 7.23 (d, 1H), 7.18 (dd, 1H), 4.36 (s, 2H), 2.77 (s, 3H), 2.35 (s, 3H)

Example 33: Preparation of N-(2-fluoro-4-(trifluoromethyl)phenyl)-3-((methylamino)methyl)-1-(pyridin-3-ylsulfonyl)-1H-indol-6-amine hydrochloride

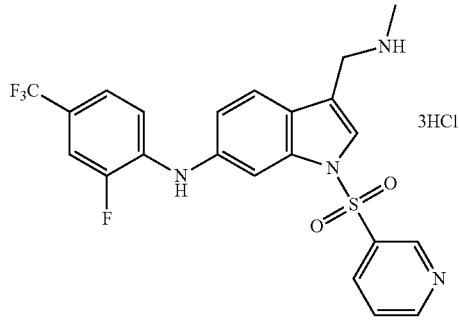 [SMILES: CNCc1cn(S(=O)(=O)c2cccnc2)c2cc(Nc3ccc(C(F)(F)F)cc3F)ccc12]

¹H NMR (500 MHz, CD₃OD): 9.14 (d, 1H), 8.83 (dd, 1H), 8.39 (td, 1H), 7.93 (s, 1H), 7.84 (d, 1H), 7.71 (d, 1H), 7.63 (q, 1H), 7.47 (d, 1H), 7.41 (d, 1H), 7.35 (t, 1H), 7.27 (dd, 1H), 4.38 (s, 2H), 2.77 (s, 3H)

Example 34: Preparation of N-(2-chloro-4-(trifluoromethyl)phenyl)-3-((methylamino)methyl)-1-(pyridin-3-ylsulfonyl)-1H-indol-6-amine hydrochloride

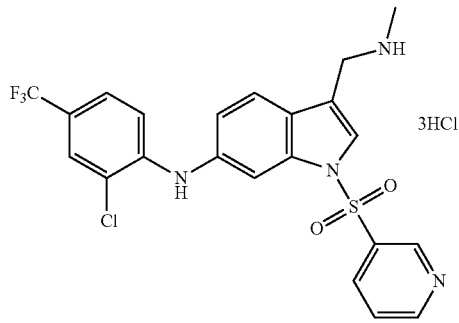 [SMILES: CNCc1cn(S(=O)(=O)c2cccnc2)c2cc(Nc3ccc(C(F)(F)F)cc3Cl)ccc12]

¹H NMR (500 MHz, CD₃OD): 9.05 (s, 1H), 8.80 (d, 1H), 8.31 (d, 1H), 7.81 (s, 1H), 7.64 (s, 1H), 7.58-7.62 (m, 2H), 7.43 (d, 1H), 7.24 (dd, 1H), 7.16 (d, 1H), 7.09 (dd, 1H), 4.31 (s, 2H), 2.73 (s, 3H)

Example 35: Preparation of N-(2,4-Bis(trifluoromethyl)phenyl)-3-((methylamino)methyl)-1-(pyridin-3-ylsulfonyl)-1H-indol-6-amine hydrochloride

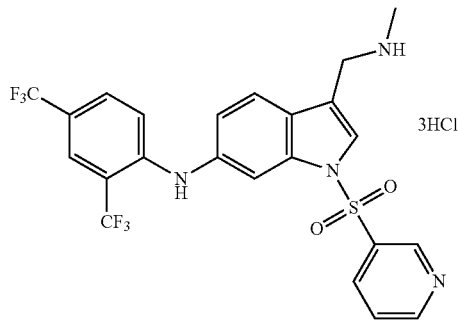 [SMILES: CNCc1cn(S(=O)(=O)c2cccnc2)c2cc(Nc3ccc(C(F)(F)F)cc3C(F)(F)F)ccc12]

$^1$H NMR (300 MHz, CD$_3$OD): 9.15 (s, 1H), 8.82 (d, 1H), 8.39 (d, 1H), 7.95 (s, 1H), 7.91 (s, 1H), 7.85 (s, 1H), 7.67-7.74 (m, 2H), 7.61 (q, 1H), 7.28 (d, 1H), 7.20 (d, 1H), 4.37 (s, 2H), 2.76 (s, 3H)

Example 36: Preparation of 3-methyl-4-((3-((methylamino)methyl)-1-(pyridin-3-ylsulfonyl)-1H-indol-6-yl)amino)benzonitrile hydrochloride

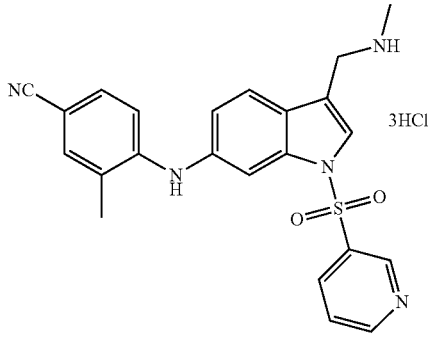 [SMILES: CNCc1cn(S(=O)(=O)c2cccnc2)c2cc(Nc3ccc(C#N)cc3C)ccc12]

$^1$H NMR (500 MHz, CD$_3$OD): 9.10 (d, 1H), 8.85 (d, 1H), 8.38 (td, 1H), 7.90 (s, 1H), 7.74-7.76 (m, 1H), 7.65-7.69 (m, 2H), 7.54 (s, 1H), 7.46 (d, 1H), 7.25 (d, 1H), 7.19 (dd, 1H), 4.35 (s, 2H), 2.76 (s, 3H), 2.33 (s, 3H)

Example 37: Preparation of 3-ethyl-4-((3-((methylamino)methyl)-1-(pyridin-3-ylsulfonyl)-1H-indol-6-yl)amino)benzonitrile hydrochloride

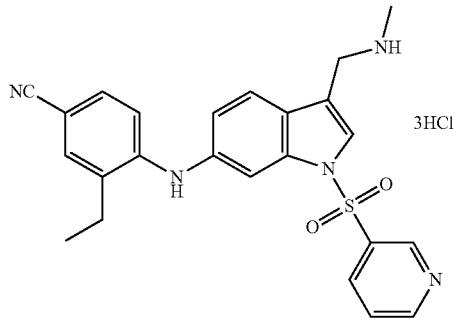 [SMILES: CCc1cc(C#N)ccc1Nc1ccc2c(CNC)cn(S(=O)(=O)c3cccnc3)c2c1]

$^1$H NMR (500 MHz, CD$_3$OD): 9.13 (d, 1H), 8.84 (dd, 1H), 8.38 (td, 1H), 7.93 (s, 1H), 7.81 (d, 1H), 7.70 (d, 1H), 7.64 (q, 1H), 7.54 (d, 1H), 7.45 (dd, 1H), 7.24 (dd, 1H), 7.13 (d, 1H), 4.38 (s, 2H), 2.78 (s, 3H), 2.75 (q, 2H), 1.31 (t, 3H)

Example 38: Preparation of 3-fluoro-4-((3-((methylamino)methyl)-1-(pyridin-3-ylsulfonyl)-1H-indol-6-yl)amino)benzonitrile hydrochloride

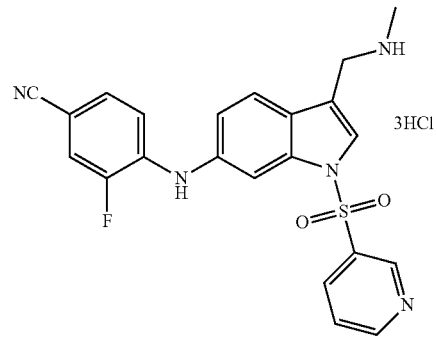

$^1$H NMR (500 MHz, CD$_3$OD): 9.13 (dd, 1H), 8.81 (td, 1H), 8.38 (td, 1H), 8.21 (d, 1H), 7.98 (d, 1H), 7.91 (dd, 1H), 7.73 (d, 1H), 7.65 (d, 1H), 7.58-7.61 (m, 1H), 7.55 (dd, 1H), 7.32 (dd, 1H), 4.38 (d, 2H), 2.76 (d, 3H)

Example 39: Preparation of 3-chloro-4-((3-((methylamino)methyl)-1-(pyridin-3-ylsulfonyl)-1H-indol-6-yl)amino)benzonitrile hydrochloride

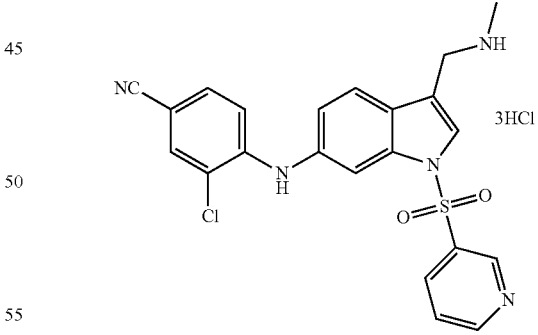

$^1$H NMR (500 MHz, CD$_3$OD): 9.15 (dd, 1H), 8.81 (td, 1H), 8.42 (td, 1H), 8.23 (d, 1H), 8.00 (d, 1H), 7.96 (dd, 1H), 7.78 (d, 1H), 7.65 (d, 1H), 7.61-7.63 (m, 1H), 7.54 (dd, 1H), 7.30 (dd, 1H), 4.36 (d, 2H), 2.75 (d, 3H)

Example 40: Preparation of 4-((3-((methylamino)methyl)-1-(pyridin-3-ylsulfonyl)-1H-indol-6-yl)amino)-3-(trifluoromethyl)benzonitrile hydrochloride

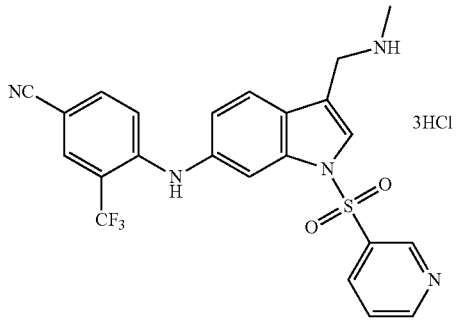 [SMILES: CNCc1cn(S(=O)(=O)c2cccnc2)c2cc(Nc3ccc(C#N)cc3C(F)(F)F)ccc12]

$^1$H NMR (500 MHz, CD$_3$OD): 9.16 (dd, 1H), 8.84 (td, 1H), 8.44 (td, 1H), 8.25 (d, 1H), 8.03 (d, 1H), 7.97 (dd, 1H), 7.79 (d, 1H), 7.71 (d, 1H), 7.63-7.65 (m, 1H), 7.60 (dd, 1H), 7.32 (dd, 1H), 4.39 (d, 2H), 2.77 (d, 3H)

Example 41: Preparation of N-(2-chloro-4-nitrophenyl)-3-((methylamino)methyl)-1-(pyridin-3-ylsulfonyl)-1H-indol-6-amine hydrochloride

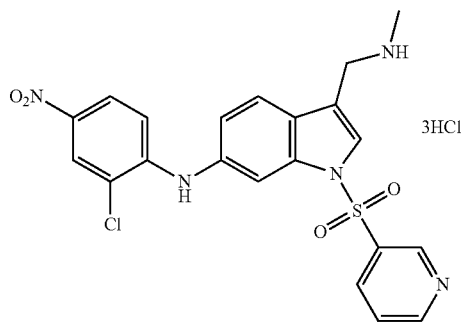 [SMILES: CNCc1cn(S(=O)(=O)c2cccnc2)c2cc(Nc3ccc([N+](=O)[O-])cc3Cl)ccc12]

$^1$H NMR (500 MHz, CD$_3$OD): 9.18 (d, 1H), 8.86 (dd, 1H), 8.44 (td, 1H), 8.43 (d, 1H), 8.07 (dd, 1H), 8.04 (s, 1H), 8.00 (d, 1H), 7.81 (d, 1H), 7.64 (q, 1H), 7.38 (dd, 1H), 7.07 (dd, 1H), 4.40 (s, 2H), 2.79 (s, 3H)

Example 42: Preparation of N-(2-methyl-4-nitrophenyl)-3-((methylamino)methyl)-1-(pyridin-3-ylsulfonyl)-1H-indol-6-amine hydrochloride

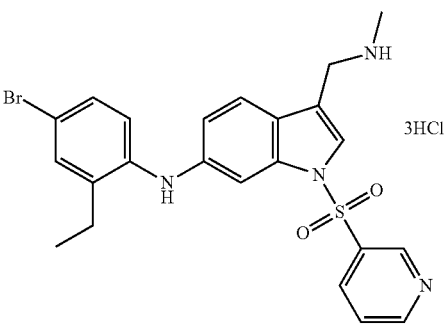 [SMILES: CCc1cc(Br)ccc1Nc1ccc2c(CNC)cn(S(=O)(=O)c3cccnc3)c2c1]

$^1$H NMR (500 MHz, CD$_3$OD): 9.19 (d, 1H), 8.86 (dd, 1H), 8.46 (td, 1H), 8.10 (d, 1H), 7.99 (s, 1H), 7.97 (d, 1H), 7.91 (d, 1H), 7.76 (d, 1H), 7.68 (q, 1H), 7.32 (dd, 1H), 7.06 (dd, 1H), 4.40 (s, 2H), 2.79 (s, 3H), 2.41 (s, 3H)

Example 43: Preparation of N-(4-bromo-2-ethylphenyl)-3-((methylamino)methyl)-1-(pyridin-3-ylsulfonyl)-1H-indol-6-amine hydrochloride

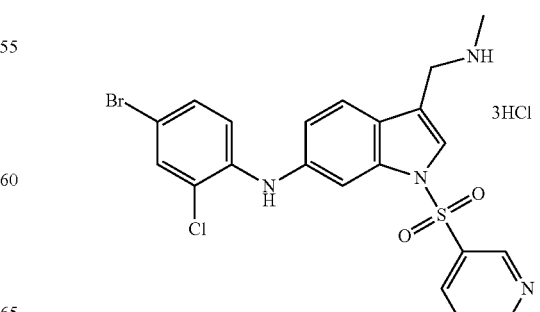

$^1$H NMR (500 MHz, CD$_3$OD): 9.13 (d, 1H), 8.82 (dd, 1H), 8.31 (td, 1H), 7.90 (s, 1H), 7.83 (d, 1H), 7.67 (d, 1H), 7.61 (q, 1H), 7.51 (d, 1H), 7.42 (dd, 1H), 7.20 (dd, 1H), 7.09 (d, 1H), 4.35 (s, 2H), 2.77 (s, 3H), 2.74 (q, 2H), 1.33 (t, 3H)

Example 44: Preparation of N-(4-bromo-2-chlorophenyl)-3-((methylamino)methyl)-1-(pyridin-3-ylsulfonyl)-1H-indol-6-amine hydrochloride ¹H NMR (500 MHz, CD₃OD): 9.11 (d, 1H), 8.83 (dd, 1H), 8.37 (td, 1H), 8.04 (s, 1H), 7.79 (d, 1H), 7.61-7.65 (m, 3H), 7.39 (dd, 1H), 7.13-7.18 (m, 2H), 4.33 (s, 2H), 2.73 (s, 3H)

Example 45: Preparation of N-(4-bromo-2-(trifluoromethyl)phenyl)-3-((methylamino)methyl)-1-(pyridin-3-ylsulfonyl)-1H-indol-6-amine hydrochloride

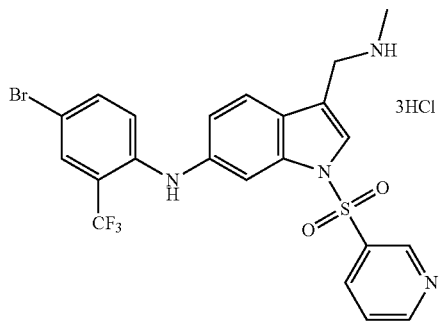 [SMILES: CNCc1cn(S(=O)(=O)c2cccnc2)c2cc(Nc3ccc(Br)cc3C(F)(F)F)ccc12]

¹H NMR (500 MHz, CD₃OD): 9.17 (d, 1H), 8.84 (dd, 1H), 8.44 (td, 1H), 8.25 (d, 1H), 8.05 (s, 1H), 7.72 (d, 1H), 7.63 (q, 1H), 7.56 (dd, 1H), 7.39 (dd, 1H), 7.13-7.18 (m, 2H), 4.38 (s, 2H), 2.76 (s, 3H)

Example 46: Preparation of N-(4-bromo-2-(trifluoromethoxy)phenyl)-3-((methylamino)methyl)-1-(pyridin-3-ylsulfonyl)-1H-indol-6-amine hydrochloride

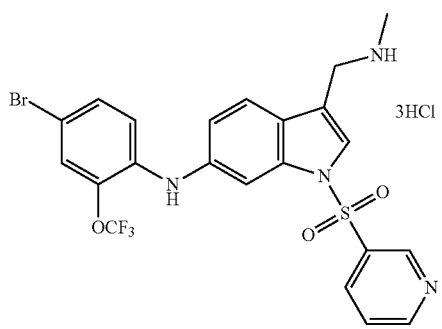 [SMILES: CNCc1cn(S(=O)(=O)c2cccnc2)c2cc(Nc3ccc(Br)cc3OC(F)(F)F)ccc12]

¹H NMR (500 MHz, CD₃OD): 9.17 (d, 1H), 8.84 (dd, 1H), 8.44 (td, 1H), 8.25 (d, 1H), 8.04 (s, 1H), 7.71 (d, 1H), 7.63 (q, 1H), 7.56 (dd, 1H), 7.37 (dd, 1H), 7.15-7.20 (m, 2H), 4.38 (s, 2H), 2.76 (s, 3H)

Example 47: Preparation of 3-methyl-4-((3-((methylamino)methyl)-1-(pyridin-3-ylsulfonyl)-1H-indol-6-yl)amino)phenol hydrochloride

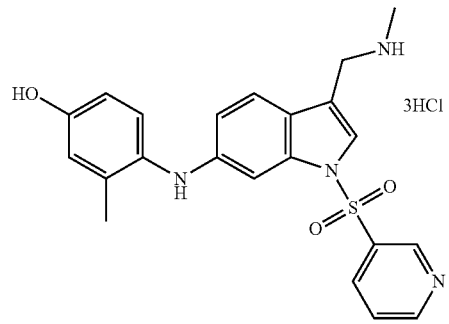 [SMILES: CNCc1cn(S(=O)(=O)c2cccnc2)c2cc(Nc3ccc(O)cc3C)ccc12]

¹H NMR (500 MHz, CD₃OD): 8.98 (dd, 2H), 8.32 (dd, 1H), 7.79 (s, 1H), 7.71 (q, 1H), 7.56 (d, 1H), 7.33 (d, 1H), 7.08 (d, 1H), 7.68-7.00 (m, 2H), 6.86 (dd, 1H), 4.33 (s, 2H), 2.76 (s, 3H), 2.16 (s, 3H)

Example 48: Preparation of N-(4-methoxy-2-methylphenyl)-3-((methylamino)methyl)-1-(pyridin-3-ylsulfonyl)-1H-indol-6-amine hydrochloride

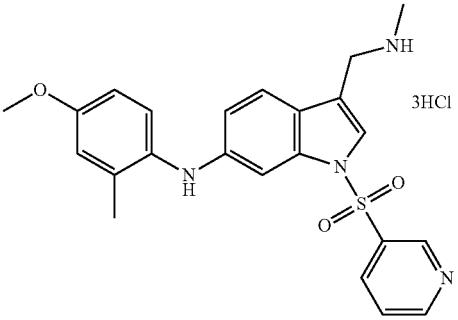 [SMILES: CNCc1cn(S(=O)(=O)c2cccnc2)c2cc(Nc3ccc(OC)cc3C)ccc12]

¹H NMR (500 MHz, CD₃OD): 8.96 (d, 1H), 8.81 (dd, 1H), 8.21 (td, 1H), 7.71 (s, 1H), 7.59 (q, 1H), 7.47 (d, 1H), 7.08-7.16 (m, 2H), 6.93 (d, 1H), 6.85 (dd, 1H), 6.80 (dd, 1H), 4.30 (s, 2H), 3.84 (s, 3H), 2.74 (s, 3H), 2.16 (s, 3H)

Example 49: Preparation of N-(2-fluoro-4-methoxyphenyl)-3-((methylamino)methyl)-1-(pyridin-3-ylsulfonyl)-1H-indol-6-amine hydrochloride

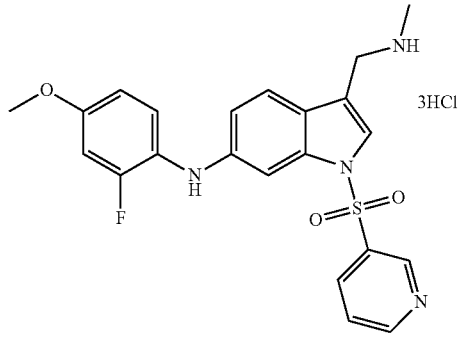 [SMILES: CNCc1cn(S(=O)(=O)c2cccnc2)c2cc(Nc3ccc(OC)cc3F)ccc12]

$^1$H NMR (500 MHz, CD$_3$OD): 9.06 (s, 1H), 8.81 (d, 1H), 8.27 (dd, 1H), 7.78 (s, 1H), 7.63 (s, 1H), 7.57 (q, 1H), 7.51 (d, 1H), 7.22 (d, 1H), 7.13 (dd, 1H), 6.94 (s, 1H), 6.83 (d, 1H), 4.28 (s, 2H), 3.96 (s, 3H), 2.71 (s, 3H)

Example 50: Preparation of N-(4-methoxy-2-(trifluoromethoxy)phenyl)-3-((methylamino)methyl)-1-(pyridin-3-ylsulfonyl)-1H-indol-6-amine hydrochloride

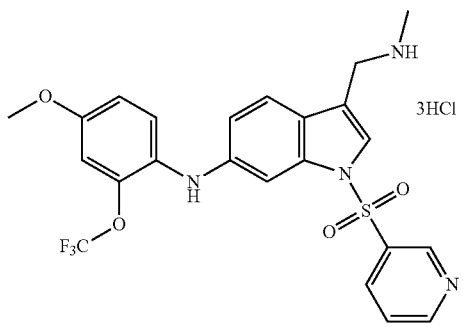 [SMILES: CNCc1cn(S(=O)(=O)c2cccnc2)c2cc(Nc3ccc(OC)cc3OC(F)(F)F)ccc12]

$^1$H NMR (500 MHz, CD$_3$OD): 9.08 (s, 1H), 8.80 (d, 1H), 8.33 (dd, 1H), 7.79 (s, 1H), 7.67 (s, 1H), 7.61 (q, 1H), 7.57 (d, 1H), 7.21 (d, 1H), 7.13 (dd, 1H), 6.95 (s, 1H), 6.85 (d, 1H), 4.31 (s, 2H), 3.90 (s, 3H), 2.73 (s, 3H)

Example 51: Preparation of N-(4-methoxy-2-(trifluoromethyl)phenyl)-3-((methylamino)methyl)-1-(pyridin-3-ylsulfonyl)-1H-indol-6-amine hydrochloride

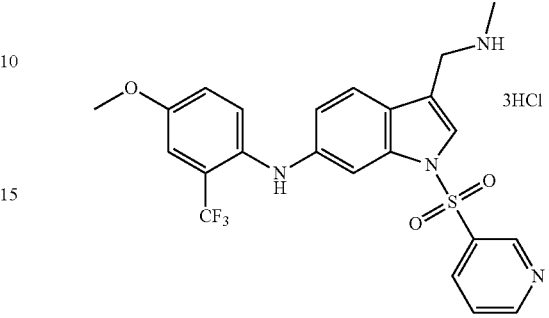

$^1$H NMR (500 MHz, CD$_3$OD): 9.05 (s, 1H), 8.78 (d, 1H), 8.24 (dd, 1H), 7.79 (s, 1H), 7.62 (s, 1H), 7.52 (q, 1H), 7.46 (d, 1H), 7.18 (d, 1H), 7.10 (dd, 1H), 6.91 (s, 1H), 6.84 (d, 1H), 4.27 (s, 2H), 3.94 (s, 3H), 2.73 (s, 3H)

Example 52: Preparation of N-(4-methoxy-2-nitrophenyl)-3-((methylamino)methyl)-1-(pyridin-3-ylsulfonyl)-1H-indol-6-amine hydrochloride

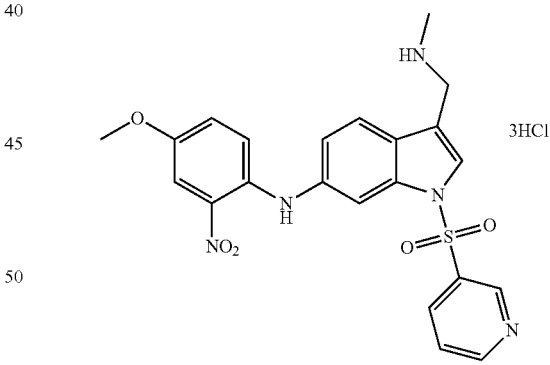

$^1$H NMR (500 MHz, CD$_3$OD): 9.12 (s, 1H), 8.82 (d, 1H), 8.39 (d, 1H), 7.93 (s, 1H), 7.89 (d, 1H), 7.71 (d, 1H), 7.68 (d, 1H), 7.61-7.63 (m, 1H), 7.26 (dd, 1H), 7.23 (s, 1H), 7.22 (s, 1H), 4.36 (s, 2H), 3.85 (s, 3H), 2.75 (s, 3H)

Example 53: Preparation of N-(2-methyl-4-(trifluoromethoxy)phenyl)-3-((methylamino)methyl)-1-(pyridin-3-ylsulfonyl)-1H-indol-6-amine hydrochloride

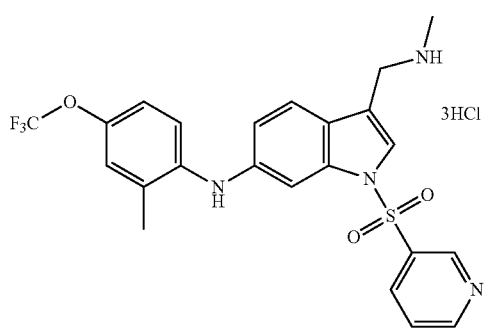 [SMILES: CNCc1cn(S(=O)(=O)c2cccnc2)c2cc(Nc3ccc(OC(F)(F)F)cc3C)ccc12]

¹H NMR (500 MHz, CD₃OD): 8.48 (s, 1H), 8.20 (d, 1H), 8.04 (s, 1H), 8.02 (d, 1H), 7.93 (t, 2H), 7.66 (d, 1H), 7.54-7.57 (m, 1H), 7.26 (d, 1H), 7.15 (dd, 1H), 6.71 (d, 1H), 4.87 (s, 2H), 2.74 (s, 3H), 2.32 (s, 3H)

Example 54: Preparation of N-(2-fluoro-4-(trifluoromethoxy)phenyl)-3-((methylamino)methyl)-1-(pyridin-3-ylsulfonyl)-1H-indol-6-amine hydrochloride

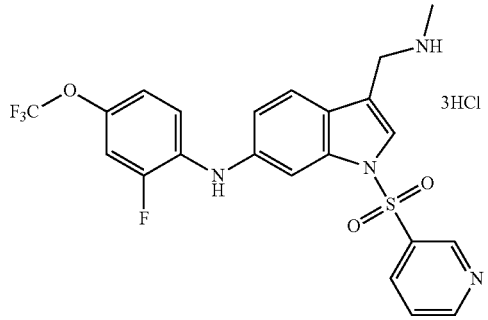 [SMILES: CNCc1cn(S(=O)(=O)c2cccnc2)c2cc(Nc3ccc(OC(F)(F)F)cc3F)ccc12]

¹H NMR (500 MHz, CD₃OD): 9.07 (d, 1H), 8.80 (dd, 1H), 8.32 (td, 1H), 7.81 (s, 1H), 7.58-7.63 (m, 3H), 7.31 (t, 1H), 7.21 (d, 1H), 7.08-7.11 (m, 2H), 4.88 (s, 2H), 2.74 (s, 3H)

Example 55: Preparation of N-(2-chloro-4-(trifluoromethoxy)phenyl)-3-((methylamino)methyl)-1-(pyridin-3-ylsulfonyl)-1H-indol-6-amine hydrochloride

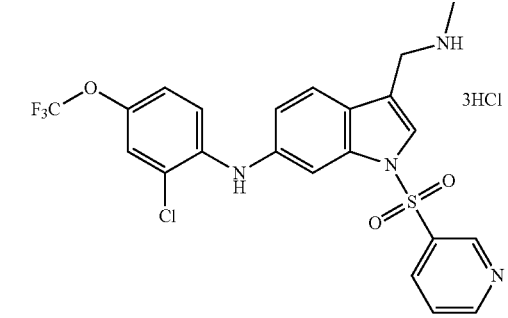

¹H NMR (500 MHz, CD₃OD): 9.07 (d, 1H), 8.81 (dd, 1H), 8.31 (td, 1H), 7.82 (s, 1H), 7.61-7.63 (m, 3H), 7.34 (t, 1H), 7.26 (d, 1H), 7.09-7.12 (m, 2H), 4.89 (s, 2H), 2.76 (s, 3H)

Example 56: Preparation of N-(2-methoxy-4-(trifluoromethoxy)phenyl)-3-((methylamino)methyl)-1-(pyridin-3-ylsulfonyl)-1H-indol-6-amine hydrochloride ¹H NMR (500 MHz, CD₃OD): 9.13 (s, 1H), 8.82 (d, 1H), 8.39 (dd, 1H), 7.81 (s, 1H), 7.65-7.68 (m, 2H), 7.57 (d, 1H), 7.21 (d, 1H), 7.13 (dd, 1H), 6.95 (s, 1H), 6.85 (d, 1H), 4.31 (s, 2H), 3.90 (s, 3H), 2.74 (s, 3H)

Example 57: Preparation of methyl 3-chloro-4-((3-((methylamino)methyl)-1-(pyridin-3-ylsulfonyl)-1H-indol-6-yl)amino)benzoate hydrochloride

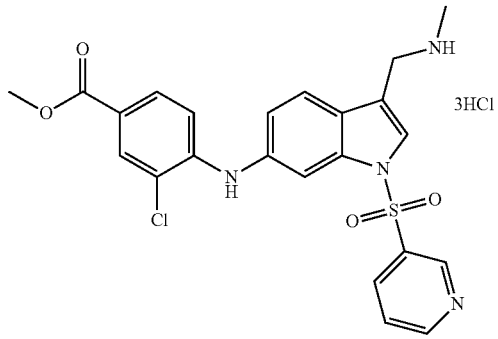 [SMILES: CNCc1cn(S(=O)(=O)c2cccnc2)c2cc(Nc3ccc(C(=O)OC)cc3Cl)ccc12]

$^1$H NMR (500 MHz, CD$_3$OD): 9.09 (d, 1H), 8.88 (dd, 1H), 8.35 (td, 1H), 7.86 (s, 1H), 7.63-7.67 (m, 3H), 7.36 (t, 1H), 7.29 (d, 1H), 7.08-7.12 (m, 2H), 4.88 (s, 2H), 3.99 (s, 3H), 2.77 (s, 3H)

Example 58: Preparation of N-(2,5-difluorophenyl)-3-((methylamino)methyl)-1-(pyridin-3-ylsulfonyl)-1H-indol-6-amine hydrochloride

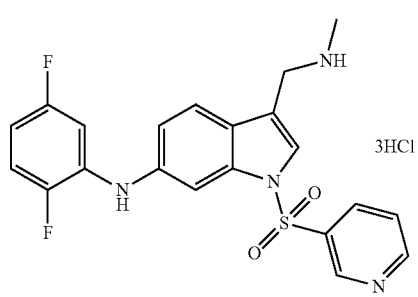 [SMILES: CNCc1cn(S(=O)(=O)c2cccnc2)c2cc(Nc3cc(F)ccc3F)ccc12]

$^1$H NMR (300 MHz, DMSO-d$_6$): 9.11 (d, 1H), 8.88 (dd, 1H), 8.35 (td, 1H), 7.94 (s, 1H), 7.63-7.72 (m, 3H), 7.24-7.32 (m, 1H), 7.14 (dd, 1H), 6.92-6.99 (m, 1H), 6.68-6.76 (m, 1H), 4.22 (t, 2H), 2.52 (s, 3H)

Example 59: Preparation of N-(2-fluoro-5-methyl-phenyl)-3-((methylamino)methyl)-1-(pyridin-3-yl-sulfonyl)-1H-indol-6-amine hydrochloride

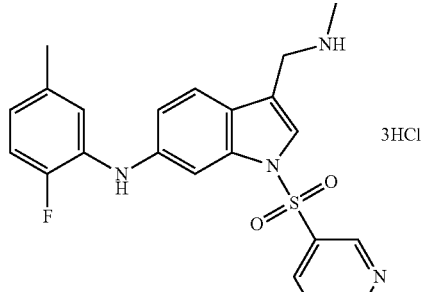

$^1$H NMR (500 MHz, CD$_3$OD): 9.02 (s, 1H), 8.71 (d, 1H), 8.22 (d, 1H), 7.67 (s, 1H), 7.64 (q, 1H), 7.40 (d, 1H), 7.16 (s, 1H), 7.11-7.15 (m, 1H), 7.07 (dd, 1H), 7.00-7.03 (m, 1H), 6.94 (dd, 1H), 4.24 (s, 2H), 2.76 (s, 3H), 2.22 (s, 3H)

Example 60: Preparation of N-(2,6-difluorophenyl)-3-((methylamino)methyl)-1-(pyridin-3-ylsulfonyl)-1H-indol-6-amine hydrochloride

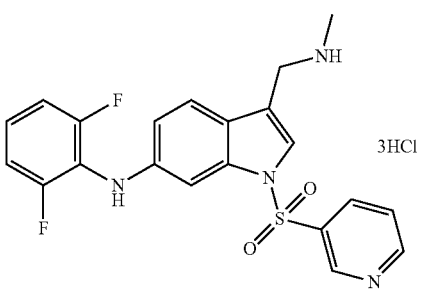 [SMILES: CNCc1cn(S(=O)(=O)c2cccnc2)c2cc(Nc3c(F)cccc3F)ccc12]

$^1$H NMR (500 MHz, CD$_3$OD): 9.08 (s, 1H), 8.76 (d, 1H), 8.25 (d, 1H), 7.87 (s, 1H), 7.66 (s, 1H), 7.55-7.61 (m, 2H), 7.49 (d, 1H), 7.27 (dd, 1H), 7.20 (d, 1H), 7.14 (dd, 1H), 4.33 (s, 2H), 2.75 (s, 3H)

Example 61: Preparation of N-(2-chloro-6-methyl-phenyl)-3-((methylamino)methyl)-1-(pyridin-3-yl-sulfonyl)-1H-indol-6-amine hydrochloride

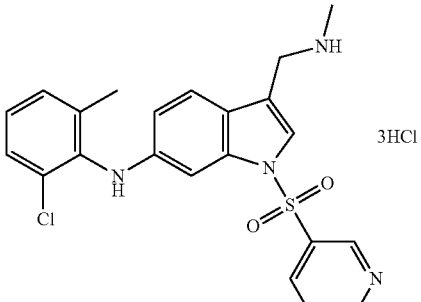

$^1$H NMR (500 MHz, CD$_3$OD): 9.06 (s, 1H), 8.74 (d, 1H), 8.25 (d, 1H), 7.67 (s, 1H), 7.61 (q, 1H), 7.36 (d, 1H), 7.15 (s, 1H), 7.08-7.12 (m, 1H), 7.04 (dd, 1H), 6.99-7.01 (m, 1H), 6.91 (dd, 1H), 4.24 (s, 2H), 2.77 (s, 3H), 2.23 (s, 3H)

Example 62: Preparation of N-(3,4-difluorophenyl)-3-((methylamino)methyl)-1-(pyridin-3-ylsulfonyl)-1H-indol-6-amine hydrochloride

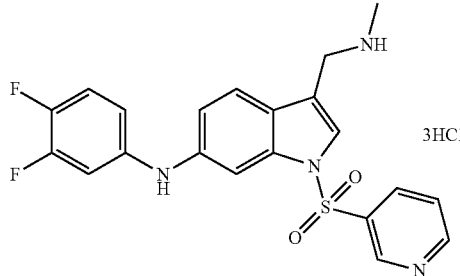 [SMILES: CNCc1cn(S(=O)(=O)c2cccnc2)c2cc(Nc3ccc(F)c(F)c3)ccc12]

¹H NMR (500 MHz, CD₃OD): 9.06 (s, 1H), 8.78 (d, 1H), 8.25 (d, 1H), 7.86 (s, 1H), 7.62 (s, 1H), 7.54-7.59 (m, 2H), 7.48 (d, 1H), 7.25 (dd, 1H), 7.18 (d, 1H), 7.13 (dd, 1H), 4.31 (s, 2H), 2.74 (s, 3H)

Example 63: Preparation of N-(3,5-dimethoxyphenyl)-3-((methylamino)methyl)-1-(pyridin-3-ylsulfonyl)-1H-indol-6-amine hydrochloride

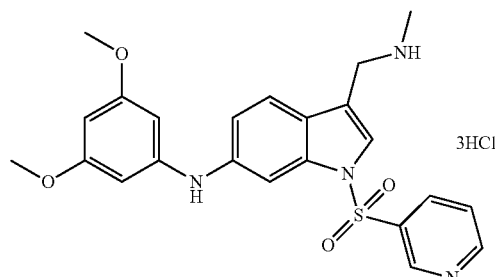

¹H NMR (300 MHz, CD₃OD): 9.14 (s, 1H), 8.85 (s, 1H), 8.40 (td, 1H), 7.91 (s, 1H), 7.80 (d, 1H), 7.63-7.70 (m, 2H), 7.23 (dd, 1H), 6.61 (dd, 2H), 4.89 (s, 6H), 4.37 (s, 3H), 2.78 (s, 3H)

Example 64: Preparation of N-(3,5-dichlorophenyl)-3-((methylamino)methyl)-1-(pyridin-3-ylsulfonyl)-1H-indol-6-amine hydrochloride

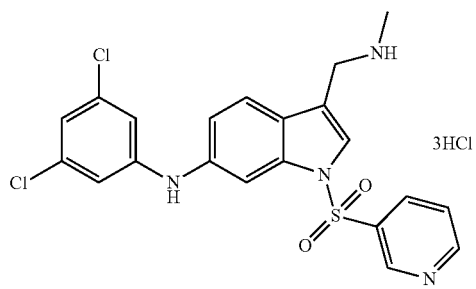 [SMILES: CNCc1cn(S(=O)(=O)c2cccnc2)c2cc(Nc3cc(Cl)cc(Cl)c3)ccc12]

¹H NMR (500 MHz, CD₃OD): 9.09 (s, 1H), 8.80 (d, 1H), 8.31 (d, 1H), 7.89 (s, 1H), 7.65 (s, 1H), 7.61-7.63 (m, 2H), 7.51 (d, 1H), 7.27 (dd, 1H), 7.21 (d, 1H), 7.15 (dd, 1H), 4.33 (s, 2H), 2.73 (s, 3H)

Example 65: Preparation of N-(2,3-difluoro-4-methylphenyl)-3-((methylamino)methyl)-1-(pyridin-3-ylsulfonyl)-1H-indol-6-amine hydrochloride

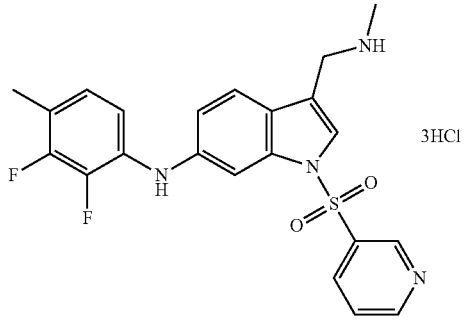 [SMILES: CNCc1cn(S(=O)(=O)c2cccnc2)c2cc(Nc3ccc(C)c(F)c3F)ccc12]

¹H NMR (500 MHz, CD₃OD): 9.05 (s, 1H), 8.79 (d, 1H), 8.29 (d, 1H), 7.78 (s, 1H), 7.59 (q, 1H), 7.55-7.56 (m, 2H), 7.04 (dd, 1H), 6.94-6.98 (m, 2H), 4.30 (s, 2H), 2.73 (s, 3H), 2.29 (s, 3H)

Example 66: Preparation of N-(4-fluoro-2,3-dimethylphenyl)-3-((methylamino)methyl)-1-(pyridin-3-ylsulfonyl)-1H-indol-6-amine hydrochloride

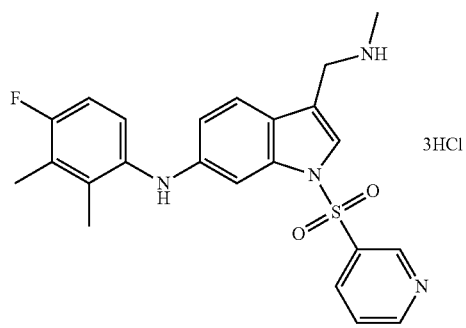 [SMILES: CNCc1cn(S(=O)(=O)c2cccnc2)c2cc(Nc3ccc(F)c(C)c3C)ccc12]

¹H NMR (400 MHz, DMSO-d₆): 8.95-9.08 (m, 3H), 8.89 (dd, 1H), 8.44 (br, 1H), 8.32 (d, 1H), 7.90 (s, 1H), 7.65-7.70 (m, 2H), 7.50 (s, 1H), 7.26 (q, 1H), 7.00-7.06 (m, 2H), 4.16-4.19 (m, 2H), 2.56 (s, 3H), 2.21 (s, 3H), 1.98 (s, 3H)

Example 67: Preparation of 3-((methylamino)methyl)-1-(pyridin-3-ylsulfonyl)-N-(2,3,4-trifluorophenyl)-1H-indol-6-amine hydrochloride

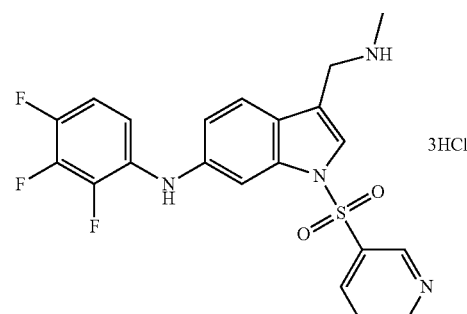

¹H NMR (400 MHz, DMSO-d₆): 8.95-9.08 (m, 3H), 8.89 (dd, 1H), 8.44 (br, 1H), 8.32 (d, 1H), 7.90 (s, 1H), 7.65-7.70 (m, 2H), 7.50 (s, 1H), 7.26 (q, 1H), 7.00-7.06 (m, 2H), 4.21-4.23 (m, 2H), 2.56 (s, 3H)

Example 68: Preparation of N-(2,4-difluoro-3-methoxyphenyl)-3-((methylamino)methyl)-1-(pyridin-3-ylsulfonyl)-1H-indol-6-amine hydrochloride

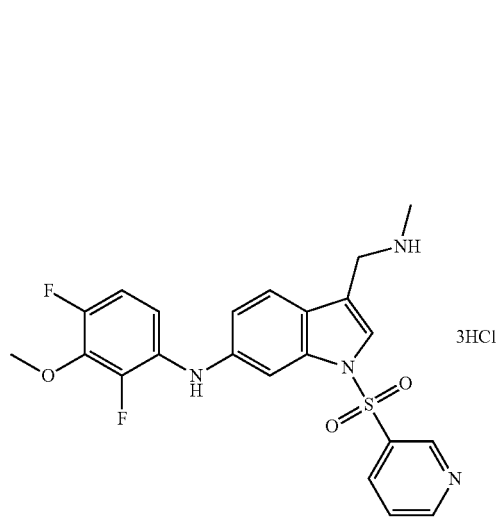 [SMILES: CNCc1cn(S(=O)(=O)c2cccnc2)c2cc(Nc3ccc(F)c(OC)c3F)ccc12]

¹H NMR (500 MHz, CD₃OD): 9.06 (s, 1H), 8.81 (d, 1H), 8.25 (d, 1H), 7.75 (s, 1H), 7.60-7.63 (m, 1H), 7.55 (d, 1H), 7.46 (s, 1H), 7.04-7.06 (m, 1H), 6.98-7.01 (m, 2H), 4.27 (s, 2H), 3.95 (s, 3H), 2.71 (s, 3H)

Example 69: Preparation of N-(3-ethoxy-2,4-difluorophenyl)-3-((methylamino)methyl)-1-(pyridin-3-ylsulfonyl)-1H-indol-6-amine hydrochloride

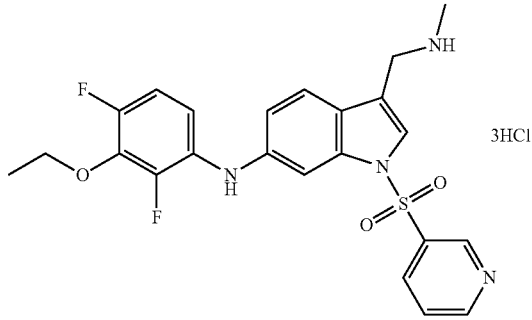 [SMILES: CCOc1c(F)ccc(Nc2ccc3c(CNC)cn(S(=O)(=O)c4cccnc4)c3c2)c1F]

¹H NMR (500 MHz, CD₃OD): 9.06 (d, 1H), 8.81 (dd, 1H), 8.29 (td, 1H), 7.74 (s, 1H), 7.62 (q, 1H), 7.54 (d, 1H), 7.50 (s, 1H), 6.94-7.02 (m, 3H), 4.25-4.26 (m, 4H), 2.71 (s, 3H), 1.42 (t, 3H)

Example 70: Preparation of N-(2,3-difluoro-4-methoxyphenyl)-3-((methylamino)methyl)-1-(pyridin-3-ylsulfonyl)-1H-indol-6-amine hydrochloride

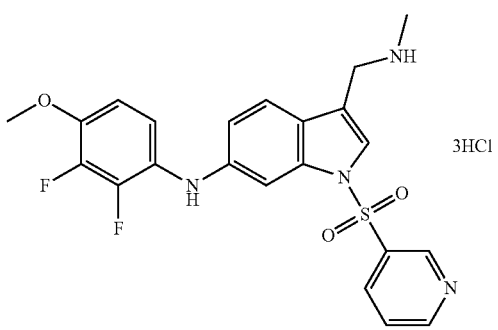 [SMILES: CNCc1cn(S(=O)(=O)c2cccnc2)c2cc(Nc3ccc(OC)c(F)c3F)ccc12]

¹H NMR (500 MHz, CD₃OD): 9.05 (s, 1H), 8.80 (d, 1H), 8.27 (d, 1H), 7.74 (s, 1H), 7.59-7.61 (m, 1H), 7.51 (d, 1H), 7.41 (s, 1H), 7.01-7.03 (m, 1H), 6.93-6.99 (m, 2H), 4.29 (s, 2H), 3.92 (s, 3H), 2.72 (s, 3H)

Example 71: Preparation of N-(4-ethoxy-2,3-difluorophenyl)-3-((methylamino)methyl)-1-(pyridin-3-ylsulfonyl)-1H-indol-6-amine hydrochloride

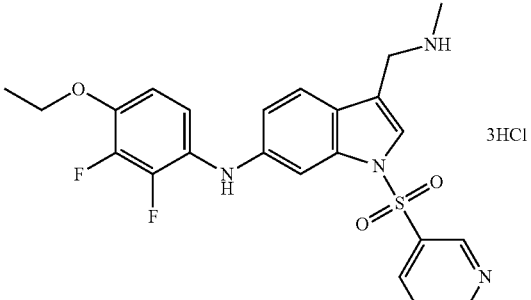

¹H NMR (500 MHz, CD3OD): 9.05 (s, 1H), 8.80 (d, 1H), 8.27-8.29 (m, 1H), 7.75 (s, 1H), 7.59-7.62 (m, 1H), 7.52 (d, 1H), 7.41 (s, 1H), 6.90-6.99 (m, 3H), 4.29 (s, 2H), 4.14-4.16 (m, 2H), 2.72 (s, 3H), 1.43 (t, 3H)

Example 72: Preparation of N-(2,5-difluoro-4-methylphenyl)-3-((methylamino)methyl)-1-(pyridin-3-ylsulfonyl)-1H-indol-6-amine hydrochloride

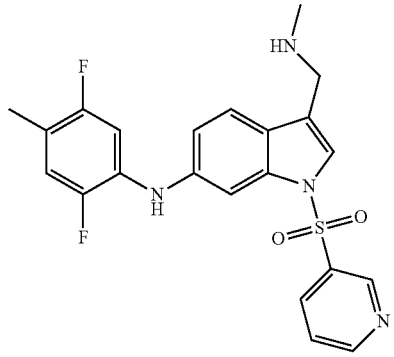

3HCl

¹H NMR (500 MHz, CD₃OD): 9.09 (d, 1H), 8.82 (dd, 1H), 8.36 (td, 1H), 7.83 (s, 1H), 7.60-7.65 (m, 3H), 7.01-7.12 (m, 2H), 6.95 (q, 1H), 4.34 (s, 2H), 2.76 (s, 3H), 2.26 (s, 3H)

Example 73: Preparation of N-(4,5-difluoro-2-methylphenyl)-3-((methylamino)methyl)-1-(pyridin-3-ylsulfonyl)-1H-indol-6-amine hydrochloride

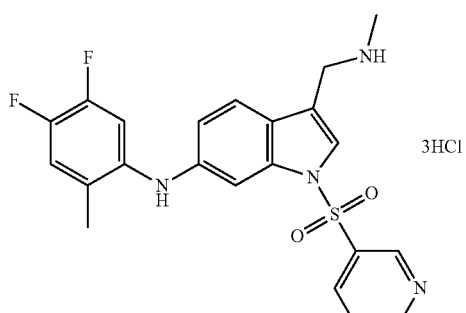

3HCl

¹H NMR (400 MHz, DMSO-d₆): 9.04 (d, 3H), 8.89 (dd, 1H), 8.29 (d, 1H), 7.86 (s, 1H), 7.68 (q, 1H), 7.63 (d, 1H), 7.40 (s, 1H), 7.34 (t, 1H), 7.03 (q, 1H), 6.95 (dd, 1H), 4.20-4.22 (m, 2H), 2.56 (s, 3H), 2.14 (s, 3H)

Example 74: Preparation of 3-((methylamino)methyl)-1-(pyridin-3-ylsulfonyl)-N-(2,4,5-trifluorophenyl)-1H-indol-6-amine hydrochloride

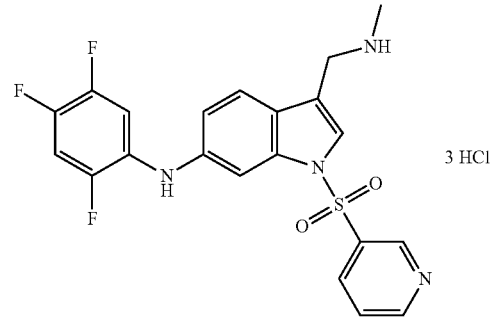 [SMILES: CNCc1cn(S(=O)(=O)c2cccnc2)c2cc(Nc3cc(F)c(F)cc3F)ccc12]

3 HCl

¹H NMR (500 MHz, CD₃OD): 9.09 (d, 1H), 8.82 (d, 1H), 8.36 (td, 1H), 7.85 (s, 1H), 7.61-7.64 (m, 3H), 7.26-7.32 (m, 1H), 7.14-7.19 (m, 1H), 7.10 (dd, 1H), 4.35 (s, 2H), 2.76 (s, 3H)

Example 75: Preparation of N-(4-chloro-2,5-dimethylphenyl)-3-((methylamino)methyl)-1-(pyridin-3-ylsulfonyl)-1H-indol-6-amine hydrochloride

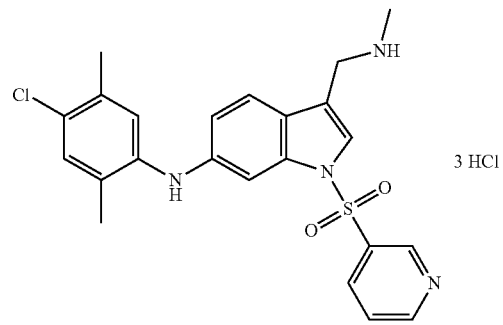 [SMILES: CNCc1cn(S(=O)(=O)c2cccnc2)c2cc(Nc3cc(C)c(Cl)cc3C)ccc12]

3 HCl

¹H NMR (500 MHz, CD₃OD): 9.03 (d, 1H), 8.82 (d, 1H), 8.28 (td, 1H), 7.76 (s, 1H), 7.61 (q, 1H), 7.53 (d, 1H), 7.39 (d, 1H), 7.27 (s, 1H), 7.11 (s, 1H), 6.95 (dd, 1H), 4.31 (s, 2H), 2.75 (s, 3H), 2.33 (s, 3H), 2.17 (s, 3H)

Example 76: Preparation of 3-((methylamino)methyl)-1-(pyridin-3-ylsulfonyl)-N-(2,4,5-trichlorophenyl)-1H-indol-6-amine hydrochloride

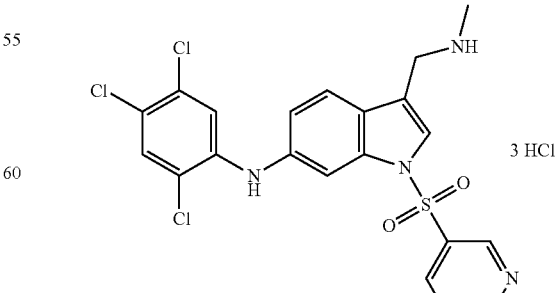

3 HCl

¹H NMR (500 MHz, CD₃OD): 9.05 (d, 1H), 8.87 (dd, 1H), 8.25 (d, 1H), 7.84 (s, 1H), 7.65 (q, 1H), 7.59 (d, 1H), 7.41 (s, 1H), 7.32 (t, 1H), 6.99 (q, 1H), 6.87 (dd, 1H), 4.22 (s, 2H), 2.55 (s, 3H)

Example 77: Preparation of N-(2,4-dichloro-5-methoxyphenyl)-3-((methylamino)methyl)-1-(pyridin-3-ylsulfonyl)-1H-indol-6-amine hydrochloride

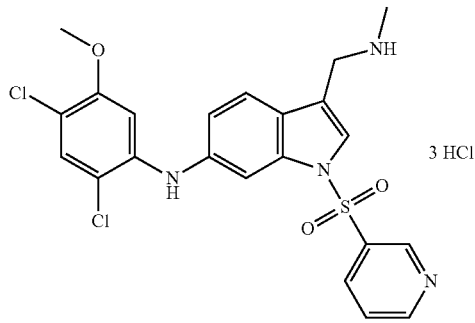 [SMILES: CNCc1cn(S(=O)(=O)c2cccnc2)c2cc(Nc3cc(OC)c(Cl)cc3Cl)ccc12]

¹H NMR (500 MHz, CD₃OD): 9.06 (d, 1H), 8.87 (dd, 1H), 8.26 (d, 1H), 7.88 (s, 1H), 7.66 (q, 1H), 7.61 (d, 1H), 7.44 (s, 1H), 7.33 (t, 1H), 7.01 (q, 1H), 6.88 (dd, 1H), 4.26 (s, 2H), 4.01 (s, 3H), 2.54 (s, 3H)

Example 78: Preparation of N-(2,5-difluoro-4-(trifluoromethyl)phenyl)-3-((methylamino)methyl)-1-(pyridin-3-ylsulfonyl)-1H-indol-6-amine hydrochloride

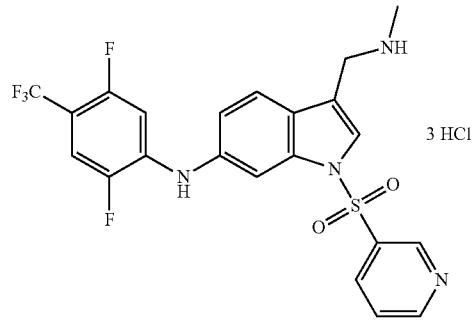 [SMILES: CNCc1cn(S(=O)(=O)c2cccnc2)c2cc(Nc3cc(F)c(C(F)(F)F)cc3F)ccc12]

¹H NMR (500 MHz, CD₃OD): 9.11 (d, 1H), 8.83 (dd, 1H), 8.38 (td, 1H), 7.90 (s, 1H), 7.71 (d, 1H), 7.65-7.69 (m, 2H), 7.62 (q, 1H), 7.10-7.14 (m, 2H), 4.36 (s, 2H), 2.77 (s, 3H)

Example 79: Preparation of N-(4-bromo-2,5-difluorophenyl)-3-((methylamino)methyl)-1-(pyridin-3-ylsulfonyl)-1H-indol-6-amine hydrochloride

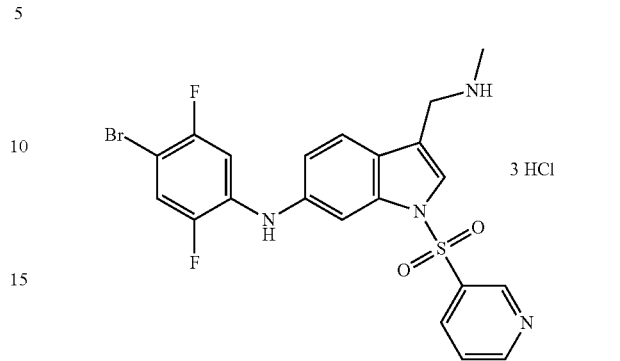

¹H NMR (500 MHz, CD₃OD): 9.17 (d, 1H), 8.84 (td, 1H), 8.45 (dd, 1H), 8.25 (d, 1H), 8.04 (s, 1H), 7.76 (d, 1H), 7.72 (d, 1H), 7.63 (q, 1H), 7.56 (dd, 1H), 7.46 (q, 1H), 4.37 (s, 2H), 2.77 (s, 3H)

Example 80: Preparation of N-mesityl-3-((methylamino)methyl)-1-(pyridin-3-ylsulfonyl)-1H-indol-6-amine hydrochloride

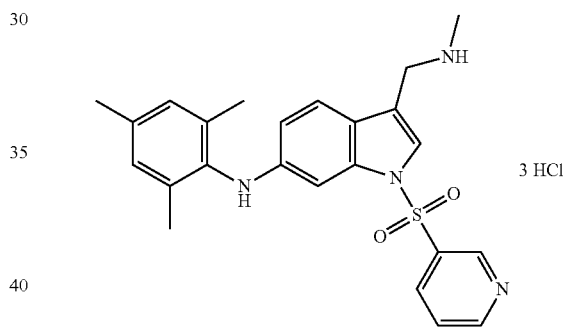

¹H NMR (500 MHz, CD₃OD): 8.88 (d, 1H), 8.80 (dd, 1H), 8.11 (td, 1H), 7.66 (s, 1H), 7.57 (q, 1H), 7.45 (d, 1H), 7.04 (s, 2H), 6.79 (s, 1H), 6.71 (d, 1H), 4.29 (s, 2H), 2.74 (s, 3H), 2.36 (s, 3H), 2.11 (s, 6H)

Example 81: Preparation of N-(4-fluoro-2,6-dimethylphenyl)-3-((methylamino)methyl)-1-(pyridin-3-ylsulfonyl)-1H-indol-6-amine hydrochloride

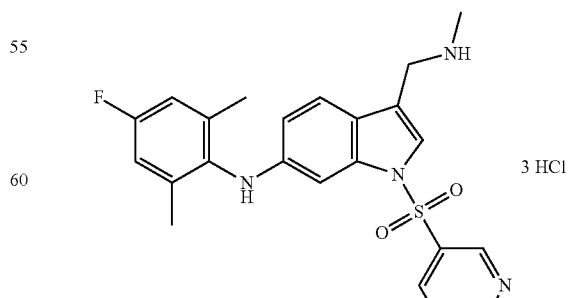

¹H NMR (500 MHz, CD₃OD): 8.88 (d, 1H), 8.80 (dd, 1H), 8.13 (td, 1H), 7.69 (s, 1H), 7.59 (q, 1H), 7.47 (d, 1H), 6.98 (d, 2H), 6.79 (s, 1H), 6.71 (d, 1H), 4.30 (s, 2H), 2.74 (s, 3H), 2.15 (s, 6H)

Example 82: Preparation of 3-((methylamino)methyl)-1-(pyridin-3-ylsulfonyl)-N-(2,4,6-trifluorophenyl)-1H-indol-6-amine hydrochloride

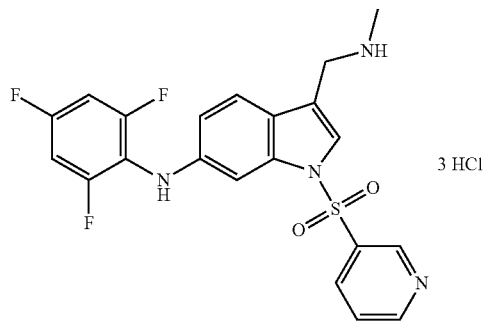 [SMILES: CNCc1cn(S(=O)(=O)c2cccnc2)c2cc(Nc3c(F)cc(F)cc3F)ccc12]

¹H NMR (500 MHz, CD₃OD): 9.03 (d, 1H), 8.82 (dd, 1H), 8.28 (td, 1H), 7.70 (s, 1H), 7.63 (q, 1H), 7.54 (d, 1H), 7.23 (s, 1H), 7.08 (t, 2H), 6.86 (dd, 1H), 4.32 (s, 2H), 2.74 (s, 3H)

Example 83: Preparation of N-(2-chloro-4,6-difluorophenyl)-3-((methylamino)methyl)-1-(pyridin-3-ylsulfonyl)-1H-indol-6-amine hydrochloride

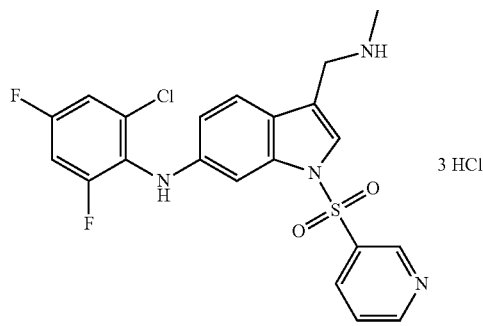

¹H NMR (500 MHz, CD₃OD): 9.03 (d, 1H), 8.82 (dd, 1H), 8.28 (td, 1H), 7.70 (s, 1H), 7.63 (q, 1H), 7.54 (d, 1H), 7.23 (s, 1H), 7.08 (t, 2H), 6.86 (dd, 1H), 4.32 (s, 2H), 2.74 (s, 3H)

Example 84: Preparation of N-(2,6-dichloro-4-fluorophenyl)-3-((methylamino)methyl)-1-(pyridin-3-ylsulfonyl)-1H-indol-6-amine hydrochloride

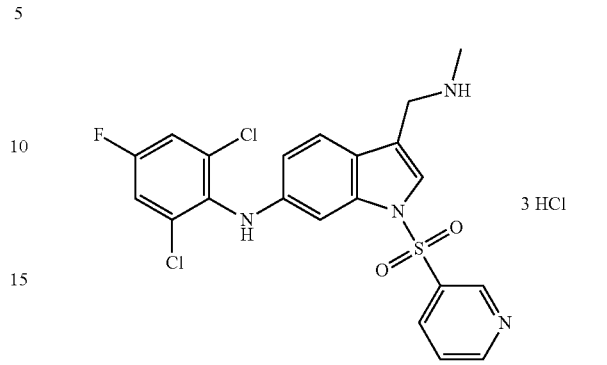

¹H NMR (500 MHz, CD₃OD): 7.44 (d, 1H), 7.25 (dd, 1H), 6.68 (td, 1H), 6.20 (s, 1H), 6.10 (s, 2H), 6.04 (q, 1H), 5.99 (d, 1H), 5.52 (s, 1H), 5.26 (dd, 1H), 2.75 (s, 2H), 1.18 (s, 3H)

Example 85: Preparation of N-(4-chloro-2,6-dimethylphenyl)-3-((methylamino)methyl)-1-(pyridin-3-ylsulfonyl)-1H-indol-6-amine hydrochloride

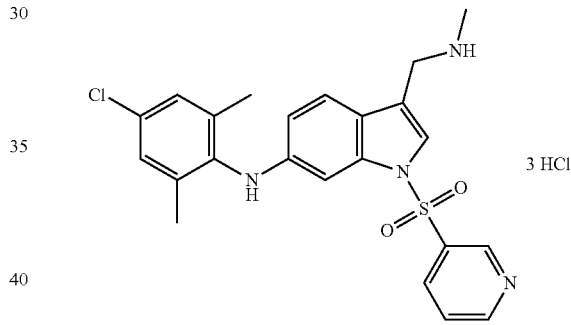

¹H NMR (500 MHz, CD₃OD): 8.90 (d, 1H), 8.80 (dd, 1H), 8.15 (td, 1H), 7.70 (s, 1H), 7.59 (q, 1H), 7.49 (d, 1H), 7.25 (s, 2H), 6.83 (s, 1H), 6.71 (dd, 1H), 4.30 (s, 2H), 2.74 (s, 3H), 2.14 (s, 6H)

Example 86: Preparation of N-(4-chloro-2,6-difluorophenyl)-3-((methylamino)methyl)-1-(pyridin-3-ylsulfonyl)-1H-indol-6-amine hydrochloride

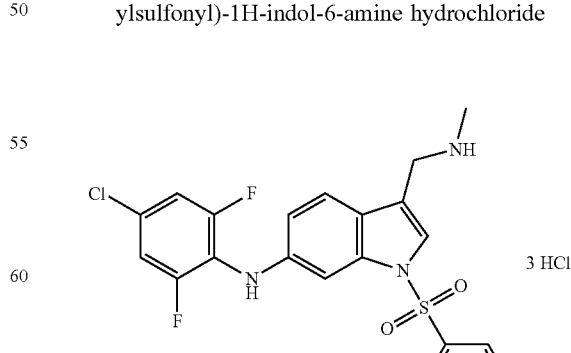

¹H NMR (500 MHz, CD₃OD): 9.05 (d, 1H), 8.82 (dd, 1H), 8.30 (td, 1H), 7.79 (s, 1H), 7.63 (q, 1H), 7.56 (d, 1H), 7.26-7.30 (m, 3H), 6.90 (d, 1H), 4.32 (s, 2H), 2.75 (s, 3H)

Example 87: Preparation of 3-((methylamino)methyl)-1-(pyridin-3-ylsulfonyl)-N-(2,4,6-trichlorophenyl)-1H-indol-6-amine hydrochloride

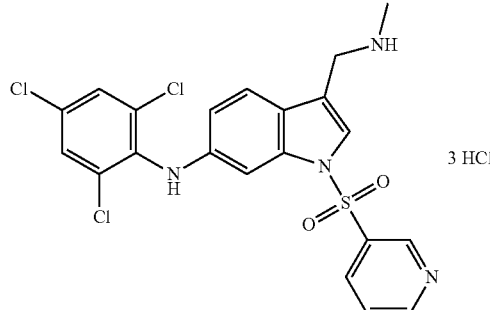

¹H NMR (500 MHz, CD₃OD): 8.98 (d, 1H), 8.81 (dd, 1H), 8.24 (td, 1H), 7.75 (s, 1H), 7.61 (q, 1H), 7.54 (d, 1H), 7.48 (d, 2H), 7.01 (d, 1H), 6.80 (dd, 1H), 4.31 (s, 2H), 2.74 (s, 3H)

Example 88: Preparation of N-(2,6-difluoro-4-methoxyphenyl)-3-((methylamino)methyl)-1-(pyridin-3-ylsulfonyl)-1H-indol-6-amine hydrochloride

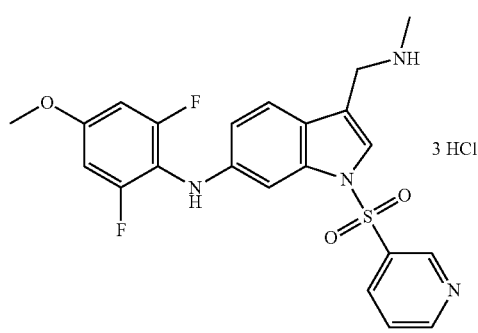 [SMILES: CNCc1cn(S(=O)(=O)c2cccnc2)c2cc(Nc3c(F)cc(OC)cc3F)ccc12]

¹H NMR (500 MHz, CD₃OD): 9.01 (d, 1H), 8.81 (dd, 1H), 8.27 (td, 1H), 7.73 (s, 1H), 7.62 (q, 1H), 7.51 (d, 1H), 7.16 (s, 1H), 6.83 (dd, 1H), 6.78 (d, 2H), 4.31 (s, 2H), 3.88 (s, 3H), 2.74 (s, 3H)

Example 89: Preparation of N-(4-ethoxy-2,6-difluorophenyl)-3-((methylamino)methyl)-1-(pyridin-3-ylsulfonyl)-1H-indol-6-amine hydrochloride

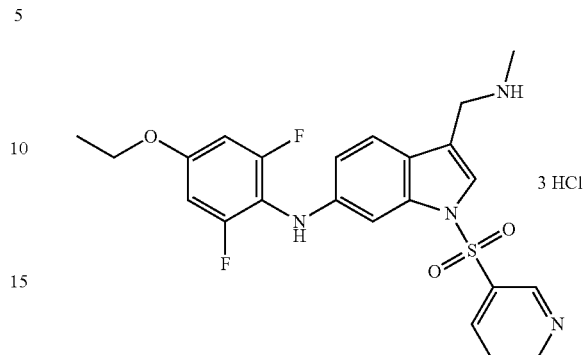

¹H NMR (500 MHz, CD₃OD): 9.01 (d, 1H), 8.81 (dd, 1H), 8.26 (td, 1H), 7.73 (s, 1H), 7.61 (q, 1H), 7.50 (d, 1H), 7.16 (s, 1H), 6.83 (dd, 1H), 6.76 (d, 2H), 4.30 (s, 2H), 4.11 (q, 2H), 2.74 (s, 3H), 1.45 (t, 3H)

Example 90: Preparation of N-(4-bromo-2,6-dimethylphenyl)-3-((methylamino)methyl)-1-(pyridin-3-ylsulfonyl)-1H-indol-6-amine hydrochloride

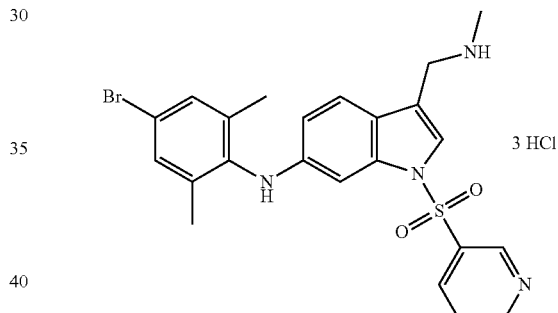

¹H NMR (500 MHz, CD₃OD): 8.90 (d, 1H), 8.80 (dd, 1H), 8.15 (td, 1H), 7.70 (s, 1H), 7.58 (q, 1H), 7.48 (d, 1H), 7.30 (s, 2H), 6.84 (dd, 1H), 6.70 (d, 1H), 4.30 (s, 2H), 2.74 (s, 3H), 2.15 (s, 6H)

Example 91: Preparation of N-(2-bromo-4,6-difluorophenyl)-3-((methylamino)methyl)-1-(pyridin-3-ylsulfonyl)-1H-indol-6-amine hydrochloride

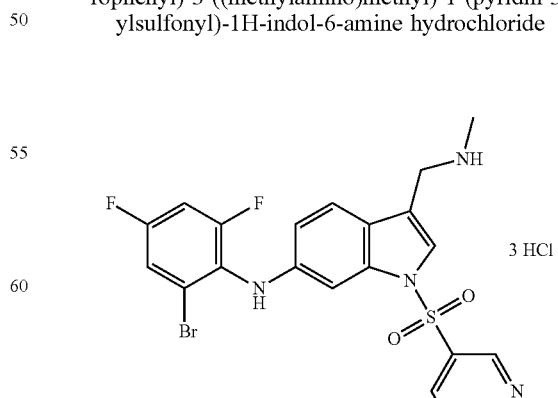

¹H NMR (500 MHz, CD₃OD): 9.17 (d, 1H), 8.84 (dd, 1H), 8.44 (td, 1H), 8.25 (d, 1H), 8.04 (s, 1H), 7.71 (s, 1H), 7.65 (q, 1H), 7.57 (dd, 1H), 7.30 (s, 1H), 6.83 (dd, 1H), 4.38 (s, 2H), 2.74 (s, 3H)

Example 92: Preparation of N-(4-bromo-2,6-difluorophenyl)-3-((methylamino)methyl)-1-(pyridin-3-ylsulfonyl)-1H-indol-6-amine hydrochloride

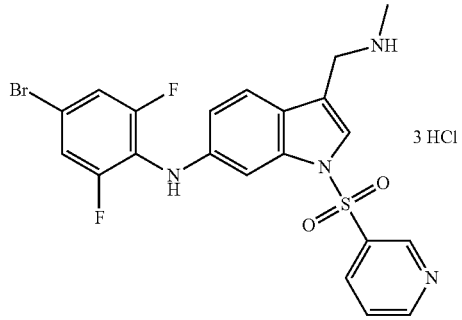

¹H NMR (500 MHz, CD₃OD): 9.15 (d, 1H), 8.81 (dd, 1H), 8.40 (td, 1H), 8.19 (d, 1H), 7.99 (s, 1H), 7.67 (s, 1H), 7.61 (q, 1H), 7.52 (dd, 1H), 7.25 (s, 1H), 6.85 (dd, 1H), 4.36 (s, 2H), 2.75 (s, 3H)

Example 93: Preparation of N-(2,4-dibromo-6-fluorophenyl)-3-((methylamino)methyl)-1-(pyridin-3-ylsulfonyl)-1H-indol-6-amine hydrochloride

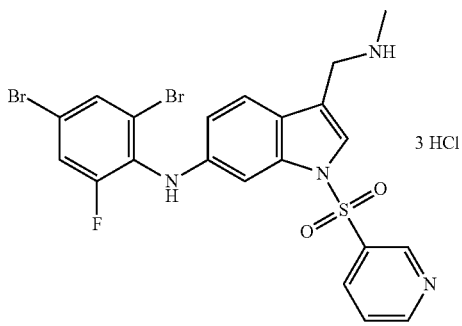 [SMILES: CNCc1cn(S(=O)(=O)c2cccnc2)c2cc(Nc3c(C)cc(Br)cc3C)ccc12]

¹H NMR (500 MHz, CD₃OD): 9.18 (d, 1H), 8.83 (dd, 1H), 8.45 (td, 1H), 8.24 (d, 1H), 8.06 (s, 1H), 7.73 (s, 1H), 7.63 (q, 1H), 7.55 (dd, 1H), 7.27 (s, 1H), 6.80 (dd, 1H), 4.39 (s, 2H), 2.77 (s, 3H)

Example 94: Preparation of N-(4-chloro-2-methyl-6-nitrophenyl)-3-((methylamino)methyl)-1-(pyridin-3-ylsulfonyl)-1H-indol-6-amine hydrochloride

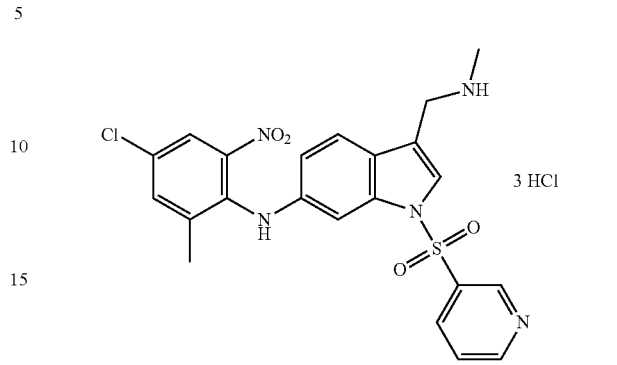

¹H NMR (500 MHz, CD₃OD): 9.08 (d, 1H), 8.81 (d, 1H), 8.33 (td, 1H), 7.82 (s, 1H), 7.63 (q, 1H), 7.59 (d, 1H), 7.50 (s, 1H), 6.95-7.03 (m, 3H), 4.34 (s, 2H), 4.03 (s, 3H), 2.76 (s, 3H)

Example 95: Preparation of 3-((methylamino)methyl)-1-(pyridin-3-ylsulfonyl)-N-(2,3,5,6-tetrafluorophenyl)-1H-indol-6-amine hydrochloride

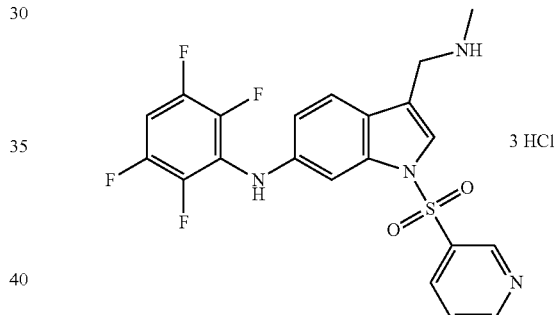

¹H NMR (500 MHz, CD₃OD): 9.07 (d, 1H), 8.82 (d, 1H), 8.32 (td, 1H), 7.85 (s, 1H), 7.60 (d, 2H), 7.47 (s, 1H), 7.15-7.20 (m, 1H), 6.99 (d, 1H), 4.35 (s, 2H), 2.76 (s, 3H)

Example 96: Preparation of 3-((methylamino)methyl)-1-(pyridin-3-ylsulfonyl)-N-(2,3,5,6-tetrafluoro-4-(trifluoromethyl)phenyl)-1H-indol-6-amine hydrochloride

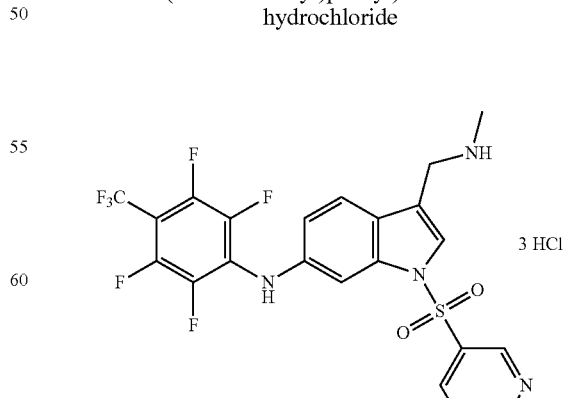

¹H NMR (500 MHz, CD₃OD): 9.13 (d, 1H), 8.83 (dd, 1H), 8.40 (td, 1H), 7.94 (s, 1H), 7.68-7.70 (m, 2H), 7.63 (q, 1H), 7.12 (d, 1H), 4.37 (s, 2H), 2.77 (s, 3H)

Example 97: Preparation of N-(2,3-dihydrobenzo[b][1,4]dioxin-6-yl)-3-((methylamino)methyl)-1-(pyridin-3-ylsulfonyl)-1H-indol-6-amine hydrochloride

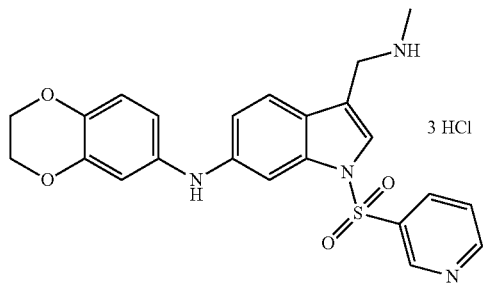 [SMILES: CNCc1cn(S(=O)(=O)c2cccnc2)c2cc(Nc3ccc4c(c3)OCCO4)ccc12]

¹H NMR (300 MHz, CD₃OD): 9.10 (s, 1H), 8.86 (d, 1H), 8.37 (td, 1H), 7.77 (br, 1H), 7.70 (q, 1H), 7.52-7.60 (m, 2H), 7.01 (br, 1H), 6.85 (br, 1H), 6.65-6.69 (m, 2H), 4.30-4.34 (m, 6H), 2.79 (s, 3H)

Example 98: Preparation of 3-((methylamino)methyl)-N-(3-methylpyridin-2-yl)-1-(pyridin-3-ylsulfonyl)-1H-indol-6-amine hydrochloride

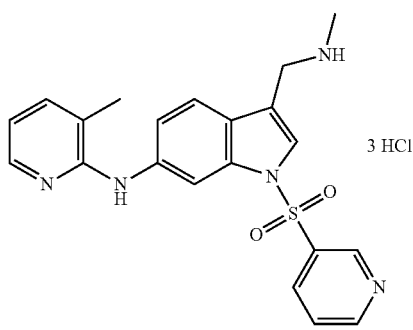 [SMILES: CNCc1cn(S(=O)(=O)c2cccnc2)c2cc(Nc3ncccc3C)ccc12]

¹H NMR (500 MHz, CD₃OD): 9.20 (s, 1H), 8.74-8.77 (m, 2H), 8.43 (d, 1H), 8.04 (d, 1H), 7.82 (s, 1H), 7.58 (d, 1H), 7.53 (q, 1H), 7.41-7.49 (m, 2H), 6.82-6.87 (m, 1H), 4.31 (s, 2H), 2.72 (s, 3H), 2.31 (s, 3H)

Example 99: Preparation of N-(3-fluoropyridin-2-yl)-3-((methylamino)methyl)-1-(pyridin-3-ylsulfonyl)-1H-indol-6-amine hydrochloride

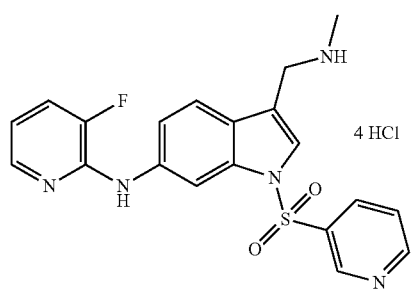 [SMILES: CNCc1cn(S(=O)(=O)c2cccnc2)c2cc(Nc3ncccc3F)ccc12]

¹H NMR (500 MHz, CD₃OD): 9.23 (s, 1H), 8.76-8.78 (m, 2H), 8.47 (d, 1H), 8.06 (d, 1H), 7.86 (s, 1H), 7.63 (d, 1H), 7.58 (q, 1H), 7.47-7.53 (m, 2H), 6.86-6.89 (m, 1H), 4.34 (s, 2H), 2.74 (s, 3H)

Example 100: Preparation of N-(3-chloropyridin-2-yl)-3-((methylamino)methyl)-1-(pyridin-3-ylsulfonyl)-1H-indol-6-amine hydrochloride

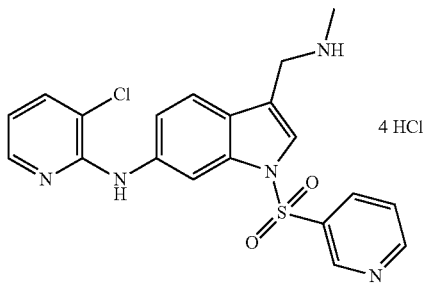 [SMILES: CNCc1cn(S(=O)(=O)c2cccnc2)c2cc(Nc3ncccc3Cl)ccc12]

¹H NMR (400 MHz, DMSO-d₆): 9.23 (d, 1H), 9.09 (br, 2H), 8.87 (dd, 1H), 8.71 (s, 1H), 8.49 (d, 1H), 8.41-8.45 (m, 1H), 8.19 (dd, 1H), 7.95 (s, 1H), 7.84 (dd, 1H), 7.62-7.71 (m, 3H), 6.91 (q, 1H), 4.23-4.26 (m, 2H), 2.56 (s, 3H)

Example 101: Preparation of 3-((methylamino)methyl)-1-(pyridin-3-ylsulfonyl)-N-(3-(trifluoromethyl)pyridin-2-yl)-1H-indol-6-amine hydrochloride

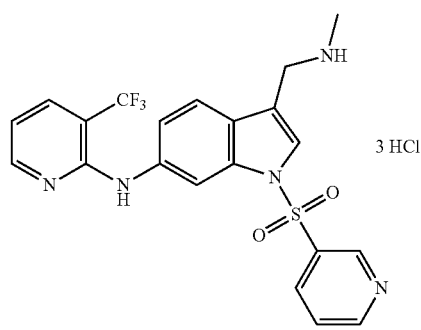 [SMILES: CNCc1cn(S(=O)(=O)c2cccnc2)c2cc(Nc3ncccc3C(F)(F)F)ccc12]

¹H NMR (300 MHz, CD₃OD): 9.28 (s, 1H), 8.85 (s, 1H), 8.55 (d, 1H), 8.48 (d, 1H), 8.27 (s, 1H), 8.17 (s, 1H), 8.10 (d, 1H), 8.00 (d, 1H), 7.67 (q, 1H), 7.47 (d, 1H), 7.19 (t, 1H), 4.44 (s, 2H), 2.78 (s, 3H)

Example 102: Preparation of N-(3-bromopyridin-2-yl)-3-((methylamino)methyl)-1-(pyridin-3-ylsulfonyl)-1H-indol-6-amine hydrochloride

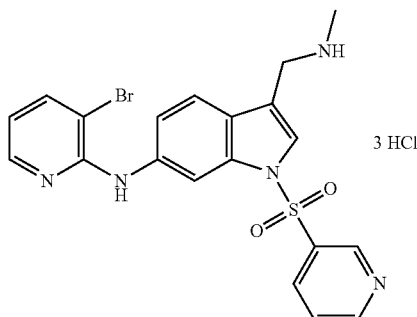

3 HCl $^1$H NMR (400 MHz, DMSO-d$_6$): 9.25 (d, 1H), 9.10 (br, 2H), 8.89 (dd, 1H), 8.75 (s, 1H), 8.51 (d, 1H), 8.44-8.49 (m, 1H), 8.22 (dd, 1H), 7.98 (s, 1H), 7.85 (dd, 1H), 7.63-7.72 (m, 3H), 6.95 (q, 1H), 4.22-4.27 (m, 2H), 2.58 (s, 3H)

Example 103: Preparation of N-(5-chloro-4-methylpyridin-2-yl)-3-((methylamino)methyl)-1-(pyridin-3-ylsulfonyl)-1H-indol-6-amine hydrochloride

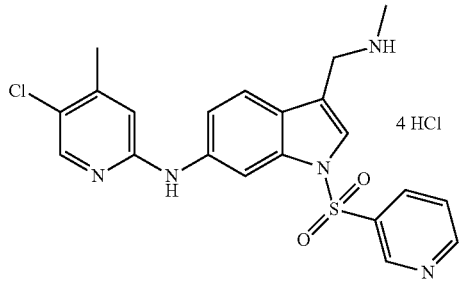 [SMILES: CNCc1cn(S(=O)(=O)c2cccnc2)c2cc(Nc3cc(C)c(Cl)cn3)ccc12]

4 HCl $^1$H NMR (500 MHz, CD$_3$OD): 9.25 (br, 1H), 8.85 (br, 1H), 8.48 (d, 1H), 8.40 (s, 1H), 8.11 (s, 1H), 8.08 (s, 1H), 7.98 (s, 2H), 7.81 (d, 1H), 7.38 (d, 1H), 4.40 (s, 2H), 2.78 (s, 3H), 2.46 (s, 3H)

Example 104: Preparation of N-(5-chloro-6-methylpyridin-2-yl)-3-((methylamino)methyl)-1-(pyridin-3-ylsulfonyl)-1H-indol-6-amine hydrochloride

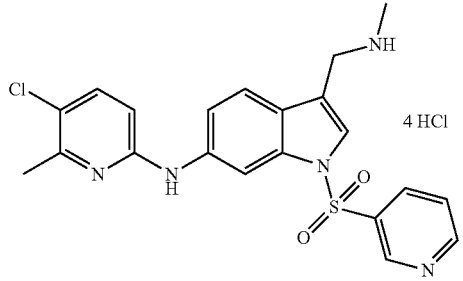 [SMILES: CNCc1cn(S(=O)(=O)c2cccnc2)c2cc(Nc3ccc(Cl)c(C)n3)ccc12]

4 HCl $^1$H NMR (400 MHz, DMSO-d$_6$): 9.53 (br, 1H), 9.14 (d, 2H), 9.01 (s, 1H), 8.81 (dd, 1H), 8.33 (d, 1H), 7.89 (d, 1H), 7.58-7.65 (m, 3H), 7.32 (dd, 1H), 6.74 (d, 1H), 4.17-4.20 (m, 2H), 2.52 (s, 3H), 2.50 (s, 3H)

Example 105: Preparation of 3-((methylamino)methyl)-N-(2-methylpyridin-3-yl)-1-(pyridin-3-ylsulfonyl)-1H-indol-6-amine hydrochloride

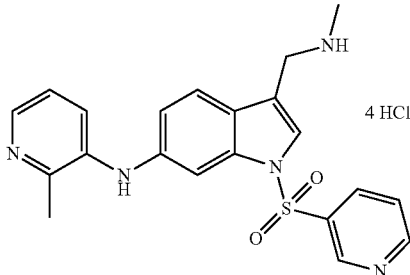

4 HCl $^1$H NMR (500 MHz, CD$_3$OD): 9.19 (br, 1H), 8.85 (s, 1H), 8.39 (td, 1H), 8.13 (d, 1H), 7.99 (s, 1H), 7.94 (d, 1H), 7.89 (s, 1H), 7.79 (d, 1H), 7.63-7.67 (m, 2H), 7.29 (dd, 1H), 4.40 (s, 2H), 2.78 (s, 3H), 2.55 (s, 3H)

Example 106: Preparation of N-(2-fluoropyridin-3-yl)-3-((methylamino)methyl)-1-(pyridin-3-ylsulfonyl)-1H-indol-6-amine hydrochloride

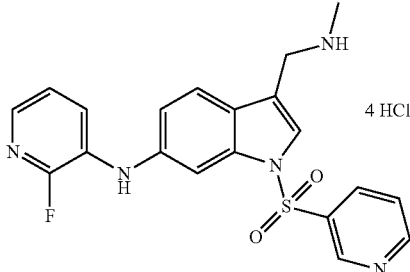

4 HCl $^1$H NMR (500 MHz, CD$_3$OD): 9.12 (d, 1H), 8.83 (dd, 1H), 8.37 (td, 1H), 7.85 (s, 1H), 7.61-7.74 (m, 5H), 7.27-7.29 (m, 1H), 7.19 (dd, 1H), 4.32 (s, 2H), 2.74 (s, 3H)

Example 107: Preparation of N-(2-chloropyridin-3-yl)-3-((methylamino)methyl)-1-(pyridin-3-ylsulfonyl)-1H-indol-6-amine hydrochloride

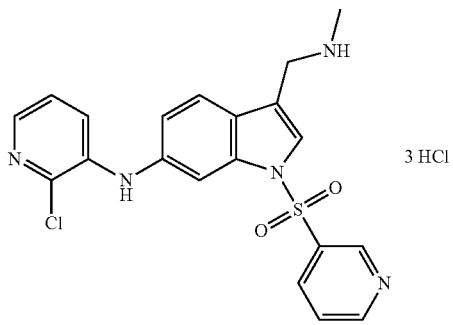 [SMILES: CNCc1cn(S(=O)(=O)c2cccnc2)c2cc(Nc3cccnc3Cl)ccc12]

3 HCl

¹H NMR (500 MHz, CD₃OD): 9.15 (d, 1H), 8.84 (dd, 1H), 8.41 (td, 1H), 7.87 (s, 1H), 7.64-7.75 (m, 4H), 7.29-7.35 (m, 2H), 7.24 (dd, 1H), 4.35 (s, 2H), 2.75 (s, 3H)

Example 108: Preparation of N-(2-methoxypyridin-3-yl)-3-((methylamino)methyl)-1-(pyridin-3-ylsulfonyl)-1H-indol-6-amine hydrochloride

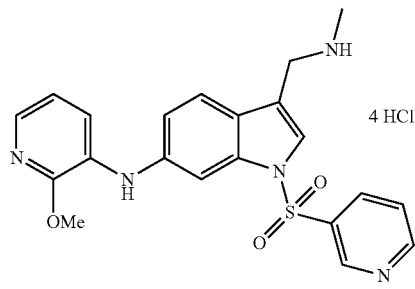 [SMILES: CNCc1cn(S(=O)(=O)c2cccnc2)c2cc(Nc3cccnc3OC)ccc12]

¹H NMR (500 MHz, CD₃OD): 9.10 (d, 1H), 8.82 (dd, 1H), 8.34 (td, 1H), 8.21 (d, 1H), 7.90 (s, 1H), 7.76 (d, 1H), 7.68 (d, 2H), 7.59 (q, 1H), 7.50 (q, 1H), 7.14 (dd, 1H), 4.34 (s, 2H), 3.99 (s, 3H), 2.73 (s, 3H)

Example 109: Preparation of 3-((methylamino)methyl)-1-(pyridin-3-ylsulfonyl)-N-(2-(trifluoromethyl)pyridin-3-yl)-1H-indol-6-amine hydrochloride

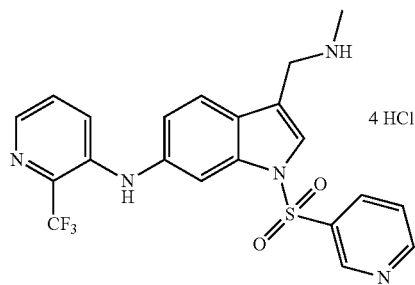 [SMILES: CNCc1cn(S(=O)(=O)c2cccnc2)c2cc(Nc3cccnc3C(F)(F)F)ccc12]

¹H NMR (500 MHz, CD₃OD): 9.12 (d, 1H), 8.84 (dd, 1H), 8.38 (td, 1H), 8.24 (d, 1H), 7.93 (s, 1H), 7.78 (d, 1H), 7.70 (d, 2H), 7.63 (q, 1H), 7.54 (q, 1H), 7.18 (dd, 1H), 4.37 (s, 2H), 2.77 (s, 3H)

Example 110: Preparation of N-(5-bromopyridin-3-yl)-3-((methylamino)methyl)-1-(pyridin-3-ylsulfonyl)-1H-indol-6-amine hydrochloride

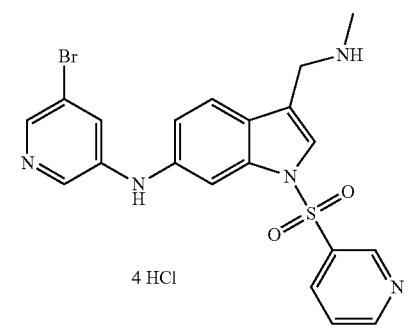 [SMILES: CNCc1cn(S(=O)(=O)c2cccnc2)c2cc(Nc3cncc(Br)c3)ccc12]

¹H NMR (500 MHz, CD₃OD): 9.17 (br, 1H), 8.85 (d, 1H), 8.42 (td, 2H), 8.33 (s, 1H), 7.90-8.04 (m, 2H), 7.96 (d, 1H), 7.85 (d, 1H), 7.65 (q, 1H), 7.34 (dd, 1H), 4.44 (s, 2H), 2.78 (s, 3H)

Example 111: Preparation of N-(2,6-dimethylpyridin-3-yl)-3-((methylamino)methyl)-1-(pyridin-3-ylsulfonyl)-1H-indol-6-amine hydrochloride

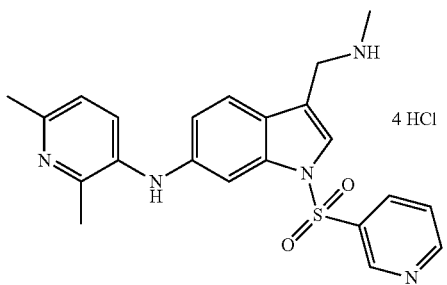 [SMILES: CNCc1cn(S(=O)(=O)c2cccnc2)c2cc(Nc3ccc(C)nc3C)ccc12]

¹H NMR (400 MHz, DMSO-d₆): 9.19 (br, 2H), 9.09 (d, 1H), 8.87 (d, 1H), 8.52 (br, 1H), 8.34 (d, 1H), 7.96 (s, 1H), 7.89 (d, 1H), 7.74 (d, 1H), 7.64-7.67 (m, 2H), 7.52 (d, 1H), 7.10 (dd, 1H), 4.19-4.22 (m, 2H), 2.61-2.65 (m, 6H), 2.51 (s, 3H)

Example 112: Preparation of N-(2-fluoro-6-methylpyridin-3-yl)-3-((methylamino)methyl)-1-(pyridin-3-ylsulfonyl)-1H-indol-6-amine hydrochloride

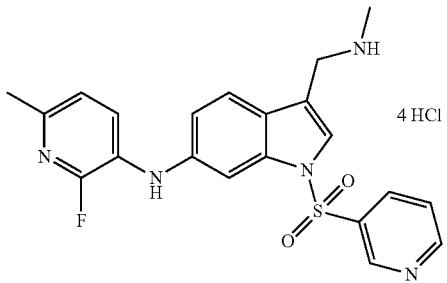 [SMILES: CNCc1cn(S(=O)(=O)c2cccnc2)c2cc(Nc3ccc(C)nc3F)ccc12]

¹H NMR (500 MHz, CD₃OD): 9.07 (s, 1H), 8.80 (d, 1H), 8.32 (d, 1H), 7.81 (s, 1H), 7.58-7.64 (m, 4H), 7.12 (d, 1H), 7.07 (dd, 1H), 4.31 (s, 2H), 2.73 (s, 3H), 2.44 (s, 3H)

Example 113: Preparation of N-(2-chloro-6-methylpyridin-3-yl)-3-((methylamino)methyl)-1-(pyridin-3-ylsulfonyl)-1H-indol-6-amine hydrochloride

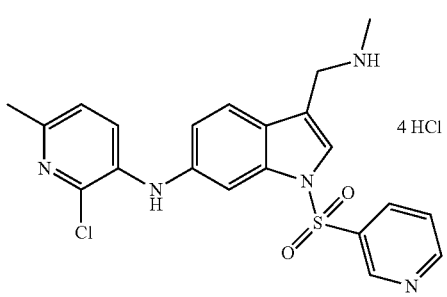 [SMILES: CNCc1cn(S(=O)(=O)c2cccnc2)c2cc(Nc3ccc(C)nc3Cl)ccc12]

¹H NMR (500 MHz, CD₃OD): 9.08 (s, 1H), 8.80 (d, 1H), 8.33 (d, 1H), 7.79 (s, 1H), 7.67 (d, 1H), 7.58-7.61 (m, 2H), 7.52 (d, 1H), 7.18 (d, 1H), 7.11 (dd, 1H), 4.25 (s, 2H), 2.69 (s, 3H), 2.46 (s, 3H)

Example 114: Preparation of N-(2-methoxy-6-methylpyridin-3-yl)-3-((methylamino)methyl)-1-(pyridin-3-ylsulfonyl)-1H-indol-6-amine hydrochloride

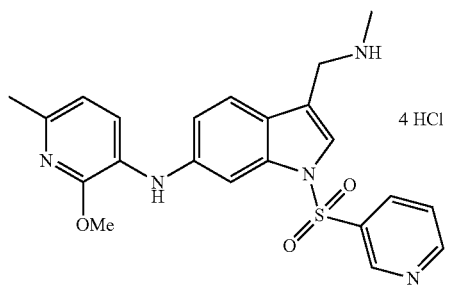 [SMILES: CNCc1cn(S(=O)(=O)c2cccnc2)c2cc(Nc3ccc(C)nc3OC)ccc12]

¹H NMR (400 MHz, DMSO-d₆): 9.10 (s, 2H), 9.04 (d, 1H), 8.89 (dd, 1H), 8.29 (d, 1H), 7.86 (s, 1H), 7.65-7.70 (m, 1H), 7.62 (d, 1H), 7.31 (d, 1H), 6.99 (dd, 1H), 6.86 (dd, 1H), 4.19-4.22 (m, 2H), 4.02 (s, 3H), 2.65 (s, 3H), 2.33 (s, 3H)

Example 115: Preparation of N-(6-methyl-2-(trifluoromethyl)pyridin-3-yl)-3-((methylamino)methyl)-1-(pyridin-3-ylsulfonyl)-1H-indol-6-amine hydrochloride

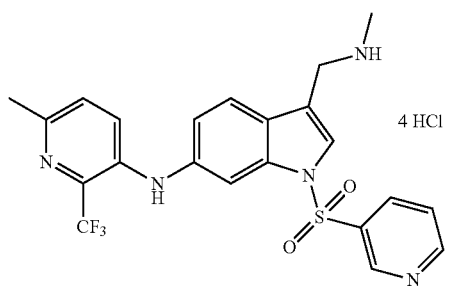

¹H NMR (500 MHz, CD₃OD): 9.14 (d, 1H), 8.84 (dd, 1H), 8.39 (td, 1H), 7.94 (s, 1H), 7.84 (d, 1H), 7.72 (d, 1H), 7.64 (q, 1H), 7.53 (s, 2H), 7.25 (dd, 1H), 4.38 (s, 2H), 2.78 (s, 3H), 2.60 (s, 3H)

Example 116: Preparation of N-(6-fluoro-2-methylpyridin-3-yl)-3-((methylamino)methyl)-1-(pyridin-3-ylsulfonyl)-1H-indol-6-amine hydrochloride

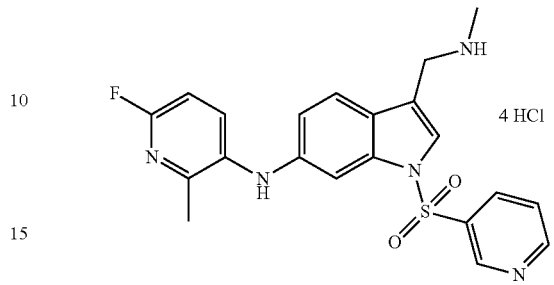

¹H NMR (500 MHz, CD₃OD): 9.08 (br, 1H), 8.85 (d, 1H), 8.34 (td, 1H), 7.82 (s, 1H), 7.72 (t, 1H), 7.65-7.68 (m, 1H), 7.59 (d, 1H), 7.37 (d, 1H), 6.97 (dd, 1H), 6.93 (dd, 1H), 4.34 (s, 2H), 2.76 (s, 3H), 2.39 (s, 3H)

Example 117: Preparation of N-(2-bromo-6-fluoropyridin-3-yl)-3-((methylamino)methyl)-1-(pyridin-3-ylsulfonyl)-1H-indol-6-amine hydrochloride

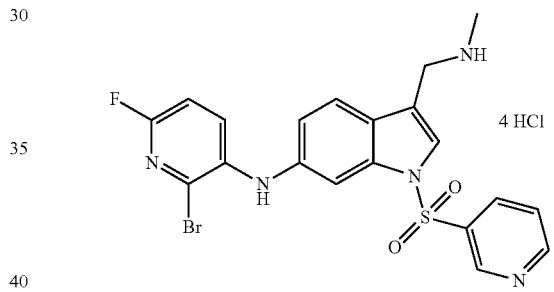

¹H NMR (500 MHz, CD₃OD): 9.29 (br, 1H), 8.81 (d, 2H), 8.59 (d, 1H), 7.90 (s, 1H), 7.85 (t, 1H), 7.62-7.65 (m, 2H), 7.33 (dd, 1H), 6.69 (d, 1H), 4.36 (s, 2H), 2.77 (s, 3H)

Example 118: Preparation of N-(6-chloro-2-methylpyridin-3-yl)-3-((methylamino)methyl)-1-(pyridin-3-ylsulfonyl)-1H-indol-6-amine hydrochloride

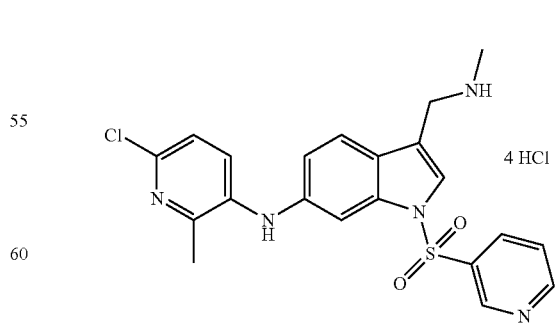

¹H NMR (500 MHz, CD₃OD): 9.17 (d, 1H), 8.86 (dd, 1H), 8.43 (td, 1H), 7.94 (s, 1H), 7.67-7.74 (m, 4H), 7.47 (d, 1H), 7.17 (d, 1H), 4.38 (s, 2H), 2.77 (s, 3H), 2.60 (s, 3H)

Example 119: Preparation of N-(2,6-dichloropyridin-3-yl)-3-((methylamino)methyl)-1-(pyridin-3-ylsulfonyl)-1H-indol-6-amine hydrochloride

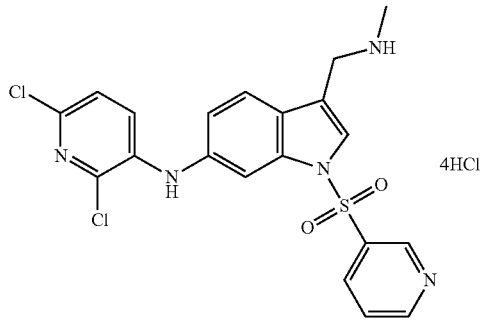 [SMILES: CNCc1cn(S(=O)(=O)c2cccnc2)c2cc(Nc3ccc(Cl)nc3Cl)ccc12]

¹H NMR (300 MHz, CD₃OD): 9.24 (s, 1H), 8.89 (s, 1H), 8.54 (d, 1H), 7.97 (s, 1H), 7.80 (s, 1H), 7.69-7.76 (m, 2H), 7.54 (d, 1H), 7.31 (d, 1H), 7.20 (d, 1H), 4.36 (s, 2H), 2.76 (s, 3H)

Example 120: Preparation of N-(6-chloro-2-methoxypyridin-3-yl)-3-((methylamino)methyl)-1-(pyridin-3-ylsulfonyl)-1H-indol-6-amine hydrochloride

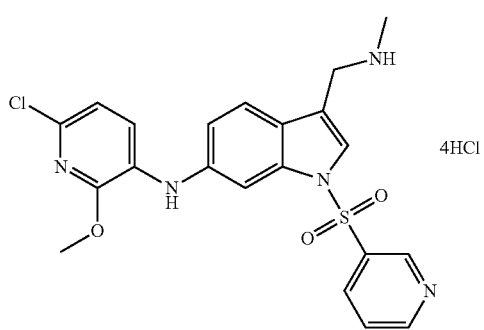 [SMILES: CNCc1cn(S(=O)(=O)c2cccnc2)c2cc(Nc3ccc(Cl)nc3OC)ccc12]

¹H NMR (500 MHz, CD₃OD): 9.10 (s, 1H), 8.80 (d, 1H), 8.34 (dd, 1H), 7.83 (s, 1H), 7.71 (s, 1H), 7.61 (d, 2H), 7.43 (d, 1H), 7.14-7.17 (m, 1H), 6.91 (d, 1H), 4.32 (s, 2H), 4.01 (s, 3H), 2.74 (s, 3H)

Example 121: Preparation of N-(6-chloro-2-(trifluoromethyl)pyridin-3-yl)-3-((methylamino)methyl)-1-(pyridin-3-ylsulfonyl)-1H-indol-6-amine hydrochloride

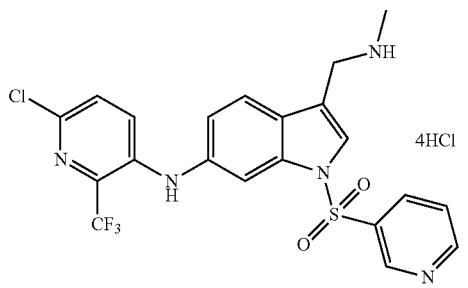 [SMILES: CNCc1cn(S(=O)(=O)c2cccnc2)c2cc(Nc3ccc(Cl)nc3C(F)(F)F)ccc12]

¹H NMR (500 MHz, CD₃OD): 9.11 (s, 1H), 8.76 (d, 1H), 8.31 (dd, 1H), 7.80 (s, 1H), 7.67 (s, 1H), 7.58 (d, 2H), 7.39 (d, 1H), 7.10-7.13 (m, 1H), 6.88 (d, 1H), 4.30 (s, 2H), 2.71 (s, 3H)

Example 122: Preparation of N-(6-methoxy-2-methylpyridin-3-yl)-3-((methylamino)methyl)-1-(pyridin-3-ylsulfonyl)-1H-indol-6-amine hydrochloride

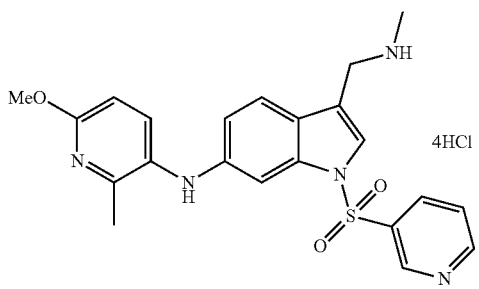 [SMILES: CNCc1cn(S(=O)(=O)c2cccnc2)c2cc(Nc3ccc(OC)nc3C)ccc12]

¹H NMR (400 MHz, DMSO-d₆): 9.08 (br, 2H), 8.99 (d, 1H), 8.89 (dd, 1H), 8.23 (d, 1H), 7.79 (s, 1H), 7.75 (d, 1H), 7.68 (q, 1H), 7.55 (d, 1H), 7.47 (d, 1H), 7.12 (d, 1H), 6.70-6.79 (m, 2H), 4.17-4.19 (m, 2H), 3.98 (s, 3H), 2.45 (s, 3H), 2.27 (s, 3H)

Example 123: Preparation of N-(2-chloro-6-methoxypyridin-3-yl)-3-((methylamino)methyl)-1-(pyridin-3-ylsulfonyl)-1H-indol-6-amine hydrochloride

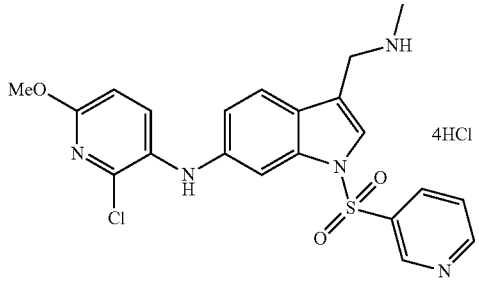

¹H NMR (500 MHz, CD₃OD): 9.03 (s, 1H), 8.79 (d, 1H), 8.27 (d, 1H), 7.75 (s, 1H), 7.62 (d, 1H), 7.59 (q, 1H), 7.52 (d, 1H), 7.36 (s, 1H), 6.91 (dd, 1H), 6.82 (d, 1H), 4.29 (s, 2H), 3.93 (s, 3H), 2.72 (s, 3H)

Example 124: Preparation of N-(2-methyl-6-(trifluoromethyl)pyridin-3-yl)-3-((methylamino)methyl)-1-(pyridin-3-ylsulfonyl)-1H-indol-6-amine hydrochloride

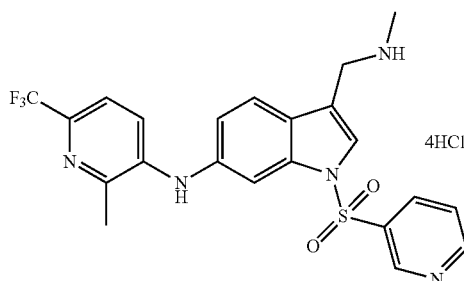

¹H NMR (500 MHz, CD₃OD): 9.17 (br, 1H), 8.86 (br, 1H), 8.41 (d, 1H), 7.95 (s, 1H), 7.85 (d, 1H), 7.73 (d, 1H), 7.65 (q, 1H), 7.55 (s, 2H), 7.26 (dd, 1H), 4.38 (s, 2H), 2.78 (s, 3H), 2.61 (s, 3H)

Example 125: Preparation of N-(2-chloro-6-(trifluoromethyl)pyridin-3-yl)-3-((methylamino)methyl)-1-(pyridin-3-ylsulfonyl)-1H-indol-6-amine hydrochloride

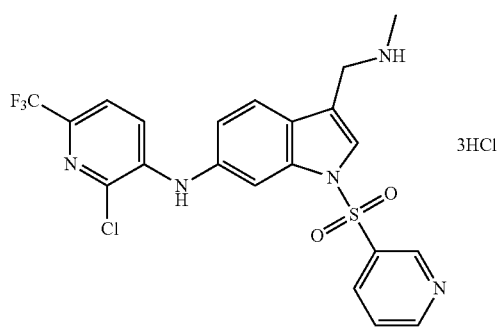 [SMILES: CNCc1cn(S(=O)(=O)c2cccnc2)c2cc(Nc3ccc(C(F)(F)F)nc3Cl)ccc12]

¹H NMR (500 MHz, CD₃OD): 9.13 (s, 1H), 8.77 (d, 1H), 8.33 (dd, 1H), 7.82 (s, 1H), 7.70 (s, 1H), 7.61 (d, 2H), 7.42 (d, 1H), 7.11-7.16 (m, 1H), 6.91 (d, 1H), 4.32 (s, 2H), 2.75 (s, 3H)

Example 126: Preparation of N-(5-chloro-2-methylpyridin-3-yl)-3-((methylamino)methyl)-1-(pyridin-3-ylsulfonyl)-1H-indol-6-amine hydrochloride

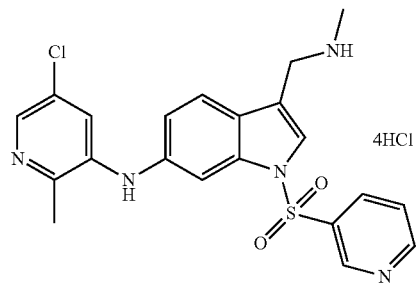 [SMILES: CNCc1cn(S(=O)(=O)c2cccnc2)c2cc(Nc3cc(Cl)cnc3C)ccc12]

¹H NMR (400 MHz, DMSO-d₆): 9.14 (br, 1H), 9.09 (d, 1H), 8.86 (d, 1H), 8.35 (d, 1H), 8.13 (s, 1H), 7.96 (s, 1H), 7.73 (d, 1H), 7.69 (s, 1H), 7.65 (q, 1H), 7.45 (s, 1H), 7.15 (d, 1H), 4.19-4.22 (m, 2H), 2.52 (s, 3H), 2.48 (s, 3H)

Example 127: Preparation of N-(2-chloro-4-methylpyridin-3-yl)-3-((methylamino)methyl)-1-(pyridin-3-ylsulfonyl)-1H-indol-6-amine hydrochloride

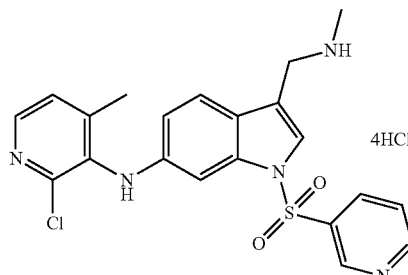

¹H NMR (500 MHz, CD₃OD): 9.17 (d, 1H), 8.83 (d, 1H), 8.42 (td, 1H), 8.02 (s, 1H), 7.99 (d, 1H), 7.91 (d, 1H), 7.84 (d, 1H), 7.61 (q, 1H), 7.33 (dd, 1H), 6.67 (d, 1H), 4.26 (s, 2H), 2.71 (s, 3H), 2.26 (s, 3H)

Example 128: Preparation of N-(3-chloropyridin-4-yl)-3-((methylamino)methyl)-1-(pyridin-3-ylsulfonyl)-1H-indol-6-amine hydrochloride

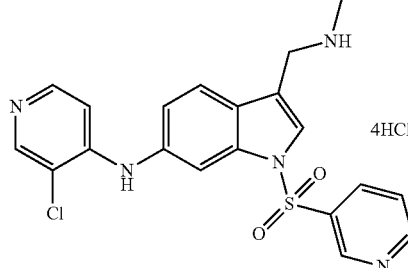

¹H NMR (500 MHz, CD₃OD): 9.19 (d, 1H), 8.85 (d, 1H), 8.46 (td, 1H), 8.08 (s, 1H), 8.02 (d, 2H), 7.93 (d, 1H), 7.86 (d, 1H), 7.63 (q, 1H), 7.36 (dd, 1H), 6.70 (d, 1H), 4.42 (s, 2H), 2.79 (s, 3H)

Example 129: Preparation of 3-((methylamino)methyl)-1-(pyridin-3-ylsulfonyl)-N-(3-(trifluoromethyl)pyridin-4-yl)-1H-indol-6-amine hydrochloride

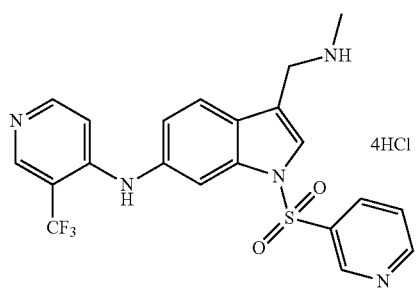 [SMILES: CNCc1cn(S(=O)(=O)c2cccnc2)c2cc(Nc3ccncc3C(F)(F)F)ccc12]

¹H NMR (500 MHz, CD₃OD): 9.17 (d, 1H), 8.83 (d, 1H), 8.43 (td, 1H), 8.05 (s, 1H), 8.00 (d, 2H), 7.91 (d, 1H), 7.83 (d, 1H), 7.59 (q, 1H), 7.33 (dd, 1H), 6.65 (d, 1H), 4.38 (s, 2H), 2.79 (s, 3H)

Example 130: Preparation of N-(3-chloro-2-methoxypyridin-4-yl)-3-((methylamino)methyl)-1-(pyridin-3-ylsulfonyl)-1H-indol-6-amine hydrochloride

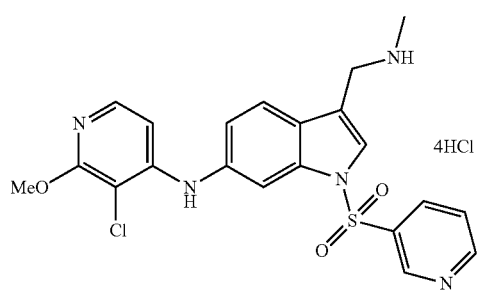 [SMILES: CNCc1cn(S(=O)(=O)c2cccnc2)c2cc(Nc3ccnc(OC)c3Cl)ccc12]

¹H NMR (500 MHz, CD₃OD): 9.22 (d, 1H), 8.85 (dd, 1H), 8.61 (s, 1H), 8.45-8.48 (m, 1H), 8.18 (d, 1H), 8.12-8.13 (m, 1H), 7.94 (d, 1H), 7.64 (q, 1H), 7.44 (dd, 1H), 6.96 (d, 1H), 4.52 (s, 2H), 4.17 (s, 3H), 2.56 (s, 3H)

Example 131: Preparation of N-(3-bromo-2-methoxypyridin-4-yl)-3-((methylamino)methyl)-1-(pyridin-3-ylsulfonyl)-1H-indol-6-amine hydrochloride

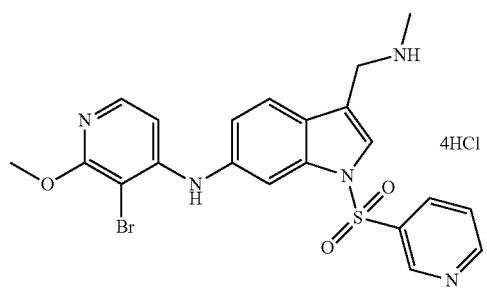 [SMILES: CNCc1cn(S(=O)(=O)c2cccnc2)c2cc(Nc3ccnc(OC)c3Br)ccc12]

¹H NMR (500 MHz, CD₃OD): 9.22 (d, 1H), 8.85 (dd, 1H), 8.61 (s, 1H), 8.18 (d, 1H), 8.12-8.13 (m, 1H), 8.08 (dd, 1H), 7.94 (d, 1H), 7.64 (q, 1H), 7.44 (dd, 1H), 6.96 (d, 1H), 4.42 (s, 2H), 4.15 (s, 3H), 2.79 (s, 3H)

Example 132: Preparation of N-(2,3-dichloropyridin-4-yl)-3-((methylamino)methyl)-1-(pyridin-3-ylsulfonyl)-1H-indol-6-amine hydrochloride

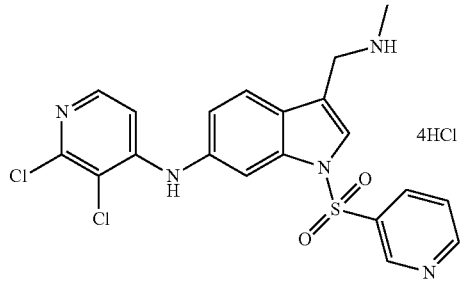 [SMILES: CNCc1cn(S(=O)(=O)c2cccnc2)c2cc(Nc3ccnc(Cl)c3Cl)ccc12]

¹H NMR (500 MHz, CD₃OD): 9.21 (d, 1H), 8.85 (d, 1H), 8.47 (d, 1H), 8.12 (s, 1H), 8.06 (d, 1H), 7.99 (d, 1H), 7.92 (d, 1H), 7.65 (q, 1H), 7.40 (dd, 1H), 6.84 (d, 1H), 4.44 (s, 2H), 2.79 (s, 3H)

Example 133: Preparation of N-(3-bromo-2-chloropyridin-4-yl)-3-((methylamino)methyl)-1-(pyridin-3-ylsulfonyl)-1H-indol-6-amine hydrochloride

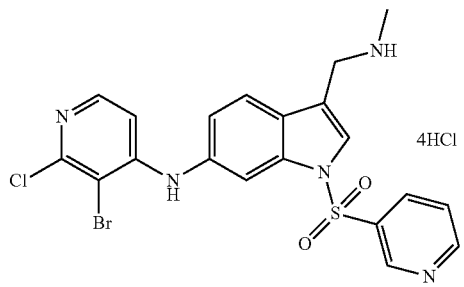 [SMILES: CNCc1cn(S(=O)(=O)c2cccnc2)c2cc(Nc3ccnc(Cl)c3Br)ccc12]

¹H NMR (400 MHz, CD₃OD): 9.18 (d, 1H), 8.82 (dd, 1H), 8.45 (td, 1H), 8.11 (s, 1H), 8.04 (d, 1H), 7.91 (d, 1H), 7.78 (d, 1H), 7.63 (q, 1H), 7.36 (dd, 1H), 6.66 (d, 1H), 4.44 (s, 2H), 2.75 (s, 3H)

Example 134: Preparation of 3-((methylamino)methyl)-1-(pyridin-3-ylsulfonyl)-N-(2,3,5-trifluoropyridin-4-yl)-1H-indol-6-amine hydrochloride

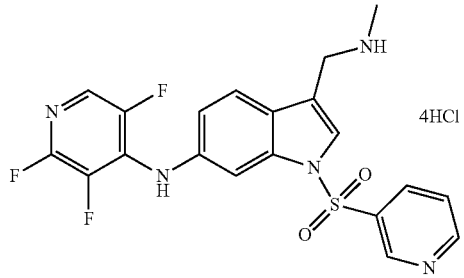 [SMILES: CNCc1cn(S(=O)(=O)c2cccnc2)c2cc(Nc3c(F)cnc(F)c3F)ccc12]

¹H NMR (500 MHz, CD₃OD): 9.18 (d, 1H), 8.79 (d, 1H), 8.42 (d, 1H), 8.11 (s, 1H), 7.95 (d, 1H), 7.88 (d, 1H), 7.60 (q, 1H), 7.34 (dd, 1H), 6.83 (d, 1H), 4.45 (s, 2H), 2.77 (s, 3H)

Example 135: Preparation of N-3-((methylamino)methyl)-1-(pyridin-3-ylsulfonyl)-1H-indol-6-yl)quinolin-6-amine hydrochloride

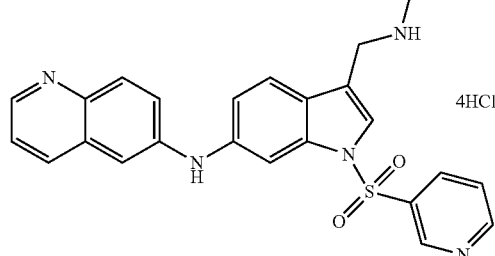

$^1$H NMR (500 MHz, CD$_3$OD): 9.00 (d, 2H), 8.55-8.67 (m, 2H), 8.35-8.43 (m, 3H), 8.03 (d, 1H), 7.75 (t, 1H), 7.35-7.46 (m, 2H), 7.24 (s, 1H), 6.98 (d, 1H), 6.82 (d, 1H), 4.27 (s, 2H), 2.79 (s, 3H)

Example 136: Preparation of N-(2-fluoro-4-methylphenyl)-1-((3-fluorophenyl)sulfonyl)-3-((methylamino)methyl)-1H-indol-6-amine hydrochloride The compound of Example 136 was prepared as shown in Reaction Scheme 2 below.

[Reaction Scheme 2]

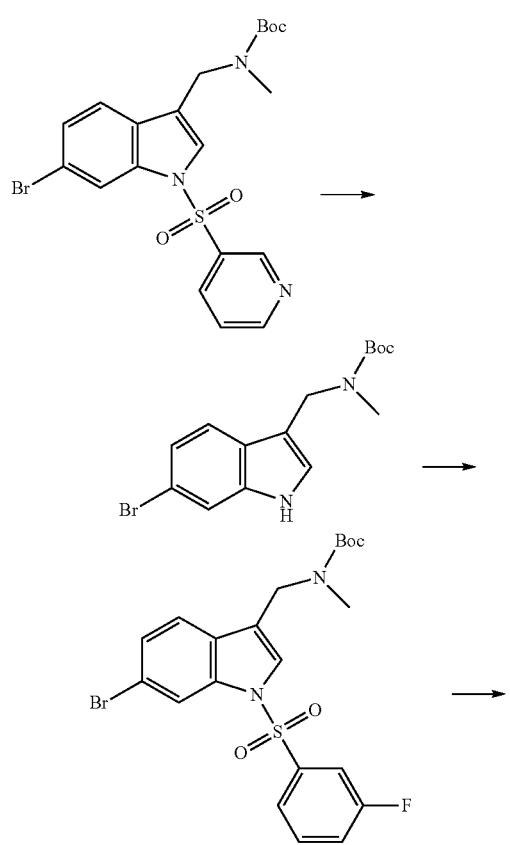

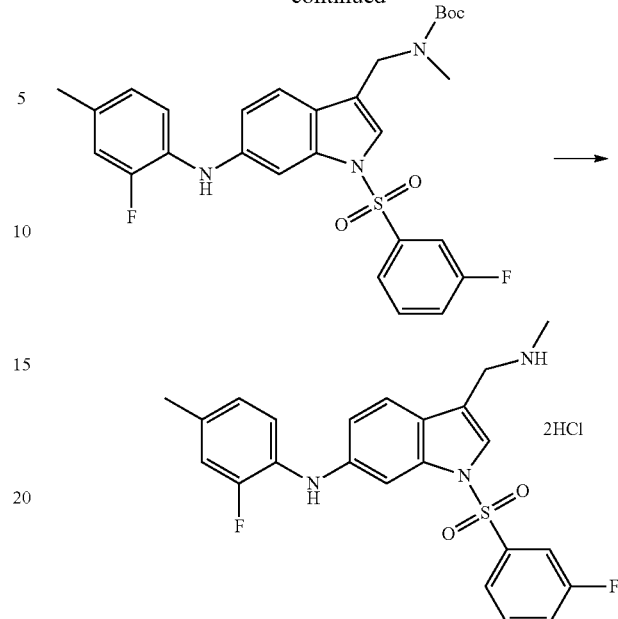

Step 1: Preparation of tert-butyl ((6-bromo-1H-indol-3-yl)methyl)(methyl)carbamate Tert-butyl ((6-bromo-1-(pyridin-3-ylsulfonyl)-1H-indol-3-yl)methyl)(methyl)carbamate (500 mg, 1.0 mmole) was added with 2 ml of 1M tetrabutylammonium fluoride-tetrahydrofuran solution and stirred at 80° C. for 2 hours. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:3 (v/v)) to obtain 310 mg of a title compound (yield: 87.8%).

$^1$H NMR (500 MHz, CDCl$_3$): 8.11 (br, 1H), 7.52-7.60 (m, 2H), 7.22 (d, 1H), 7.10 (s, 1H), 4.56 (s, 2H), 2.73-2.78 (m, 3H), 1.49 (s, 9H)

Step 2: Preparation of tert-butyl ((6-bromo-1-((3-fluorophenyl)sulfonyl)-1H-indol-3-yl)methyl)(methyl)carbamate Tert-butyl ((6-bromo-1H-indol-3-yl)methyl)(methyl)carbamate (220 mg, 0.6 mmole) was dissolved in 5 ml of N,N-dimethylformamide solution, cooled to 0° C., and dropwisely added with sodium hydride (60% in oil)(52 mg, 1.3 mmol). The reaction mixture was stirred at 0° C. for 30 minutes, added with 3-fluorobenzenesulfonyl chloride (189 mg, 0.9 mmol), and stirred at room temperature for 2 hours. The resultant was added with an aqueous ammonium chloride solution and then extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:4 (v/v)) to obtain 310 mg of a title compound (yield: 96.2%).

$^1$H NMR (500 MHz, CDCl$_3$): 8.16 (s, 1H), 7.65 (d, 1H), 7.54 (dd, 2H), 7.44-7.49 (m, 1H), 7.38 (t, 2H), 7.28 (d, 1H), 4.48 (s, 2H), 2.70-2.78 (m, 3H), 1.47 (s, 9H)

Step 3: Preparation of tert-butyl ((6-((2-fluoro-4-methylphenyl)amino)-1-((3-fluorophenyl)sulfonyl)-1H-indol-3-yl)methyl)(methyl)carbamate Tert-butyl ((6-bromo-1-((3-fluorophenyl)sulfonyl)-1H-indol-3-yl)methyl)(methyl)carbamate (30 mg, 0.06 mmole); tris(dibenzylideneacetone)dipalladium(0) (3.5 mg, 0.006 mmole); tri-tert-butylphosphine, 50% solution in toluene (2.3 µl, 0.009 mmole); 4,5-Bis(diphenylphosphino)-9,9-dime; and 2-fluoro-4-methylaniline (11 mg, 0.09 mmole) were suspended in 1 ml of toluene solution, and stirred at 110° C. for 24 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 12 mg of a title compound (yield: 36.8%).

$^1$H NMR (300 MHz, CDCl$_3$): 7.61 (d, 2H), 7.55 (dd, 1H), 7.43-7.48 (m, 2H), 7.26-7.31 (m, 2H), 7.16 (t, 1H), 6.88-6.97 (m, 3H), 4.47 (s, 2H), 2.73-2.75 (m, 3H), 2.33 (s, 3H), 1.47 (s, 9H)

Step 4: Preparation of N-(2-fluoro-4-methylphenyl)-1-((3-fluorophenyl)sulfonyl)-3-((methylamino)methyl)-1H-indol-6-amine hydrochloride Tert-butyl ((6-((2-fluoro-4-methylphenyl)amino)-1-((3-fluorophenyl)sulfonyl)-1H-indol-3-yl)methyl)(methyl)carbamate (10 mg, 0.02 mmole) was added with 1 ml of 1.25 M HCl-methanol solution and stirred at room temperature for 15 hours. The reaction mixture was concentrated under reduced pressure, and the resulting residue was recrystallized with diethyl ether to obtain 6 mg of a title compound (yield: 63%).

$^1$H NMR (500 MHz, CD$_3$OD): 7.75 (s, 2H), 7.53-7.69 (m, 2H), 7.47 (d, 1H), 7.44-7.46 (m, 2H), 7.29 (s, 1H), 7.15 (d, 1H), 7.09 (d, 1H), 7.02 (dd, 1H), 4.30 (s, 2H), 2.73 (s, 3H), 2.33 (s, 3H)

In Examples 137 through 145 below, compounds were prepared in the same manner as in Example 136 except that reactants were appropriately changed as necessary depending on the structures of the compounds to be prepared and in consideration of Reaction Scheme 2.

Example 137: Preparation of N-(2-chloro-4-methylphenyl)-1-((3-fluorophenyl)sulfonyl)-3-((methylamino)methyl)-1H-indol-6-amine hydrochloride

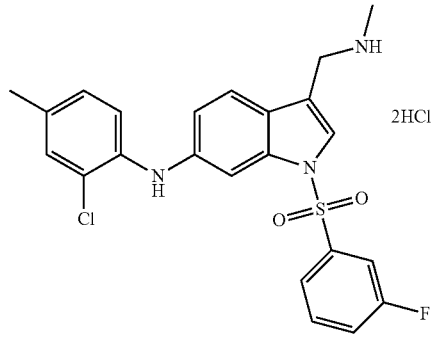 [SMILES: CNCc1cn(S(=O)(=O)c2cccc(F)c2)c2cc(Nc3ccc(C)cc3Cl)ccc12]

$^1$H NMR (500 MHz, CD$_3$OD): 7.72-7.75 (m, 2H), 7.64-7.69 (m, 1H), 7.58-7.62 (m, 1H), 7.54 (d, 1H), 7.48 (s, 1H), 7.44 (td, 1H), 7.29 (s, 1H), 7.15 (d, 1H), 7.09 (d, 1H), 7.03 (dd, 1H), 4.30 (s, 2H), 2.72 (s, 3H), 2.33 (s, 3H)

Example 138: Preparation of N-(4-fluoro-2-methylphenyl)-1-((3-fluorophenyl)sulfonyl)-3-((methylamino)methyl)-1H-indol-6-amine hydrochloride

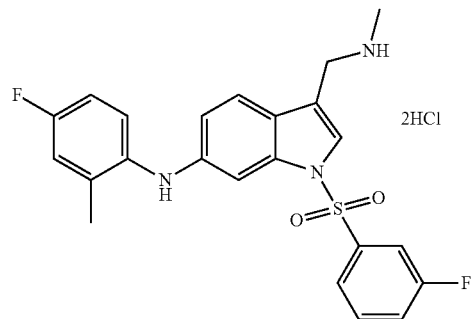 [SMILES: CNCc1cn(S(=O)(=O)c2cccc(F)c2)c2cc(Nc3ccc(F)cc3C)ccc12]

$^1$H NMR (500 MHz, CD$_3$OD): 7.70 (s, 1H), 7.67 (d, 1H), 7.53-7.60 (m, 2H), 7.48 (d, 1H), 7.43-7.45 (m, 1H), 7.12-7.14 (m, 2H), 7.07 (dd, 1H), 7.97 (td, 1H), 6.84 (dd, 1H), 4.28 (s, 2H), 2.72 (s, 3H), 2.17 (s, 3H)

Example 139: Preparation of N-(2-fluoro-4-methoxyphenyl)-1-((3-fluorophenyl)sulfonyl)-3-((methylamino)methyl)-1H-indol-6-amine hydrochloride

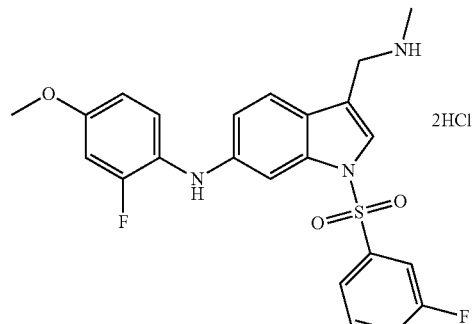

$^1$H NMR (500 MHz, CD$_3$OD): 7.67-7.69 (m, 2H), 7.56-7.60 (m, 2H), 7.47 (d, 1H), 7.43 (td, 1H), 7.26 (s, 1H), 7.19 (t, 1H), 6.88 (dd, 1H), 6.84 (dd, 1H), 6.79 (d, 1H), 4.27 (s, 2H), 3.83 (s, 3H), 2.71 (s, 3H)

Example 140: Preparation of 1-((3-fluorophenyl)sulfonyl)-N-(2-methyl-4-(trifluoromethoxy)phenyl)-3-((methylamino)methyl)-1H-indol-6-amine hydrochloride

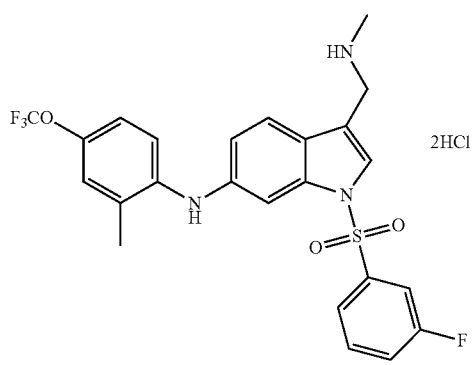 [SMILES: CNCc1cn(S(=O)(=O)c2cccc(F)c2)c2cc(Nc3ccc(OC(F)(F)F)cc3C)ccc12]

$^1$H NMR (500 MHz, CD$_3$OD): 7.74 (s, 1H), 7.69 (d, 1H), 7.57-7.61 (m, 2H), 7.53 (d, 1H), 7.45 (td, 1H), 7.34 (d, 1H), 7.16-7.18 (m, 2H), 7.08 (d, 1H), 6.97 (dd, 1H), 4.30 (s, 3H), 2.73 (s, 3H), 2.23 (s, 3H)

Example 141: Preparation of N-(6-chloro-2-methoxypyridin-3-yl)-1-((3-fluorophenyl)sulfonyl)-3-((methylamino)methyl)-1H-indol-6-amine hydrochloride

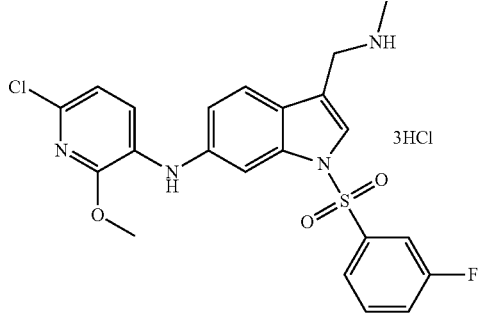

$^1$H NMR (500 MHz, CD$_3$OD): 7.82 (s, 1H), 7.79 (d, 1H), 7.71 (d, 1H), 7.70 (s, 1H), 7.58-7.63 (m, 2H), 7.00-7.46 (m, 1H), 7.16 (d, 1H), 7.14 (d, 1H), 6.88 (d, 1H), 4.32 (s, 2H), 4.00 (s, 3H), 2.73 (s, 3H)

Example 142: Preparation of N-(2,6-dichloropyridin-3-yl)-1-((3-fluorophenyl)sulfonyl)-3-((methylamino)methyl)-1H-indol-6-amine hydrochloride

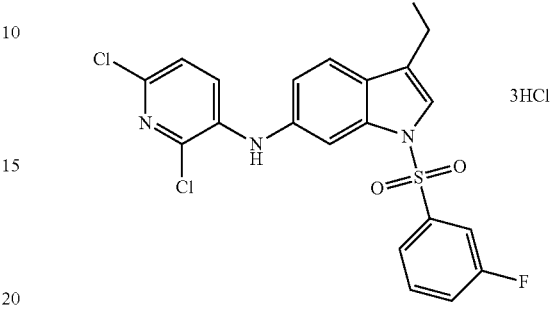

$^1$H NMR (500 MHz, CD$_3$OD): 7.87 (s, 1H), 7.82 (d, 1H), 7.75 (s, 1H), 7.67 (d, 1H), 7.61-7.62 (m, 1H), 7.50 (d, 1H), 7.46 (td, 1H), 7.26 (d, 1H), 7.17 (d, 1H), 7.10 (d, 1H), 4.33 (s, 2H), 2.74 (s, 3H)

Example 143: Preparation of N-(6-chloro-2-(trifluoromethyl)pyridin-3-yl)-1-((3-fluorophenyl)sulfonyl)-3-((methylamino)methyl)-1H-indol-6-amine hydrochloride

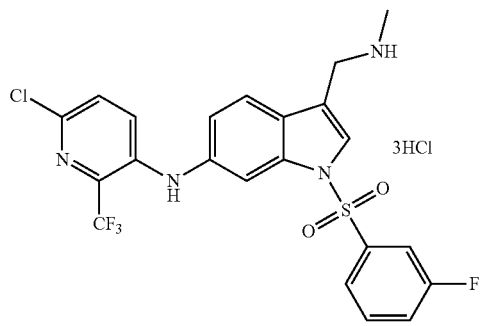 [SMILES: CNCc1cn(S(=O)(=O)c2cccc(F)c2)c2cc(Nc3ccc(Cl)nc3OC)ccc12]

$^1$H NMR (500 MHz, CD$_3$OD): 7.98 (s, 1H), 7.92 (s, 1H), 7.86 (d, 1H), 7.78-7.80 (m, 1H), 7.77 (d, 1H), 7.62 (q, 1H), 7.53 (d, 1H), 7.43-7.48 (m, 2H), 7.31 (dd, 1H), 4.37 (s, 2H), 2.75 (s, 3H)

Example 144: Preparation of N-(2-chloro-6-methoxypyridin-3-yl)-1-((3-fluorophenyl)sulfonyl)-3-((methylamino)methyl)-1H-indol-6-amine hydrochloride

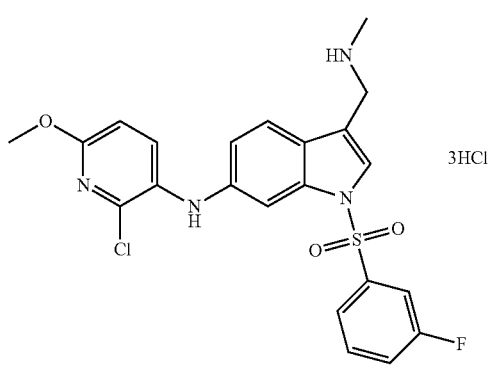 [SMILES: CNCc1cn(S(=O)(=O)c2cccc(F)c2)c2cc(Nc3ccc(OC)nc3Cl)ccc12]

$^1$H NMR (500 MHz, CD$_3$OD): 7.70-7.73 (m, 2H), 7.58-7.65 (m, 3H), 7.52 (d, 1H), 7.44 (td, 1H), 7.31 (d, 1H), 6.90 (dd, 1H), 6.80 (d, 1H), 4.29 (s, 2H), 3.93 (s, 3H), 2.72 (s, 3H)

Example 145: Preparation of N-(2-chloro-6-(trifluoromethyl)pyridin-3-yl)-1-((3-fluorophenyl)sulfonyl)-3-((methylamino)methyl)-1H-indol-6-amine hydrochloride

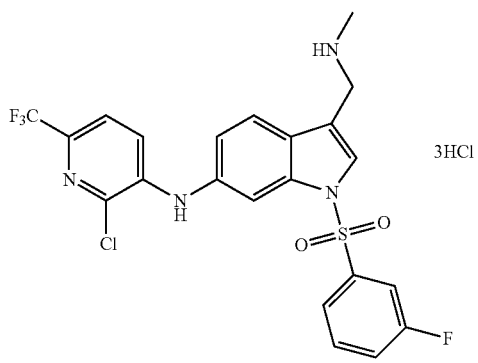 [SMILES: CNCc1cn(S(=O)(=O)c2cccc(F)c2)c2cc(Nc3ccc(C(F)(F)F)nc3Cl)ccc12]

$^1$H NMR (500 MHz, CD$_3$OD): 7.93 (d, 2H), 7.84 (d, 1H), 7.79 (d, 1H), 7.75 (d, 1H), 7.59-7.63 (m, 1H), 7.54 (d, 1H), 7.43-7.48 (m, 2H), 7.31 (dd, 1H), 4.35 (s, 2H), 2.74 (s, 3H)

Example 146: Preparation of 1-((3-chlorophenyl)sulfonyl)-N-(2-fluoro-4-methylphenyl)-3-((methylamino)methyl)-1H-indol-6-amine hydrochloride

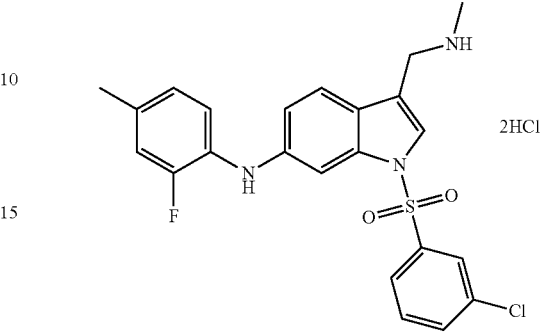

The compound was prepared in the same manner as in Example 136 except that 3-chlorobenzenesulfonyl chloride was used instead of 3-fluorobenzenesulfonyl chloride to obtain 7 mg of a title compound (yield: 73.6%).

$^1$H NMR (400 MHz, DMSO-d$_6$): 8.84 (br, 2H), 8.08 (s, 1H), 7.85-7.86 (m, 1H), 7.77-7.81 (m, 3H), 7.65 (t, 1H), 7.56 (d, 1H), 7.31-7.33 (m, 1H), 7.09-7.13 (m, 2H), 6.97 (d, 1H), 6.91 (dd, 1H), 4.18 (s, 2H), 2.63 (s, 3H), 2.32 (s, 3H)

In Examples 147 through 161 below, compounds were prepared in the same manner as in Example 146 except that reactants were appropriately changed as necessary depending on the structures of the compounds to be prepared and in consideration of Reaction Scheme 2.

Example 147: Preparation of N-(2-chloro-4-methylphenyl)-1-((3-chlorophenyl)sulfonyl)-3-((methylamino)methyl)-1H-indol-6-amine hydrochloride

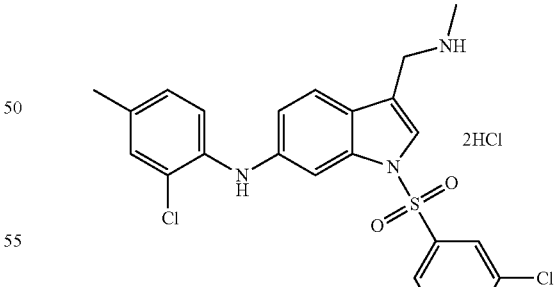

$^1$H NMR (500 MHz, CD$_3$OD): 7.90 (s, 1H), 7.83 (d, 1H), 7.72 (s, 1H), 7.69 (d, 1H), 7.53-7.56 (m, 2H), 7.48 (s, 1H), 7.30 (d, 1H), 7.16 (d, 1H), 7.11 (s, 1H), 7.03 (dd, 1H), 4.30 (s, 2H), 2.72 (s, 3H), 2.33 (s, 3H)

Example 148: Preparation of 1-((3-chlorophenyl)sulfonyl)-N-(4-methyl-2-(trifluoromethoxy)phenyl)-3-((methylamino)methyl)-1H-indol-6-amine hydrochloride

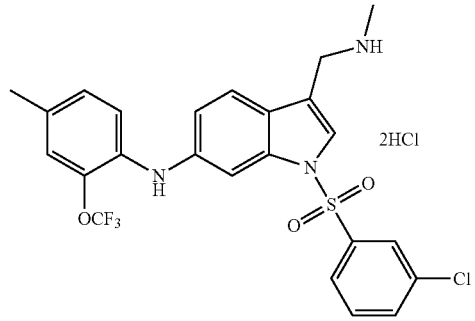 [SMILES: CNCc1cn(S(=O)(=O)c2cccc(Cl)c2)c2cc(Nc3ccc(C)cc3OC(F)(F)F)ccc12]

$^1$H NMR (500 MHz, CD$_3$OD): 7.88 (t, 1H), 7.81 (d, 1H), 7.76 (s, 1H), 7.71 (td, 1H), 7.57 (t, 2H), 7.36 (d, 1H), 7.21-7.23 (m, 2H), 7.11-7.13 (m, 1H), 6.99 (dd, 1H), 4.33 (s, 2H), 2.76 (s, 3H), 2.26 (s, 3H)

Example 149: Preparation of N-(2-chloro-4-fluorophenyl)-1-((3-chlorophenyl)sulfonyl)-3-((methylamino)methyl)-1H-indol-6-amine hydrochloride

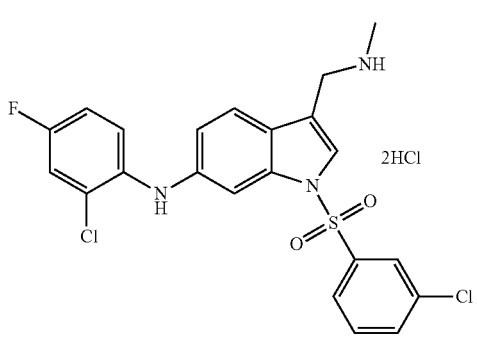 [SMILES: CNCc1cn(S(=O)(=O)c2cccc(Cl)c2)c2cc(Nc3ccc(F)cc3Cl)ccc12]

$^1$H NMR (500 MHz, CD$_3$OD): 7.92 (s, 1H), 7.86 (s, 1H), 7.78 (s, 1H), 7.71 (d, 1H), 7.56-7.59 (m, 2H), 7.47 (s, 1H), 7.35 (dd, 1H), 7.28-7.31 (m, 1H), 7.11 (td, 1H), 7.04 (d, 1H), 4.33 (s, 2H), 2.75 (s, 3H)

Example 150: Preparation of N-(4-chloro-2-fluorophenyl)-1-((3-chlorophenyl)sulfonyl)-3-((methylamino)methyl)-1H-indol-6-amine hydrochloride

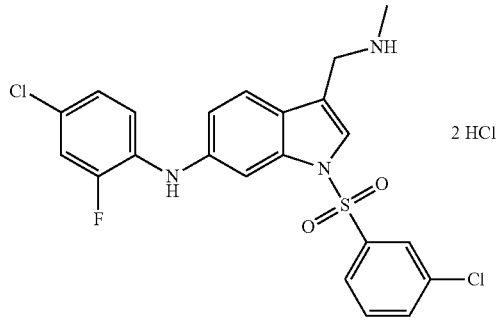 [SMILES: CNCc1cn(S(=O)(=O)c2cccc(Cl)c2)c2cc(Nc3ccc(Cl)cc3F)ccc12]

$^1$H NMR (500 MHz, CD$_3$OD): 7.89 (s, 1H), 7.82 (s, 1H), 7.74 (s, 1H), 7.68 (d, 1H), 7.52-7.55 (m, 2H), 7.43 (s, 1H), 7.31 (dd, 1H), 7.25-7.29 (m, 1H), 7.08 (td, 1H), 7.00 (d, 1H), 4.32 (s, 2H), 2.73 (s, 3H)

Example 151: Preparation of N-(4-chloro-2-(trifluoromethyl)phenyl)-1-((3-chlorophenyl)sulfonyl)-3-((methylamino)methyl)-1H-indol-6-amine hydrochloride

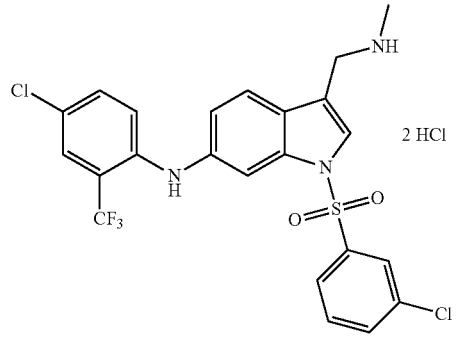 [SMILES: CNCc1cn(S(=O)(=O)c2cccc(Cl)c2)c2cc(Nc3ccc(Cl)cc3C(F)(F)F)ccc12]

$^1$H NMR (500 MHz, CD$_3$OD): 7.90 (s, 1H), 7.85 (d, 1H), 7.80 (s, 1H), 7.66 (d, 1H), 7.65 (s, 1H), 7.60-7.62 (m, 2H), 7.55 (t, 1H), 7.51 (d, 1H), 7.24 (d, 1H), 7.09 (dd, 1H), 4.32 (s, 2H), 2.73 (s, 3H)

Example 152: Preparation of N-(2-chloro-4-(trifluoromethyl)phenyl)-1-((3-chlorophenyl)sulfonyl)-3-((methylamino)methyl)-1H-indol-6-amine hydrochloride

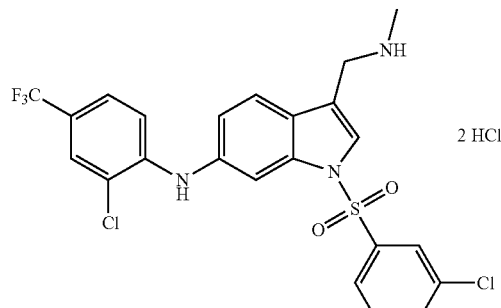

2 HCl

¹H NMR (500 MHz, CD₃OD): 7.92 (s, 1H), 7.87 (d, 1H), 7.84 (s, 1H), 7.68 (d, 1H), 7.66 (s, 1H), 7.61-7.64 (m, 2H), 7.56 (t, 1H), 7.50 (d, 1H), 7.28 (d, 1H), 7.12 (dd, 1H), 4.34 (s, 2H), 2.76 (s, 3H)

Example 153: Preparation of 1-((3-chlorophenyl)sulfonyl)-N-(2-fluoro-4-methoxyphenyl)-3-((methylamino)methyl)-1H-indol-6-amine hydrochloride

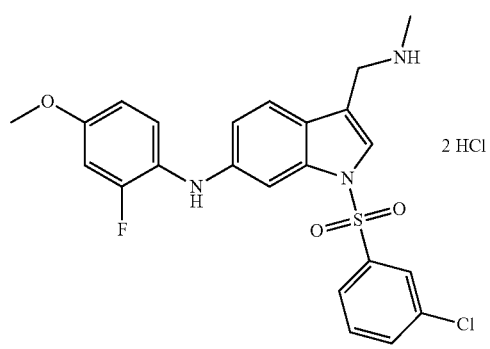 [SMILES: CNCc1cn(S(=O)(=O)c2cccc(Cl)c2)c2cc(Nc3ccc(OC)cc3F)ccc12]

2 HCl

¹H NMR (500 MHz, CD₃OD): 7.85 (t, 1H), 7.78 (d, 1H), 7.67-7.68 (m, 2H), 7.53 (t, 1H), 7.47 (s, 1H), 7.27 (s, 1H), 7.20 (t, 2H), 6.84-6.90 (m, 2H), 6.80 (dd, 1H), 4.30 (s, 2H), 3.97 (s, 3H), 2.73 (s, 3H)

Example 154: Preparation of 1-((3-chlorophenyl)sulfonyl)-N-(2-methyl-4-(trifluoromethoxy)phenyl)-3-((methylamino)methyl)-1H-indol-6-amine hydrochloride

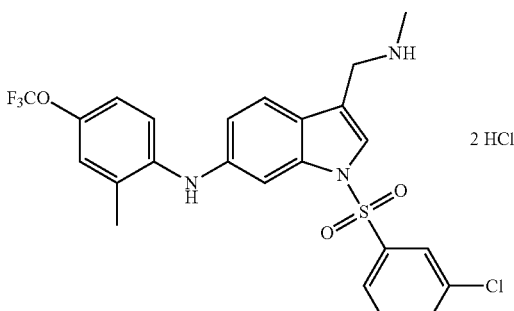

2 HCl

¹H NMR (500 MHz, CD₃OD): 7.84 (d, 1H), 7.78 (d, 1H), 7.73 (s, 1H), 7.69 (d, 1H), 7.52-7.55 (m, 2H), 7.33 (s, 1H), 7.21 (d, 2H), 7.09 (d, 1H), 6.97 (dd, 1H), 4.30 (s, 2H), 2.73 (s, 3H), 2.23 (s, 3H)

Example 155: Preparation of 1-((3-chlorophenyl)sulfonyl)-N-(2-fluoro-4-(trifluoromethoxy)phenyl)-3-((methylamino)methyl)-1H-indol-6-amine hydrochloride 2 HCl ¹H NMR (500 MHz, CD₃OD): 7.90 (d, 1H), 7.82 (d, 1H), 7.77 (s, 1H), 7.73 (d, 1H), 7.55-7.60 (m, 2H), 7.35 (s, 1H), 7.26 (d, 2H), 7.13 (d, 1H), 6.99 (dd, 1H), 4.33 (s, 2H), 2.75 (s, 3H)

Example 156: Preparation of 1-((3-chlorophenyl)sulfonyl)-N-(2,3-difluoro-4-methylphenyl)-3-((methylamino)methyl)-1H-indol-6-amine hydrochloride

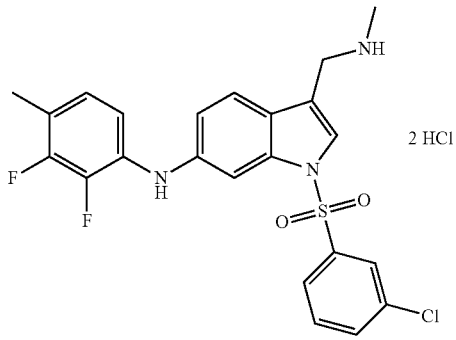 [SMILES: CNCc1cn(S(=O)(=O)c2cccc(Cl)c2)c2cc(Nc3ccc(C)c(F)c3F)ccc12]

¹H NMR (500 MHz, CD₃OD): 7.90 (d, 1H), 7.85 (dd, 1H), 7.78 (s, 1H), 7.69 (dd, 1H), 7.53-7.57 (m, 3H), 7.05 (d, 1H), 6.93-6.99 (m, 2H), 4.31 (s, 2H), 2.72 (s, 3H), 2.29 (s, 3H)

Example 157: Preparation of 1-((3-chlorophenyl)sulfonyl)-N-(2-methoxypyridin-3-yl)-3-((methylamino)methyl)-1H-indol-6-amine hydrochloride

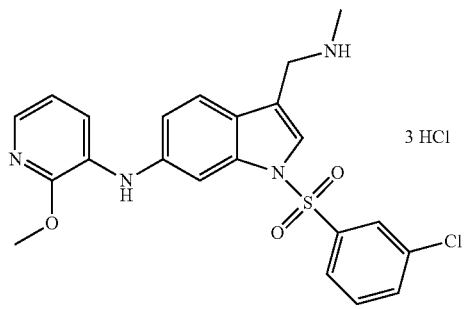 [SMILES: CNCc1cn(S(=O)(=O)c2cccc(Cl)c2)c2cc(Nc3cccnc3OC)ccc12]

¹H NMR (500 MHz, CD₃OD): 8.02 (s, 1H), 7.95 (d, 1H), 7.71-7.75 (m, 2H), 7.64 (t, 1H), 7.53 (s, 1H), 7.31 (s, 1H), 7.25 (t, 2H), 6.89-6.95 (m, 1H), 6.84 (dd, 1H), 4.33 (s, 2H), 3.99 (s, 3H), 2.75 (s, 3H)

Example 158: Preparation of 1-((3-chlorophenyl)sulfonyl)-N-(2-fluoro-6-methylpyridin-3-yl)-3-((methylamino)methyl)-1H-indol-6-amine hydrochloride

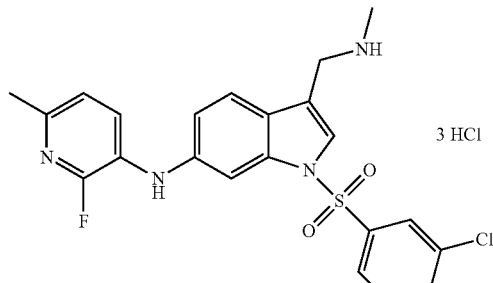

¹H NMR (500 MHz, CD₃OD): 7.88 (d, 1H), 7.82 (dd, 1H), 7.74 (s, 1H), 7.66 (dd, 1H), 7.50-7.54 (m, 3H), 7.01 (d, 1H), 6.89-6.95 (m, 2H), 4.33 (s, 2H), 2.73 (s, 3H), 2.25 (s, 3H)

Example 159: Preparation of 1-((3-chlorophenyl)sulfonyl)-N-(2,6-dichloropyridin-3-yl)-3-((methylamino)methyl)-1H-indol-6-amine hydrochloride

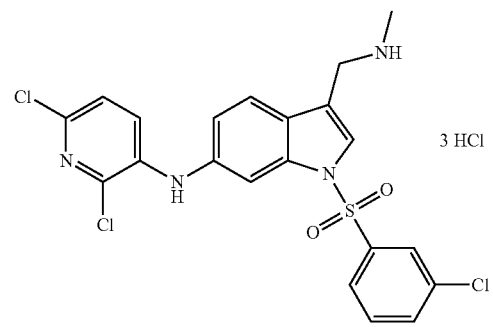 [SMILES: CNCc1cn(S(=O)(=O)c2cccc(Cl)c2)c2cc(Nc3ccc(Cl)nc3Cl)ccc12]

¹H NMR (500 MHz, CD₃OD): 7.97 (s, 1H), 7.88-7.95 (m, 2H), 7.75 (s, 1H), 7.67-7.70 (m, 2H), 7.56 (t, 1H), 7.51 (d, 1H), 7.26 (d, 1H), 7.19 (dd, 1H), 4.34 (s, 2H), 2.74 (s, 3H)

Example 160: Preparation of N-(2-chloro-6-methoxypyridin-3-yl)-1-((3-chlorophenyl)sulfonyl)-3-((methylamino)methyl)-1H-indol-6-amine hydrochloride

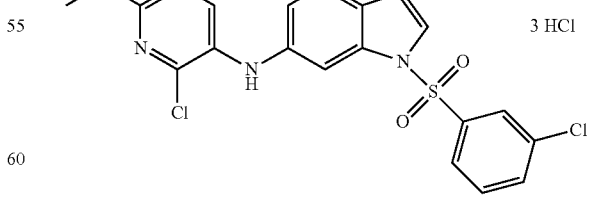

¹H NMR (500 MHz, CD₃OD): 8.82 (br, 2H), 8.00 (s, 1H), 7.83-7.89 (m, 2H), 7.80 (d, 1H), 7.64-7.68 (m, 2H), 7.58 (d, 1H), 7.25 (s, 1H), 6.91 (d, 1H), 6.84 (d, 1H), 4.19 (s, 2H), 3.86 (s, 3H), 2.62 (s, 3H)

Example 161: Preparation of N-(2-chloro-6-(trifluoromethyl)pyridin-3-yl)-1-((3-chlorophenyl)sulfonyl)-3-((methylamino)methyl)-1H-indol-6-amine hydrochloride

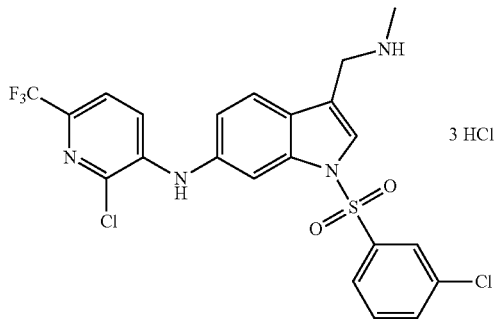 [SMILES: CNCc1cn(S(=O)(=O)c2cccc(Cl)c2)c2cc(Nc3ccc(C(F)(F)F)nc3Cl)ccc12]

¹H NMR (500 MHz, CD₃OD): 7.91-8.05 (m, 4H), 7.76 (d, 1H), 7.70 (dd, 1H), 7.55 (q, 2H), 7.43 (d, 1H), 7.31 (dd, 1H), 4.37 (s, 2H), 2.75 (s, 3H)

Example 162: Preparation of N-(2-fluoro-4-methylphenyl)-1-((3-methoxyphenyl)sulfonyl)-3-((methylamino)methyl)-1H-indol-6-amine hydrochloride

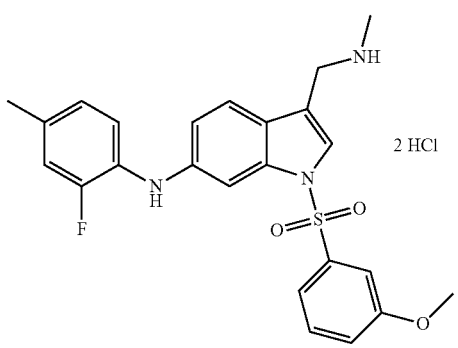

The compound was prepared in the same manner as in Example 136 except that 3-methoxybenzenesulfonyl chloride was used instead of 3-fluorobenzenesulfonyl chloride to obtain 5 mg of a title compound (yield: 52.6%).

¹H NMR (500 MHz, CD₃OD): 7.70 (s, 1H), 7.50 (d, 2H), 7.44 (d, 2H), 7.36 (s, 1H), 7.20 (d, 1H), 7.15 (t, 1H), 7.01 (d, 1H), 6.95-6.98 (m, 2H), 4.28 (s, 2H), 3.77 (s, 3H), 2.71 (s, 3H), 2.35 (s, 3H)

In Examples 163 through 173 below, compounds were prepared in the same manner as in Example 162 except that reactants were appropriately changed as necessary depending on the structures of the compounds to be prepared and in consideration of Reaction Scheme 2.

Example 163: Preparation of N-(2-chloro-4-methylphenyl)-1-((3-methoxyphenyl)sulfonyl)-3-((methylamino)methyl)-1H-indol-6-amine hydrochloride

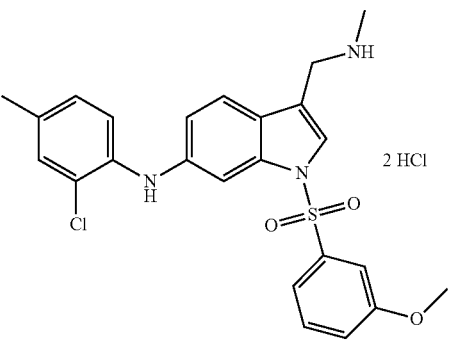

¹H NMR (500 MHz, CD₃OD): 7.75 (s, 1H), 7.52 (d, 2H), 7.42-7.47 (m, 2H), 7.37 (d, 1H), 7.28 (d, 1H), 7.21 (dd, 1H), 7.14 (d, 1H), 7.07-7.15 (m, 1H), 7.02 (d, 1H), 4.29 (s, 2H), 3.78 (s, 3H), 2.71 (s, 3H), 2.33 (s, 3H)

Example 164: Preparation of N-(4-chloro-2-fluorophenyl)-1-((3-methoxyphenyl)sulfonyl)-3-((methylamino)methyl)-1H-indol-6-amine hydrochloride

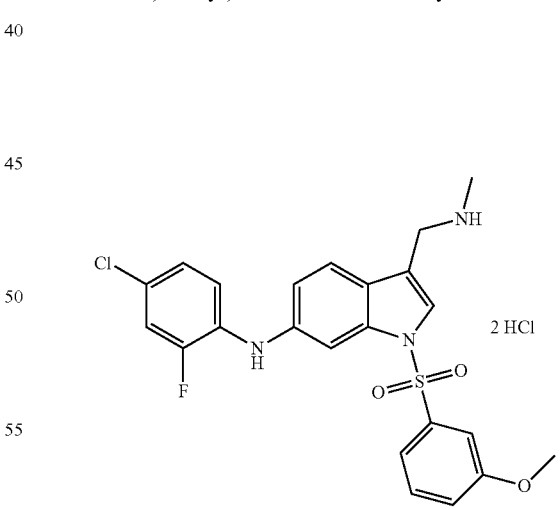

¹H NMR (500 MHz, CD₃OD): 7.80 (s, 1H), 7.62 (d, 1H), 7.59 (d, 1H), 7.48-7.49 (m, 2H), 7.42 (t, 1H), 7.21-7.28 (m, 3H), 7.14 (td, 1H), 7.08 (dd, 1H), 4.32 (s, 2H), 3.82 (s, 3H), 2.74 (s, 3H)

Example 165: Preparation of N-(4-chloro-2-(trifluoromethyl)phenyl)-1-((3-methoxyphenyl)sulfonyl)-3-((methylamino)methyl)-1H-indol-6-amine hydrochloride

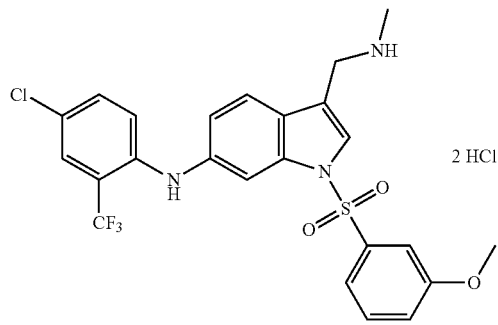 [SMILES: CNCc1cn(S(=O)(=O)c2cccc(OC)c2)c2cc(Nc3ccc(Cl)cc3C(F)(F)F)ccc12]

¹H NMR (500 MHz, CD₃OD): 7.78 (s, 1H), 7.64 (dd, 2H), 7.59 (d, 1H), 7.43-7.51 (m, 3H), 7.38 (s, 1H), 7.18-7.23 (m, 2H), 7.07 (dd, 1H), 4.60 (s, 3H), 3.79 (s, 3H), 2.68 (s, 3H)

Example 166: Preparation of N-(2-chloro-4-(trifluoromethyl)phenyl)-1-((3-methoxyphenyl)sulfonyl)-3-((methylamino)methyl)-1H-indol-6-amine hydrochloride

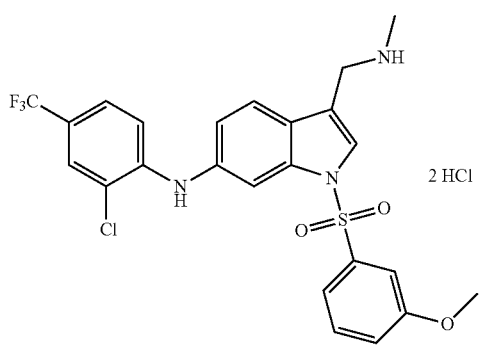 [SMILES: CNCc1cn(S(=O)(=O)c2cccc(OC)c2)c2cc(Nc3ccc(C(F)(F)F)cc3Cl)ccc12]

¹H NMR (500 MHz, CD₃OD): 7.93 (s, 1H), 7.88 (d, 1H), 7.73 (d, 1H), 7.70 (d, 1H), 7.47-7.54 (m, 3H), 7.42 (dd, 1H), 7.25-7.28 (m, 2H), 7.14 (d, 1H), 4.37 (s, 2H), 3.82 (s, 3H), 2.76 (s, 3H)

Example 167: Preparation of N-(2-fluoro-4-methoxyphenyl)-1-((3-methoxyphenyl)sulfonyl)-3-((methylamino)methyl)-1H-indol-6-amine hydrochloride ¹H NMR (500 MHz, CD₃OD): 7.70 (s, 1H), 7.41-7.50 (m, 3H), 7.36 (t, 1H), 7.34 (s, 1H), 7.20-7.24 (m, 2H), 6.90 (dd, 1H), 6.87 (dd, 1H), 6.81 (dd, 1H), 4.30 (s, 2H), 3.86 (s, 3H), 3.80 (s, 3H), 2.73 (s, 3H)

Example 168: Preparation of 1-((3-methoxyphenyl)sulfonyl)-N-(2-methyl-4-(trifluoromethoxy)phenyl)-3-((methylamino)methyl)-1H-indol-6-amine hydrochloride

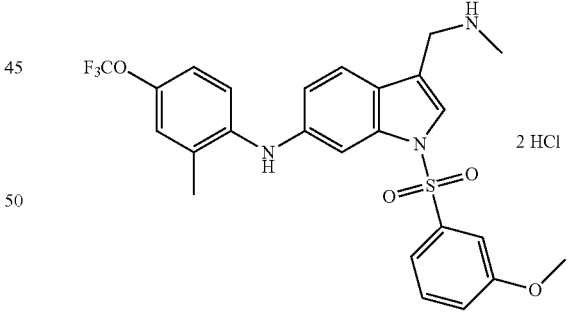

¹H NMR (500 MHz, CD₃OD): 7.75 (s, 1H), 7.55 (d, 1H), 7.42 (t, 1H), 7.36-7.39 (m, 1H), 7.34 (s, 1H), 7.33 (d, 1H), 7.2 (dd, 1H), 7.17 (d, 2H), 7.07 (d, 1H), 6.96 (dd, 1H), 4.30 (s, 2H), 3.78 (s, 3H), 2.72 (s, 3H), 2.22 (s, 3H)

Example 169: Preparation of N-(2-chloro-4-(trifluoromethoxy)phenyl)-1-((3-methoxyphenyl)sulfonyl)-3-((methylamino)methyl)-1H-indol-6-amine hydrochloride

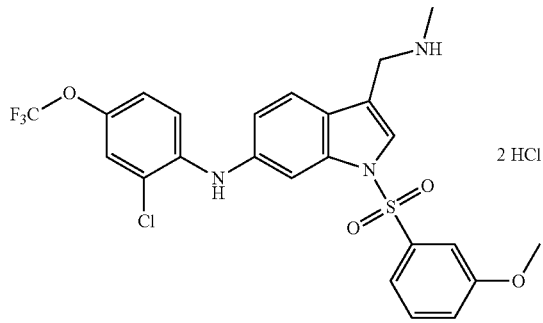 [SMILES: CNCc1cn(S(=O)(=O)c2cccc(OC)c2)c2cc(Nc3ccc(OC(F)(F)F)cc3Cl)ccc12]

¹H NMR (500 MHz, CD₃OD): 7.84 (s, 1H), 7.69 (d, 1H), 7.63 (d, 1H), 7.44-7.49 (m, 2H), 7.40-7.41 (m, 2H), 7.19-7.23 (m, 2H), 7.12-7.15 (m, 2H), 4.33 (s, 2H), 3.79 (s, 3H), 2.73 (s, 3H)

Example 170: Preparation of N-(2,3-difluoro-4-methylphenyl)-1-((3-methoxyphenyl)sulfonyl)-3-((methylamino)methyl)-1H-indol-6-amine hydrochloride

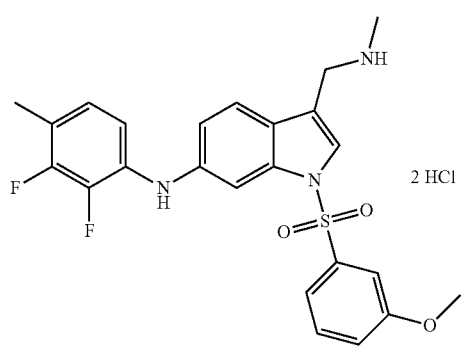

¹H NMR (500 MHz, CD₃OD): 7.77 (s, 1H), 7.59 (d, 1H), 7.57 (d, 1H), 7.48-7.49 (m, 2H), 7.40 (t, 1H), 7.23-7.25 (m, 1H), 7.05 (dd, 1H), 6.97 (t, 2H), 4.32 (s, 2H), 3.81 (s, 3H), 2.74 (s, 3H), 2.31 (s, 3H)

Example 171: Preparation of N-(2-fluoro-6-methylpyridin-3-yl)-1-((3-methoxyphenyl)sulfonyl)-3-((methylamino)methyl)-1H-indol-6-amine hydrochloride

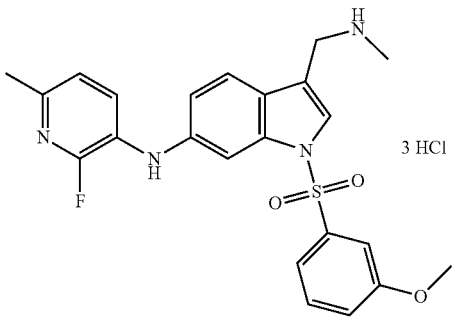

¹H NMR (500 MHz, CD₃OD): 7.80 (s, 1H), 7.58-7.59 (m, 3H), 7.46 (d, 2H), 7.39 (s, 1H), 7.21-7.22 (m, 1H), 7.10 (d, 1H), 7.05 (dd, 1H), 4.32 (s, 2H), 3.79 (s, 3H), 2.72 (s, 3H), 2.43 (s, 3H)

Example 172: Preparation of N-(2-chloro-6-methylpyridin-3-yl)-1-((3-methoxyphenyl)sulfonyl)-3-((methylamino)methyl)-1H-indol-6-amine hydrochloride

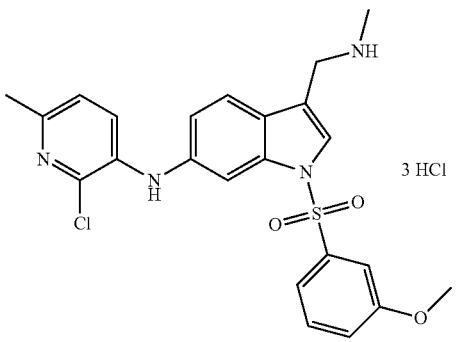

¹H NMR (500 MHz, CD₃OD): 8.18 (d, 1H), 7.89 (s, 1H), 7.83 (d, 1H), 7.72 (d, 1H), 7.66 (d, 1H), 7.58 (d, 1H), 7.51 (s, 1H), 7.43-7.44 (m, 1H), 7.25 (d, 1H), 7.10 (d, 1H), 4.38 (s, 2H), 3.82 (s, 3H), 2.81 (s, 3H), 2.77 (s, 3H)

Example 173: Preparation of N-(2-chloro-6-methoxypyridin-3-yl)-1-((3-methoxyphenyl)sulfonyl)-3-((methylamino)methyl)-1H-indol-6-amine hydrochloride

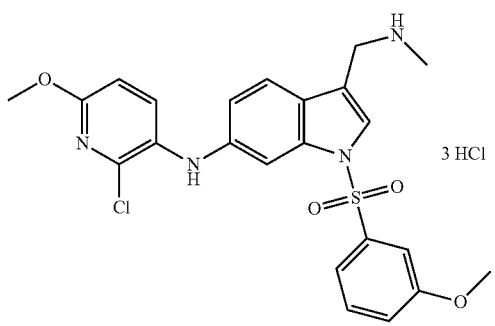

$^1$H NMR (500 MHz, CD$_3$OD): 7.75 (s, 1H), 7.61 (d, 1H), 7.52 (d, 1H), 7.40-7.46 (m, 2H), 7.35 (d, 1H), 7.33 (d, 1H), 7.20 (dd, 1H), 6.91 (dd, 1H), 6.80 (d, 1H), 4.30 (s, 2H), 3.92 (s, 3H), 3.80 (s, 3H), 2.71 (s, 3H)

Example 174: Preparation of 1-((3-(difluoromethoxy)phenyl)sulfonyl)-N-(2-fluoro-4-methylphenyl)-3-((methylamino)methyl)-1H-indol-6-amine hydrochloride

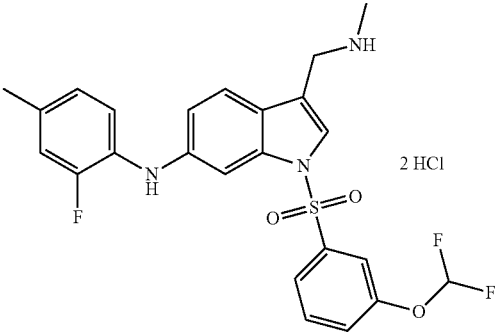 [SMILES: CNCc1cn(S(=O)(=O)c2cccc(OC(F)F)c2)c2cc(Nc3ccc(C)cc3F)ccc12]

The compound was prepared in the same manner as in Example 136 except that 3-(difluoromethoxy)benzenesulfonyl chloride was used instead of 3-fluorobenzenesulfonyl chloride to obtain 6.5 mg of a title compound (yield: 68.4%).
$^1$H NMR (500 MHz, CD$_3$OD): 7.75 (d, 1H), 7.70 (s, 1H), 7.58-7.61 (m, 2H), 7.50 (d, 1H), 7.44-7.46 (m, 2H), 7.16 (t, 1H), 7.02 (d, 1H), 6.98 (d, 2H), 4.28 (s, 2H), 2.71 (s, 3H), 2.35 (s, 3H)

In Examples 175 through 182 below, compounds were prepared in the same manner as in Example 174 except that reactants were appropriately changed as necessary depending on the structures of the compounds to be prepared and in consideration of Reaction Scheme 2.

Example 175: Preparation of N-(2-chloro-4-methylphenyl)-1-((3-(difluoromethoxy)phenyl)sulfonyl)-3-((methylamino)methyl)-1H-indol-6-amine hydrochloride

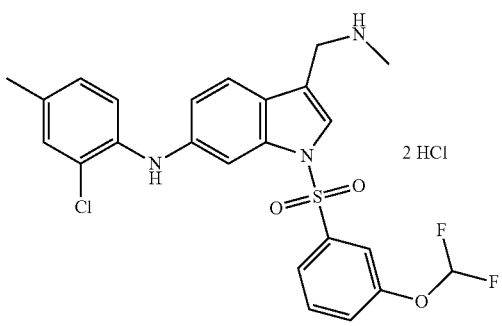 [SMILES: CNCc1cn(S(=O)(=O)c2cccc(OC(F)F)c2)c2cc(Nc3ccc(C)cc3Cl)ccc12]

$^1$H NMR (500 MHz, CD$_3$OD): 7.75-7.79 (d, 2H), 7.65 (t, 1H), 7.63 (t, 1H), 7.56 (d, 1H), 7.53 (d, 1H), 7.48 (dd, 1H), 7.32 (s, 1H), 7.19 (d, 1H), 7.12 (dd, 1H), 7.05 (dd, 1H), 4.32 (s, 2H), 2.74 (s, 3H), 2.36 (s, 3H)

Example 176: Preparation of N-(4-chloro-2-fluorophenyl)-1-((3-(difluoromethoxy)phenyl)sulfonyl)-3-((methylamino)methyl)-1H-indol-6-amine hydrochloride

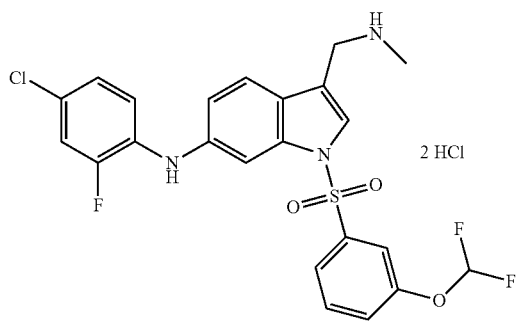 [SMILES: CNCc1cn(S(=O)(=O)c2cccc(OC(F)F)c2)c2cc(Nc3ccc(Cl)cc3F)ccc12]

$^1$H NMR (500 MHz, CD$_3$OD): 7.80-7.81 (d, 2H), 7.68 (t, 1H), 7.59-7.65 (m, 3H), 7.48 (dd, 1H), 7.24-7.29 (m, 2H), 7.16 (td, 1H), 7.09-7.11 (m, 1H), 4.33 (s, 2H), 2.74 (s, 3H)

Example 177: Preparation of N-(4-chloro-2-(trifluoromethyl)phenyl)-1-((3-(difluoromethoxy)phenyl)sulfonyl)-3-((methylamino)methyl)-1H-indol-6-amine hydrochloride

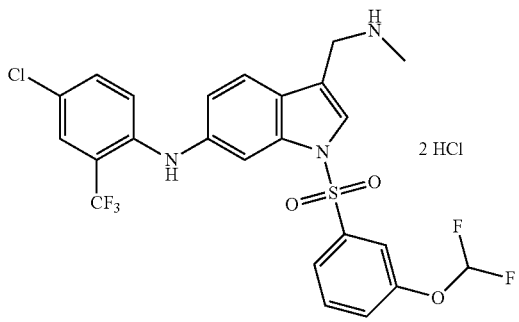 [SMILES: CNCc1cn(S(=O)(=O)c2cccc(OC(F)F)c2)c2cc(Nc3ccc(Cl)cc3C(F)(F)F)ccc12]

$^1$H NMR (500 MHz, CD$_3$OD): 7.84 (s, 1H), 7.81 (dd, 1H), 7.66-7.68 (m, 3H), 7.63 (q, 2H), 7.52 (dd, 1H), 7.49 (dd, 1H), 7.25 (d, 1H), 7.12 (dd, 1H), 4.34 (s, 2H), 2.74 (s, 3H)

Example 178: Preparation of 1-((3-(difluoromethoxy)phenyl)sulfonyl)-N-(2-fluoro-4-methoxyphenyl)-3-((methylamino)methyl)-1H-indol-6-amine hydrochloride

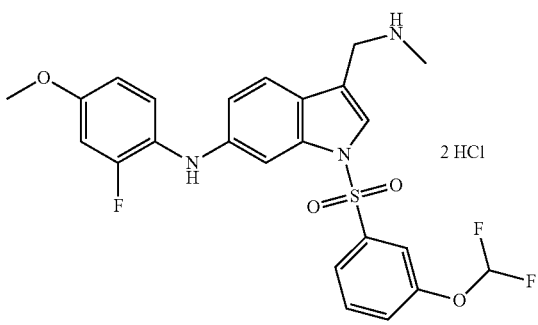 [SMILES: CNCc1cn(S(=O)(=O)c2cccc(OC(F)F)c2)c2cc(Nc3ccc(OC)cc3F)ccc12]

$^1$H NMR (500 MHz, CD$_3$OD): 7.73 (d, 1H), 7.68 (s, 1H), 7.59-7.62 (m, 2H), 7.46-7.49 (m, 2H), 7.32 (s, 1H), 7.23 (t, 1H), 6.90 (dd, 1H), 6.87 (dd, 1H), 6.82 (dd, 1H), 4.27 (s, 2H), 3.86 (s, 3H), 2.71 (s, 3H)

Example 179: Preparation of 1-((3-(difluoromethoxy)phenyl)sulfonyl)-N-(2-methyl-4-(trifluoromethoxy)phenyl)-3-((methylamino)methyl)-1H-indol-6-amine hydrochloride

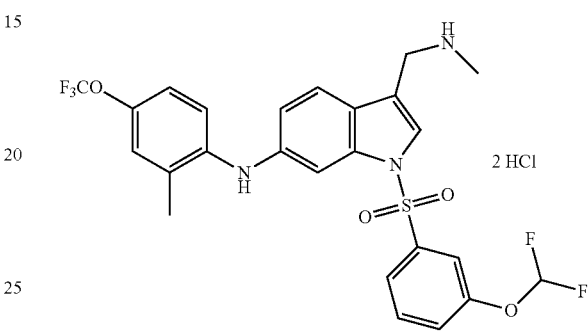

$^1$H NMR (500 MHz, CD$_3$OD): 7.78 (d, 2H), 7.62 (t, 1H), 7.59 (t, 1H), 7.51 (d, 1H), 7.48 (d, 1H), 7.45 (dd, 1H), 7.29 (s, 1H), 7.14 (d, 1H), 7.06 (dd, 1H), 7.01 (dd, 1H), 4.31 (s, 2H), 2.73 (s, 3H), 2.33 (s, 3H)

Example 180: Preparation of N-(2,3-difluoro-4-methylphenyl)-1-((3-(difluoromethoxy)phenyl)sulfonyl)-3-((methylamino)methyl)-1H-indol-6-amine hydrochloride

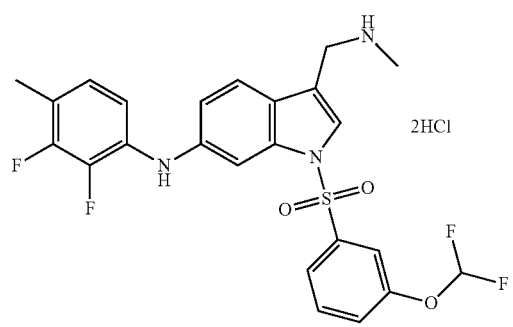 [SMILES: CNCc1cn(S(=O)(=O)c2cccc(OC(F)F)c2)c2cc(Nc3ccc(C)c(F)c3F)ccc12]

$^1$H NMR (500 MHz, CD$_3$OD): 7.78-7.80 (m, 2H), 7.67 (t, 1H), 7.63 (t, 1H), 7.57-7.58 (m, 2H), 7.48 (dd, 1H), 7.05-7.07 (m, 1H), 6.98 (t, 2H), 4.32 (s, 2H), 2.74 (s, 3H), 2.31 (s, 3H)

Example 181: Preparation of 1-((3-(difluoromethoxy)phenyl)sulfonyl)-N-(2-fluoro-6-methylpyridin-3-yl)-3-((methylamino)methyl)-1H-indol-6-amine hydrochloride

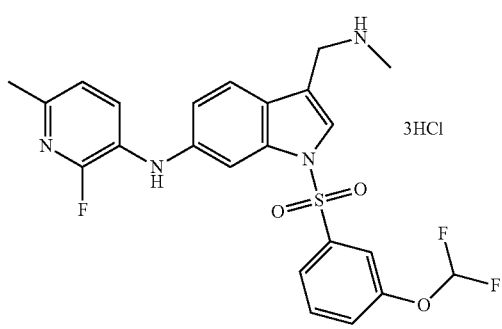 [SMILES: CNCc1cn(S(=O)(=O)c2cccc(OC(F)F)c2)c2cc(Nc3ccc(C)nc3F)ccc12]

$^1$H NMR (500 MHz, CD$_3$OD): 7.77-7.83 (m, 2H), 7.71 (t, 1H), 7.61-7.66 (m, 3H), 7.46-7.49 (m, 1H), 7.17 (dd, 1H), 7.14 (d, 1H), 7.09-7.10 (m, 1H), 4.34 (s, 2H), 2.75 (s, 3H), 2.44 (s, 3H)

Example 182: Preparation of N-(2-chloro-6-methoxypyridin-3-yl)-1-((3-(difluoromethoxy)phenyl)sulfonyl)-3-((methylamino)methyl)-1H-indol-6-amine hydrochloride

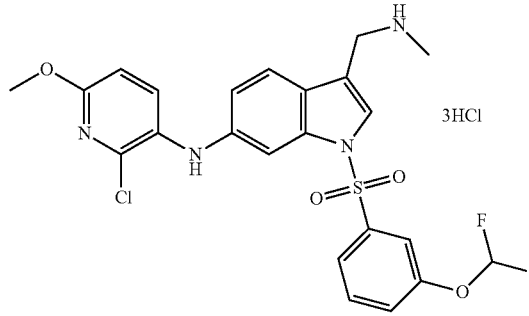

$^1$H NMR (500 MHz, CD$_3$OD): 7.75-7.77 (m, 2H), 7.64-7.65 (m, 2H), 7.61 (d, 1H), 7.55 (d, 1H), 7.47 (dd, 1H), 7.36 (d, 1H), 6.92-6.94 (m, 1H), 6.83 (d, 1H), 4.31 (s, 2H), 3.95 (s, 3H), 2.73 (s, 3H)

Example 183: Preparation of N-(2-fluoro-4-methylphenyl)-3-((methylamino)methyl)-1-((3-(trifluoromethyl)phenyl)sulfonyl)-1H-indol-6-amine hydrochloride

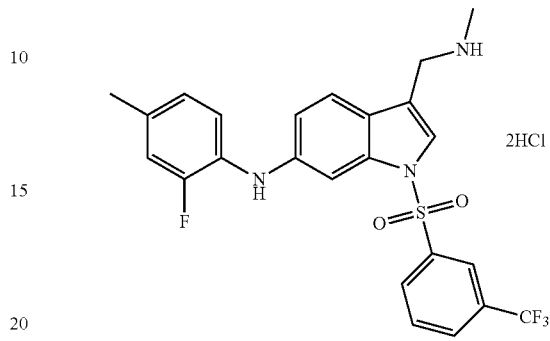

The compound was prepared in the same manner as in Example 136 except that 3-(trifluoromethyl)benzenesulfonyl chloride was used instead of 3-fluorobenzenesulfonyl chloride to obtain 7 mg of a title compound (yield: 73.3%).

$^1$H NMR (400 MHz, DMSO-d$_6$): 8.84 (br, 2H), 8.09-8.15 (m, 3H), 7.87 (t, 1H), 7.81 (s, 1H), 7.55 (d, 1H), 7.33 (s, 1H), 7.07-7.13 (m, 2H), 6.89-6.96 (m, 2H), 4.17 (s, 2H), 2.63 (d, 3H), 2.28 (s, 3H)

In Examples 184 through 195 below, compounds were prepared in the same manner as in Example 183 except that reactants were appropriately changed as necessary depending on the structures of the compounds to be prepared and in consideration of Reaction Scheme 2.

Example 184: Preparation of N-(2-chloro-4-methylphenyl)-3-((methylamino)methyl)-1-((3-(trifluoromethyl)phenyl)sulfonyl)-1H-indol-6-amine hydrochloride

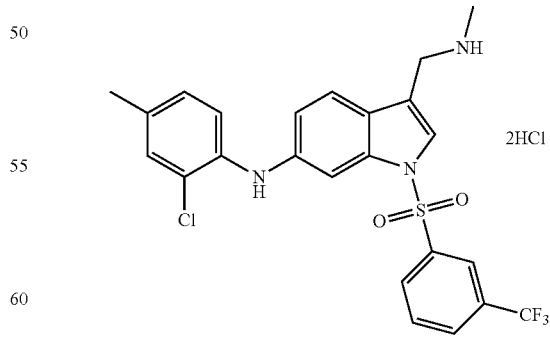

$^1$H NMR (500 MHz, CD$_3$OD): 7.89 (s, 1H), 7.81 (d, 1H), 7.70 (s, 1H), 7.67 (d, 1H), 7.51-7.55 (m, 2H), 7.45 (s, 1H), 7.29 (d, 1H), 7.14 (d, 1H), 7.08 (s, 1H), 7.01 (dd, 1H), 4.31 (s, 2H), 2.73 (s, 3H), 2.33 (s, 3H)

Example 185: Preparation of N-(4-chloro-2-fluorophenyl)-3-((methylamino)methyl)-1-((3-(trifluoromethyl)phenyl)sulfonyl)-1H-indol-6-amine hydrochloride

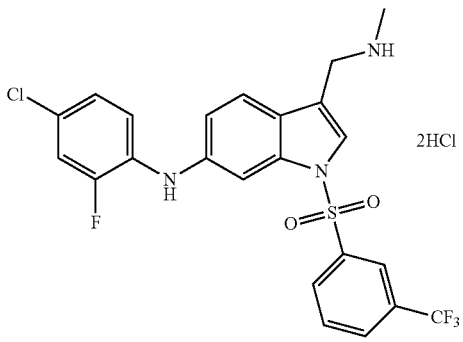 [SMILES: CNCc1cn(S(=O)(=O)c2cccc(C(F)(F)F)c2)c2cc(Nc3ccc(Cl)cc3F)ccc12]

$^1$H NMR (500 MHz, CD$_3$OD): 7.90 (s, 1H), 7.83 (s, 1H), 7.76 (s, 1H), 7.69 (d, 1H), 7.55-7.59 (m, 2H), 7.45 (s, 1H), 7.36 (dd, 1H), 7.29-7.33 (m, 1H), 7.13 (td, 1H), 7.05 (d, 1H), 4.34 (s, 2H), 2.75 (s, 3H)

Example 186: Preparation of N-(4-chloro-2-(trifluoromethyl)phenyl)-3-((methylamino)methyl)-1-((3-(trifluoromethyl)phenyl)sulfonyl)-1H-indol-6-amine hydrochloride

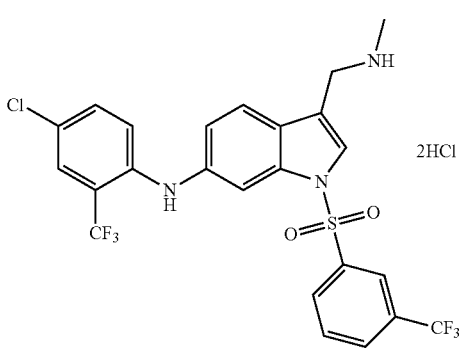 [SMILES: CNCc1cn(S(=O)(=O)c2cccc(C(F)(F)F)c2)c2cc(Nc3ccc(Cl)cc3C(F)(F)F)ccc12]

$^1$H NMR (500 MHz, CD$_3$OD): 7.89 (s, 1H), 7.85 (d, 1H), 7.80 (s, 1H), 7.66 (d, 1H), 7.65 (s, 1H), 7.60-7.62 (m, 2H), 7.55 (t, 1H), 7.51 (d, 1H), 7.24 (d, 1H), 7.09 (dd, 1H), 4.32 (s, 2H), 2.74 (s, 3H)

Example 187: Preparation of N-(2-chloro-4-(trifluoromethyl)phenyl)-3-((methylamino)methyl)-1-((3-(trifluoromethyl)phenyl)sulfonyl)-1H-indol-6-amine hydrochloride

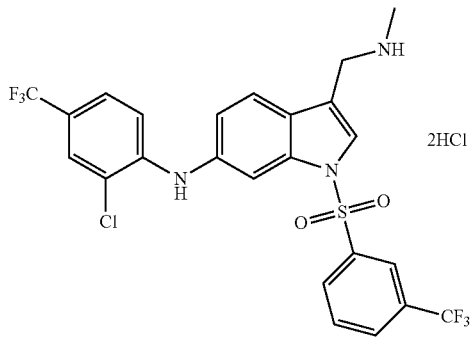 [SMILES: CNCc1cn(S(=O)(=O)c2cccc(C(F)(F)F)c2)c2cc(Nc3ccc(C(F)(F)F)cc3Cl)ccc12]

$^1$H NMR (500 MHz, CD$_3$OD): 7.93 (s, 1H), 7.87 (d, 1H), 7.84 (s, 1H), 7.68 (d, 1H), 7.66 (s, 1H), 7.61-7.64 (m, 2H), 7.56 (t, 1H), 7.50 (d, 1H), 7.28 (d, 1H), 7.12 (dd, 1H), 4.34 (s, 2H), 2.76 (s, 3H)

Example 188: Preparation of N-(2-fluoro-4-methoxyphenyl)-3-((methylamino)methyl)-1-((3-(trifluoromethyl)phenyl)sulfonyl)-1H-indol-6-amine hydrochloride

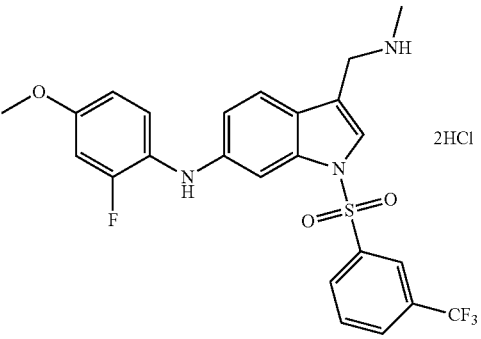 [SMILES: CNCc1cn(S(=O)(=O)c2cccc(C(F)(F)F)c2)c2cc(Nc3ccc(OC)cc3F)ccc12]

$^1$H NMR (500 MHz, CD$_3$OD): 7.88 (d, 1H), 7.78 (d, 1H), 7.67-7.68 (m, 2H), 7.52 (t, 1H), 7.46 (s, 1H), 7.27 (s, 1H), 7.20 (t, 2H), 6.81-6.88 (m, 2H), 6.80 (dd, 1H), 4.31 (s, 2H), 3.98 (s, 3H), 2.23 (s, 3H)

Example 189: Preparation of N-(2-methyl-4-(trifluoromethoxy)phenyl)-3-((methylamino)methyl)-1-((3-(trifluoromethyl)phenyl)sulfonyl)-1H-indol-6-amine hydrochloride

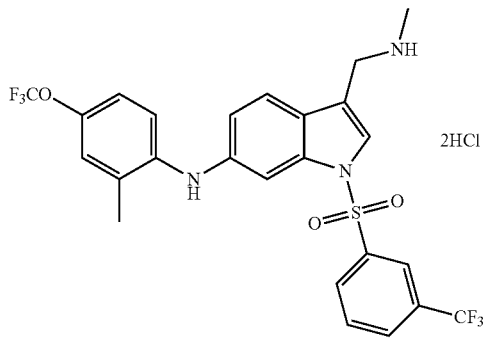 [SMILES: CNCc1cn(S(=O)(=O)c2cccc(C(F)(F)F)c2)c2cc(Nc3ccc(OC(F)(F)F)cc3C)ccc12]

$^1$H NMR (500 MHz, CD$_3$OD): 7.84 (d, 1H), 7.78 (d, 1H), 7.73 (s, 1H), 7.69 (d, 1H), 7.52-7.55 (m, 2H), 7.33 (s, 1H), 7.21 (d, 2H), 7.09 (d, 1H), 6.97 (dd, 1H), 4.30 (s, 2H), 2.73 (s, 3H), 2.23 (s, 3H)

Example 190: Preparation of N-(2-methoxy-4-(trifluoromethoxy)phenyl)-3-((methylamino)methyl)-1-((3-(trifluoromethyl)phenyl)sulfonyl)-1H-indol-6-amine hydrochloride

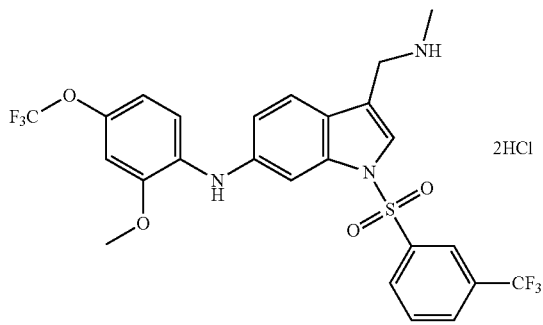 [SMILES: CNCc1cn(S(=O)(=O)c2cccc(C(F)(F)F)c2)c2cc(Nc3ccc(OC(F)(F)F)cc3OC)ccc12]

$^1$H NMR (500 MHz, CD$_3$OD): 8.20 (d, 1H), 8.17 (s, 1H), 7.99 (d, 1H), 7.80 (s, 1H), 7.78 (d, 1H), 7.68 (s, 1H), 7.56 (d, 1H), 7.21 (d, 1H), 7.12 (dd, 1H), 6.95 (s, 1H), 6.82 (d, 1H), 4.31 (s, 2H), 3.90 (s, 3H), 2.72 (s, 3H)

Example 191: Preparation of N-(2,3-difluoro-4-methylphenyl)-3-((methylamino)methyl)-1-((3-(trifluoromethyl)phenyl)sulfonyl)-1H-indol-6-amine hydrochloride

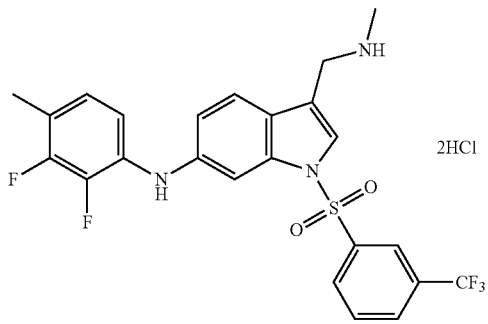 [SMILES: CNCc1cn(S(=O)(=O)c2cccc(C(F)(F)F)c2)c2cc(Nc3ccc(C)c(F)c3F)ccc12]

$^1$H NMR (500 MHz, CD$_3$OD): 8.17 (d, 1H), 8.15 (s, 1H), 7.99 (d, 1H), 7.80 (d, 1H), 7.77 (s, 1H), 7.54-7.55 (m, 2H), 7.03 (dd, 1H), 6.96 (d, 2H), 4.29 (s, 2H), 2.70 (s, 3H), 2.29 (s, 3H)

Example 192: Preparation of N-(2-chloro-6-methylpyridin-3-yl)-3-((methylamino)methyl)-1-((3-(trifluoromethyl)phenyl)sulfonyl)-1H-indol-6-amine hydrochloride

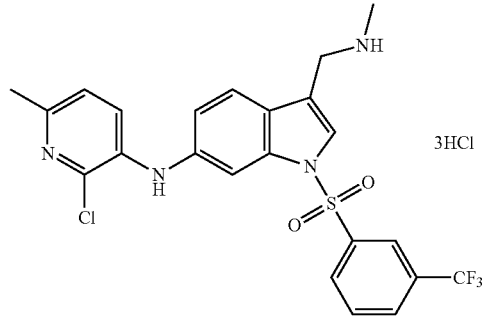 [SMILES: CNCc1cn(S(=O)(=O)c2cccc(C(F)(F)F)c2)c2cc(Nc3ccc(C)nc3Cl)ccc12]

$^1$H NMR (500 MHz, CD$_3$OD): 8.22 (d, 1H), 8.18 (s, 1H), 8.00 (d, 1H), 7.86 (s, 1H), 7.80 (t, 1H), 7.66 (s, 1H), 7.62 (d, 1H), 7.54 (d, 1H), 7.17 (d, 1H), 7.11 (dd, 1H), 4.33 (s, 2H), 2.72 (s, 3H), 2.47 (s, 3H)

Example 193: Preparation of N-(2,6-dichloropyridin-3-yl)-3-((methylamino)methyl)-1-((3-(trifluoromethyl)phenyl)sulfonyl)-1H-indol-6-amine hydrochloride

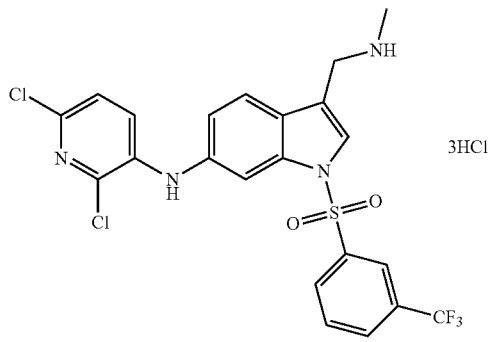 [SMILES: CNCc1cn(S(=O)(=O)c2cccc(C(F)(F)F)c2)c2cc(Nc3ccc(Cl)nc3Cl)ccc12]

¹H NMR (500 MHz, CD₃OD): 7.99 (s, 1H), 7.85-7.91 (m, 2H), 7.73 (s, 1H), 7.65-7.69 (m, 2H), 7.55 (t, 1H), 7.48 (d, 1H), 7.24 (d, 1H), 7.16 (dd, 1H), 4.32 (s, 2H), 2.71 (s, 3H)

Example 194: Preparation of N-(6-methoxy-2-methylpyridin-3-yl)-3-((methylamino)methyl)-1-((3-(trifluoromethyl)phenyl)sulfonyl)-1H-indol-6-amine hydrochloride

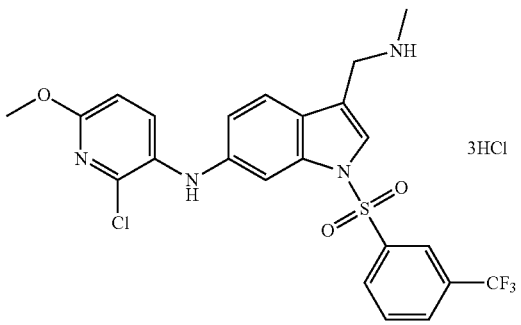 [SMILES: CNCc1cn(S(=O)(=O)c2cccc(C(F)(F)F)c2)c2cc(Nc3ccc(OC)nc3Cl)ccc12]

¹H NMR (500 MHz, CD₃OD): 8.13-8.15 (m, 2H), 7.99 (d, 1H), 7.78 (t, 1H), 7.75 (s, 1H), 7.62 (d, 1H), 7.52 (d, 1H), 7.34 (s, 1H), 6.90 (dd, 1H), 6.80 (d, 1H), 4.29 (s, 2H), 3.93 (s, 3H), 2.71 (s, 3H)

Example 195: Preparation of N-(2-chloro-6-(trifluoromethyl)pyridin-3-yl)-3-((methylamino)methyl)-1-((3-(trifluoromethyl)phenyl)sulfonyl)-1H-indol-6-amine hydrochloride

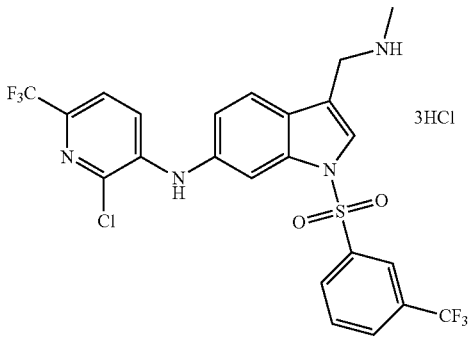 [SMILES: CNCc1cn(S(=O)(=O)c2cccc(C(F)(F)F)c2)c2cc(Nc3ccc(C(F)(F)F)nc3Cl)ccc12]

¹H NMR (500 MHz, CD₃OD): 7.93-8.07 (m, 4H), 7.78 (d, 1H), 7.71 (dd, 1H), 7.59 (q, 2H), 7.48 (d, 1H), 7.34 (dd, 1H), 4.35 (s, 2H), 2.74 (s, 3H)

Example 196: Preparation of N-(2-chloro-4-methylphenyl)-3-((methylamino)methyl)-1-((3-(trifluoromethoxy)phenyl)sulfonyl)-1H-indol-6-amine hydrochloride

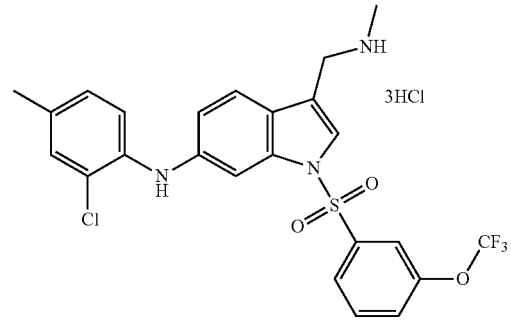 [SMILES: CNCc1cn(S(=O)(=O)c2cccc(OC(F)(F)F)c2)c2cc(Nc3ccc(C)cc3Cl)ccc12]

The compound was prepared in the same manner as in Example 136 except that 3-(trifluoromethoxy)benzenesulfonyl chloride was used instead of 3-fluorobenzenesulfonyl chloride to obtain 7 mg of a title compound (yield: 73.3%).

¹H NMR (500 MHz, CD₃OD): 7.93 (d, 1H), 7.78-7.80 (m, 2H), 7.71 (t, 1H), 7.64 (d, 1H), 7.57 (d, 1H), 7.52 (d, 1H), 7.32 (s, 1H), 7.19 (d, 1H), 7.11 (dd, 1H), 7.06 (dd, 1H), 4.33 (s, 2H), 2.74 (s, 3H), 2.35 (s, 3H)

In Examples 197 through 205 below, compounds were prepared in the same manner as in Example 196 except that reactants were appropriately changed as necessary depending on the structures of the compounds to be prepared and in consideration of Reaction Scheme 2.

Example 197: Preparation of N-(4-chloro-2-fluoro-phenyl)-3-((methylamino)methyl)-1-((3-(trifluoromethoxy)phenyl)sulfonyl)-1H-indol-6-amine hydrochloride

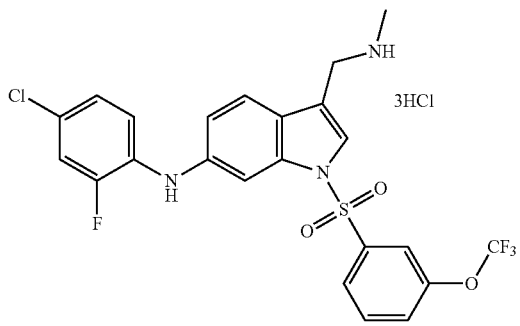 [SMILES: CNCc1cn(S(=O)(=O)c2cccc(OC(F)(F)F)c2)c2cc(Nc3ccc(Cl)cc3F)ccc12]

$^1$H NMR (500 MHz, CD$_3$OD): 7.88 (s, 1H), 7.82 (s, 1H), 7.74 (s, 1H), 7.68 (d, 1H), 7.52-7.55 (m, 2H), 7.43 (s, 1H), 7.31 (dd, 1H), 7.24-7.30 (m, 1H), 7.08 (td, 1H), 7.01 (d, 1H), 4.32 (s, 2H), 2.75 (s, 3H)

Example 198: Preparation of N-(2-chloro-4-(trifluoromethyl)phenyl)-3-((methylamino)methyl)-1-((3-(trifluoromethoxy)phenyl)sulfonyl)-1H-indol-6-amine hydrochloride

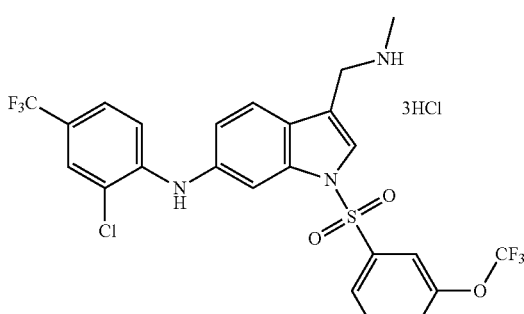

$^1$H NMR (500 MHz, CD$_3$OD): 7.95 (s, 1H), 7.86 (d, 1H), 7.81 (s, 1H), 7.68 (d, 1H), 7.61 (s, 1H), 7.56-7.59 (m, 2H), 7.53 (t, 1H), 7.49 (d, 1H), 7.27 (d, 1H), 7.11 (dd, 1H), 4.32 (s, 2H), 2.73 (s, 3H)

Example 199: Preparation of N-(2-fluoro-4-methoxyphenyl)-3-(methylamino)methyl)-1-((3-(trifluoromethoxy)phenyl)sulfonyl)-1H-indol-6-amine hydrochloride

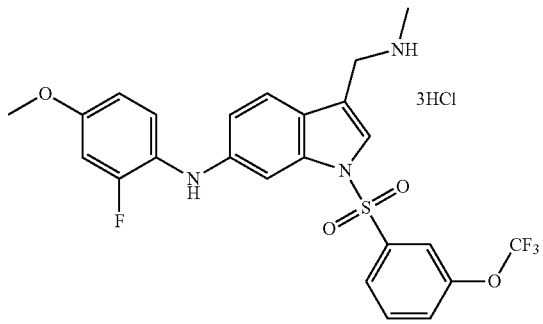 [SMILES: CNCc1cn(S(=O)(=O)c2cccc(OC(F)(F)F)c2)c2cc(Nc3ccc(OC)cc3F)ccc12]

$^1$H NMR (500 MHz, CD$_3$OD): 7.89 (d, 1H), 7.76 (s, 1H), 7.68-7.71 (m, 2H), 7.63 (d, 1H), 7.50 (d, 1H), 7.32 (s, 1H), 7.23 (t, 1H), 6.92 (dd, 1H), 6.86 (dd, 1H), 6.81 (dd, 1H), 4.30 (s, 2H), 3.85 (s, 3H), 2.73 (s, 3H)

Example 200: Preparation of N-(2-methyl-4-(trifluoromethoxy)phenyl)-3-((methylamino)methyl)-1-((3-(trifluoromethoxy)phenyl)sulfonyl)-1H-indol-6-amine hydrochloride

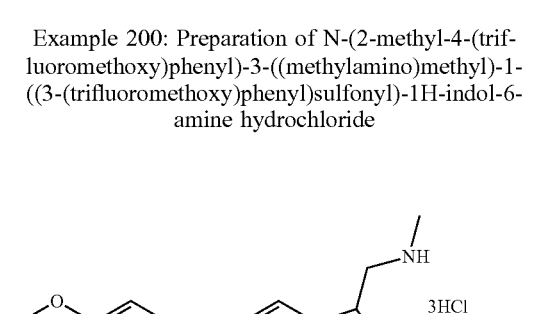

$^1$H NMR (500 MHz, CD$_3$OD): 7.78 (s, 1H), 7.59 (d, 1H), 7.44 (t, 1H), 7.38-7.42 (m, 1H), 7.36 (s, 1H), 7.31 (d, 1H), 7.20 (dd, 1H), 7.14 (d, 2H), 7.03 (d, 1H), 6.94 (dd, 1H), 4.31 (s, 2H), 2.72 (s, 3H), 2.22 (s, 3H)

Example 201: Preparation of N-(2-chloro-4-(trifluoromethoxy)phenyl)-3-((methylamino)methyl)-1-((3-(trifluoromethoxy)phenyl)sulfonyl)-1H-indol-6-amine hydrochloride

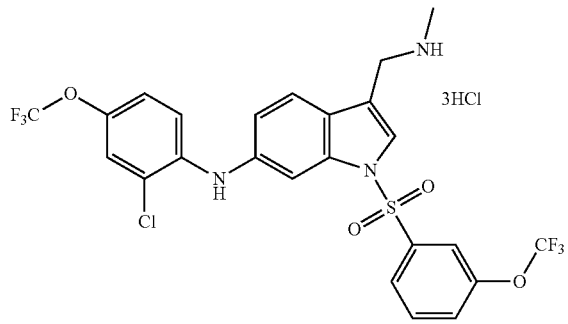 [SMILES: CNCc1cn(S(=O)(=O)c2cccc(OC(F)(F)F)c2)c2cc(Nc3ccc(OC(F)(F)F)cc3OC)ccc12]

¹H NMR (500 MHz, CD₃OD): 7.98 (td, 1H), 7.90 (s, 1H), 7.86 (s, 1H), 7.67-7.73 (m, 3H), 7.64 (td, 1H), 7.42 (d, 1H), 7.26 (d, 1H), 7.16-7.19 (m, 2H), 4.37 (s, 2H), 2.76 (s, 3H)

Example 202: Preparation of N-(2-methoxy-4-(trifluoromethoxy)phenyl)-3-((methylamino)methyl)-1-((3-(trifluoromethoxy)phenyl)sulfonyl)-1H-indol-6-amine hydrochloride

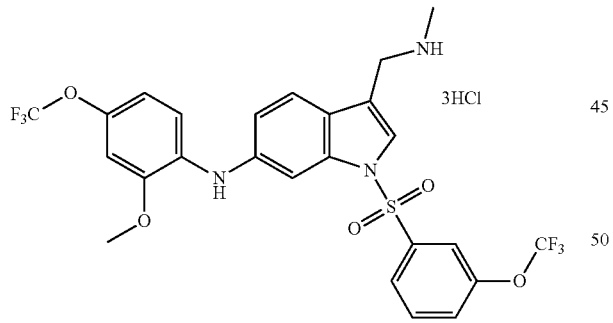

¹H NMR (500 MHz, CD₃OD): 7.85 (t, 1H), 7.78 (d, 1H), 7.67-7.68 (m, 2H), 7.53 (t, 1H), 7.47 (s, 1H), 7.27 (s, 1H), 7.20 (t, 1H), 6.84-6.90 (m, 2H), 6.80 (dd, 1H), 4.30 (s, 2H), 3.97 (s, 3H), 2.73 (s, 3H)

Example 203: Preparation of N-(2,3-difluoro-4-methylphenyl)-3-((methylamino)methyl)-1-((3-(trifluoromethoxy)phenyl)sulfonyl)-1H-indol-6-amine hydrochloride

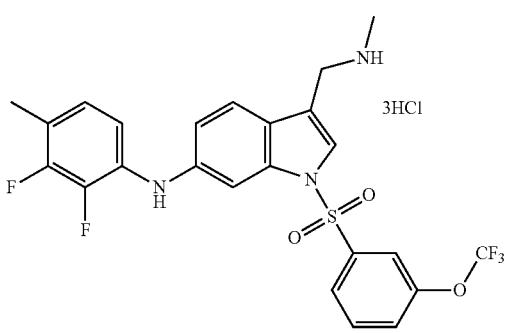 [SMILES: CNCc1cn(S(=O)(=O)c2cccc(OC(F)(F)F)c2)c2cc(Nc3ccc(C)c(F)c3F)ccc12]

¹H NMR (500 MHz, CD₃OD): 7.94 (d, 1H), 7.80-7.81 (m, 2H), 7.71 (t, 1H), 7.64 (dd, 1H), 7.59 (d, 1H), 7.56 (s, 1H), 7.06 (dd, 1H), 6.98 (d, 2H), 4.34 (s, 2H), 2.75 (s, 3H), 2.31 (s, 3H)

Example 204: Preparation of N-(2-fluoro-6-methylpyridin-3-yl)-3-((methylamino)methyl)-1-((3-(trifluoromethoxy)phenyl)sulfonyl)-1H-indol-6-amine hydrochloride

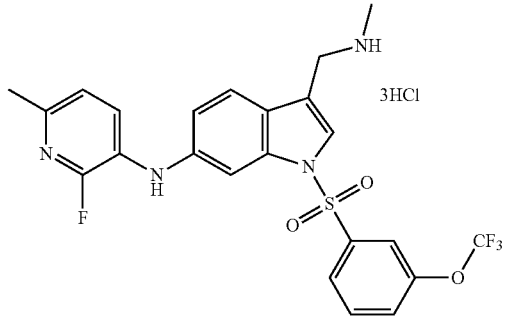 [SMILES: CNCc1cn(S(=O)(=O)c2cccc(OC(F)(F)F)c2)c2cc(Nc3ccc(C)nc3F)ccc12]

¹H NMR (500 MHz, CD₃OD): 7.95-8.00 (m, 1H), 7.83-7.90 (m, 2H), 7.61-7.67 (m, 5H), 7.13 (d, 1H), 7.10 (dd, 1H), 4.34 (s, 2H), 2.75 (s, 3H), 2.46 (s, 3H)

Example 205: Preparation of N-(2-chloro-6-methyl-pyridin-3-yl)-3-((methylamino)methyl)-1-((3-(trifluoromethoxy)phenyl)sulfonyl)-1H-indol-6-amine hydrochloride

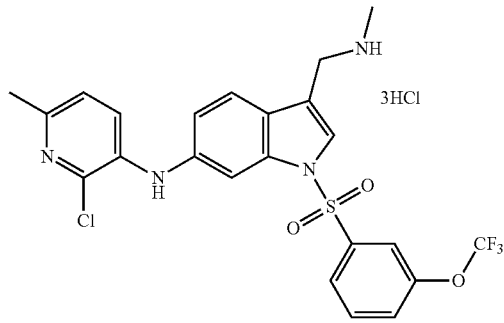

¹H NMR (500 MHz, CD₃OD): 7.98 (d, 1H), 7.86 (s, 2H), 7.72 (t, 1H), 7.69 (d, 1H), 7.65 (d, 2H), 7.58 (d, 2H), 7.21 (d, 1H), 7.15 (dd, 1H), 4.35 (s, 2H), 2.75 (s, 3H), 2.50 (s, 3H)

Example 206: Preparation of N-(2-fluoro-4-methylphenyl)-3-((methylamino)methyl)-1-((4-(trifluoromethoxy)phenyl)sulfonyl)-1H-indol-6-amine hydrochloride

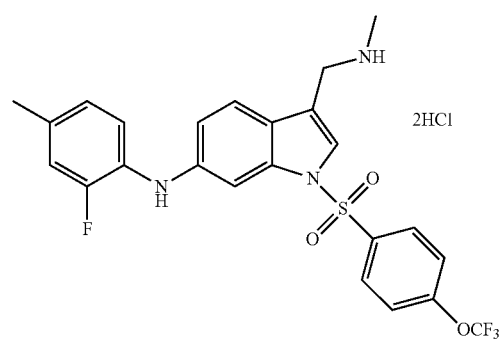 [SMILES: CNCc1cn(S(=O)(=O)c2ccc(OC(F)(F)F)cc2)c2cc(Nc3ccc(C)cc3F)ccc12]

The compound was prepared in the same manner as in Example 136 except that 4-(trifluoromethoxy)benzenesulfonyl chloride was used instead of 3-fluorobenzenesulfonyl chloride to obtain 7 mg of a title compound (yield: 62.8%).

¹H NMR (500 MHz, CD₃OD): 8.04 (d, 2H), 7.74 (s, 1H), 7.54 (d, 1H), 7.49 (d, 3H), 7.18 (t, 1H), 7.06 (d, 1H), 7.01 (dd, 1H), 6.99 (d, 1H), 4.31 (s, 2H), 2.74 (s, 3H), 2.37 (s, 3H)

In Examples 207 through 209 below, compounds were prepared in the same manner as in Example 206 except that reactants were appropriately changed as necessary depending on the structures of the compounds to be prepared and in consideration of Reaction Scheme 2.

Example 207: Preparation of N-(2-chloro-4-methylphenyl)-3-((methylamino)methyl)-1-((4-(trifluoromethoxy)phenyl)sulfonyl)-1H-indol-6-amine hydrochloride ¹H NMR (500 MHz, CD₃OD): 8.02 (d, 2H), 7.74 (s, 1H), 7.54 (d, 1H), 7.51 (dd, 1H), 7.46 (d, 2H), 7.29 (s, 1H), 7.15 (d, 1H), 7.08 (d, 1H), 7.03 (dd, 1H), 4.29 (s, 2H), 2.72 (s, 3H), 2.32 (s, 3H)

Example 208: Preparation of N-(2-chloro-4-(trifluoromethyl)phenyl)-3-((methylamino)methyl)-1-((4-(trifluoromethoxy)phenyl)sulfonyl)-1H-indol-6-amine hydrochloride

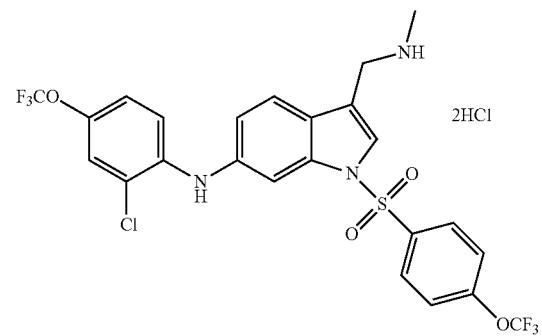 [SMILES: CNCc1cn(S(=O)(=O)c2ccc(OC(F)(F)F)cc2)c2cc(Nc3ccc(OC(F)(F)F)cc3Cl)ccc12]

¹H NMR (500 MHz, CD₃OD): 8.14 (d, 2H), 7.90 (d, 1H), 7.89 (s, 1H), 7.72 (s, 1H), 7.70 (t, 1H), 7.50 (d, 2H), 7.42 (d, 1H), 7.30 (dd, 1H), 7.19 (d, 1H), 4.31 (s, 2H), 2.73 (s, 3H)

Example 209: Preparation of N-(2-methyl-4-(trifluoromethoxy)phenyl)-3-((methylamino)methyl)1-((4-(trifluoromethoxy)phenyl)sulfonyl)-1H-indol-6-amine hydrochloride

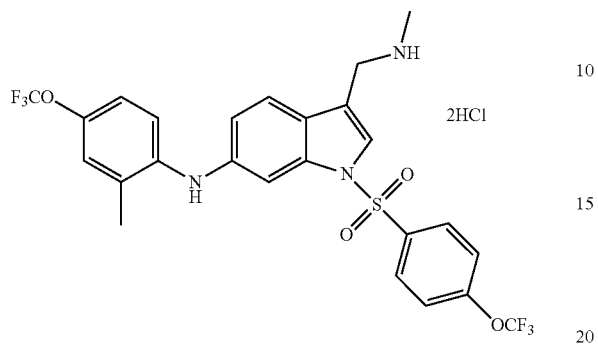

¹H NMR (400 MHz, DMSO-d₆): 9.04 (s, 2H), 7.99 (d, 2H), 7.83 (s, 2H), 7.61-7.64 (m, 2H), 7.37 (s, 1H), 7.25 (s, 1H), 7.10-7.15 (m, 2H), 6.98 (d, 1H), 5.73 (s, 1H), 4.19 (s, 2H), 2.61 (s, 3H), 2.25 (s, 3H)

Example 210: Preparation of N-(2-fluoro-4-methylphenyl)-1-((5-fluoropyridin-3-yl)sulfonyl)-3-((methylamino)methyl)-1H-indol-6-amine hydrochloride

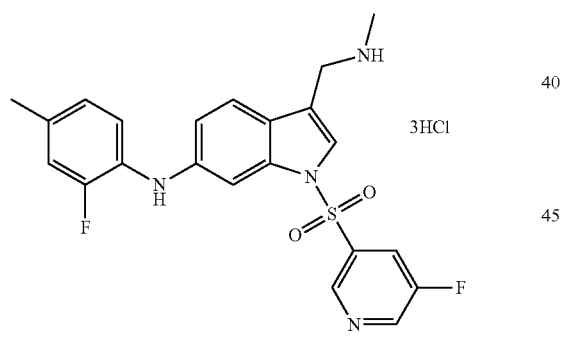

The compound was prepared in the same manner as in Example 136 except that 5-fluoropyridin-3-sulfonyl chloride was used instead of 3-fluorobenzenesulfonyl chloride to obtain 5.5 mg of a title compound (yield: 58%).

¹H NMR (500 MHz, CD₃OD): 8.90 (s, 1H), 8.76 (d, 1H), 8.10-8.12 (m, 1H), 7.73 (s, 1H), 7.52 (d, 1H), 7.43 (s, 1H), 7.16 (t, 1H), 6.98-7.02 (m, 3H), 4.30 (s, 2H), 2.74 (s, 3H), 2.35 (s, 3H)

In Examples 211 through 218 below, compounds were prepared in the same manner as in Example 210 except that reactants were appropriately changed as necessary depending on the structures of the compounds to be prepared and in consideration of Reaction Scheme 2.

Example 211: Preparation of N-(2-chloro-4-methylphenyl)-1-((5-fluoropyridin-3-yl)sulfonyl)-3-((methylamino)methyl)-1H-indol-6-amine hydrochloride

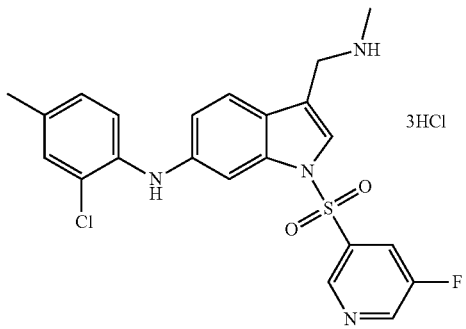 [SMILES: CNCc1cn(S(=O)(=O)c2cncc(F)c2)c2cc(Nc3ccc(C)cc3Cl)ccc12]

¹H NMR (500 MHz, CD₃OD): 8.90 (s, 1H), 8.76 (d, 1H), 8.12-8.14 (m, 1H), 7.76 (s, 1H), 7.55 (d, 1H), 7.48 (s, 1H), 7.30 (s, 1H), 7.16 (d, 1H), 7.11 (dd, 1H), 7.04 (dd, 1H), 4.30 (s, 2H), 2.74 (s, 3H), 2.33 (s, 3H)

Example 212: Preparation of N-(4-fluoro-2-methylphenyl)-1-((5-fluoropyridin-3-yl)sulfonyl)-3-((methylamino)methyl)-1H-indol-6-amine hydrochloride

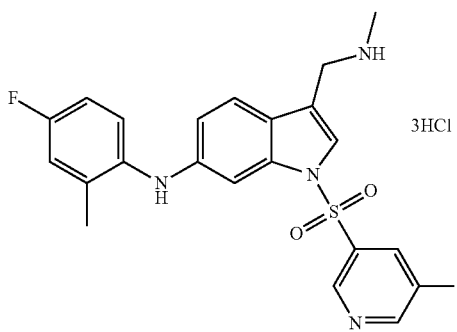

¹H NMR (500 MHz, CD₃OD): 8.89 (s, 1H), 8.80 (s, 1H), 8.06 (d, 1H), 7.72 (s, 1H), 7.51 (d, 1H), 7.15-7.20 (m, 2H), 7.09 (dd, 1H), 6.98-7.01 (m, 1H), 6.88 (dd, 1H), 4.31 (s, 2H), 2.76 (s, 3H), 2.21 (s, 3H)

Example 213: Preparation of N-(2-chloro-4-fluoro-phenyl)-1-((5-fluoropyridin-3-yl)sulfonyl)-3-((methylamino)methyl)-1H-indol-6-amine hydrochloride

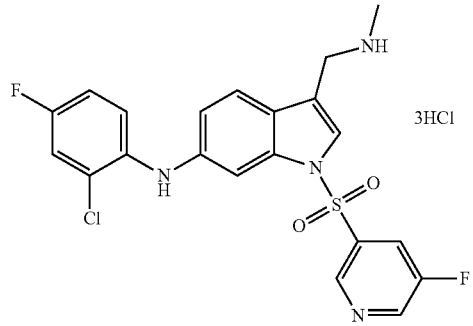 [SMILES: CNCc1cn(S(=O)(=O)c2cncc(F)c2)c2cc(Nc3ccc(F)cc3Cl)ccc12]

¹H NMR (500 MHz, CD₃OD): 8.95 (s, 1H), 8.80 (s, 1H), 8.16 (dd, 1H), 7.81 (s, 1H), 7.60 (d, 1H), 7.49 (s, 1H), 7.28-7.48 (m, 2H), 7.09-7.13 (m, 1H), 7.05 (dd, 1H), 4.34 (s, 2H), 2.77 (s, 3H)

Example 214: Preparation of 1-((5-fluoropyridin-3-yl)sulfonyl)-N-(4-methoxy-2-(trifluoromethoxy)phenyl)-3-((methylamino)methyl)-1H-indol-6-amine hydrochloride

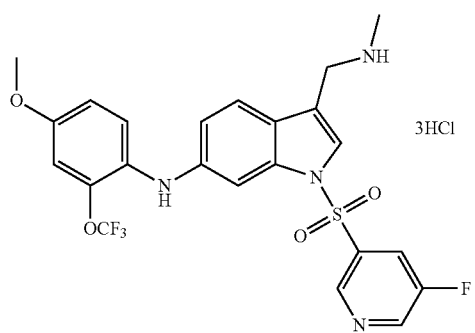 [SMILES: CNCc1cn(S(=O)(=O)c2cncc(F)c2)c2cc(Nc3ccc(OC)cc3OC(F)(F)F)ccc12]

¹H NMR (500 MHz, CDCl₃): 8.90 (s, 1H), 8.63 (s, 1H), 7.81 (td, 1H), 7.72 (s, 1H), 7.47 (d, 1H), 7.36 (s, 1H), 7.15 (d, 1H), 7.09 (dd, 1H), 6.78-7.08 (m, 2H), 6.21 (s, 1H), 3.93 (s, 3H), 3.83 (s, 2H), 2.49 (s, 3H)

Example 215: Preparation of N-(2-chloro-4-(trifluoromethoxy)phenyl)-1-((5-fluoropyridin-3-yl)sulfonyl)-3-((methylamino)methyl)-1H-indol-6-amine hydrochloride

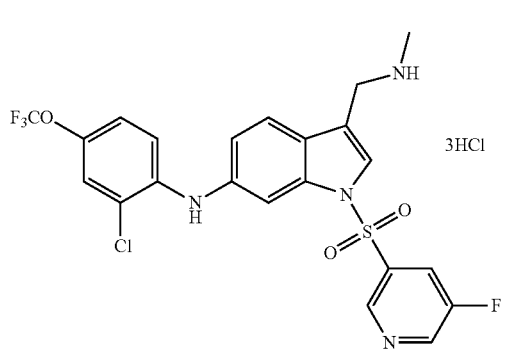 [SMILES: CNCc1cn(S(=O)(=O)c2cncc(F)c2)c2cc(Nc3ccc(OC(F)(F)F)cc3Cl)ccc12]

¹H NMR (500 MHz, CD₃OD): 8.95 (s, 1H), 8.77 (s, 1H), 8.21 (td, 1H), 7.86 (s, 1H), 7.69 (s, 1H), 7.65 (d, 1H), 7.41 (s, 1H), 7.25 (d, 1H), 7.17 (dd, 2H), 4.34 (s, 2H), 2.75 (s, 3H)

Example 216: Preparation of 1-((5-fluoropyridin-3-yl)sulfonyl)-N-(2-methoxy-4-(trifluoromethoxy)phenyl)-3-((methylamino)methyl)-1H-indol-6-amine hydrochloride

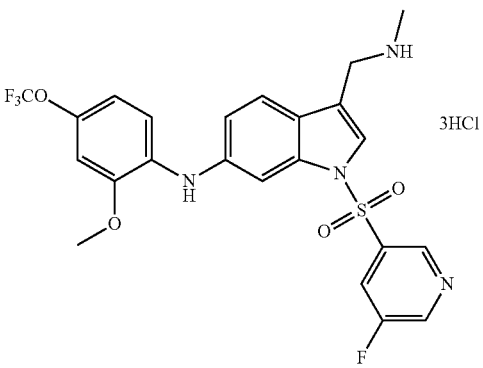 [SMILES: CNCc1cn(S(=O)(=O)c2cncc(F)c2)c2cc(Nc3ccc(OC(F)(F)F)cc3OC)ccc12]

¹H NMR (500 MHz, CD₃OD): 8.93 (s, 1H), 8.77 (d, 1H), 8.16-8.19 (m, 1H), 7.78 (s, 1H), 7.65 (d, 1H), 7.57 (d, 1H), 7.21 (d, 1H), 7.14 (dd, 1H), 6.96 (s, 1H), 6.84 (d, 1H), 4.31 (s, 2H), 3.90 (s, 3H), 2.74 (s, 3H)

Example 217: Preparation of N-(2-chloro-6-methoxypyridin-3-yl)-1-((5-fluoropyridin-3l1)sulfonyl)-3-((methylamino)methyl)-1H-indol-6-amine hydrochloride

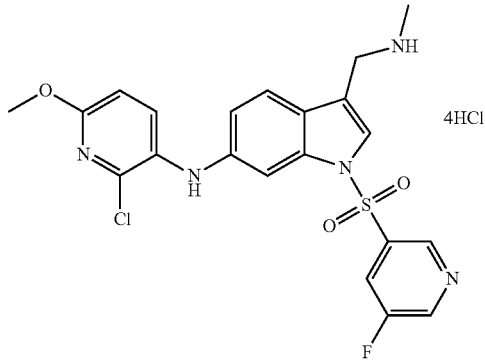 [SMILES: CNCc1cn(S(=O)(=O)c2cncc(F)c2)c2cc(Nc3ccc(OC)nc3Cl)ccc12]

¹H NMR (500 MHz, CD₃OD): 8.89 (s, 1H), 8.77 (d, 1H), 8.12 (d, 1H), 7.74 (s, 1H), 7.62 (d, 1H), 7.53 (d, 1H), 7.34 (s, 1H), 6.91 (dd, 1H), 6.81 (d, 1H), 7.10 (d, 1H), 4.30 (s, 2H), 3.93 (s, 1H), 2.73 (s, 3H)

Example 218: Preparation of N-(2-chloro-6-(trifluoromethyl)pyridin-3-yl)-1-((5-fluoropyridin-3-yl)sulfonyl)-3-((methylamino)methyl)-1H-indol-6-amine hydrochloride

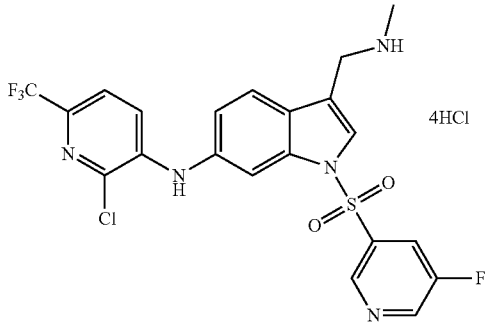 [SMILES: CNCc1cn(S(=O)(=O)c2cncc(F)c2)c2cc(Nc3ccc(C(F)(F)F)nc3Cl)ccc12]

¹H NMR (500 MHz, CD₃OD): 8.90 (s, 1H), 8.68 (s, 1H), 8.12-8.14 (m, 1H), 7.92 (s, 1H), 7.87 (s, 1H), 7.71 (d, 1H), 7.37 (d, 1H), 7.27 (dd, 1H), 7.13 (d, 1H), 4.26 (s, 2H), 2.69 (s, 3H)

Example 219: Preparation of N-(2-chloro-4-methylphenyl)-1-((4-methoxyphenyl)sulfonyl)-3-((methylamino)methyl)-1H-indol-6-amine hydrochloride

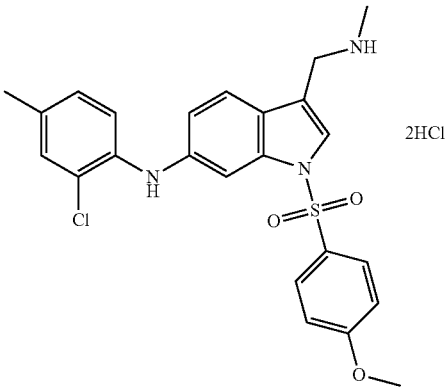

The compound was prepared in the same manner as in Example 136 except that 4-methoxybenzenesulfonyl chloride was used instead of 3-fluorobenzenesulfonyl chloride, and 2-chloro-4-methylaniline was used instead of 2-fluoro-4-methylaniline, based on Reaction Scheme 2, to obtain 7 mg of a title compound (yield: 73.5%).

¹H NMR (500 MHz, CD₃OD): 7.83 (d, 2H), 7.71 (s, 1H), 7.52 (d, 2H), 7.28 (s, 1H), 7.14 (d, 1H), 7.07 (d, 1H), 7.00-7.04 (d, 3H), 4.27 (s, 2H), 3.83 (s, 3H), 2.70 (s, 3H), 2.32 (s, 3H)

Example 220: Preparation of N-(2-chloro-4-methylphenyl)-1-((4-(difluoromethoxy)phenyl)sulfonyl)-3-((methylamino)methyl)-1H-indol-6-amine hydrochloride

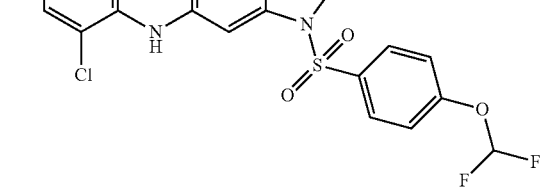

The compound was prepared in the same manner as in Example 219 except that 4-(difluoromethoxy)benzenesulfonyl chloride was used instead of 4-methoxybenzenesulfonyl chloride to obtain 6 mg of a title compound (yield: 62.8%).

¹H NMR (500 MHz, CD₃OD): 7.98 (d, 2H), 7.77 (s, 1H), 7.56 (d, 1H), 7.54 (d, 1H), 7.30-7.32 (m, 3H), 7.16 (t, 1H), 7.10 (dd, 1H), 7.05 (dd, 1H), 4.32 (s, 2H), 2.74 (s, 3H), 2.35 (s, 3H)

Example 221: Preparation of N-(2-chloro-4-methyl-phenyl)-3-((methylamino)methyl)-1-((4-(trifluoromethyl)phenyl)sulfonyl)-1H-indol-6-amine hydrochloride

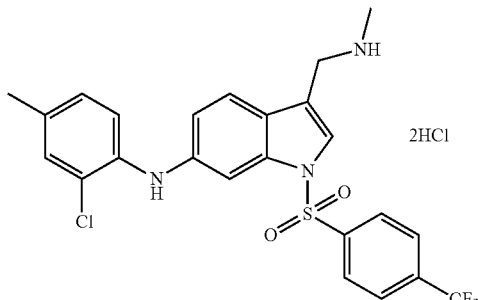

The compound was prepared in the same manner as in Example 219 except that 4-(trifluoromethyl)benzenesulfonyl chloride was used instead of 4-methoxybenzenesulfonyl chloride to obtain 6 mg of a title compound (yield: 62.8%).

$^1$H NMR (500 MHz, CD$_3$OD): 8.09 (d, 2H), 7.88 (d, 2H), 7.74 (s, 1H), 7.51-7.53 (m, 2H), 7.29 (s, 1H), 7.15 (d, 1H), 7.08 (d, 1H), 7.03 (dd, 1H), 4.27 (s, 2H), 2.71 (s, 3H), 2.33 (s, 3H)

Example 222: Preparation of N-(2-fluoro-4-methyl-phenyl)-3-((methylamino)methyl)-1-(phenylsulfonyl)-1H-indol-6-amine hydrochloride The compound was prepared as shown in Reaction Scheme 3 below.

[Reaction Scheme 3]

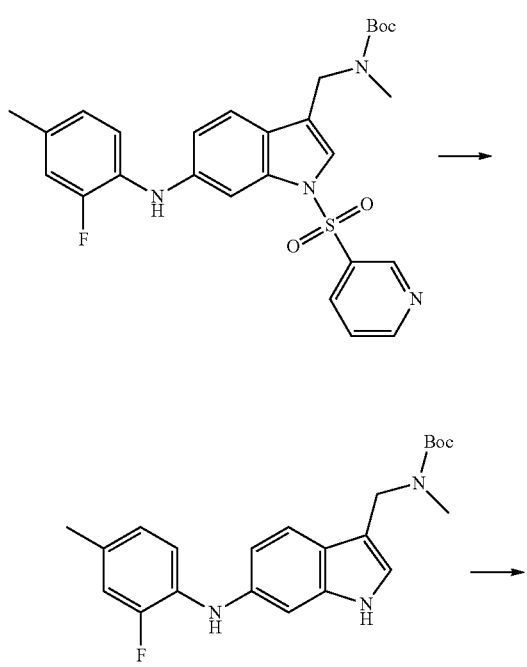

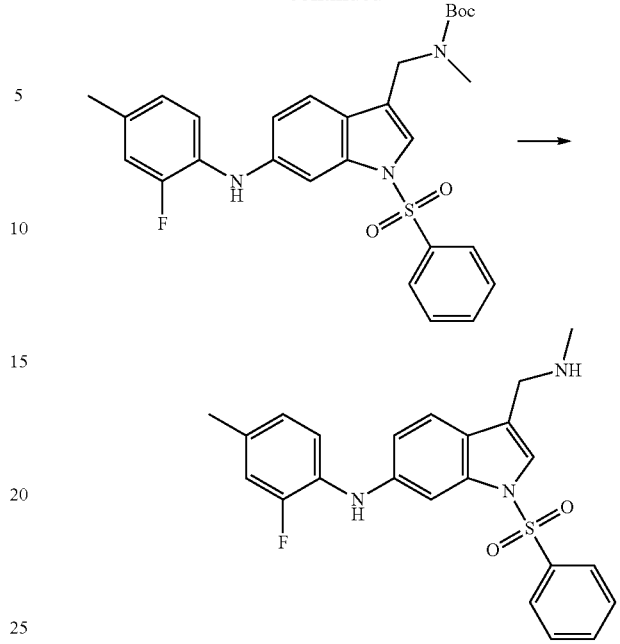

Step 1: Preparation of tert-butyl ((6-((2-fluoro-4-methylphenyl)amino)-1H-indol-3-yl)methyl)(methyl)carbamate Tert-butyl ((6-((2-fluoro-4-methylphenyl)amino)-1-(pyridin-3-ylsulfonyl)-1H-indol-3-yl)methyl)(methyl)carbamate (100 mg, 0.2 mmole) was added with 1 ml of 1M tetrabutylammonium fluoride-tetrahydrofuran solution, and stirred at 80° C. for 1 hour. The reaction mixture was added with water and extracted with ethyl acetate. The resulting separated organic layer was washed with saturated brine, dried on anhydrous magnesium sulfate and concentrated under reduced pressure. The resulting residue was purified by silica gel column chromatography (ethyl acetate:n-hexane=1:3 (v/v)) to obtain 40 mg of a title compound (yield: 54.8%).

$^1$H NMR (500 MHz, CDCl$_3$): 7.65 (s, 1H), 7.54-7.56 (m, 1H), 7.46 (d, 2H), 7.14 (t, 1H), 6.85-6.96 (m, 2H), 4.39 (s, 2H), 2.70 (s, 3H), 2.28 (s, 3H), 1.43 (s, 9H)

Step 2: Preparation of tert-butyl ((6-((2-fluoro-4-methylphenyl)amino)-1-(phenylsulfonyl)-1H-indol-3-yl)methyl)(methyl)carbamate Tert-butyl ((6-((2-fluoro-4-methylphenyl)amino)-1H-indol-3-yl)methyl)(methyl)carbamate (20 mg, 0.05 mmole) was dissolved in 1 ml of N,N-dimethylformamide solution, cooled to 0° C., and dropwisely added with sodium hydride (60% in oil)(4 mg, 0.1 mmol). The reaction mixture was stirred at 0° C. for 30 minutes, added with benzenesulfonyl chloride (11 mg, 0.06 mmole), and stirred at room temperature for 2 hours. The resulting reaction mixture was added with an aqueous ammonium chloride solution and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 20 mg of a title compound (yield: 74%).

¹H NMR (300 MHz, CD₃OD): 7.85 (s, 1H), 7.82 (d, 1H), 7.65 (s, 1H), 7.54-7.56 (m, 1H), 7.46 (d, 2H), 7.34 (br, 1H), 7.14 (t, 1H), 6.85-6.96 (m, 4H), 4.47 (s, 2H), 2.73 (s, 3H), 2.32 (s, 3H), 1.48 (s, 9H)

Step 3: Preparation of N-(2-fluoro-4-methylphenyl)-3-((methylamino)methyl)-1-(phenylsulfonyl)-1H-indol-6-amine hydrochloride Tert-butyl (((6-((2-fluoro-4-methylphenyl)amino)-1-(phenylsulfonyl)-1H-indol-3-yl)methyl)(methyl)carbamate (20 mg, 0.04 mmole) was added with 1 ml of 1.25 M HCl-methanol solution, and stirred at room temperature for 15 hours. The reaction mixture was concentrated under reduced pressure, and the resulting residue was recrystallized with diethyl ether to obtain 12 mg of a title compound (yield: 63%).

¹H NMR (300 MHz, CD₃OD): 7.85 (d, 2H), 7.60-7.66 (m, 2H), 7.52 (t, 3H), 7.45 (d, 1H), 7.13 (t, 1H), 7.01 (d, 1H), 6.94 (dd, 2H), 4.08 (s, 2H), 2.58 (s, 3H), 2.34 (s, 3H)

In Examples 223 through 242 below, compounds were prepared in the same manner as in Example 222 except that reactants were appropriately changed as necessary depending on the structures of the compounds to be prepared and in consideration of Reaction Scheme 3.

Example 223: Preparation of N-(2-fluoro-4-methylphenyl)-3-((methylamino)methyl)-1-(o-tolylsulfonyl)-1H-indol-6-amine hydrochloride

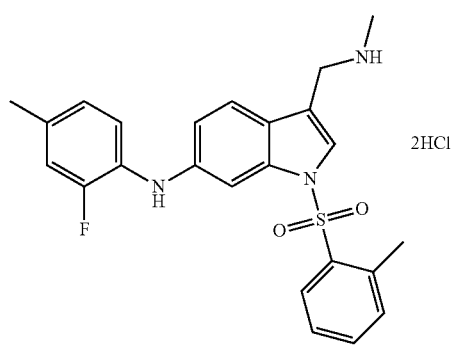

¹H NMR (300 MHz, CD₃OD): 7.88 (d, 2H), 7.63-7.69 (m, 2H), 7.53 (t, 2H), 7.48 (d, 1H), 7.16 (t, 1H), 7.05 (d, 1H), 6.99 (dd, 2H), 4.08 (s, 2H), 2.61 (s, 3H), 2.34 (s, 3H), 2.30 (s, 3H)

Example 224: Preparation of N-(2-fluoro-4-methylphenyl)-1-((2-fluorophenyl)sulfonyl)-3-((methylamino)methyl)-1H-indol-6-amine hydrochloride

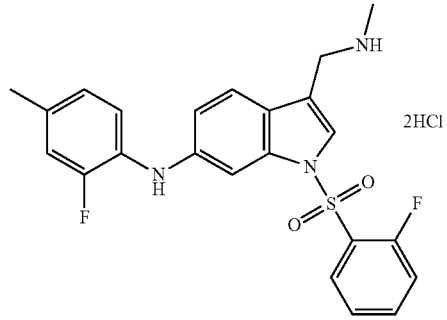 [SMILES: CNCc1cn(S(=O)(=O)c2ccccc2F)c2cc(Nc3ccc(C)cc3F)ccc12]

¹H NMR (300 MHz, CD₃OD): 7.88 (d, 2H), 7.60-7.66 (m, 1H), 7.50 (t, 3H), 7.43 (d, 1H), 7.10 (t, 1H), 7.02 (d, 1H), 6.96 (dd, 2H), 4.05 (s, 2H), 2.59 (s, 3H), 2.32 (s, 3H)

Example 225: Preparation of 1-((2-chlorophenyl)sulfonyl)-N-(2-fluoro-4-methylphenyl)-3-((methylamino)methyl)-1H-indol-6-amine hydrochloride

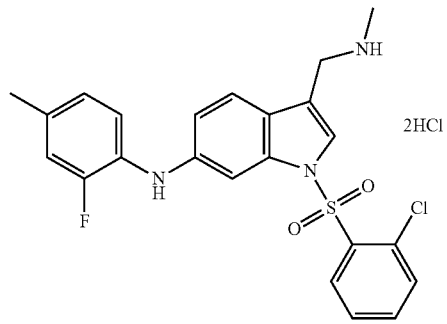 [SMILES: CNCc1cn(S(=O)(=O)c2ccccc2Cl)c2cc(Nc3ccc(C)cc3F)ccc12]

¹H NMR (300 MHz, CD₃OD): 9.40 (s, 1H), 8.88 (d, 1H), 8.68 (d, 1H), 8.49 (s, 1H), 8.24-8.30 (m, 2H), 8.13 (s, 1H), 7.92 (d, 1H), 7.74-7.78 (m, 1H), 7.68 (d, 1H), 7.22 (dd, 1H), 4.35 (s, 2H), 2.78 (s, 3H), 2.37 (s, 3H)

Example 226: Preparation of N-(2-fluoro-4-methylphenyl)-3-((methylamino)methyl)-1-(m-tolylsulfonyl)-1H-indol-6-amine hydrochloride

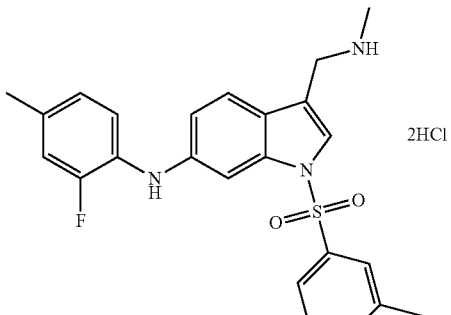

¹H NMR (400 MHz, DMSO-d₆): 8.83 (br, 2H), 8.03 (s, 1H), 7.74 (s, 1H), 7.66 (s, 1H), 7.62 (d, 1H), 7.47-7.55 (m, 3H), 7.32 (s, 1H), 7.10 (t, 2H), 6.96 (d, 1H), 6.88 (dd, 1H), 4.16-4.18 (m, 2H), 2.53 (s, 3H), 2.33 (s, 3H), 2.26 (s, 3H)

Example 227: Preparation of 3-((6-((2-fluoro-4-methylphenyl)amino)-3-((methylamino)methyl)-1H-indol-1-yl)sulfonyl)benzonitrile hydrochloride

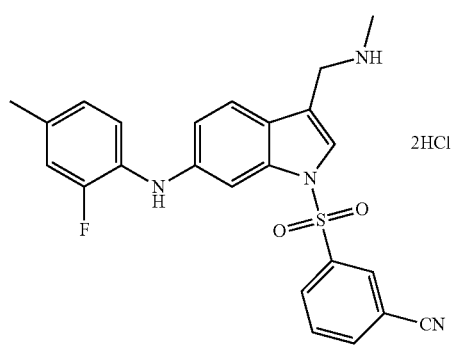 [SMILES: CNCc1cn(S(=O)(=O)c2cccc(C#N)c2)c2cc(Nc3ccc(C)cc3F)ccc12]

¹H NMR (300 MHz, CD₃OD): 8.25 (s, 1H), 8.15 (d, 1H), 8.02 (d, 1H), 7.74 (t, 2H), 7.52 (d, 1H), 7.39 (s, 1H), 7.15 (t, 1H), 7.06 (d, 1H), 7.01 (d, 1H), 6.98 (dd, 1H), 4.30 (s, 2H), 2.73 (s, 3H), 2.36 (s, 3H)

Example 228: Preparation of 1-((3-bromophenyl)sulfonyl)-N-(2-fluoro-4-methylphenyl)-3-((methylamino)methyl)-1H-indol-6-amine hydrochloride

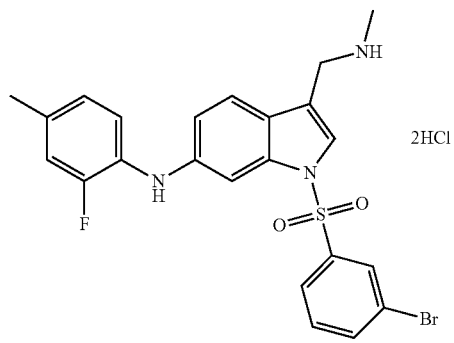 [SMILES: CNCc1cn(S(=O)(=O)c2cccc(Br)c2)c2cc(Nc3ccc(C)cc3F)ccc12]

¹H NMR (500 MHz, CD₃OD): 7.65 (s, 1H), 7.51-7.58 (m, 2H), 7.21-7.31 (m, 3H), 7.06-7.12 (m, 2H), 6.88-7.03 (m, 3H), 4.29 (s, 2H), 2.30 (s, 3H), 2.27 (s, 3H)

Example 229: Preparation of N-(2-fluoro-4-methylphenyl)-3-((methylamino)methyl)-1-tosyl-1H-indol-6-amine hydrochloride

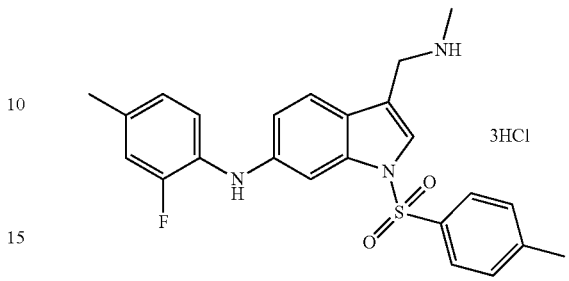

¹H NMR (500 MHz, CD₃OD): 7.89 (d, 2H), 7.68 (d, 2H), 7.50 (t, 2H), 7.43 (d, 1H), 7.14 (t, 1H), 7.01 (d, 1H), 6.95 (dd, 2H), 4.11 (s, 2H), 2.59 (s, 3H), 2.34 (s, 3H), 2.26 (s, 3H)

Example 230: Preparation of 1-((4-chlorophenyl)sulfonyl)-N-(2-fluoro-4-methylphenyl)-3-((methylamino)methyl)-1H-indol-6-amine hydrochloride

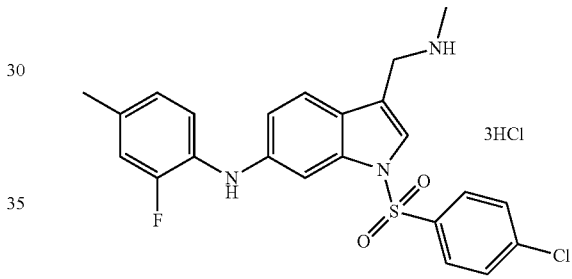

¹H NMR (500 MHz, CD₃OD): 8.80 (s, 1H), 8.62 (d, 1H), 8.51 (d, 1H), 8.39 (s, 1H), 8.19-8.25 (m, 2H), 8.06 (s, 1H), 7.88 (d, 1H), 7.68-7.72 (m, 1H), 7.62 (d, 1H), 7.16 (dd, 1H), 4.33 (s, 2H), 2.78 (s, 3H), 2.36 (s, 3H)

Example 231: Preparation of 1-((4-(tert-butyl)phenyl)sulfonyl)-N-(2-fluoro-4-methylphenyl)-3-((methylamino)methyl)-1H-indol-6-amine hydrochloride

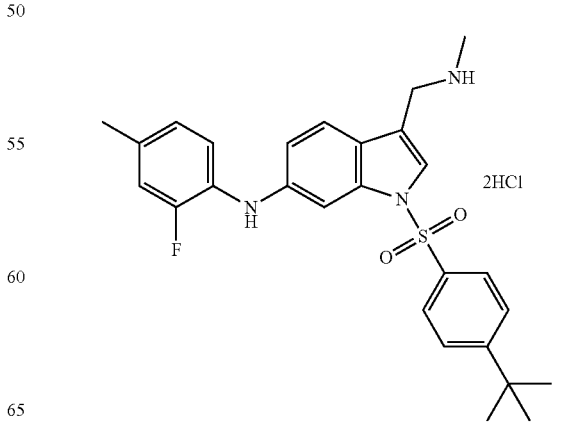

¹H NMR (300 MHz, CD₃OD): 9.77 (br, 2H), 7.75-7.81 (m, 3H), 7.63 (s, 2H), 7.45-7.48 (m, 2H), 7.15-7.19 (m, 1H), 6.84-6.97 (m, 3H), 4.19 (br, 2H), 2.53 (s, 3H), 2.31 (s, 3H), 1.25 (s, 9H)

Example 232: Preparation of 1-([1,1'-biphenyl]-4-ylsulfonyl)-N-(2-fluoro-4-methylphenyl)-3-((methylamino)methyl)-1H-indol-6-amine hydrochloride

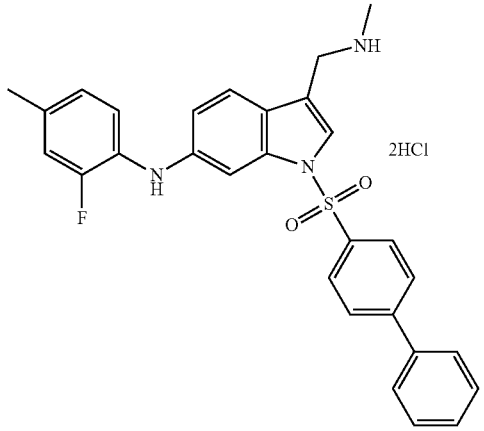 [SMILES: CNCc1cn(S(=O)(=O)c2ccc(-c3ccccc3)cc2)c2cc(Nc3ccc(C)cc3F)ccc12]

¹H NMR (500 MHz, CD₃OD): 7.91 (d, 2H), 7.70 (s, 1H), 7.63 (d, 2H), 7.52 (d, 2H), 7.39-7.46 (m, 4H), 7.17 (d, 1H), 6.96 (t, 2H), 6.85 (d, 1H), 5.78 (s, 1H), 3.84 (s, 2H), 2.48 (d, 3H), 2.32 (s, 3H)

Example 233: Preparation of N-(2-fluoro-4-methylphenyl)-3-((methylamino)methyl)-1-(naphthalen-1-ylsulfonyl)-1H-indol-6-amine hydrochloride

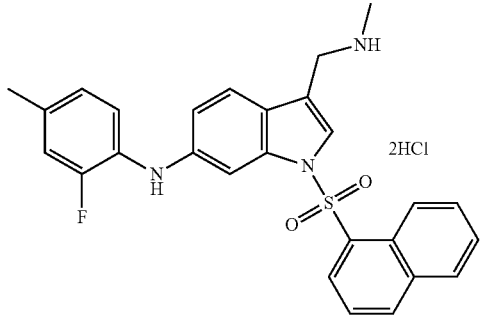 [SMILES: CNCc1cn(S(=O)(=O)c2cccc3ccccc23)c2cc(Nc3ccc(C)cc3F)ccc12]

¹H NMR (300 MHz, CDCl₃): 7.90 (d, 2H), 7.72 (s, 1H), 7.61 (d, 2H), 7.48 (d, 2H), 7.39-7.43 (m, 3H), 7.14 (d, 1H), 6.94 (t, 2H), 6.81 (d, 1H), 3.91 (s, 2H), 2.46 (d, 3H), 2.33 (s, 3H)

Example 234: Preparation of 1-((2,3-dichlorophenyl)sulfonyl)-N-(2-fluoro-4-methylphenyl)-3-((methylamino)methyl)-1H-indol-6-amine hydrochloride

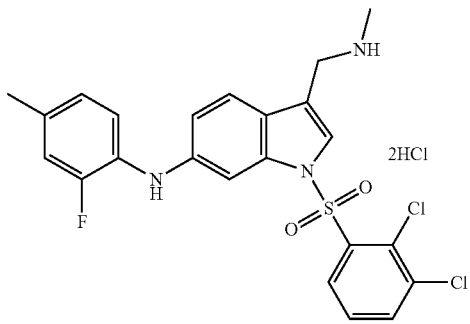 [SMILES: CNCc1cn(S(=O)(=O)c2cccc(Cl)c2Cl)c2cc(Nc3ccc(C)cc3F)ccc12]

¹H NMR (500 MHz, CD₃OD): 8.08 (d, 1H), 7.81 (dd, 1H), 7.67-7.71 (m, 2H), 7.53 (d, 1H), 7.42 (s, 1H), 7.17 (t, 1H), 7.05 (d, 1H), 6.98-7.03 (m, 2H), 4.32 (s, 2H), 2.77 (s, 3H), 2.36 (s, 3H)

Example 235: Preparation of 1-((2,4-dichlorophenyl)sulfonyl)-N-(2-fluoro-4-methylphenyl)-3-((methylamino)methyl)-1H-indol-6-amine hydrochloride

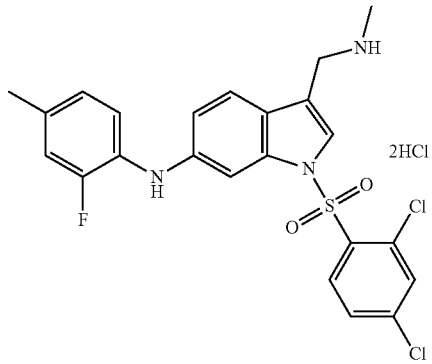 [SMILES: CNCc1cn(S(=O)(=O)c2ccc(Cl)cc2Cl)c2cc(Nc3ccc(C)cc3F)ccc12]

¹H NMR (500 MHz, CD₃OD): 8.06 (d, 1H), 7.78 (dd, 1H), 7.62-7.68 (m, 2H), 7.51 (d, 1H), 7.41 (s, 1H), 7.15 (t, 1H), 7.03 (d, 1H), 6.95-7.00 (m, 2H), 4.35 (s, 2H), 2.75 (s, 3H), 2.33 (s, 3H)

Example 236: Preparation of 1-((2,5-dimethylphenyl)sulfonyl)-N-(2-fluoro-4-methylphenyl)-3-((methylamino)methyl)-1H-indol-6-amine hydrochloride

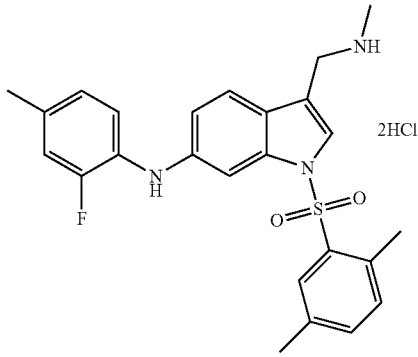

$^{1}$H NMR (500 MHz, CD$_3$OD): 7.90 (d, 2H), 7.71 (d, 2H), 7.56 (t, 2H), 7.45 (d, 1H), 7.16 (t, 1H), 7.07 (d, 1H), 6.99 (dd, 1H), 4.12 (s, 2H), 2.56 (s, 3H), 2.32 (s, 3H), 2.26 (s, 3H), 2.24 (s, 3H)

Example 237: Preparation of 1-((3,4-difluorophenyl)sulfonyl)-N-(2-fluoro-4-methylphenyl)-3-((methylamino)methyl)-1H-indol-6-amine hydrochloride

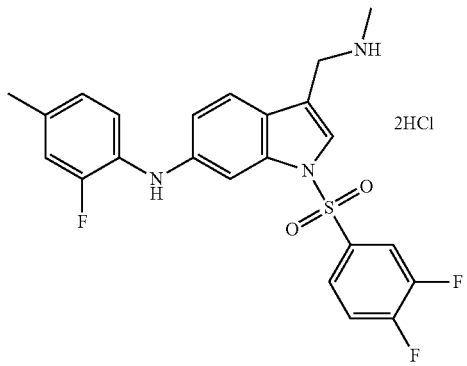 [SMILES: CNCc1cn(S(=O)(=O)c2ccc(F)c(F)c2)c2cc(Nc3ccc(C)cc3F)ccc12]

$^{1}$H NMR (300 MHz, CDCl$_3$): 7.59-7.69 (m, 2H), 7.57 (d, 1H), 7.22-7.29 (m, 3H), 7.13-7.20 (m, 1H), 6.88-6.98 (m, 3H), 5.76 (s, 1H), 4.47 (s, 2H), 2.75 (s, 3H), 2.33 (s, 3H)

Example 238: Preparation of 1-((3,4-dichlorophenyl)sulfonyl)-N-(2-fluoro-4-methylphenyl)-3-((methylamino)methyl)-1H-indol-6-amine hydrochloride

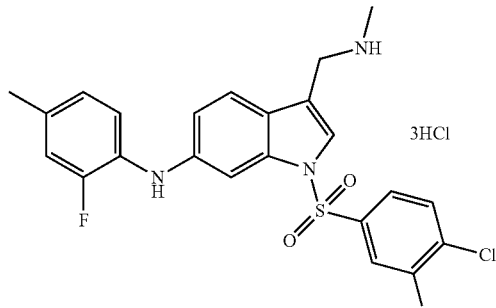

$^{1}$H NMR (500 MHz, CD$_3$OD): 8.07 (d, 1H), 7.82 (dd, 1H), 7.70-7.73 (m, 2H), 7.55 (d, 1H), 7.45 (s, 1H), 7.19 (t, 1H), 7.06 (d, 1H), 7.00-7.03 (m, 2H), 4.31 (s, 2H), 2.75 (s, 3H), 2.38 (s, 3H)

Example 239: Preparation of 1-((3,5-dimethylphenyl)sulfonyl)-N-(2-fluoro-4-methylphenyl)-3-((methylamino)methyl)-1H-indol-6-amine hydrochloride

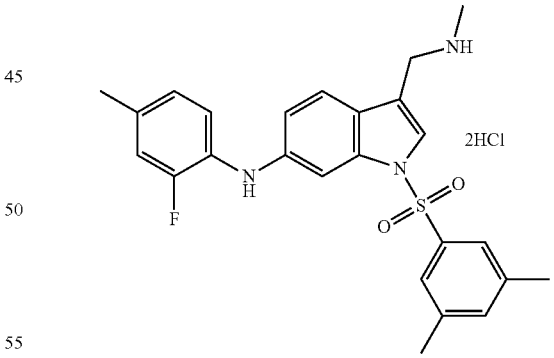

$^{1}$H NMR (500 MHz, CD$_3$OD): 7.91 (d, 2H), 7.73 (d, 2H), 7.58 (t, 2H), 7.48 (d, 1H), 7.18 (t, 1H), 7.10 (d, 1H), 6.95 (dd, 1H), 4.11 (s, 2H), 2.59 (s, 3H), 2.35 (s, 3H), 2.28 (s, 3H), 2.22 (s, 3H)

Example 240: Preparation of N-(2-fluoro-4-methylphenyl)-3-((methylamino)methyl)-1-((2,3,4-trichlorophenyl)sulfonyl)-1H-indol-6-amine hydrochloride

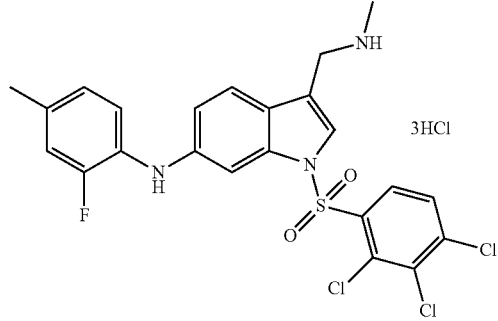 [SMILES: CNCc1cn(S(=O)(=O)c2ccc(Cl)c(Cl)c2Cl)c2cc(Nc3ccc(C)cc3F)ccc12]

¹H NMR (500 MHz, CD₃OD): 8.05 (d, 1H), 7.81 (dd, 1H), 7.70 (s, 1H), 7.50 (d, 1H), 7.43 (s, 1H), 7.15 (t, 1H), 7.02 (d, 1H), 6.93-6.99 (m, 2H), 4.33 (s, 2H), 2.76 (s, 3H), 2.33 (s, 3H)

Example 241: Preparation of 1-((5-bromopyridin-3-yl)sulfonyl)-N-(2-fluoro-4-methylphenyl)-3-((methylamino)methyl)-1H-indol-6-amine hydrochloride

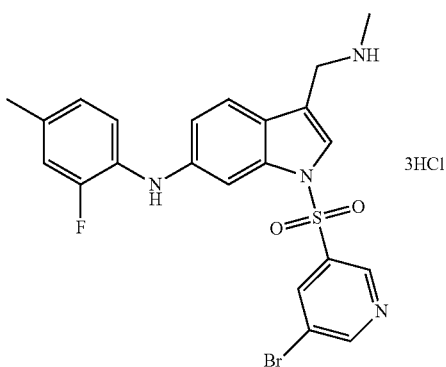 [SMILES: CNCc1cn(S(=O)(=O)c2cncc(Br)c2)c2cc(Nc3ccc(C)cc3F)ccc12]

¹H NMR (300 MHz, CDCl₃): 8.61 (d, 1H), 7.78 (dd, 1H), 7.61 (s, 1H), 7.32 (d, 1H), 7.11 (t, 1H), 6.84-6.90 (m, 3H), 6.67 (d, 1H), 5.72 (s, 1H), 4.47 (s, 2H), 2.72 (d, 3H), 2.31 (s, 3H)

Example 242: Preparation of N-(2-fluoro-4-methylphenyl)-1-((6-methoxypyridin-3-yl)sulfonyl)-3-((methylamino)methyl)-1H-indol-6-amine hydrochloride

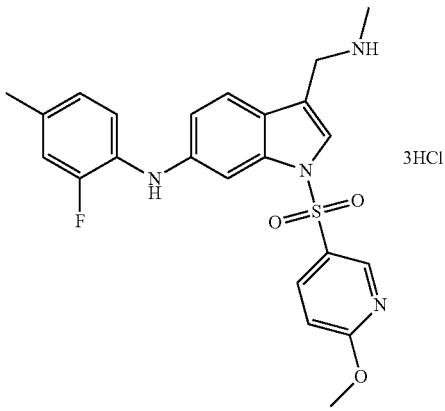 [SMILES: CNCc1cn(S(=O)(=O)c2ccc(OC)nc2)c2cc(Nc3ccc(C)cc3F)ccc12]

¹H NMR (300 MHz, CDCl₃): 8.67 (d, 1H), 7.86 (dd, 1H), 7.62 (s, 1H), 7.31 (d, 1H), 7.16 (t, 1H), 6.89-6.96 (m, 4H), 6.72 (d, 1H), 5.77 (s, 1H), 4.47 (s, 2H), 3.94 (s, 3H), 2.73 (d, 3H), 2.33 (s, 3H)

Example 243: Preparation of N-methyl-1-(6-phenyl-1-(pyridin-3-ylsulfonyl)-1H-indol-3-yl)methanamine The compound was prepared as shown in Reaction Scheme 4 below.

[Reaction Scheme 4]

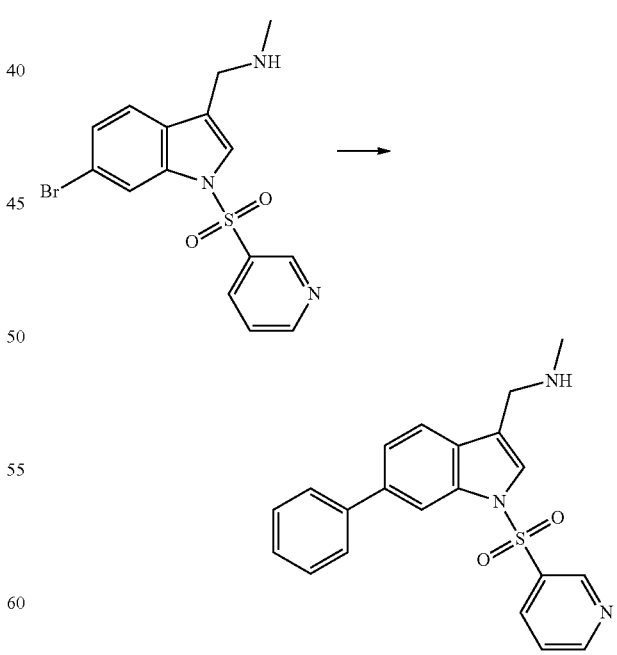

1-(6-bromo-1-(pyridin-3-ylsulfonyl)-1H-indol-3-yl)-N-methylmethanamine (30 mg, 0.08 mmol), phenyl boric acid (12 mg, 0.09 mmol), Tetrakis (triphenylphosphine)palladium(0) (6 mg, 0.005 mmol), and 2 M potassium carbonate (79 μl, 0.1 mmol) were suspended in 0.5 ml of toluene, and stirred at 100° C. for 24 hours. The reaction mixture was filtered with celite, and the resulting filtrate was added with water and then extracted with ethyl acetate. The resulting extract was washed with saturated brine, dried on anhydrous magnesium sulfate, and concentrated under reduced pressure. The resulting residue was purified by silica gel column chromatography (methanol:dichloromethane=1:30 (v/v)) to obtain 19 mg of a title compound (yield: 64%).

$^1$H NMR (500 MHz, CD$_3$OD): 9.11 (d, 1H), 8.74 (dd, 1H), 8.35 (td, 1H), 8.18 (d, 1H), 7.75 (s, 1H), 7.70 (d, 1H), 7.63 (t, 1H), 7.51-7.58 (m, 3H), 7.48 (t, 1H), 7.40 (td, 2H), 3.86 (s, 2H), 2.43 (s, 3H)

In Examples 244 through 250 below, compounds were prepared in the same manner as in Example 243 except that reactants were appropriately changed as necessary depending on the structures of the compounds to be prepared and in consideration of Reaction Scheme 4.

Example 244: Preparation of 1-(6-(3-chlorophenyl)-1-(pyridin-3-ylsulfonyl)-1H-indol-3-yl)-N-methylmethanamine

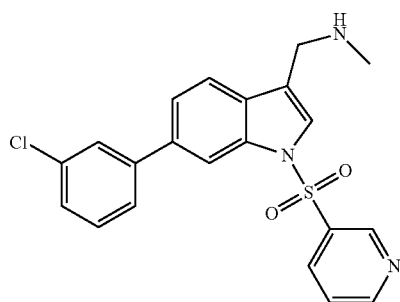 [SMILES: CNCc1cn(S(=O)(=O)c2cccnc2)c2cc(-c3cccc(Cl)c3)ccc12]

$^1$H NMR (500 MHz, CD$_3$OD): 9.13 (d, 1H), 8.76 (dd, 1H), 8.37 (td, 1H), 8.21 (d, 1H), 7.76 (s, 1H), 7.73 (d, 1H), 7.66 (t, 1H), 7.55-7.62 (m, 3H), 7.49 (t, 1H), 7.41 (td, 1H), 3.91 (s, 2H), 2.45 (s, 3H)

Example 245: Preparation of N-(3-(3-((methylamino)methyl)-1-(pyridin-3-ylsulfonyl)-1H-indol-6-yl)phenyl)acetamide

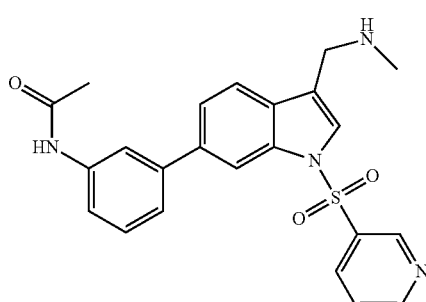

$^1$H NMR (500 MHz, CD$_3$OD): 9.14 (d, 1H), 8.77 (dd, 1H), 8.40 (td, 1H), 8.23 (d, 1H), 7.96 (t, 1H), 7.79 (s, 1H), 7.73 (d, 1H), 7.56-7.61 (m, 3H), 7.42-7.46 (m, 2H), 3.99 (s, 2H), 2.51 (s, 3H), 2.20 (s, 3H)

Example 246: Preparation of 4-(3-((methylamino)methyl)-1-(pyridin-3-ylsulfonyl)-1H-indol-6-yl)aniline

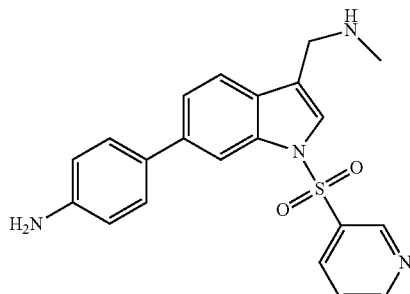

$^1$H NMR (500 MHz, CD$_3$OD): 9.12 (d, 1H), 8.76 (dd, 1H), 8.36 (td, 1H), 8.13 (s, 1H), 7.75 (s, 1H), 7.66 (d, 1H), 7.57 (q, 1H), 7.54 (dd, 1H), 7.44 (d, 2H), 6.85 (d, 2H), 4.03 (s, 2H), 2.54 (s, 3H)

Example 247: Preparation of 1-(6-([1,1'-biphenyl]-4-yl)-1-(pyridin-3-ylsulfonyl)-1H-indol-3-yl)-N-methylmethanamine

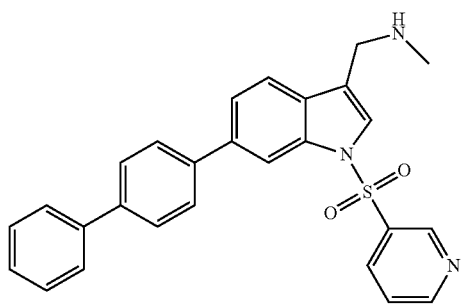 [SMILES: CNCc1cn(S(=O)(=O)c2cccnc2)c2cc(-c3ccc(-c4ccccc4)cc3)ccc12]

$^1$H NMR (500 MHz, CD$_3$OD): 9.20 (d, 1H), 8.83 (dd, 1H), 8.46 (td, 1H), 8.15 (s, 1H), 8.13 (s, 1H), 7.91 (d, 1H), 7.62 (q, 1H), 7.58 (d, 1H), 7.53 (dd, 1H), 6.47 (s, 1H), 3.94 (s, 2H), 2.47 (s, 3H)

Example 248: Preparation of 1-(6-(6-methoxypyridin-3-yl)-1-(pyridin-3-ylsulfonyl)-1H-indol-3-yl)-N-methylmethanamine

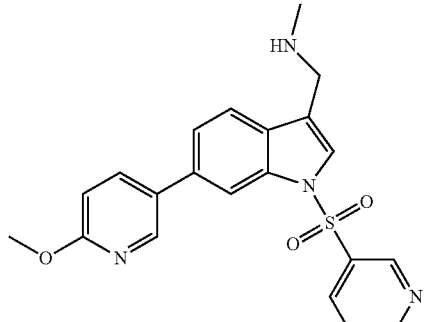

¹H NMR (300 MHz, CDCl₃): 9.09 (s, 1H), 8.76 (d, 1H), 8.40 (d, 1H), 8.12-8.15 (m, 2H), 7.82 (dd, 1H), 7.36-7.50 (m, 4H), 6.86 (d, 1H), 4.50 (s, 2H), 4.00 (s, 3H), 2.74 (s, 3H)

Example 249: Preparation of N-methyl-1-(6-(1-methyl-1H-pyrazol-4-yl)-1-(pyridin-3-ylsulfonyl)-1H-indol-3-yl)methanamine

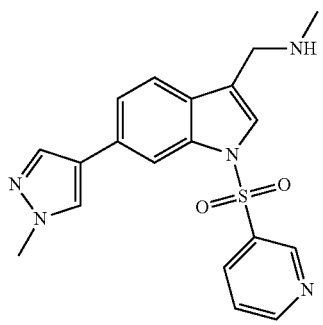 [SMILES: CNCc1cn(S(=O)(=O)c2cccnc2)c2cc(-c3cnn(C)c3)ccc12]

¹H NMR (500 MHz, CD₃OD): 9.19 (d, 1H), 8.80 (dd, 1H), 8.46 (td, 1H), 8.17 (s, 1H), 8.13 (s, 1H), 7.97 (s, 1H), 7.93 (s, 1H), 7.75 (d, 1H), 7.59-7.62 (m, 2H), 4.38 (s, 2H), 3.98 (s, 3H), 2.77 (s, 3H)

Example 250: Preparation of N-methyl-1-(6-(1-methyl-1H-pyrazol-5-yl)-1-(pyridin-3-ylsulfonyl)-1H-indol-3-yl)methanamine

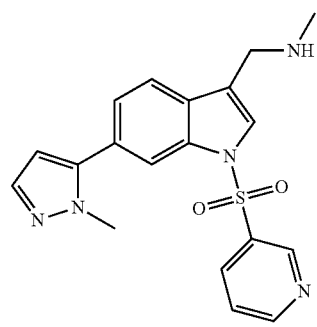 [SMILES: CNCc1cn(S(=O)(=O)c2cccnc2)c2cc(-c3ccnn3C)ccc12]

¹H NMR (500 MHz, CD₃OD): 9.19 (d, 1H), 8.80 (dd, 1H), 8.46 (td, 1H), 8.17 (s, 1H), 8.13 (s, 1H), 7.97 (s, 1H), 7.93 (s, 1H), 7.75 (d, 1H), 7.59-7.62 (m, 2H), 4.44 (s, 2H), 3.90 (s, 3H), 2.80 (s, 3H)

Example 251: Preparation of 1-(6-(4-methoxyphenyl)-1-(pyridin-3-ylsulfonyl)-1H-indol-3-yl)-N-methylmethanamine hydrochloride The compound was prepared as shown in Reaction Scheme 5 below.

[Reaction Scheme 5]

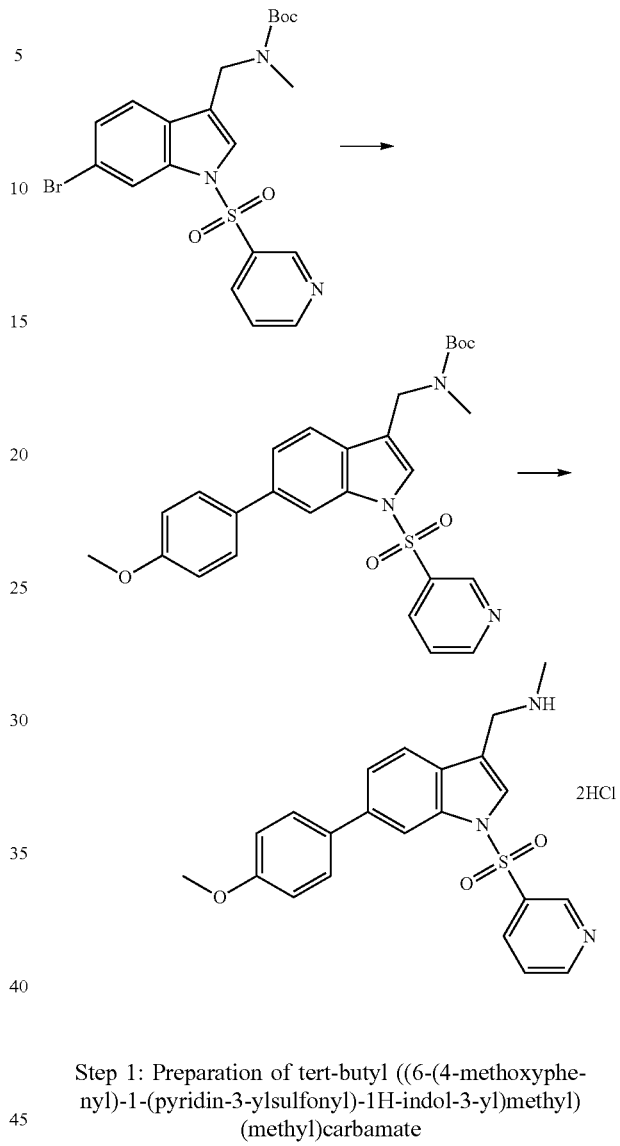

Step 1: Preparation of tert-butyl ((6-(4-methoxyphenyl)-1-(pyridin-3-ylsulfonyl)-1H-indol-3-yl)methyl)(methyl)carbamate Tert-butyl ((6-bromo-1-(pyridin-3-ylsulfonyl)-1H-indol-3-yl)methyl)(methyl)carbamate (20 mg, 0.04 mmol), (4-methoxyphenyl)boronic acid (9.5 mg, 0.06 mmol), Tetrakis(triphenylphosphine)palladium(0) (9.6 mg, 0.008 mmol), and potassium carbonate (11 mg, 0.08 mmol) were suspended in 1 ml of toluene, and then reacted in a microwave reactor maintained at 170° C. for 30 minutes. The reaction mixture was filtered with celite, and the resulting filtrate was added with water and extracted with ethyl acetate. The resulting extract was washed with saturated brine, dried on anhydrous magnesium sulfate and concentrated under reduced pressure. The resulting residue was purified by silica gel column chromatography (ethyl acetate:n-hexane=1:3 (v/v)) to obtain 18 mg of a title compound (yield: 85.7%).

¹H NMR (300 MHz, CDCl₃): 9.11 (d, 1H), 8.75 (dd, 1H), 8.10-8.18 (m, 3H), 7.57 (d, 2H), 7.48 (d, 2H), 7.35-7.39 (m, 1H), 7.02 (d, 3H), 4.52 (s, 2H), 3.90 (s, 3H), 2.75 (s, 3H), 1.50 (s, 9H)

Step 2: Preparation of 1-(6-(4-methoxyphenyl)-1-(pyridin-3-ylsulfonyl)-1H-indol-3-yl)-N-methylmethanamine hydrochloride Tert-butyl ((6-(4-methoxyphenyl)-1-(pyridin-3-ylsulfonyl)-1H-indol-3-yl)methyl)(methyl)carbamate (15 mg, 0.03 mmol) was added with 1 ml of 1.25 M HCl-methanol solution, and stirred at room temperature for 1 hour. The reaction mixture was concentrated under reduced pressure, and the resulting residue was recrystallized with diethyl ether to obtain 7 mg of a title compound (yield: 50%).

$^1$H NMR (300 MHz, CD$_3$OD): 9.24 (s, 1H), 8.83 (s, 1H), 8.50 (d, 1H), 8.18 (s, 1H), 8.02 (s, 1H), 7.79 (d, 1H), 7.59-7.68 (m, 4H), 7.05 (d, 2H), 4.40 (s, 2H), 3.86 (s, 3H), 2.76 (s, 3H)

In Examples 252 through 260 below, compounds were prepared in the same manner as in Example 251 except that reactants were appropriately changed as necessary depending on the structures of the compounds to be prepared and in consideration of Reaction Scheme 5.

Example 252: Preparation of 1-(6-(2-fluoro-4-methylphenyl)-1-(pyridin-3-ylsulfonyl)-1H-indol-3-yl)-N-methylmethanamine hydrochloride

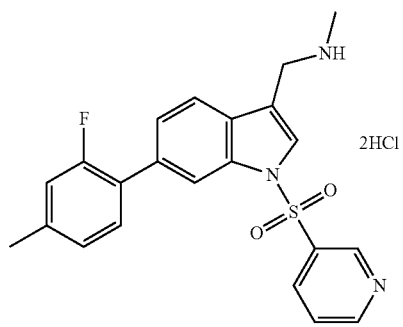 [SMILES: CNCc1cn(S(=O)(=O)c2cccnc2)c2cc(-c3ccc(C)cc3F)ccc12]

$^1$H NMR (300 MHz, CD$_3$OD): 9.14 (s, 1H), 8.79 (d, 1H), 8.40 (d, 1H), 8.19 (s, 1H), 8.03 (s, 1H), 7.81 (d, 1H), 7.59 (q, 1H), 7.54 (d, 1H), 7.40 (t, 1H), 7.13 (d, 1H), 7.09 (d, 1H), 4.40 (s, 2H), 2.76 (s, 3H), 2.41 (s, 3H)

Example 253: Preparation of 1-(6-(2-chloro-4-methylphenyl)-1-(pyridin-3-ylsulfonyl)-1H-indol-3-yl)-N-methylmethanamine hydrochloride

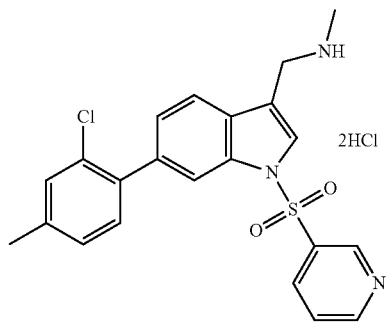 [SMILES: CNCc1cn(S(=O)(=O)c2cccnc2)c2cc(-c3ccc(C)cc3Cl)ccc12]

$^1$H NMR (300 MHz, CD$_3$OD): 9.17 (s, 1H), 8.80 (d, 1H), 8.45 (d, 1H), 8.21 (s, 1H), 8.06 (s, 1H), 7.83 (d, 1H), 7.62 (q, 1H), 7.55 (d, 1H), 7.42 (t, 1H), 7.16 (d, 1H), 7.11 (d, 1H), 4.42 (s, 2H), 2.78 (s, 3H), 2.37 (s, 3H)

Example 254: Preparation of N-methyl-1-(1-(pyridin-3-ylsulfonyl)-6-(2-(trifluoromethyl)pyridin-3-yl)-1H-indol-3-yl)methanamine hydrochloride

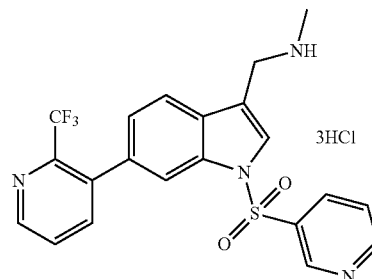

$^1$H NMR (500 MHz, DMSO-d$_6$): 9.33 (s, 2H), 9.26 (s, 1H), 8.91 (s, 1H), 8.72 (s, 1H), 8.50 (s, 1H), 8.46 (d, 1H), 8.29 (s, 1H), 8.26 (d, 1H), 8.18 (d, 1H), 8.06 (d, 1H), 7.94 (d, 1H), 7.68 (s, 1H), 4.36 (s, 2H), 2.61 (s, 3H)

Example 255: Preparation of 1-(6-(6-fluoropyridin-3-yl)-1-(pyridin-3-ylsulfonyl)-1H-indol-3-yl)-N-methylmethanamine hydrochloride

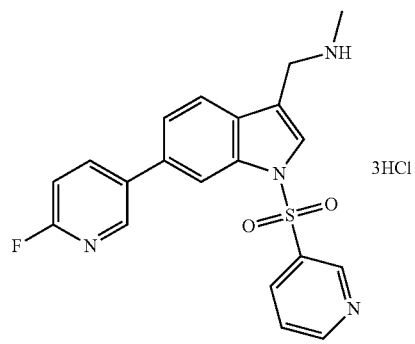 [SMILES: CNCc1cn(S(=O)(=O)c2cccnc2)c2cc(-c3ccc(F)nc3)ccc12]

$^1$H NMR (500 MHz, DMSO-d$_6$): 9.24 (s, 1H), 9.01 (s, 1H), 8.85 (d, 1H), 8.55 (d, 1H), 8.40 (s, 1H), 8.13-8.21 (m, 2H), 7.99 (d, 1H), 7.81 (d, 1H), 7.65-7.71 (m, 2H), 4.27-4.30 (m, 2H), 2.58 (s, 3H)

Example 256: Preparation of 1-(6-(2-fluoropyridin-4-yl)-1-(pyridin-3-ylsulfonyl)-1H-indol-3-yl)-N-methylmethanamine hydrochloride

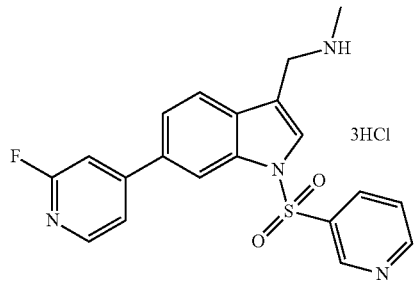 [SMILES: CNCc1cn(S(=O)(=O)c2cccnc2)c2cc(-c3ccnc(F)c3)ccc12]

$^1$H NMR (500 MHz, DMSO-d$_6$): 9.25 (s, 1H), 9.04 (s, 1H), 8.86 (d, 1H), 8.54 (d, 1H), 8.38 (s, 1H), 8.15-8.26 (m, 2H), 8.01 (d, 1H), 7.88 (d, 1H), 7.66-7.72 (m, 2H), 4.28-4.32 (m, 2H), 2.59 (s, 3H)

Example 257: Preparation of 1-(6-(6-fluoro-5-methylpyridin-3-yl)-1-(pyridin-3-ylsulfonyl)-1H-indol-3-yl)-N-methylmethanamine hydrochloride

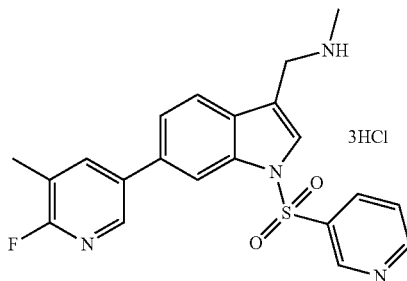

$^1$H NMR (500 MHz, DMSO-d$_6$): 9.26 (s, 1H), 9.07 (s, 1H), 8.84 (d, 1H), 8.54 (d, 1H), 8.37 (s, 1H), 8.12-8.20 (m, 2H), 7.98 (d, 1H), 7.77 (d, 1H), 7.62-7.68 (m, 1H), 4.27-4.29 (m, 2H), 2.55 (s, 3H), 2.34 (s, 3H)

Example 258: Preparation of N-methyl-1-(1-(pyridin-3-ylsulfonyl)-6-(pyrimidin-5-yl)-1H-indol-3-yl)methanamine hydrochloride

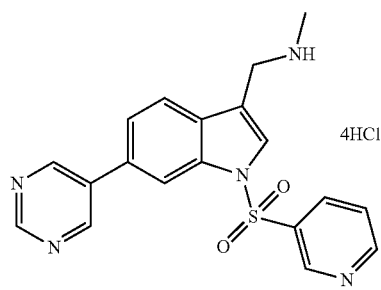 [SMILES: CNCc1cn(S(=O)(=O)c2cccnc2)c2cc(-c3cncnc3)ccc12]

$^1$H NMR (500 MHz, DMSO-d$_6$): 9.35 (d, 2H), 9.27 (s, 1H), 9.21 (s, 1H), 8.91 (s, 1H), 8.66 (d, 1H), 8.34 (s, 1H), 8.25 (s, 1H), 8.07 (d, 1H), 7.85 (d, 1H), 7.69 (s, 1H), 4.36 (s, 2H), 2.54 (s, 3H)

Example 259: Preparation of 1-(6-(2-methoxypyrimidin-5-yl)-1-(pyridin-3-ylsulfonyl)-1H-indol-3-yl)-N-methylmethanamine hydrochloride

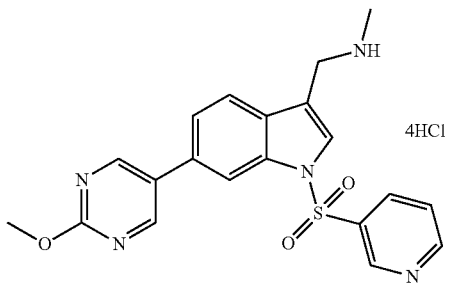 [SMILES: CNCc1cn(S(=O)(=O)c2cccnc2)c2cc(-c3cnc(OC)nc3)ccc12]

$^1$H NMR (500 MHz, DMSO-d$_6$): 9.31 (d, 1H), 9.25 (s, 1H), 9.18 (s, 1H), 8.88 (s, 1H), 8.62 (d, 1H), 8.31 (s, 1H), 8.23 (s, 1H), 8.08 (d, 1H), 7.81 (d, 1H), 7.65 (s, 1H), 4.36 (s, 2H), 3.98 (s, 3H), 2.54 (s, 3H)

Example 260: Preparation of N-methyl-1-(6-(6-methyl-3,4-dihydroquinolin-1(2H)-yl)-1-(pyridin-3-ylsulfonyl)-1H-indol-3-yl)methanamine hydrochloride

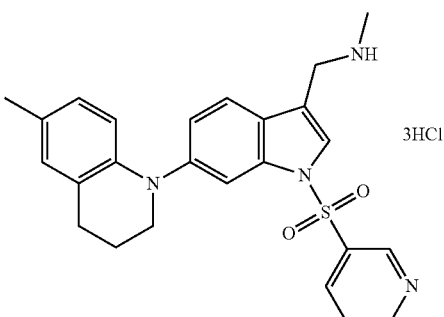

$^1$H NMR (500 MHz, DMSO-d$_6$): 9.00 (d, 2H), 8.64 (d, 1H), 8.32 (d, 1H), 7.99 (t, 1H), 7.62 (s, 1H), 7.25-7.47 (m, 3H), 7.00 (s, 2H), 4.33 (s, 2H), 3.95 (s, 3H), 3.31-3.35 (m, 2H), 2.99-3.05 (m, 2H), 2.52 (s, 3H), 1.99-2.05 (m, 2H)

Example 261: Preparation of 1-(1-((3-(difluoromethoxy)phenyl)sulfonyl)-6-(2-(trifluoromethyl)pyridin-3-yl)-1H-indol-3-yl)-N-methylmethanamine hydrochloride The compound was prepared as shown in Reaction Scheme 6 below.

[Reaction Scheme 6]

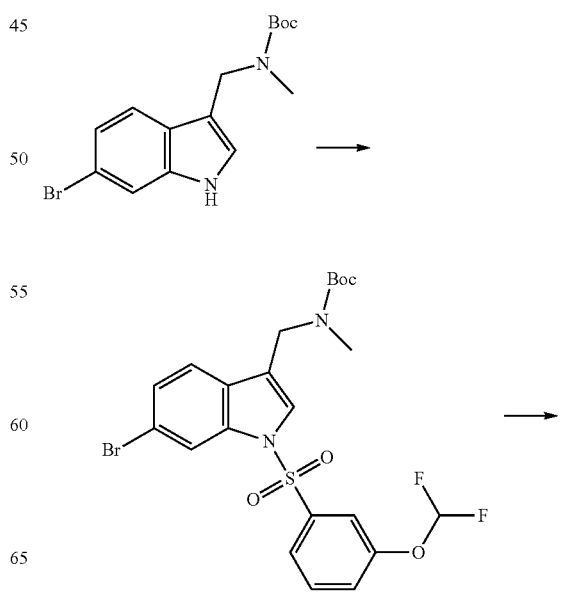

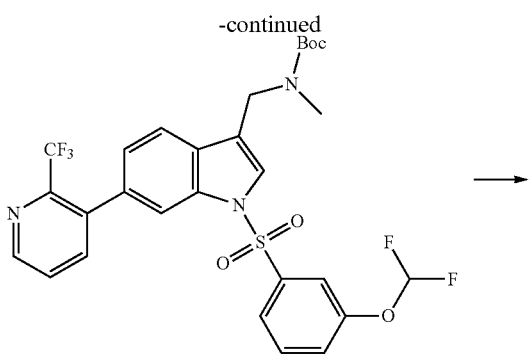

Step 1: Preparation of tert-butyl ((6-bromo-1-((3-(difluoromethoxy)phenyl)sulfonyl)-1H-indol-3-yl)methyl)(methyl)carbamate Tert-butyl ((6-bromo-1H-indol-3-yl)methyl)(methyl)carbamate (1.3 g, 3.8 mmol) was dissolved in 10 ml of N,N-dimethylformamide solution, cooled to 0° C., and dropwisely added with sodium hydride (60% in oil) (306 mg, 7.6 mmol). The reaction mixture was stirred at 0° C. for 30 minutes, added with 3-(difluoromethoxy)benzenesulfonyl chloride (1.39 g, 5.7 mmol), and stirred at room temperature for 2 hours. The resulting reaction mixture was added with an aqueous ammonium chloride solution and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:3 (v/v)) to obtain 850 mg of a title compound (yield: 41%).

$^1$H NMR (300 MHz, CDCl$_3$): 8.18 (s, 1H), 7.76 (d, 1H), 7.61 (s, 1H), 7.45-7.51 (m, 3H), 7.28 (dd, 1H), 6.45 (t, 1H), 4.55 (s, 2H), 2.78 (s, 3H), 1.61 (s, 9H)

Step 2: Preparation of tert-butyl ((1-((3-(difluoromethoxy)phenyl)sulfonyl)-6-(2-(trifluoromethyl)pyridin-3-yl)-1H-indol-3-yl)methyl)(methyl)carbamate Tert-butyl ((6-bromo-1-((3-(difluoromethoxy)phenyl)sulfonyl)-1H-indol-3-yl)methyl)(methyl)carbamate (50 mg, 0.09 mmol), (2-(trifluoromethyl)pyridin-3-yl) boric acid (26 mg, 0.1 mmol), Tetrakis(triphenylphosphine)palladium(0) (10.6 mg, 0.009 mmol), and potassium carbonate (31 mg, 0.2 mmol) were suspended in 0.5 ml of toluene, and reacted in a microwave reactor maintained at 170° C. for 30 minutes. The reaction mixture was filtered with celite, and the resulting filtrate was added with water and extracted with ethyl acetate. The resulting extract was washed with saturated brine, dried on anhydrous magnesium sulfate and concentrated under reduced pressure. The resulting residue was purified by silica gel column chromatography (methanol:dichloromethane=1:30 (v/v)) to obtain 10 mg of a title compound (yield: 17.8%).

$^1$H NMR (300 MHz, CDCl$_3$): 8.79 (d, 2H), 8.17 (s, 1H), 7.78 (d, 1H), 7.64 (s, 1H), 7.48-7.53 (m, 3H), 7.31 (dd, 1H), 7.05 (d, 1H), 6.48 (t, 1H), 4.56 (s, 2H), 2.76-2.81 (m, 3H), 1.57 (s, 9H)

Step 3: Preparation of 1-(1-((3-(difluoromethoxy)phenyl)sulfonyl)-6-(2-(trifluoromethyl)pyridin-3-yl)-1H-indol-3-yl)-N-methylmethanamine hydrochloride Tert-butyl ((1-((3-(difluoromethoxy)phenyl)sulfonyl)-6-(2-(trifluoromethyl)pyridin-3-yl)-1H-indol-3-yl)methyl)(methyl)carbamate (10 mg, 0.01 mmol) was added with 1 ml of 1.25 M HCl-methanol solution, and stirred at room temperature for 15 hours. The reaction mixture was concentrated under reduced pressure, and the resulting residue was recrystallized with diethyl ether to obtain 4 mg of a title compound (yield: 42%).

$^1$H NMR (500 MHz, CDCl$_3$): 8.90 (s, 1H), 8.63 (s, 1H), 7.81 (td, 1H), 7.72 (s, 1H), 7.47 (d, 1H), 7.36 (s, 1H), 7.15 (d, 1H), 7.09 (dd, 1H), 6.78-7.08 (m, 2H), 6.21 (s, 1H), 3.93 (s, 3H), 3.83 (s, 2H), 2.49 (s, 3H)

In Examples 262 through 266 below, compounds were prepared in the same manner as in Example 261 except that reactants were appropriately changed as necessary depending on the structures of the compounds to be prepared and in consideration of Reaction Scheme 6.

Example 262: Preparation of 1-(1-((3-(difluoromethoxy)phenyl)sulfonyl)-6-(2-fluoropyridin-4-yl)-1H-indol-3-yl)-N-methylmethanamine hydrochloride

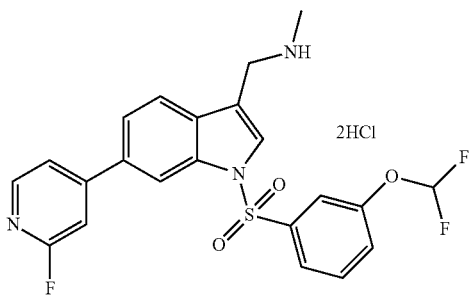 [SMILES: CNCc1cn(S(=O)(=O)c2cccc(OC(F)F)c2)c2cc(-c3ccnc(F)c3)ccc12]

$^1$H NMR (500 MHz, CDCl$_3$): 8.29 (d, 1H), 8.21 (s, 1H), 7.79 (br, 1H), 7.71 (d, 1H), 7.66 (s, 1H), 7.51-7.53 (m, 2H), 7.43-7.48 (m, 2H), 7.32 (dd, 1H), 7.16 (s, 1H), 6.49 (t, 1H), 4.54 (s, 2H), 2.74 (s, 3H)

Example 263: Preparation of 1-(1-((3-(difluoromethoxy)phenyl)sulfonyl)-6-(6-fluoro-5-methylpyridin-3-yl)-1H-indol-3-yl)-N-methylmethanamine hydrochloride

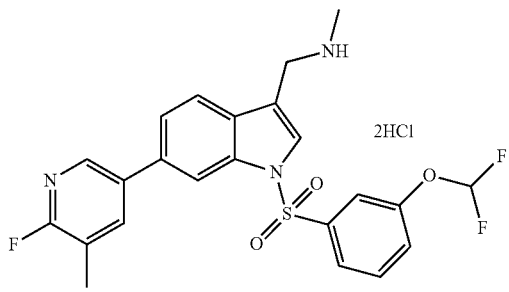 [SMILES: CNCc1cn(S(=O)(=O)c2cccc(OC(F)F)c2)c2cc(-c3cnc(F)c(C)c3)ccc12]

$^1$H NMR (500 MHz, CDCl$_3$): 8.31 (d, 1H), 8.25 (s, 1H), 7.83 (br, 1H), 7.75 (d, 1H), 7.68 (s, 1H), 7.55-7.58 (m, 2H), 7.38-7.42 (m, 1H), 7.31 (dd, 1H), 7.14 (s, 1H), 6.49 (t, 1H), 4.54 (s, 2H), 2.74 (s, 3H), 2.31 (s, 3H)

Example 264: Preparation of 1-(1-((3-(difluoromethoxy)phenyl)sulfonyl)-6-(pyrimidin-5-yl)-1H-indol-3-yl)-N-methylmethanamine hydrochloride

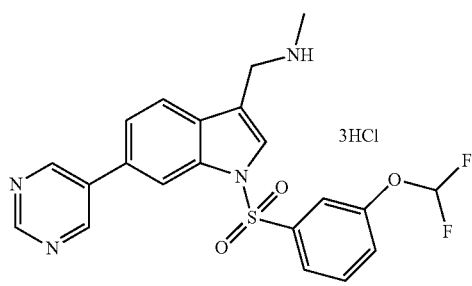 [SMILES: CNCc1cn(S(=O)(=O)c2cccc(OC(F)F)c2)c2cc(-c3cncnc3)ccc12]

$^1$H NMR (500 MHz, CDCl$_3$): 9.23 (s, 1H), 8.98 (s, 2H), 8.15 (s, 1H), 7.82 (br, 1H), 7.72 (dd, 1H), 7.65 (s, 1H), 7.53 (s, 1H), 7.46-7.51 (m, 2H), 7.32 (d, 1H), 6.50 (t, 1H), 4.55 (s, 2H), 2.75 (s, 3H)

Example 265: Preparation of 1-(1-((4-(difluoromethoxy)phenyl)sulfonyl)-6-(pyrimidin-5-yl)-1H-indol-3-yl)-N-methylmethanamine hydrochloride

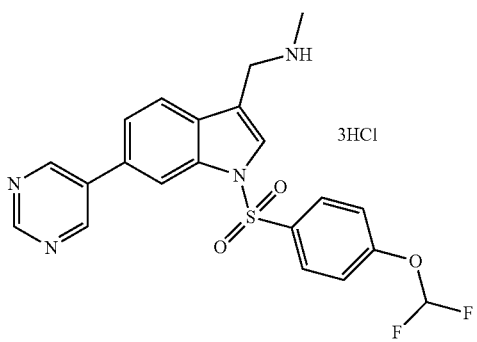 [SMILES: CNCc1cn(S(=O)(=O)c2ccc(OC(F)F)cc2)c2cc(-c3cncnc3)ccc12]

$^1$H NMR (500 MHz, CDCl$_3$): 9.18 (s, 2H), 8.95 (br, 2H), 8.22 (d, 2H), 8.11 (s, 1H), 7.98 (d, 1H), 7.77 (d, 1H), 7.33 (d, 2H), 5.91 (s, 1H), 4.29 (s, 2H), 2.55 (s, 3H)

Example 266: Preparation of 1-(1-((3-(difluoromethoxy)phenyl)sulfonyl)-6-(2-methoxypyrimidin-5-yl)-1H-indol-3-yl)-N-methylmethanamine hydrochloride

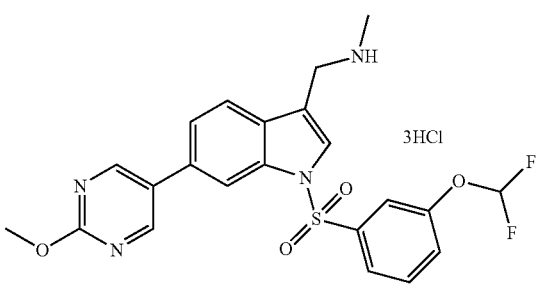 [SMILES: CNCc1cn(S(=O)(=O)c2cccc(OC(F)F)c2)c2cc(-c3cnc(OC)nc3)ccc12]

$^1$H NMR (500 MHz, CDCl$_3$): 9.21 (s, 2H), 8.98 (br, 1H), 8.24 (d, 2H), 8.15 (s, 1H), 7.99 (d, 1H), 7.79 (d, 1H), 7.36 (d, 2H), 5.88 (s, 1H), 4.29 (s, 2H), 3.99 (s, 3H), 2.53 (s, 3H)

Example 267: Preparation of 1-(6-(2-chloro-4-methylbenzyl)-1-(pyridin-3-ylsulfonyl)-1H-indol-3-yl)-N-methylmethanamine hydrochloride The compound was prepared as shown in Reaction Scheme 7 below.

[Reaction Scheme 7]

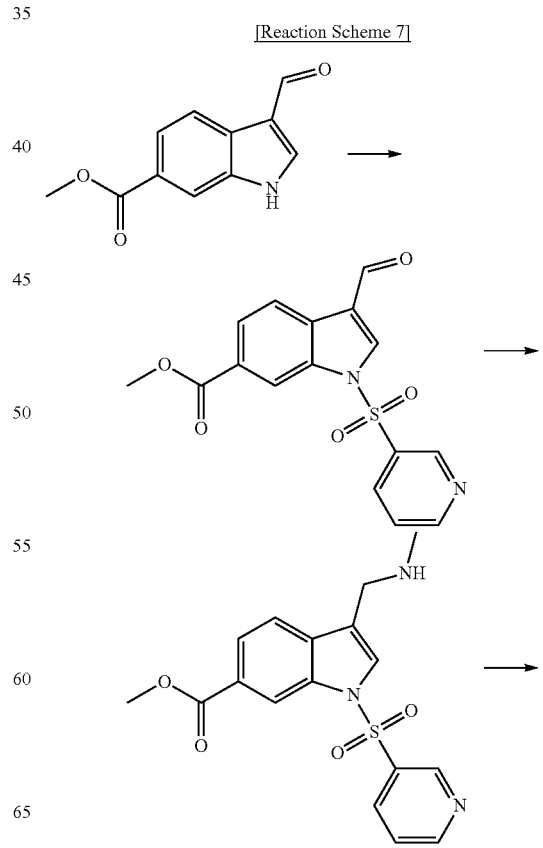

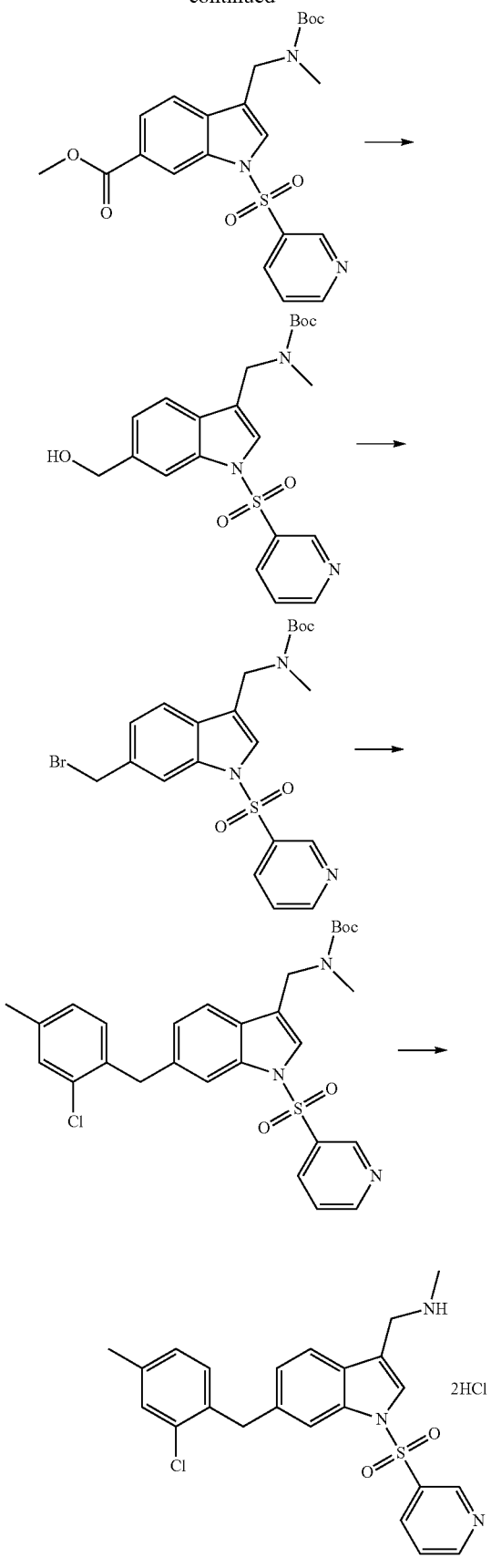

Step 1: Preparation of methyl 3-formyl-1-(pyridin-3-ylsulfonyl)-1H-indol-6-carboxylate Methyl 3-formyl-1H-indol-6-carboxylate (1 g, 4.9 mmol) was dissolved in 50 ml of N,N-dimethylformamide solution, cooled to 0° C., and dropwisely added with sodium hydride (60% in oil) (295 mg, 7.3 mmol). The reaction mixture was stirred at 0° C. for 30 minutes, added with pyridin-3-sulfonyl chloride (1.3 g, 7.3 mmol) prepared in Step 1 of Example 1, and stirred at room temperature for 3 hours. The resulting reaction mixture was added with water and recrystallized to obtain 1.2 g of a title compound (yield: 71%).

$^1$H NMR (500 MHz, CDCl$_3$): 10.14 (s, 1H), 9.25 (d, 1H), 8.87 (dd, 1H), 8.67 (d, 1H), 8.35 (d, 2H), 8.29 (t, 1H), 8.10 (t, 1H), 7.51 (dd, 1H), 4.00 (s, 3H)

Step 2: Preparation of methyl 3-((methylamino)methyl)-1-(pyridin-3-ylsulfonyl)-1H-indol-6-carboxylate Methyl 3-formyl-1-(pyridin-3-ylsulfonyl)-1H-indol-6-carboxylate (1.2 g, 3.4 mmol) prepared in Step 1, dissolved in 40 ml of methanol, was added with sodium cyanoborohydride (1.1 g, 17.4 mmole), zinc chloride (474 mg, 3.4 mmole) and 2 M methylamine-tetrahydrofuran solution (5.2 ml, 10.4 mmole), and stirred at room temperature for 5 hours. The resultant was added with a saturated sodium bicarbonate solution and extracted with ethyl acetate. The resulting extract was washed with saturated brine, dried on anhydrous magnesium sulfate, and concentrated under reduced pressure. The resulting residue was purified by silica gel column chromatography (dichloromethane:methanol=10:1 (v/v)) to obtain 500 mg of a title compound (yield: 40%).

$^1$H NMR (500 MHz, CDCl$_3$): 9.25 (d, 1H), 8.85-8.88 (m, 1H), 8.67 (d, 1H), 8.32-8.63 (m, 2H), 8.29 (t, 1H), 8.10 (t, 1H), 7.51 (q, 1H), 7.27 (d, 1H), 4.00 (s, 3H)

Step 3: Preparation of methyl 3-(((tert-butoxycarbonyl)(methyl)amino)methyl)-1-(pyridin-3-ylsulfonyl)-1H-indol-6-carboxylate Methyl 3-((methylamino)methyl)-1-(pyridin-3-ylsulfonyl)-1H-indol-6-carboxylate (500 mg, 1.4 mmol) prepared in Step 2 was dissolved in 15 ml of dichloromethane, added with triethylamine (233 μl, 1.6 mmole) and di-tert-butyl dicarbonate (455 mg, 2.1 mmole), and stirred at room temperature for 3 hours. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 350 mg of a title compound (yield: 54.8%).

$^1$H NMR (500 MHz, CDCl$_3$): 9.09 (d, 1H), 8.76 (q, 1H), 8.66 (d, 1H), 8.15 (t, 1H), 7.95 (s, 1H), 7.58-7.70 (m, 2H), 7.37-7.41 (m, 1H), 4.50 (s, 2H), 3.95 (d, 3H), 2.72 (s, 3H), 1.46 (s, 9H)

Step 4: Preparation of tert-butyl ((6-(hydroxymethyl)-1-(pyridin-3-ylsulfonyl)-1H-indol-3-yl)methyl)(methyl)carbamate Methyl 3-(((tert-butoxycarbonyl)(methyl)amino)methyl)-1-(pyridin-3-ylsulfonyl)-1H-indol-6-carboxylate (350 mg, 0.7 mmol) prepared in Step 3 was dissolved in 10 ml of tetrahydrofuran solution, added with 1.0 M diisobutylaluminum hydride-tetrahydrofuran solution (3 ml, 3.0 mmole), and stirred at room temperature for 5 hours. The resulting reaction mixture was added with an aqueous ammonium chloride solution, and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate: n-hexane=1:1 (v/v)) to obtain 200 mg of a title compound (yield: 61%).

$^1$H NMR (500 MHz, CDCl$_3$): 9.08 (d, 1H), 8.74 (d, 1H), 8.11 (dd, 1H), 8.00 (s, 1H), 7.54-7.63 (m, 2H), 7.44 (s, 1H), 7.39 (q, 2H), 4.93 (s, 2H), 4.55 (s, 2H), 2.71-2.78 (m, 3H), 1.48 (s, 9H)

Step 5: Preparation of tert-butyl ((6-(bromomethyl)-1-(pyridin-3-ylsulfonyl)-1H-indol-3-yl)methyl)(methyl)carbamate Tert-butyl ((6-(hydroxymethyl)-1-(pyridin-3-ylsulfonyl)-1H-indol-3-yl)methyl)(methyl)carbamate (50 mg, 1.1 mmol) prepared in Step 4 was dissolved in 2 ml of dichloromethane, added with triphenylphosphine (32 mg, 0.1 mmole) and tetrabromomethane (42 mg, 0.1 mmole), and stirred at room temperature for 3 hours. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate: n-hexane=1:2 (v/v)) to obtain 40 mg of a title compound (yield: 70%).

$^1$H NMR (500 MHz, CDCl$_3$): 9.08 (s, 1H), 8.77 (d, 1H), 8.14 (d, 1H), 8.04 (s, 1H), 7.63 (br, 1H), 7.46 (s, 1H), 7.40 (t, 1H), 7.31 (d, 1H), 4.63 (s, 2H), 4.49 (s, 2H), 2.71-2.77 (m, 3H), 1.48 (s, 9H)

Step 6: Preparation of tert-butyl ((6-(2-chloro-4-methylbenzyl)-1-(pyridin-3-ylsulfonyl)-1H-indol-3-yl)methyl)(methyl)carbamate Tert-butyl ((6-(bromomethyl)-1-(pyridin-3-ylsulfonyl)-1H-indol-3-yl)methyl)(methyl)carbamate (40 mg, 0.08 mmol) prepared in Step 5, (2-chloro-4-methylphenyl)boronic acid (20 mg, 0.1 mmol), [1,1'-Bis(diphenylphosphino)ferrocene]dichloropalladium(II)dichloromethane (16 mg, 0.01 mmol), and 2 M aqueous sodium carbonate solution (162 μl, 0.3 mmol) were suspended in 3 ml of dimethoxyethane solution, and reacted in a microwaver reactor maintained at 120° C. for 10 minutes. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:1 (v/v)) to obtain 30 mg of a title compound (yield: 68.8%).

$^1$H NMR (500 MHz, CD$_3$OD): 9.10 (d, 1H), 8.81 (d, 1H), 8.26 (d, 1H), 7.95 (s, 1H), 7.81 (s, 1H), 7.69 (d, 1H), 7.56 (q, 1H), 7.38 (q, 1H), 7.28-7.32 (m, 2H), 7.14 (td, 1H), 4.35 (s, 2H), 4.22 (s, 2H), 2.74 (s, 3H), 2.33 (s, 3H), 1.36 (s, 9H)

Step 7: Preparation of 1-(6-(2-chloro-4-methylbenzyl)-1-(pyridin-3-ylsulfonyl)-1H-indol-3-yl)-N-methylmethanamine hydrochloride Tert-butyl ((6-(2-chloro-4-methylbenzyl)-1-(pyridin-3-ylsulfonyl)-1H-indol-3-yl)methyl)(methyl)carbamate (11.7 mg, 0.02 mmol) prepared in Step 6 was added with 1 ml of 1.25 M HCl-methanol solution, and stirred at room temperature for 6 hours. The reaction mixture was concentrated under reduced pressure, and the resulting residue was recrystallized with diethyl ether to obtain 4 mg of a title compound (yield: 36.3%).

$^1$H NMR (500 MHz, CD$_3$OD): 9.01 (d, 1H), 8.80 (d, 1H), 8.22 (td, 1H), 7.94 (s, 1H), 7.78 (s, 1H), 7.66 (d, 1H), 7.54 (q, 1H), 7.27-7.30 (m, 2H), 7.21 (d, 1H), 7.15 (d, 1H), 4.36 (s, 2H), 4.24 (s, 2H), 2.74 (s, 3H), 2.37 (s, 3H)

In Examples 268 through 298 below, compounds were prepared in the same manner as in Example 267 except that reactants were appropriately changed as necessary depending on the structures of the compounds to be prepared and in consideration of Reaction Scheme 7.

Example 268: Preparation of 1-(6-benzyl-(pyridin-3-ylsulfonyl)-1H-indol-3-yl)-N-methylmethanamine hydrochloride

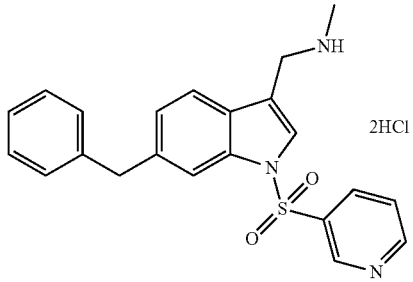 [SMILES: CNCc1cn(S(=O)(=O)c2cccnc2)c2cc(Cc3ccccc3)ccc12]

$^1$H NMR (500 MHz, CD$_3$OD): 9.14 (d, 1H), 8.82 (d, 1H), 8.39 (dd, 1H), 7.95 (s, 1H), 7.83 (s, 1H), 7.64-7.66 (m, 2H), 7.18-7.39 (m, 6H), 4.34 (s, 2H), 4.12 (s, 2H), 2.72 (s, 3H)

Example 269: Preparation of 1-(6-(2-fluorobenzyl)-1-(pyridin-3-ylsulfonyl)-1H-indol-3-yl)-N-methyl-methanamine hydrochloride

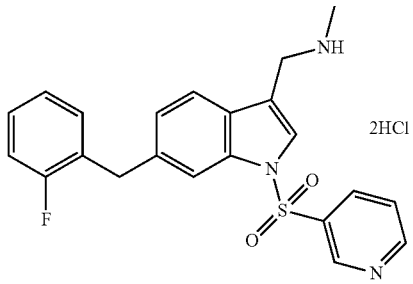 [SMILES: CNCc1cn(S(=O)(=O)c2cccnc2)c2cc(Cc3ccccc3F)ccc12]

$^1$H NMR (500 MHz, CD$_3$OD): 9.03 (d, 1H), 8.77 (dd, 1H), 8.27 (dd, 1H), 7.92 (s, 1H), 7.84 (s, 1H), 7.64 (d, 1H), 7.55 (dd, 1H), 7.25-7.29 (m, 3H), 7.08-7.15 (m, 2H), 4.37 (s, 2H), 4.15 (s, 2H), 2.71 (s, 3H)

Example 270: Preparation of N-methyl-1-(6-(4-methylbenzyl)-1-(pyridin-3-ylsulfonyl)-1H-indol-3-yl)methanamine hydrochloride

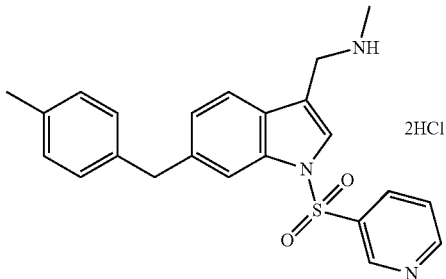 [SMILES: CNCc1cn(S(=O)(=O)c2cccnc2)c2cc(Cc3ccc(C)cc3)ccc12]

¹H NMR (500 MHz, CD₃OD): 9.04 (s, 1H), 8.78 (dd, 1H), 8.26 (dd, 1H), 7.91 (s, 1H), 7.80 (s, 1H), 7.63 (d, 1H), 7.53 (dd, 1H), 7.25 (d, 1H), 7.12 (d, 2H), 7.06 (d, 2H), 4.33 (s, 2H), 4.07 (s, 2H), 2.72 (s, 3H), 2.32 (s, 3H)

Example 271: Preparation of N-methyl-1-(1-(pyridin-3-ylsulfonyl)-6-(4-(trifluoromethoxy)benzyl)-1H-indol-3-yl)methanamine hydrochloride

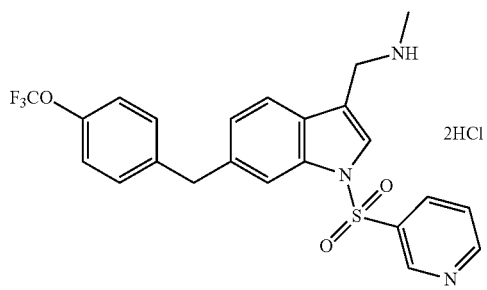 [SMILES: CNCc1cn(S(=O)(=O)c2cccnc2)c2cc(Cc3ccc(OC(F)(F)F)cc3)ccc12]

¹H NMR (500 MHz, CD₃OD): 9.09 (s, 1H), 8.78 (dd, 1H), 8.33 (dd, 1H), 7.94 (s, 1H), 7.86 (s, 1H), 7.66 (d, 1H), 7.57 (dd, 1H), 7.25-7.30 (m, 3H), 7.21 (d, 2H), 4.34 (s, 2H), 4.16 (s, 2H), 2.72 (s, 3H)

Example 272: Preparation of 1-(6-(2-fluoro-4-methylbenzyl)-1-(pyridin-3-ylsulfonyl)-1H-indol-3-yl)-N-methylmethanamine hydrochloride

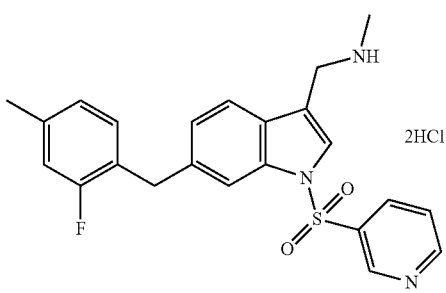 [SMILES: CNCc1cn(S(=O)(=O)c2cccnc2)c2cc(Cc3ccc(C)cc3F)ccc12]

¹H NMR (500 MHz, CD₃OD): 9.06 (d, 1H), 8.80 (d, 1H), 8.26 (d, 1H), 7.98 (s, 1H), 7.79 (s, 1H), 7.69 (d, 1H), 7.58 (q, 1H), 7.36 (q, 1H), 7.27-7.32 (m, 2H), 7.16 (td, 1H), 4.33 (s, 2H), 4.26 (s, 2H), 2.73 (s, 3H), 2.34 (s, 3H)

Example 273: Preparation of 1-(6-(2-chloro-4-fluorobenzyl)-1-(pyridin-3-ylsulfonyl)-1H-indol-3-yl)-N-methylmethanamine hydrochloride

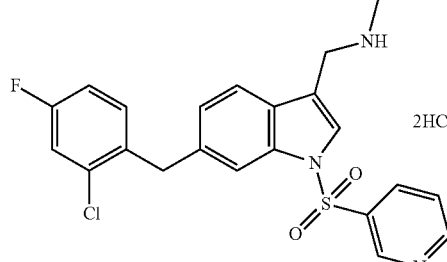

¹H NMR (500 MHz, CD₃OD): 9.08 (d, 1H), 8.78 (d, 1H), 8.24 (d, 1H), 7.93 (s, 1H), 7.78 (s, 1H), 7.66 (d, 1H), 7.54 (q, 1H), 7.34 (q, 1H), 7.25-7.29 (m, 2H), 7.10 (td, 1H), 4.34 (s, 2H), 4.25 (s, 2H), 2.73 (s, 3H)

Example 274: Preparation of 1-(6-(4-chloro-2-fluorobenzyl)-1-(pyridin-3-ylsulfonyl)-1H-indol-3-yl)-N-methylmethanamine hydrochloride

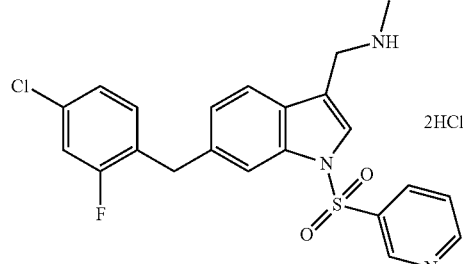

¹H NMR (500 MHz, CD₃OD): 9.05 (s, 1H), 8.79 (s, 1H), 8.29 (d, 1H), 7.94 (s, 1H), 7.86 (s, 1H), 7.66 (d, 1H), 7.55 (q, 1H), 7.17-7.28 (m, 4H), 4.34 (s, 2H), 4.14 (s, 2H), 2.72 (s, 3H)

Example 275: Preparation of 1-(6-(4-chloro-2-(trifluoromethyl)benzyl)-1-(pyridin-3-ylsulfonyl)-1H-indol-3-yl)-N-methylmethanamine hydrochloride

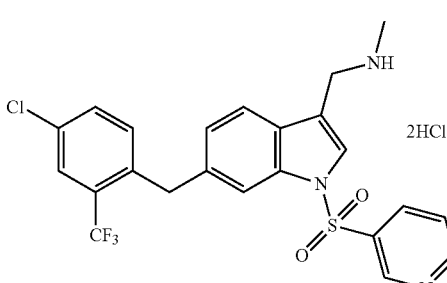

¹H NMR (500 MHz, CD₃OD): 8.99 (s, 1H), 8.79 (d, 1H), 8.24 (dd, 1H), 7.95 (s, 1H), 7.77 (s, 1H), 7.72 (s, 1H), 7.68 (d, 1H), 7.61 (dd, 1H), 7.54 (dd, 1H), 7.27 (d, 1H), 7.20 (d, 1H), 4.33 (s, 2H), 4.34 (s, 2H), 2.73 (s, 3H)

Example 276: Preparation of 1-(6-(2-chloro-4-(trifluoromethyl)benzyl)-1-(pyridin-3-ylsulfonyl)-1H-indol-3-yl)-N-methylmethanamine hydrochloride

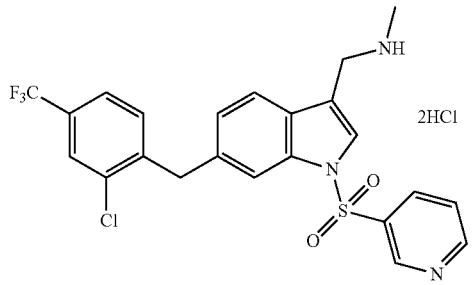 [SMILES: CNCc1cn(S(=O)(=O)c2cccnc2)c2cc(Cc3ccc(C(F)(F)F)cc3Cl)ccc12]

¹H NMR (500 MHz, CD₃OD): 8.96 (d, 1H), 8.79 (dd, 1H), 8.18 (td, 1H), 7.93 (s, 1H), 7.70 (s, 1H), 7.67 (d, 1H), 7.53 (q, 1H), 7.37 (d, 1H), 7.25 (t, 1H), 7.14 (d, 1H), 7.08 (d, 1H), 4.34 (s, 2H), 4.2

Example 277: Preparation of 1-(6-(2-fluoro-4-methoxybenzyl)-1-(pyridin-3-ylsulfonyl)-1H-indol-3-yl)-N-methylmethanamine hydrochloride

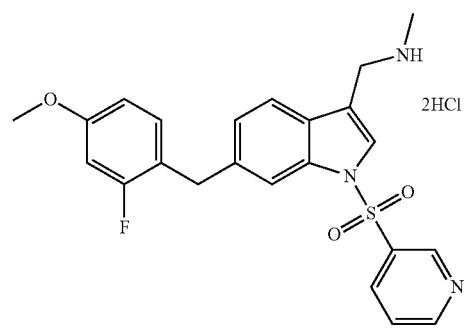 [SMILES: CNCc1cn(S(=O)(=O)c2cccnc2)c2cc(Cc3ccc(OC)cc3F)ccc12]

¹H NMR (500 MHz, CD₃OD): 9.02 (d, 1H), 8.79 (dd, 1H), 8.27 (td, 1H), 7.94 (s, 1H), 7.84 (s, 1H), 7.66 (d, 1H), 7.54 (q, 1H), 7.29 (d, 1H), 7.18 (t, 1H), 6.73-6.77 (m, 2H), 4.36 (s, 2H), 4.10 (s, 2H), 3.82 (s, 3H), 2.74 (s, 3H)

Example 278: Preparation of N-methyl-1-(6-(2-methyl-4-(trifluoromethoxy)benzyl)-1-(pyridin-3-ylsulfonyl)-1H-indol-3-yl)methanamine hydrochloride

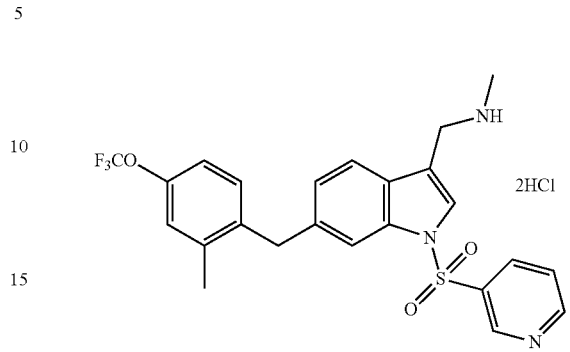

¹H NMR (500 MHz, CD₃OD): 9.04 (d, 1H), 8.80 (d, 1H), 8.28 (td, 1H), 7.98 (s, 1H), 7.87 (s, 1H), 7.79 (s, 1H), 7.70 (d, 1H), 7.64 (d, 1H), 7.53-7.56 (m, 2H), 7.29 (dd, 1H), 4.38 (d, 4H), 2.75 (s, 3H)

Example 279: Preparation of 1-(6-(2-fluoro-4-(trifluoromethoxy)benzyl)-1-(pyridin-3-ylsulfonyl)-1H-indol-3-yl)-N-methylmethanamine hydrochloride

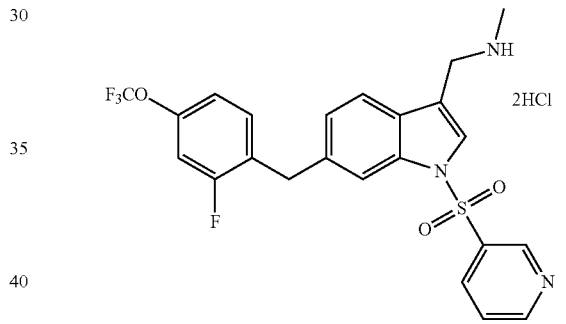

¹H NMR (500 MHz, CD₃OD): 9.06 (d, 1H), 8.79 (dd, 1H), 8.30 (td, 1H), 7.96 (s, 1H), 7.91 (s, 1H), 7.69 (d, 1H), 7.56 (q, 1H), 7.40 (t, 1H), 7.31 (d, 1H), 7.16 (d, 1H), 7.13 (d, 1H), 4.36 (s, 2H), 4.21 (s, 2H), 2.74 (s, 3H)

Example 280: Preparation of 1-(6-(2-chloro-4-(trifluoromethoxy)benzyl)-1-(pyridin-3-ylsulfonyl)-1H-indol-3-yl)-N-methylmethanamine hydrochloride

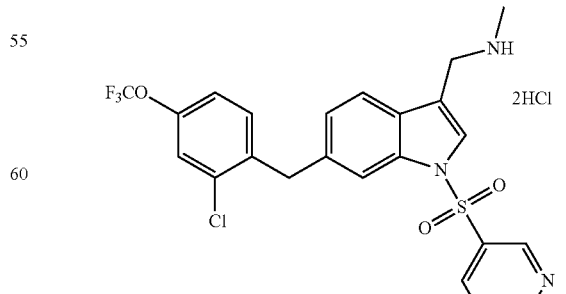

¹H NMR (500 MHz, CD₃OD): 9.04 (d, 1H), 8.79 (d, 1H), 8.27 (td, 1H), 7.96 (s, 1H), 7.83 (s, 1H), 7.69 (d, 1H), 7.55 (q, 1H), 7.46 (s, 1H), 7.45 (d, 1H), 7.29 (d, 2H), 4.36 (s, 2H), 4.32 (s, 2H), 2.75 (s, 3H)

Example 281: Preparation of 1-(6-(2-methoxy-4-(trifluoromethoxy)benzyl)-1-(pyridin-3-ylsulfonyl)-1H-indol-3-yl)-N-methylmethanamine hydrochloride

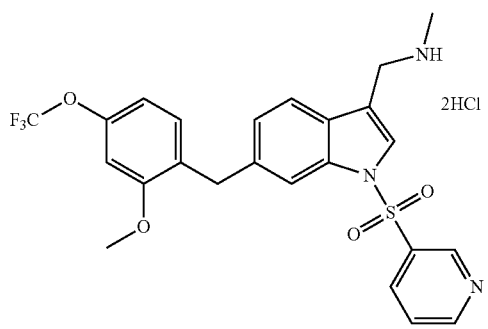 [SMILES: CNCc1cn(S(=O)(=O)c2cccnc2)c2cc(Cc3ccc(OC(F)(F)F)cc3OC)ccc12]

¹H NMR (500 MHz, CD₃OD): 9.08 (d, 1H), 8.80 (d, 1H), 8.34 (td, 1H), 7.94 (s, 1H), 7.84 (s, 1H), 7.64 (d, 1H), 7.60 (q, 1H), 7.27 (d, 1H), 7.21 (d, 1H), 6.90 (s, 1H), 6.84 (d, 1H), 4.34 (s, 2H), 4.10 (s, 2H), 3.84 (s, 3H), 2.72 (s, 3H)

Example 282: Preparation of 1-(6-((2-methoxypyridin-3-yl)methyl)-1-(pyridin-3-ylsulfonyl)-1H-indol-3-yl)-N-methylmethanamine hydrochloride

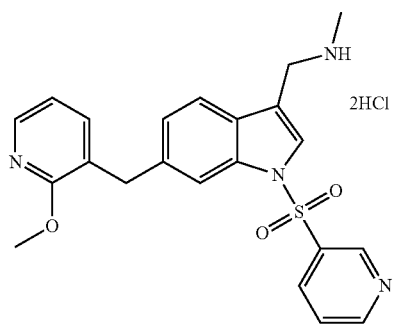 [SMILES: CNCc1cn(S(=O)(=O)c2cccnc2)c2cc(Cc3cccnc3OC)ccc12]

¹H NMR (500 MHz, CD₃OD): 9.16 (br, 1H), 8.80 (br, 1H), 8.40 (d, 1H), 8.05 (s, 1H), 7.91 (s, 1H), 7.67 (t, 2H), 7.58 (br, 1H), 7.39 (br, 2H), 7.32 (d, 1H), 4.36 (d, 4H), 4.02 (s, 3H), 2.74 (s, 3H)

Example 283: Preparation of 1-(6-((2-fluoro-6-methylpyridin-3-yl)methyl)-1-(pyridin-3-ylsulfonyl)-1H-indol-3-yl)-N-methylmethanamine hydrochloride

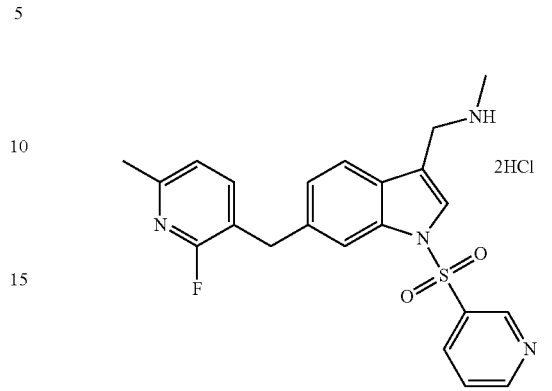

¹H NMR (500 MHz, CD₃OD): 9.07 (br, 1H), 8.80 (d, 1H), 8.32 (d, 1H), 7.97 (s, 1H), 7.91 (s, 1H), 7.68-7.73 (m, 2H), 7.58 (q, 1H), 7.29 (d, 1H), 7.17 (d, 1H), 4.36 (s, 2H), 4.15 (s, 2H), 2.74 (s, 3H), 2.48 (s, 3H)

Example 284: Preparation of 1-(6-((2-chloro-6-methylpyridin-3-yl)methyl)-1-(pyridin-3-ylsulfonyl)-1H-indol-3-yl)-N-methylmethanamine hydrochloride

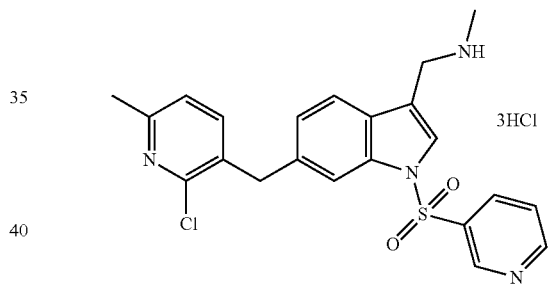

¹H NMR (500 MHz, CD₃OD): 9.10 (br, 1H), 8.82 (d, 1H), 8.33 (td, 1H), 7.99 (s, 1H), 7.88 (s, 1H), 7.77 (d, 1H), 7.72 (d, 1H), 7.60 (q, 1H), 7.36 (d, 1H), 7.29 (dd, 1H), 4.37 (s, 2H), 4.29 (s, 2H), 2.75 (s, 3H), 2.57 (s, 3H)

Example 285: Preparation of 1-(6-((2,6-dichloropyridin-3-yl)methyl)-1-(pyridin-3-ylsulfonyl)-1H-indol-3-yl)-N-methylmethanamine hydrochloride

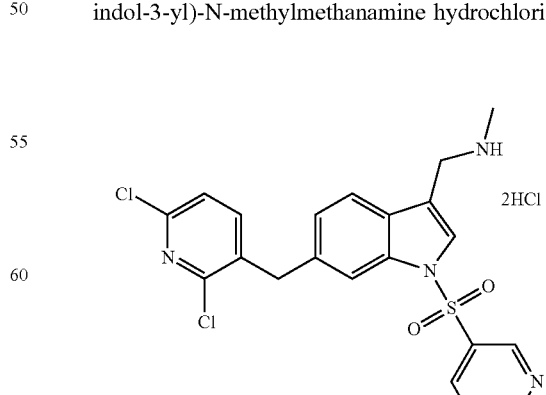

¹H NMR (500 MHz, CD₃OD): 9.12 (br, 1H), 8.86 (d, 1H), 8.35 (td, 1H), 8.02 (s, 1H), 7.91 (s, 1H), 7.79 (d, 1H), 7.75 (d, 1H), 7.62 (q, 1H), 7.37 (d, 1H), 7.31 (dd, 1H), 4.34 (s, 2H), 4.29 (s, 2H), 2.75 (s, 3H)

Example 286: Preparation of 1-(6-(2,3-difluoro-4-methylbenzyl)-1-(pyridin-3-ylsulfonyl)-1H-indol-3-yl)-N-methylmethanamine hydrochloride

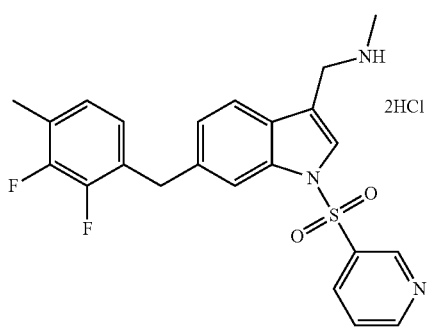 [SMILES: CNCc1cn(S(=O)(=O)c2cccnc2)c2cc(Cc3ccc(C)c(F)c3F)ccc12]

¹H NMR (500 MHz, CDCl₃): 9.02 (s, 1H), 8.77 (d, 1H), 8.28 (d, 1H), 7.93 (s, 1H), 7.86 (s, 1H), 7.66 (d, 1H), 7.53 (q, 1H), 7.27 (d, 1H), 6.99 (t, 1H), 6.93 (t, 1H), 4.34 (s, 2H), 4.15 (s, 2H), 2.76 (s, 3H), 2.29 (s, 3H)

Example 287: Preparation of 1-(6-(2,3-difluoro-4-methylbenzyl)-1-((3-fluorophenyl)sulfonyl)-1H-indol-3-yl)-N-methylmethanamine

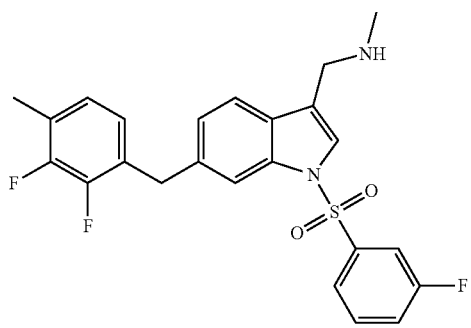 [SMILES: CNCc1cn(S(=O)(=O)c2cccc(F)c2)c2cc(Cc3ccc(C)c(F)c3F)ccc12]

¹H NMR (500 MHz, CD₃OD): 7.80 (s, 1H), 7.75 (s, 1H), 7.59 (d, 1H), 7.36-7.45 (m, 2H), 7.37 (t, 1H), 7.26 (dd, 1H), 7.15-7.19 (m, 1H), 6.99 (t, 1H), 6.92 (t, 1H), 4.15 (s, 2H), 4.08 (s, 2H), 3.79 (s, 3H), 2.52 (s, 3H)

Example 288: Preparation of 1-(6-(2,3-difluoro-4-methylbenzyl)-1-((3-(trifluoromethyl)phenyl)sulfonyl)-1H-indol-3-yl)-N-methylmethanamine

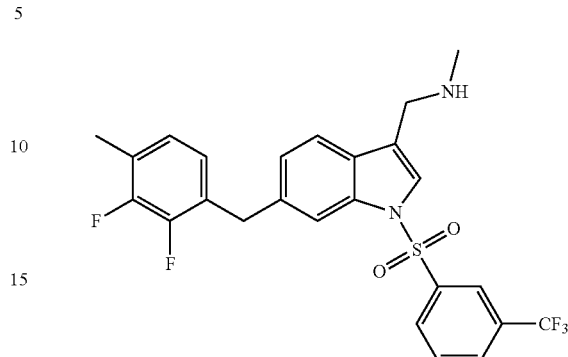

¹H NMR (500 MHz, CD₃OD): 7.78 (s, 1H), 7.71 (s, 1H), 7.55 (d, 1H), 7.31-7.42 (m, 2H), 7.33 (t, 1H), 7.24 (dd, 1H), 7.11-7.20 (m, 1H), 6.96 (t, 1H), 6.88 (t, 1H), 4.13 (s, 2H), 4.05 (s, 2H), 3.79 (s, 3H), 2.52 (s, 3H)

Example 289: Preparation of 1-(6-(2,3-difluoro-4-methylbenzyl)-1-((3-methoxyphenyl)sulfonyl)-1H-indol-3-yl)-N-methylmethanamine

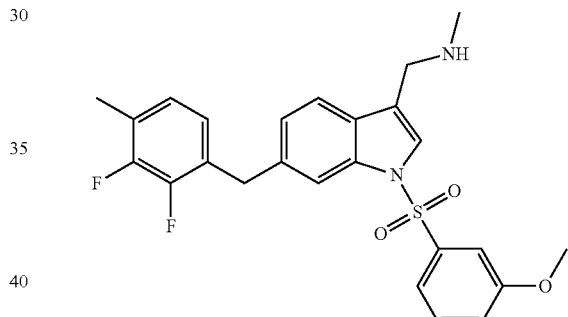

¹H NMR (500 MHz, CD₃OD): 7.83 (s, 1H), 7.71 (s, 1H), 7.57 (d, 1H), 7.35-7.41 (m, 2H), 7.31 (t, 1H), 7.21 (dd, 1H), 7.14-7.16 (m, 1H), 6.97 (t, 1H), 6.91 (t, 1H), 4.13 (s, 2H), 4.03 (s, 2H), 3.76 (s, 3H), 2.52 (s, 3H), 2.31 (s, 3H)

Example 290: Preparation of 1-(6-(2,3-difluoro-4-methylbenzyl)-1-((3-(difluoromethoxy)phenyl)sulfonyl)-1H-indol-3-yl)-N-methylmethanamine

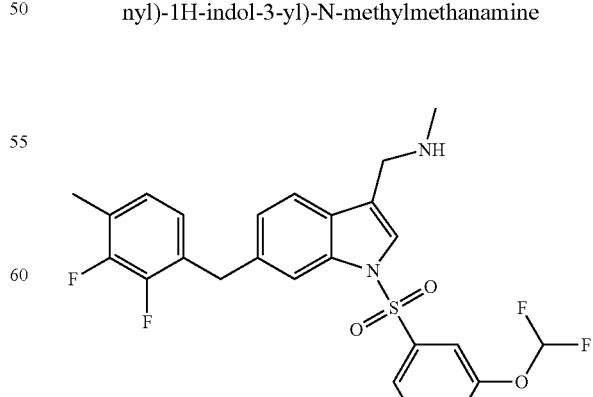

¹H NMR (500 MHz, CD₃OD): 7.83 (s, 1H), 7.73 (s, 1H), 7.71 (d, 1H), 7.61 (t, 1H), 7.58 (d, 1H), 7.51 (t, 1H), 7.40 (dd, 1H), 7.22 (d, 1H), 6.98 (t, 1H), 6.90 (t, 1H), 4.12 (s, 2H), 4.03 (s, 2H), 2.52 (s, 3H), 2.30 (s, 3H)

Example 291: Preparation of 1-(6-((2-chloro-6-methoxypyridin-3-yl)methyl)-1-(pyridin-3-ylsulfonyl)-1H-indol-3-yl)-N-methylmethanamine hydrochloride

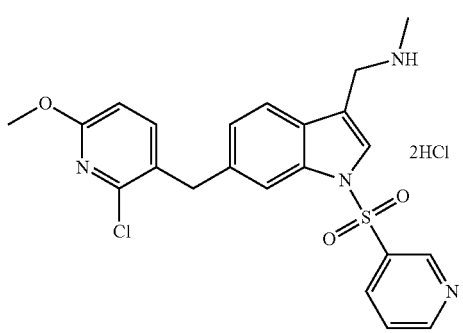 [SMILES: CNCc1cn(S(=O)(=O)c2cccnc2)c2cc(Cc3ccc(OC)nc3Cl)ccc12]

¹H NMR (500 MHz, CD₃OD): 9.05 (d, 1H), 8.78 (d, 1H), 8.28 (d, 1H), 7.95 (s, 1H), 7.82 (s, 1H), 7.67 (d, 1H), 7.61 (d, 1H), 7.55 (q, 1H), 7.26 (d, 1H), 6.76 (d, 1H), 4.35 (s, 2H), 4.18 (s, 2H), 3.97 (s, 3H), 2.73 (s, 3H)

Example 292: Preparation of 1-(6-((2-chloro-6-methoxypyridin-3-yl)methyl)-1-((3-fluorophenyl)sulfonyl)-1H-indol-3-yl)-N-methylmethanamine hydrochloride

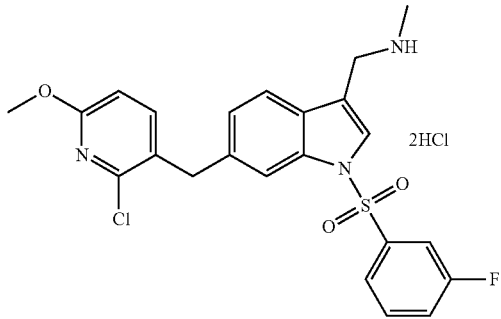 [SMILES: CNCc1cn(S(=O)(=O)c2cccc(F)c2)c2cc(Cc3ccc(OC)nc3Cl)ccc12]

¹H NMR (500 MHz, CD₃OD): 7.93 (s, 1H), 7.79 (s, 1H), 7.60-7.71 (m, 4H), 7.55 (d, 1H), 7.41 (t, 1H), 7.26 (d, 1H), 6.75 (d, 1H), 4.35 (s, 2H), 3.91 (s, 3H), 2.74 (s, 3H)

Example 293: Preparation of 1-(6-((2-chloro-6-methoxypyridin-3-yl)methyl)-1-((3-chlorophenyl)sulfonyl)-1H-indol-3-yl)-N-methylmethanamine

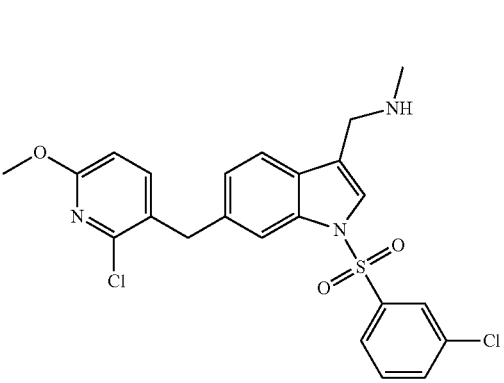 [SMILES: CNCc1cn(S(=O)(=O)c2cccc(Cl)c2)c2cc(Cc3ccc(OC)nc3Cl)ccc12]

¹H NMR (500 MHz, CD₃OD): 7.95 (s, 1H), 7.81 (s, 1H), 7.62-7.73 (m, 4H), 7.58 (d, 1H), 7.42 (t, 1H), 7.29 (d, 1H), 6.75 (d, 1H), 4.31 (s, 2H), 4.14 (s, 2H), 3.86 (s, 3H), 2.72 (s, 3H)

Example 294: Preparation of 1-(6-((2-chloro-6-methoxypyridin-3-yl)methyl)-1-((3-(trifluoromethyl)phenyl)sulfonyl)-1H-indol-3-yl)-N-methylmethanamine hydrochloride

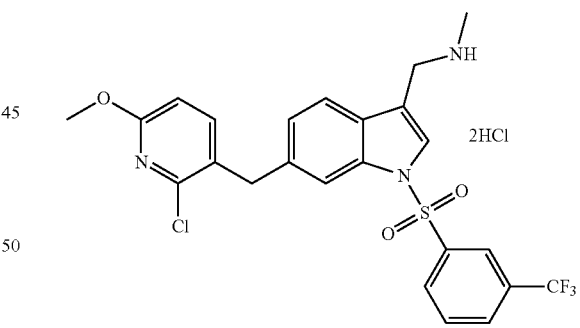

¹H NMR (500 MHz, CD₃OD): 8.18 (s, 1H), 8.17 (s, 1H), 8.00 (d, 1H), 7.98 (s, 1H), 7.87 (s, 1H), 7.76 (t, 1H), 7.69 (d, 1H), 7.61 (d, 1H), 7.28 (dd, 1H), 6.76 (d, 1H), 4.36 (s, 2H), 4.20 (s, 2H), 3.93 (s, 3H), 2.73 (s, 3H)

Example 295: Preparation of 1-(6-((2-chloro-6-methoxypyridin-3-yl)methyl)-1-((3-methoxyphenyl)sulfonyl)-1H-indol-3-yl)-N-methylmethanamine

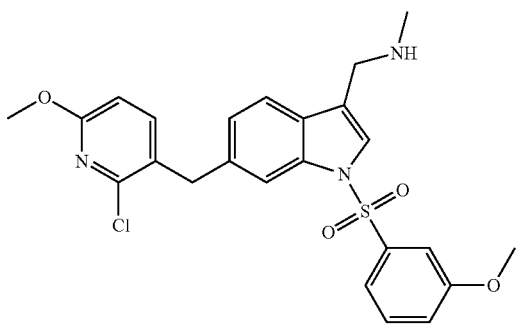

¹H NMR (500 MHz, CD₃OD): 7.80 (s, 1H), 7.74 (s, 1H), 7.59 (d, 1H), 7.56 (d, 1H), 7.38-7.39 (m, 2H), 7.32 (d, 1H), 7.21 (dd, 1H), 7.15-7.18 (m, 1H), 6.75 (d, 1H), 4.16 (s, 2H), 4.06 (s, 2H), 3.93 (s, 3H), 3.77 (s, 3H), 2.54 (s, 3H)

Example 296: Preparation of 1-(6-((2-chloro-6-methoxypyridin-3-yl)methyl)-1-((3-(difluoromethoxy)phenyl)sulfonyl)-1H-indol-3-yl)-N-methylmethanamine

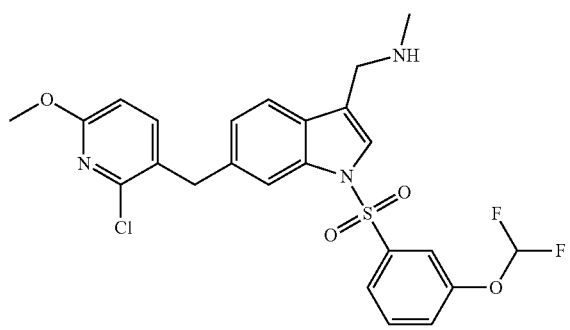 [SMILES: CNCc1cn(S(=O)(=O)c2cccc(OC(F)F)c2)c2cc(Cc3ccc(OC)nc3Cl)ccc12]

¹H NMR (500 MHz, CD₃OD): 7.80 (s, 1H), 7.72 (s, 1H), 7.70 (d, 1H), 7.62 (t, 1H), 7.59 (d, 1H), 7.56 (d, 1H), 7.53 (d, 1H), 7.40 (dd, 1H), 7.20 (d, 1H), 6.75 (d, 1H), 4.16 (s, 2H), 4.02 (s, 2H), 3.92 (s, 3H), 2.51 (s, 3H)

Example 297: Preparation of 1-(6-((2-chloro-6-methoxypyridin-3-yl)methyl)-1-((3-(trifluoromethoxy)phenyl)sulfonyl)-1H-indol-3-yl)-N-methylmethanamine

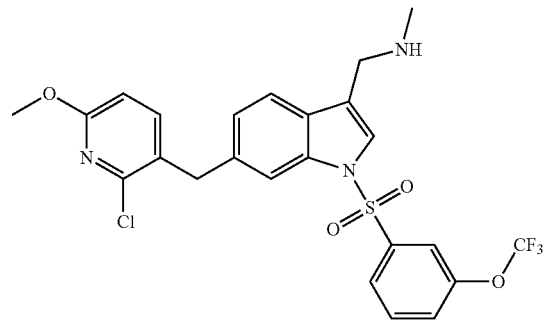 [SMILES: CNCc1cn(S(=O)(=O)c2cccc(OC(F)(F)F)c2)c2cc(Cc3ccc(OC)nc3Cl)ccc12]

¹H NMR (500 MHz, CD₃OD): 7.85 (td, 1H), 7.81 (d, 1H), 7.76 (d, 1H), 7.72 (s, 1H), 7.54-7.63 (m, 4H), 7.21 (dd, 1H), 6.74 (d, 1H), 4.17 (s, 2H), 4.03 (s, 2H), 3.93 (s, 3H), 2.50 (s, 3H)

Example 298: Preparation of 1-(6-((2-chloro-6-methoxypyridin-3-yl)methyl)-1-((4-(difluoromethoxy)phenyl)sulfonyl)-1H-indol-3-yl)-N-methylmethanamine

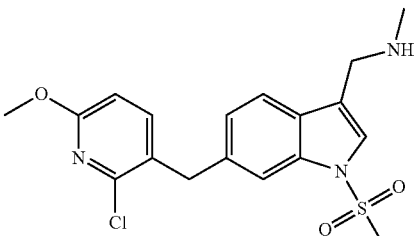

¹H NMR (500 MHz, CD₃OD): 7.84 (s, 2H), 7.69 (s, 1H), 7.55-7.60 (m, 2H), 7.15-7.19 (m, 3H), 6.74-7.03 (m, 1H), 6.70 (s, 1H), 4.29 (s, 2H), 4.11 (s, 2H), 3.85 (s, 3H), 2.68 (s, 3H)

Example 299: Preparation of 1-(6-(2-chloro-4-methylbenzyl)-1-((3-fluorophenyl)sulfonyl)-1H-indol-3-yl)-N-methylmethanamine The compound was prepared as shown in Reaction Scheme 8 below.

[Reaction Scheme 8]

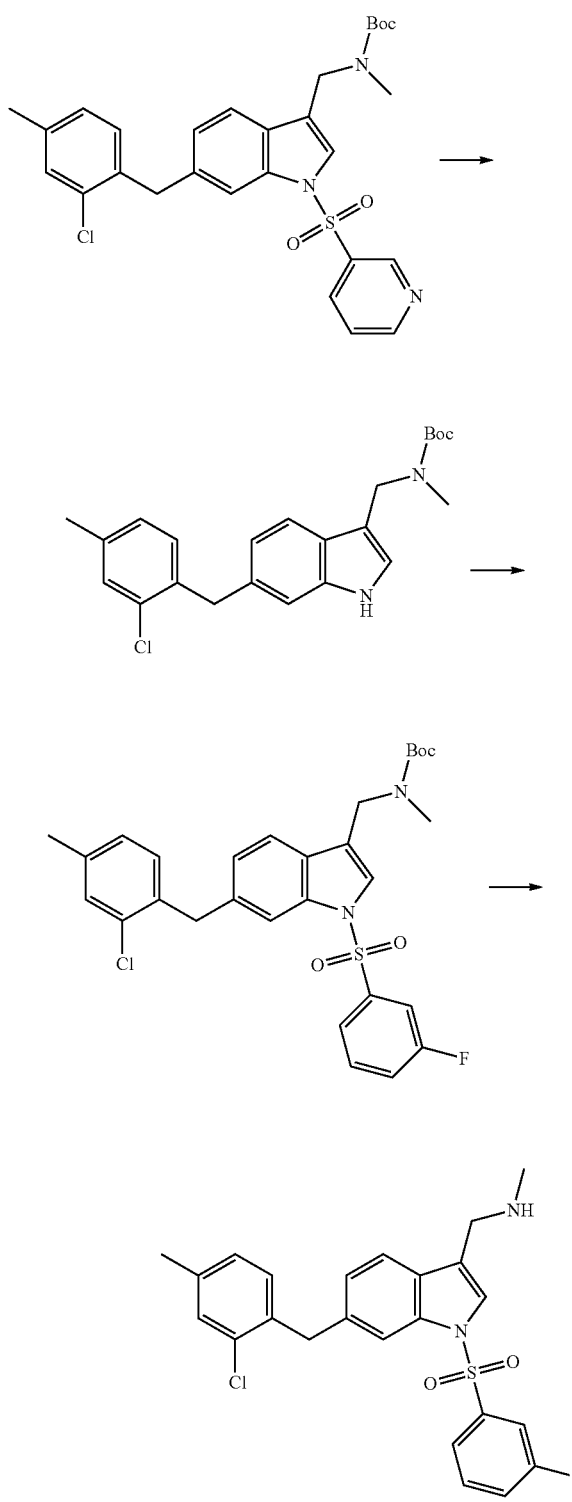

Step 1: Preparation of tert-butyl ((6-(2-chloro-4-methylbenzyl)-1H-indol-3-yl)methyl)(methyl)carbamate Tert-butyl ((6-(2-chloro-4-methylbenzyl)-1-(pyridin-3-ylsulfonyl)-1H-indol-3-yl)methyl)(methyl)carbamate (200 mg, 0.4 mmol) was dissolved in 5 ml of tetrahydrofuran solution, added with 1 ml of 1 M tetrabutylammonium fluoride-tetrahydrofuran solution, and stirred at 70° C. for 3 hours. The reaction mixture was added with water and extracted with ethyl acetate. The resulting separated organic layer was washed with saturated brine, dried on anhydrous magnesium sulfate and concentrated under reduced pressure. The resulting residue was purified by silica gel column chromatography (ethyl acetate:n-hexane=1:1 (v/v)) to obtain 120 mg of a title compound (yield: 81.6%).

$^1$H NMR (500 MHz, CD$_3$OD): 7.82 (s, 1H), 7.71 (d, 1H), 7.58 (q, 1H), 7.36 (q, 1H), 7.22-7.28 (m, 2H), 7.16 (td, 1H), 4.33 (s, 2H), 4.21 (s, 2H), 2.72 (s, 3H), 2.31 (s, 3H), 1.35 (s, 9H)

Step 2: Preparation of tert-butyl ((6-(2-chloro-4-methylbenzyl)-1-((3-fluorophenyl)sulfonyl)-1H-indol-3-yl)methyl)(methyl)carbamate Tert-butyl ((6-(2-chloro-4-methylbenzyl)-1H-indol-3-yl)methyl)(methyl)carbamate (20 mg, 0.05 mmol) prepared in Step 1 was dissolved in 2 ml of N,N-dimethylformamide solution, cooled to 0° C., and dropwisely added with sodium hydride (60% in oil) (3 mg, 0.07 mmol). The reaction mixture was stirred at 0° C. for 30 minutes, added with 3-fluorobenzenesulfonyl chloride (15 mg, 0.07 mmol) and stirred at room temperature for 3 hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 13 mg of a title compound (yield: 46.5%).

$^1$H NMR (500 MHz, CD$_3$OD): 8.23 (d, 1H), 8.11 (d, 1H), 7.89 (d, 1H), 7.78 (s, 1H), 7.65 (s, 1H), 7.54 (d, 1H), 7.48 (q, 1H), 7.36 (q, 1H), 7.21-7.28 (m, 2H), 7.11 (td, 1H), 4.31 (s, 2H), 4.18 (s, 2H), 2.71 (s, 3H), 2.32 (s, 3H), 1.33 (s, 9H)

Step 3: Preparation of 1-(6-(2-chloro-4-methylbenzyl)-1-((3-fluorophenyl)sulfonyl)-1H-indol-3-yl)-N-methylmethanamine Tert-butyl ((6-(2-chloro-4-methylbenzyl)-1-((3-fluorophenyl)sulfonyl)-1H-indol-3-yl)methyl)(methyl)carbamate (13 mg, 0.02 mmol) prepared in Step 2 was added with 0.5 ml of 1.0 M HCl-ethylacetate solution, and stirred at room temperature for 5 hours. The reaction mixture was concentrated under reduced pressure, and the resulting residue was purified by silica gel column chromatography (dichloromethane:methanol=10:1 (v/v)) to obtain 5 mg of a title compound (yield: 47%).

$^1$H NMR (500 MHz, CD$_3$OD): 7.88 (s, 1H), 7.73 (s, 1H), 7.62-7.65 (m, 2H), 7.57 (d, 1H), 7.48-7.53 (m, 1H), 7.41 (td, 1H), 7.25-7.27 (m, 2H), 7.19 (d, 1H), 7.12 (d, 1H), 4.33 (s, 2H), 4.21 (s, 2H), 2.72 (s, 3H), 2.35 (s, 3H)

In Examples 300 through 308 below, compounds were prepared in the same manner as in Example 299 except that reactants were appropriately changed as necessary depending on the structures of the compounds to be prepared and in consideration of Reaction Scheme 8.

Example 300: Preparation of 1-(6-(2-chloro-4-methylbenzyl)-1-((2-fluorophenyl)sulfonyl)-1H-indol-3-yl)-N-methylmethanamine

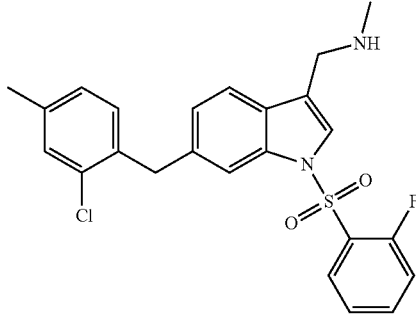 [SMILES: CNCc1cn(S(=O)(=O)c2ccccc2F)c2cc(Cc3ccc(C)cc3Cl)ccc12]

¹H NMR (500 MHz, CD₃OD): 7.95 (td, 1H), 7.82 (d, 1H), 7.67-7.72 (m, 1H), 7.61 (d, 1H), 7.54 (s, 1H), 7.34 (td, 1H), 7.20-7.25 (m, 3H), 7.11 (s, 1H), 7.09 (d, 1H), 4.18 (s, 2H), 4.15 (s, 2H), 2.62 (s, 3H), 2.36 (s, 3H)

Example 301: Preparation of 1-(6-(2-chloro-4-methylbenzyl)-1-((3-chlorophenyl)sulfonyl)-1H-indol-3-yl)-N-methylmethanamine

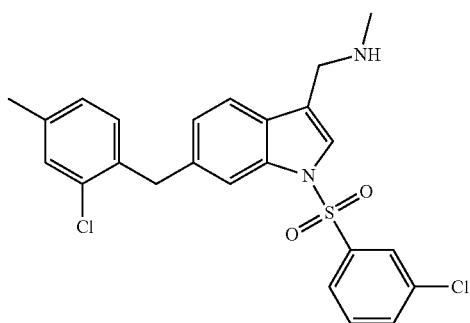 [SMILES: CNCc1cn(S(=O)(=O)c2cccc(Cl)c2)c2cc(Cc3ccc(C)cc3Cl)ccc12]

¹H NMR (500 MHz, CD₃OD): 7.89 (s, 2H), 7.70 (s, 1H), 7.64 (s, 1H), 7.49 (d, 1H), 7.26 (s, 1H), 7.10-7.17 (m, 4H), 7.06 (d, 1H), 4.18 (s, 2H), 3.98 (s, 2H), 2.48 (s, 3H), 2.36 (s, 3H)

Example 302: Preparation of 1-(6-(2-chloro-4-methylbenzyl)-1-((3-(trifluoromethyl)phenyl)sulfonyl)-1H-indol-3-yl)-N-methylmethanamine

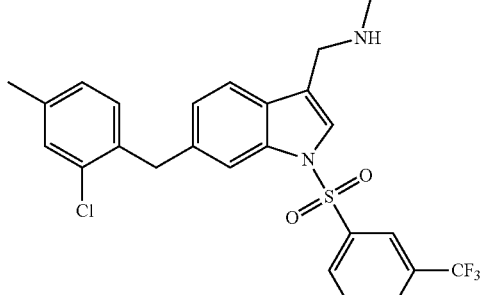

¹H NMR (500 MHz, CD₃OD): 7.91 (s, 2H), 7.68 (s, 1H), 7.66 (s, 1H), 7.51 (d, 1H), 7.28 (s, 1H), 7.12-7.19 (m, 4H), 7.10 (d, 1H), 4.16 (s, 2H), 3.99 (s, 2H), 2.42 (s, 3H), 2.33 (s, 3H)

Example 303: Preparation of 1-(6-(2-chloro-4-methylbenzyl)-1-((3-methoxyphenyl)sulfonyl)-1H-indol-3-yl)-N-methylmethanamine

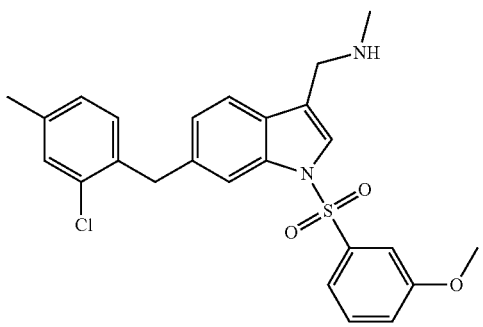

¹H NMR (500 MHz, CD₃OD): 7.78 (s, 1H), 7.74 (s, 1H), 7.57 (d, 1H), 7.35-7.37 (m, 2H), 7.30 (t, 1H), 7.27 (s, 1H), 7.21 (d, 1H), 7.10-7.18 (m, 3H), 4.20 (s, 2H), 4.09 (s, 2H), 3.76 (s, 3H), 2.56 (s, 3H), 2.36 (s, 3H)

Example 304: Preparation of 1-(6-(2-chloro-4-methylbenzyl)-1-((3-(difluoromethoxy)phenyl)sulfonyl)-1H-indol-3-yl)-N-methylmethanamine

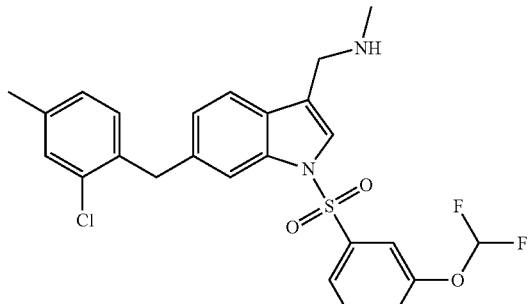

¹H NMR (500 MHz, CD₃OD): 7.75 (s, 1H), 7.67 (s, 1H), 7.63 (td, 1H), 7.57 (t, 1H), 7.54 (d, 1H), 7.48 (t, 1H), 7.37 (dd, 1H), 7.28 (s, 1H), 7.10-7.19 (m, 3H), 4.19 (s, 2H), 3.97 (s, 2H), 2.47 (s, 3H), 2.35 (s, 3H)

Example 305: Preparation of 1-(6-(2-chloro-4-methylbenzyl)-1-((3-(trifluoromethoxy)phenyl)sulfonyl)-1H-indol-3-yl)-N-methylmethanamine

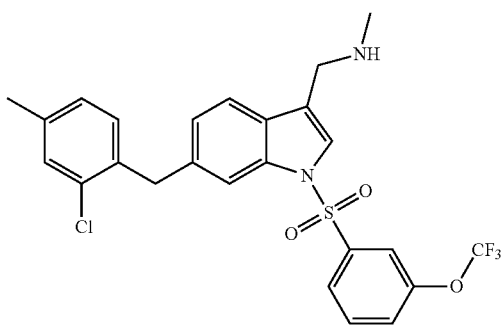 [SMILES: CNCc1cn(S(=O)(=O)c2cccc(OC(F)(F)F)c2)c2cc(Cc3ccc(C)cc3Cl)ccc12]

$^1$H NMR (500 MHz, CD$_3$OD): 7.78 (td, 1H), 7.75 (s, 1H), 7.70 (s, 1H), 7.66 (s, 1H), 7.51-7.59 (m, 3H), 7.27 (s, 1H), 7.19 (dd, 1H), 7.14-7.16 (m, 1H), 7.10 (d, 1H), 4.19 (s, 2H), 3.94 (s, 2H), 2.45 (s, 3H), 2.35 (s, 3H)

Example 306: Preparation of 1-(6-(2-chloro-4-methylbenzyl))-1-((4-fluorophenyl)sulfonyl)-1H-indol-3-yl)-N-methylmethanamine

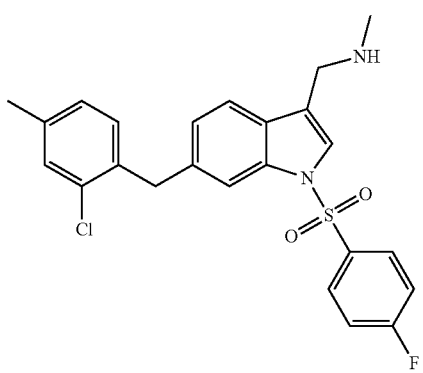 [SMILES: CNCc1cn(S(=O)(=O)c2ccc(F)cc2)c2cc(Cc3ccc(C)cc3Cl)ccc12]

$^1$H NMR (500 MHz, CD$_3$OD): 7.82-7.85 (m, 2H), 7.71 (s, 1H), 7.66 (s, 1H), 7.53 (d, 1H), 7.28 (s, 1H), 7.14-7.19 (m, 4H), 7.11 (d, 1H), 4.18 (s, 2H), 3.98 (s, 2H), 2.48 (s, 3H), 2.36 (s, 3H)

Example 307: Preparation of 1-(6-(2-chloro-4-methylbenzyl)-1-((4-methoxyphenyl)sulfonyl)-1H-indol-3-yl)-N-methylmethanamine

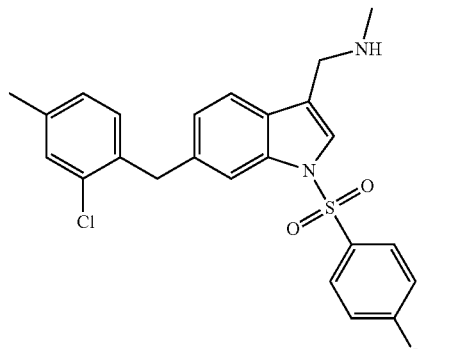

$^1$H NMR (500 MHz, CD$_3$OD): 7.69-7.72 (m, 3H), 7.65 (s, 1H), 7.52 (d, 1H), 7.28 (s, 1H), 7.14-7.17 (m, 2H), 7.11 (d, 1H), 6.89 (d, 2H), 4.18 (s, 2H), 3.98 (s, 2H), 3.80 (s, 3H), 2.49 (s, 3H), 2.36 (s, 3H)

Example 308: Preparation of 1-(6-(2-chloro-4-methylbenzyl)-1-((4-(difluoromethoxy)phenyl)sulfonyl)-1H-indol-3-yl)-N-methylmethanamine

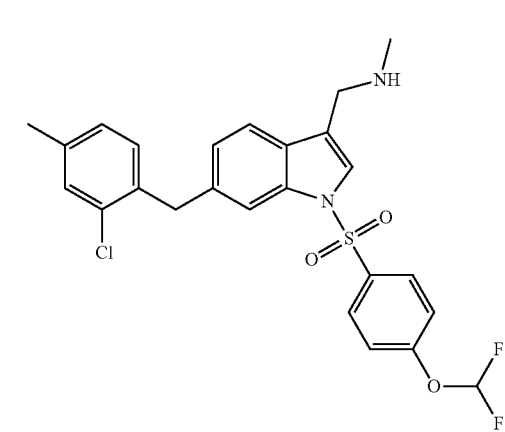 [SMILES: CNCc1cn(S(=O)(=O)c2ccc(OC(F)F)cc2)c2cc(Cc3ccc(C)cc3Cl)ccc12]

$^1$H NMR (500 MHz, CD$_3$OD): 7.83 (d, 2H), 7.73 (s, 1H), 7.69 (s, 1H), 7.55 (d, 1H), 7.29 (s, 1H), 7.20 (d, 1H), 7.11-7.17 (m, 4H), 4.19 (s, 2H), 4.01 (s, 2H), 2.52 (s, 3H), 2.36 (s, 3H)

Example 309: Preparation of 1-(6-(5-chloro-nitrophenoxy)-1-(pyridin-3-ylsulfonyl)-1H-indol-3-yl)-N-methylmethanamine hydrochloride The compound was prepared as shown in Reaction Scheme 9 below.

[Reaction Scheme 9]

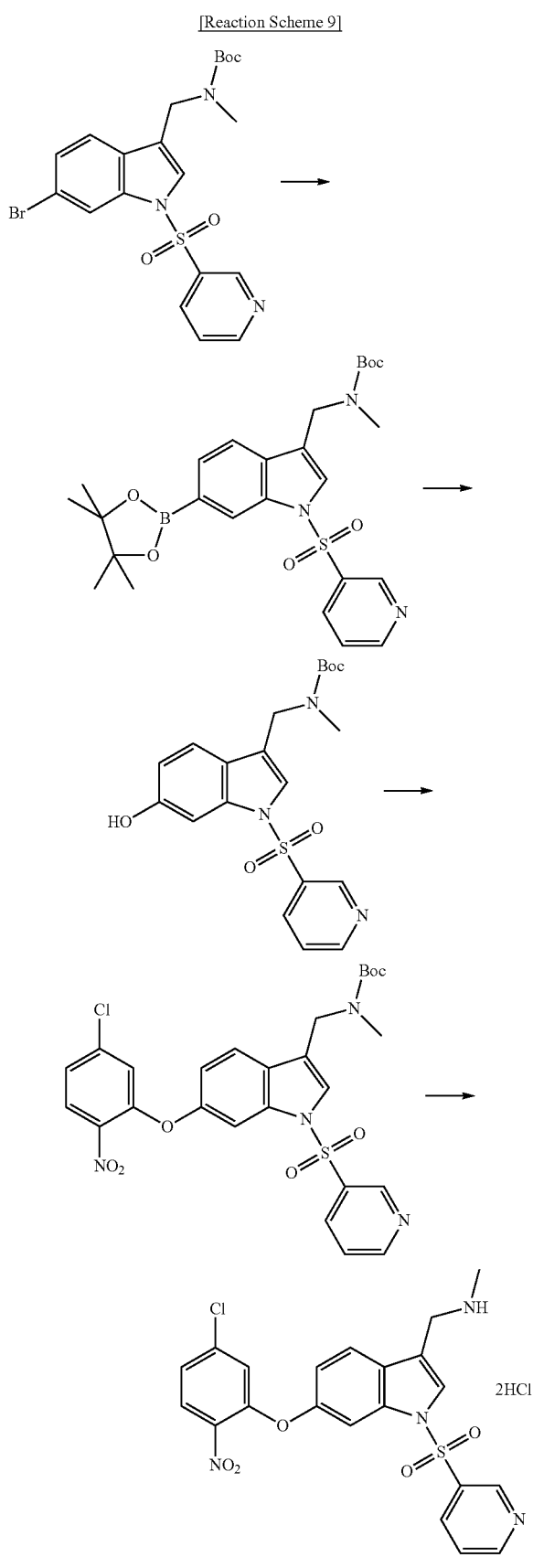

Step 1: Preparation of tert-butyl methyl((1-(pyridin-3-ylsulfonyl)-6-(4,4,5,5-tetramethyl-1,3,2-dioxaborolan-2-yl)-1H-indol-3-yl)methyl)carbamate Tert-butyl ((6-bromo-1-(pyridin-3-ylsulfonyl)-1H-indol-3-yl)methyl)(methyl)carbamate (2.9 g, 6.0 mmol), Bis(pinacolato)diboron (2.3 g, 9.0 mmole), 1,1'-Bis(diphenylphosphino)ferrocene-palladium(II) dichloride (490 mg, 0.6 mmole), and potassium acetate (1.77 mg, 18.1 mmole) were suspended in 50 ml of 1,2-dimethoxyethane solution, and stirred at 90° C. for 15 hours. The reaction mixture was filtered with celite and concentrated under reduced pressure. The resulting residue was purified by silica gel column chromatography (ethyl acetate:n-hexane=1:3 (v/v)) to obtain 3.99 g of a title compound (over yield).

$^1$H NMR (500 MHz, CDCl$_3$): 9.10 (d, 1H), 8.78 (q, 1H), 8.69 (d, 1H), 8.17 (t, 1H), 7.98 (s, 1H), 7.61-7.72 (m, 2H), 7.33-7.39 (m, 1H), 4.32 (s, 2H), 2.71 (s, 3H), 1.33 (s, 9H), 1.12-1.25 (m, 12H)

Step 2: Preparation of tert-butyl ((6-hydroxy-1-(pyridin-3-ylsulfonyl)-1H-indol-3-yl)methyl)(methyl)carbamate Tert-butyl methyl((1-(pyridin-3-ylsulfonyl)-6-(4,4,5,5-tetramethyl-1,3,2-dioxaborolan-2-yl)-1H-indol-3-yl)methyl)carbamate (3.99 g, 7.56 mmol) prepared in Step 1 was dissolved in 100 ml of 1,2-dimethoxyethane solution, added with sodium hydroxide (275 mg, 6.88 mmole) and hydrogen peroxide (34.5%. 2.36 ml, 27.2 mmole), and stirred at room temperature for 2 hours. The reaction mixture was concentrated under reduced pressure, and the resulting residue was added with water and ethyl acetate, and extracted via acidification by adding citric acid. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 2.2 g of a title compound (yield: 87%).

$^1$H NMR (500 MHz, CDCl$_3$): 9.07 (s, 1H), 8.78 (d, 1H), 8.11 (d, 1H), 8.02 (s, 1H), 7.61 (br, 1H), 7.44 (s, 1H), 7.36 (t, 1H), 7.30 (d, 1H), 4.38 (s, 2H), 2.36 (s, 3H), 1.46 (s, 9H)

Step 3: Preparation of tert-butyl ((6-(5-chloro-2-nitrophenoxy)-1-(pyridin-3-ylsulfonyl)-1H-indol-3-yl)methyl)(methyl)carbamate Tert-butyl ((6-hydroxy-1-(pyridin-3-ylsulfonyl)-1H-indol-3-yl)methyl)(methyl)carbamate (30 mg, 0.07 mmol) prepared in Step 2 was dissolved in 0.5 ml of N,N-dimethylformamide solution, added with cesium carbonate (47 mg, 0.1 mmol) and 4-chloro-2-fluoro-1-nitrobenzene (13 mg, 0.07 mmole), and reacted in a microwave reactor maintained at 110° C. for 5 minutes. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:1 (v/v)) to obtain 27 mg of a title compound (yield: 65.8%).

$^1$H NMR (500 MHz, CDCl$_3$): 9.04 (s, 1H), 8.79 (d, 1H), 8.10 (dd, 1H), 7.96 (d, 1H), 7.72 (s, 2H), 7.47 (s, 1H), 7.43 (d, 1H), 7.18 (dd, 1H), 7.01 (d, 1H), 6.88 (s, 1H), 4.56 (s, 2H), 2.75 (s, 3H), 1.48 (s, 9H)

Step 4: Preparation of 1-(6-(5-chloro-nitrophenoxy)-1-(pyridin-3-ylsulfonyl)-1H-indol-3-yl)-N-methylmethanamine hydrochloride Tert-butyl ((6-(5-chloro-2-nitrophenoxy)-1-(pyridin-3-ylsulfonyl)-1H-indol-3-yl)methyl)(methyl)carbamate (25 mg, 0.04 mmol) prepared in Step 3 was added with 0.5 ml of 1.25 M HCl-methanol solution, and stirred at room temperature for 12 hours. The reaction mixture was concentrated under reduced pressure, and the resulting residue was purified by recrystallizing with dichloromethane to obtain 17 mg of a title compound (yield: 71.4%).

$^1$H NMR (500 MHz, CD$_3$OD): 9.05 (s, 1H), 8.80 (d, 1H), 8.31 (d, 1H), 8.01 (dd, 1H), 7.76 (d, 1H), 7.68 (td, 1H), 7.61 (q, 1H), 7.56 (d, 1H), 7.41 (td, 1H), 7.12 (d, 1H), 7.08 (dd, 1H), 4.35 (s, 2H), 2.76 (s, 3H)

In Examples 310 through 314 below, compounds were prepared in the same manner as in Example 309 except that reactants were appropriately changed as necessary depending on the structures of the compounds to be prepared and in consideration of Reaction Scheme 9.

Example 310: Preparation of N-methyl-1-(6-(2-nitrophenoxy)-1-(pyridin-3-ylsulfonyl)-1H-indol-3-yl)methanamine hydrochloride

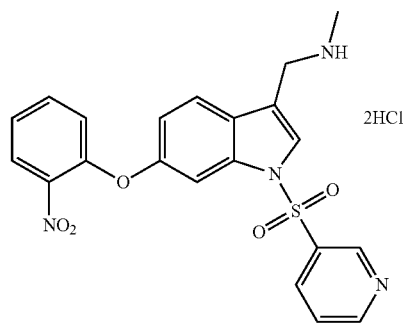 [SMILES: CNCc1cn(S(=O)(=O)c2cccnc2)c2cc(Oc3ccccc3[N+](=O)[O-])ccc12]

$^1$H NMR (500 MHz, CD$_3$OD): 9.07 (s, 1H), 8.83 (d, 1H), 8.34 (d, 1H), 8.05 (dd, 1H), 8.00 (s, 1H), 7.78 (d, 1H), 7.72 (td, 1H), 7.64 (q, 1H), 7.61 (d, 1H), 7.43 (td, 1H), 7.15 (d, 1H), 7.14 (dd, 1H), 4.37 (s, 2H), 2.75 (s, 3H)

Example 311: Preparation of 1-(6-(2-chloro-4-(trifluoromethyl)phenoxy)-1-(pyridin-3-ylsulfonyl)-1H-indol-3-yl)-N-methylmethanamine hydrochloride

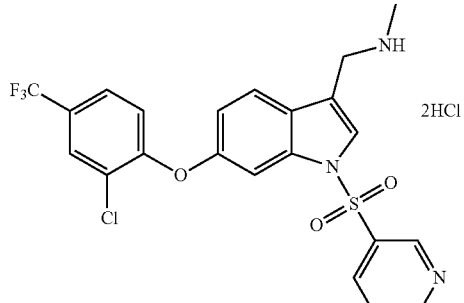

$^1$H NMR (500 MHz, CD$_3$OD): 8.98 (d, 2H), 8.42 (d, 1H), 8.07 (s, 1H), 8.88 (d, 2H), 7.81 (q, 1H), 7.75 (s, 1H), 7.68 (d, 1H), 7.05 (dd, 1H), 6.79 (d, 1H), 4.47 (s, 2H), 2.76 (s, 3H)

Example 312: Preparation of 1-(6-((3-chloro-5-(trifluoromethyl)pyridin-2-yl)oxy)-1-(pyridin-3-ylsulfonyl)-1H-indol-3-yl)-N-methylmethanamine hydrochloride

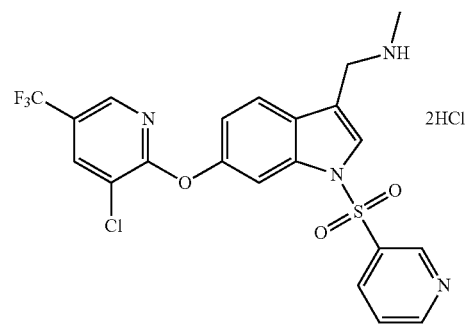 [SMILES: CNCc1cn(S(=O)(=O)c2cccnc2)c2cc(Oc3ncc(C(F)(F)F)cc3Cl)ccc12]

$^1$H NMR (500 MHz, CD$_3$OD): 9.16 (s, 1H), 8.83 (d, 1H), 8.42 (br, 1H), 8.33 (s, 2H), 8.03-8.04 (m, 1H), 7.96 (d, 1H), 7.81-7.83 (m, 1H), 7.59-7.63 (m, 1H), 7.23 (dd, 1H), 4.40 (s, 2H), 2.76 (s, 3H)

Example 313: Preparation of 1-(6-((5-fluoropyrimidin-2-yl)oxy)-1-(pyridin-3-ylsulfonyl)-1H-indol-3-yl)-N-methylmethanamine hydrochloride

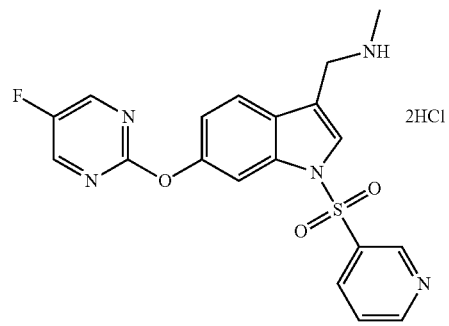 [SMILES: CNCc1cn(S(=O)(=O)c2cccnc2)c2cc(Oc3ncc(F)cn3)ccc12]

$^1$H NMR (500 MHz, CD$_3$OD): 9.26 (s, 1H), 8.88 (d, 1H), 8.55-8.58 (m, 3H), 8.07 (s, 1H), 7.94 (d, 1H), 7.82 (d, 1H), 7.72-7.75 (m, 1H), 7.23 (dd, 1H), 4.40 (s, 2H), 2.76 (s, 3H)

Example 314: Preparation of 1-(6-((6-chloropyrimidin-4-yl)oxy)-1-(pyridin-3-ylsulfonyl)-1H-indol-3-yl)-N-methylmethanamine hydrochloride

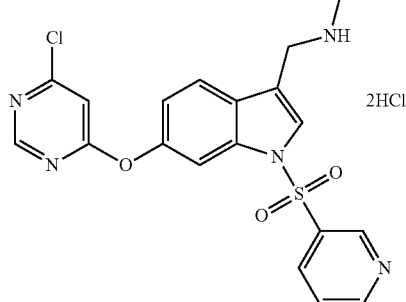

$^1$H NMR (500 MHz, CD$_3$OD): 9.17 (s, 1H), 8.83 (d, 1H), 8.56 (s, 1H), 8.45 (d, 1H), 8.05 (s, 1H), 7.97 (d, 1H), 7.83 (d, 1H), 7.60-7.62 (m, 1H), 7.23-7.25 (m, 2H), 4.40 (s, 2H), 2.76 (s, 3H)

Example 315: Preparation of N-(2-chloro-6-methoxypyridin-3-yl)-N-methyl-3-((methylamino)methyl)-1-((3-(trifluoromethyl)phenyl)sulfonyl)-1H-indol-6-amine hydrochloride The compound was prepared as shown in Reaction Scheme 10 below.

[Reaction Scheme 10]

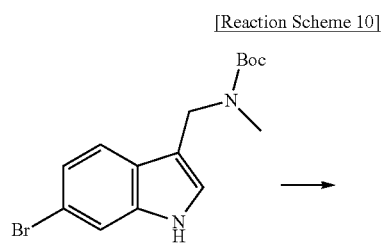

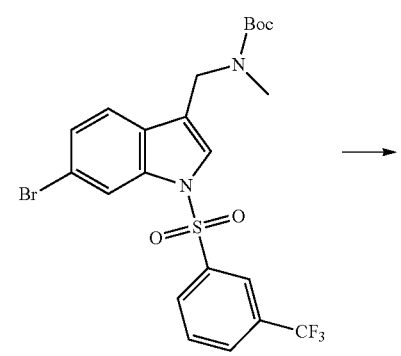

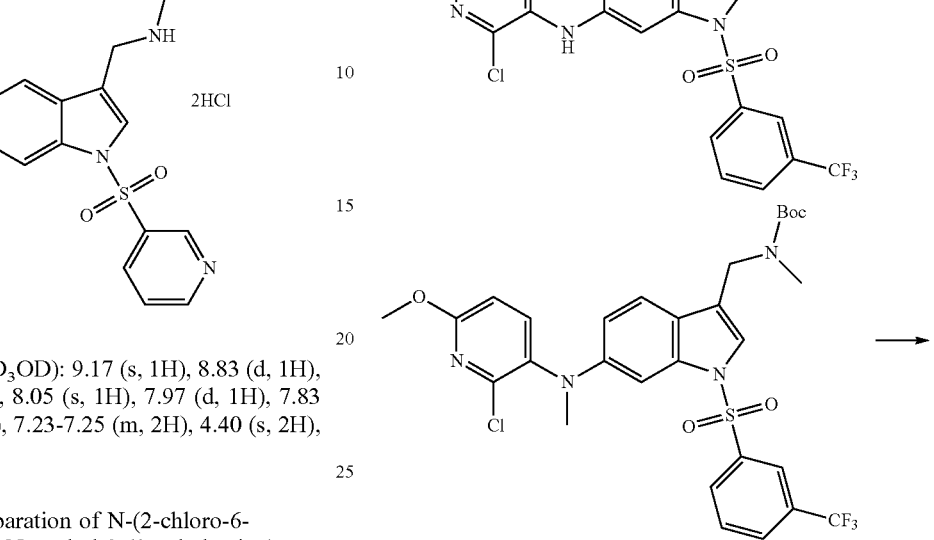

Step 1: Preparation of tert-butyl ((6-bromo-1-((3-(trifluoromethyl)phenyl)sulfonyl)-1H-indol-3-yl)methyl)(methyl)carbamate Tert-butyl ((6-bromo-1H-indol-3-yl)methyl)(methyl)carbamate (485 mg, 1.4 mmol) was dissolved in 5 ml of N,N-dimethylformamide solution, cooled to 0° C., and dropwisely added with sodium hydride (60% in oil) (114 mg, 2.8 mmol). The reaction mixture was stirred at 0° C. for 30 minutes, added with 3-(trifluoromethyl)benzenesulfonyl chloride (342 μl, 2.1 mmol), and stirred at room temperature for 2 hours. The resulting reaction mixture was added with an aqueous ammonium chloride solution and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:3 (v/v)) to obtain 420 mg of a title compound (yield: 54%).

$^1$H NMR (300 MHz, CDCl$_3$): 8.16 (s, 1H), 7.72 (d, 1H), 7.58 (s, 1H), 7.41-7.48 (m, 3H), 7.26 (dd, 1H), 6.45 (t, 1H), 4.51 (s, 2H), 2.76 (s, 3H), 1.58 (s, 9H)

Step 2: Preparation of tert-butyl ((6-((2-chloro-6-methoxypyridin-3-yl)amino)-1-((3-(trifluoromethyl)phenyl)sulfonyl)-1H-indol-3-yl)methyl)(methyl)carbamate Tert-butyl ((6-bromo-1-((3-(trifluoromethyl)phenyl)sulfonyl)-1H-indol-3-yl)methyl)(methyl)carbamate (50 mg, 0.09 mmol) prepared in Step 1; Bis(dibenzylideneacetone)palladium(0) (5.3 mg, 0.009 mmole); tri-tert-butylphosphine, 50% solution in toluene (6.6 μl, 0.04 mmole); 4,5-Bis(diphenylphosphino)-9,9-dimethylxanthene (8 mg, 0.01 mmole); cesium carbonate (48 mg, 0.1 mmole); and 2-chloro-6-methoxypyridin-3-amine (22 mg, 0.1 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:3 (v/v)) to obtain 30 mg of a title compound (yield: 52.5%).

$^1$H NMR (500 MHz, CDCl$_3$): 8.10 (s, 1H), 7.95 (d, 1H), 7.81 (d, 1H), 7.62 (t, 1H), 7.53 (d, 1H), 7.16-7.35 (m, 3H), 6.79 (d, 1H), 6.51 (dd, 1H), 4.47 (s, 2H), 4.01 (s, 3H), 3.23 (s, 3H), 1.45 (s, 9H)

Step 3: Preparation of tert-butyl ((6-((2-chloro-6-methoxypyridin-3-yl)(methyl)amino)-1-((3-(trifluoromethyl)phenyl)sulfonyl)-1H-indol-3-yl)methyl)(methyl)carbamate Tert-butyl ((6-((2-chloro-6-methoxypyridin-3-yl)amino)-1-((3-(trifluoromethyl)phenyl)sulfonyl)-1H-indol-3-yl)methyl)(methyl)carbamate (30 mg, 0.04 mmol) prepared in Step 2 was dissolved in 1 ml of N,N-dimethylformamide solution, cooled to 0° C., and dropwisely added with sodium hydride (60% in oil) (3 mg, 0.07 mmol). The reaction mixture was stirred at 0° C. for 30 minutes, added with iodomethane (14 mg, 0.09 mmol), and stirred at room temperature for 3 hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:3 (v/v)) to obtain 20 mg of a title compound (yield: 65.3%).

$^1$H NMR (500 MHz, CDCl$_3$): 8.09 (s, 1H), 7.93 (d, 1H), 7.79 (d, 1H), 7.59 (t, 1H), 7.49 (d, 1H), 7.15-7.37 (m, 3H), 6.77 (d, 1H), 6.47 (dd, 1H), 4.44 (s, 2H), 3.99 (s, 3H), 3.26 (s, 3H), 2.68-2.75 (m, 3H), 1.47 (s, 9H)

Step 4: Preparation of N-(2-chloro-6-methoxypyridin-3-yl)-N-methyl-3-((methylamino)methyl)-1-((3-(trifluoromethyl)phenyl)sulfonyl)-1H-indol-6-amine hydrochloride Tert-butyl ((6-((2-chloro-6-methoxypyridin-3-yl)(methyl)amino)-1-((3-(trifluoromethyl)phenyl)sulfonyl)-1H-indol-3-yl)methyl)(methyl)carbamate (20 mg, 0.03 mmol) prepared in Step 3 was dissolved in 1 ml of 1.25 M HCl-methanol solution, and stirred at room temperature for 5 hours. The reaction mixture was concentrated under reduced pressure to obtain 10 mg of a title compound (yield: 59.5%).

$^1$H NMR (500 MHz, CDCl$_3$): 9.87 (br, 1H), 8.15 (s, 1H), 8.07 (br, 1H), 7.82 (br, 1H), 7.75 (s, 1H), 7.51-7.60 (m, 2H), 7.43 (d, 1H), 7.09 (s, 1H), 6.74 (d, 1H), 6.53 (s, 1H), 4.14 (s, 2H), 3.98 (s, 3H), 3.23 (s, 3H), 2.49 (s, 3H)

Example 316: Preparation of N-(2-methoxy-4-(trifluoromethoxy)phenyl)-N-(3-((methylamino)methyl)-1-(pyridin-3-ylsulfonyl)-1H-indol-6-yl)formamide The compound was prepared as shown in Reaction Scheme 11 below.

[Reaction Scheme 11]

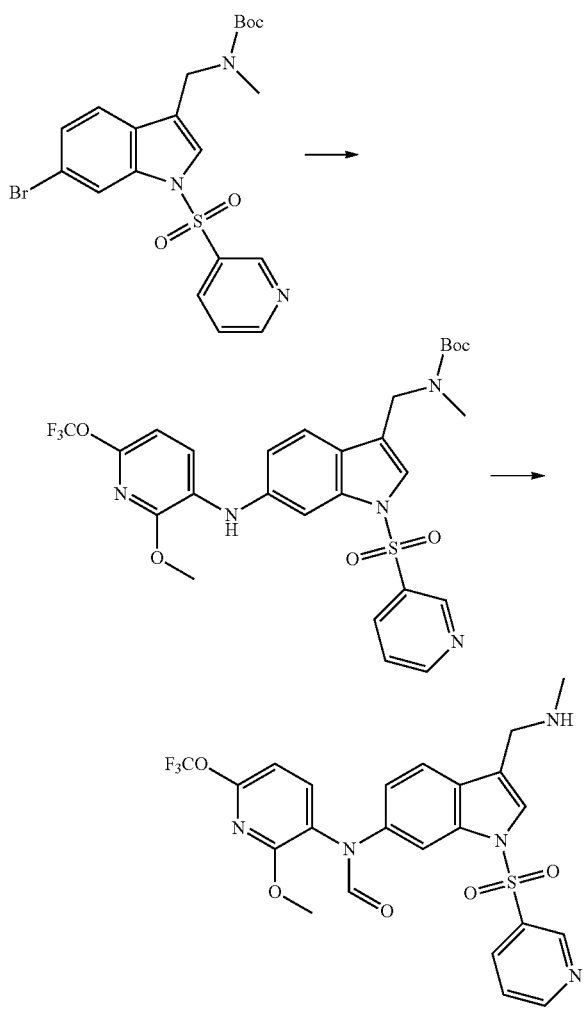

Step 1: Preparation of tert-butyl ((6-((2-methoxy-6-(trifluoromethoxy)pyridin-3-yl)amino)-1-(pyridin-3-ylsulfonyl)-1H-indol-3-yl)methyl)(methyl)carbamate Tert-butyl ((6-bromo-1-(pyridin-3-ylsulfonyl)-1H-indol-3-yl)methyl)(methyl)carbamate (50 mg, 0.1 mmol); Bis(dibenzylideneacetone)palladium(0) (6 mg, 0.01 mmole); tri-tert-butylphosphine, 50% solution in toluene (7.5 μl, 0.01 mmole); 4,5-Bis(diphenylphosphino)-9,9-dimethylxanthene (9 mg, 0.01 mmole); cesium carbonate (55 mg, 0.1 mmole); and 2-methoxy-4-(trifluoromethoxy)aniline (32 mg, 0.1 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 26 mg of a title compound (yield: 41.2%).

$^1$H NMR (500 MHz, CDCl$_3$): 8.12 (s, 1H), 8.01 (d, 1H), 7.93 (d, 1H), 7.78 (d, 1H), 7.60 (t, 1H), 7.51 (d, 1H), 7.11-7.28 (m, 3H), 6.75 (d, 1H), 6.48 (dd, 1H), 4.45 (s, 2H), 3.99 (s, 3H), 3.22 (s, 3H), 1.46 (s, 9H)

Step 2: Preparation of N-(2-methoxy-4-(trifluoromethoxy)phenyl)-N-(3-((methylamino)methyl)-1-(pyridin-3-ylsulfonyl)-1H-indol-6-yl)formamide Tert-butyl ((6-((2-methoxy-4-(trifluoromethoxy)phenyl)amino)-1-(pyridin-3-ylsulfonyl)-1H-indol-3-yl)methyl)(methyl)carbamate (25 mg, 0.04 mmol) prepared in Step 1 was added with formic acid (4.6 µl, 0.1 mmole) and zinc oxide (1.6 mg, 0.02 mmole), and stirred at 80° C. for 12 hours. The reaction mixture was concentrated under reduced pressure, and the resulting residue was purified by silica gel column chromatography (dichloromethane:methanol=10:1 (v/v)) to obtain 10 mg of a title compound (yield: 45.4%).

$^1$H NMR (500 MHz, CD$_3$OD): 9.07 (d, 1H), 8.68 (s, 1H), 8.39 (s, 1H), 8.23 (d, 1H), 8.13 (s, 1H), 8.10 (d, 1H), 7.77 (s, 1H), 7.54 (d, 1H), 7.37-7.40 (m, 1H), 7.07-7.10 (m, 1H), 6.91 (d, 1H), 4.01 (s, 2H), 3.80 (s, 3H), 2.47 (s, 3H)

Example 317: Preparation of N-(2-chloro-6-methoxypyridin-3-yl)-3-((ethylamino)methyl)-1-((3-(trifluoromethyl)phenyl)sulfonyl)-1H-indol-6-amine The compound was prepared as shown in Reaction Scheme 12.

[Reaction Scheme 12]

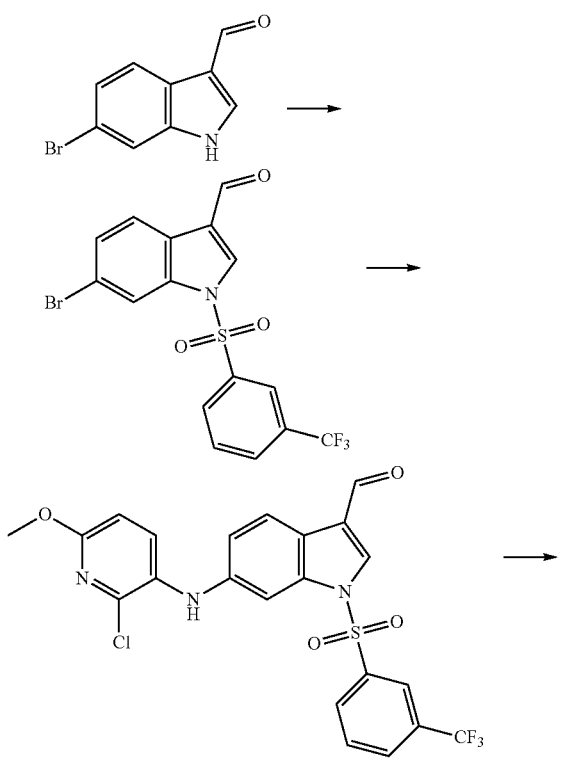

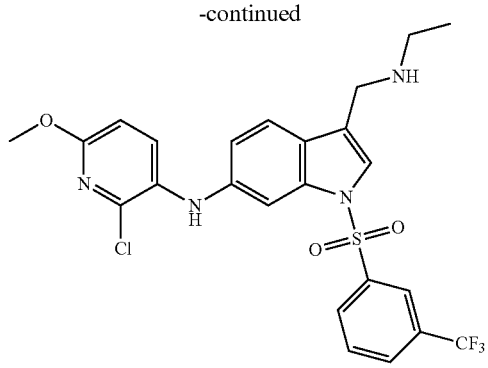

Step 1: Preparation of 6-bromo-1-((3-(trifluoromethyl)phenyl)sulfonyl)-1H-indol-3-carbaldehyde 6-bromo-1H-indol-3-carbaldehyde (224 mg, 1.0 mmol) was dissolved in 1 ml of N,N-dimethylformamide solution, cooled to 0° C., and dropwisely added with sodium hydride (60% in oil) (60 mg, 1.5 mmol). The reaction mixture was stirred at 0° C. for 30 minutes, added with 3-(trifluoromethyl)benzenesulfonyl chloride (402 µl, 1.5 mmol), and stirred at room temperature for 3 hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:3 (v/v)) to obtain 330 mg of a title compound (yield: 76.3%).

$^1$H NMR (500 MHz, CDCl$_3$): 10.14 (s, 1H), 9.26 (d, 1H), 8.85 (dd, 1H), 8.69 (d, 1H), 8.36 (d, 2H), 8.31 (t, 1H), 8.14 (t, 1H), 7.53 (dd, 1H)

Step 2: Preparation of 6-((2-chloro-6-methoxypyridin-3-yl)amino)-1-((3-(trifluoromethyl)phenyl)sulfonyl)-1H-indol-3-carbaldehyde 6-bromo-1-((3-(trifluoromethyl)phenyl)sulfonyl)-1H-indol-3-carbaldehyde (50 mg, 0.1 mmol) prepared in Step 1; Bis(dibenzylideneacetone)palladium(0) (6.6 mg, 0.01 mmole); tri-tert-butylphosphine, 50% solution in toluene (8.3 µl, 0.01 mmole); 4,5-Bis(diphenylphosphino)-9,9-dimethylxanthene (10 mg, 0.01 mmole); cesium carbonate (61 mg, 0.1 mmole); and 2-chloro-6-methoxypyridin-3-amine (27.5 mg, 0.1 mmole) were suspended in 2 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 50 mg of a title compound (yield: 85%).

$^1$H NMR (500 MHz, CDCl$_3$): 10.05 (s, 1H), 8.17 (s, 1H), 8.11 (d, 1H), 8.08 (s, 1H), 8.06 (d, 1H), 7.90 (d, 1H), 7.70 (t, 1H), 7.56 (d, 1H), 7.42 (d, 1H), 6.98 (dd, 1H), 6.72 (d, 1H), 3.96 (s, 3H)

Step 3: Preparation of N-(2-chloro-6-methoxypyridin-3-yl)-3-((ethylamino)methyl)-1-((3-(trifluoromethyl)phenyl)sulfonyl)-1H-indol-6-amine 6-((2-chloro-6-methoxypyridin-3-yl)amino)-1-((3-(trifluoromethyl)phenyl)sulfonyl)-1H-indol-3-carbaldehyde (50 mg, 0.1 mmol) prepared in Step 2, dissolved in 1 ml of methanol, was added with sodium cyanoborohydride (34 mg, 0.5 mmole) and 2 M ethylamine-methanol solution (272 µl, 0.5 mmole), and stirred at 60° C. for 5 hours. The reaction mixture was added with a saturated sodium bicarbonate solution and extracted with ethyl acetate. The resulting extract was washed with saturated brine, dried on anhydrous magnesium sulfate, and concentrated under reduced pressure. The resulting residue was purified by silica gel column chromatography (dichloromethane:methanol=10:1 (v/v)) to obtain 23 mg of a title compound (yield: 43.5%).

$^1$H NMR (500 MHz, CDCl$_3$): 8.09 (s, 1H), 8.01 (d, 1H), 7.80 (d, 1H), 7.61 (t, 1H), 7.51 (d, 2H), 7.47 (d, 2H), 6.90 (dd, 1H), 6.67 (s, 1H), 5.78 (s, 1H), 3.94 (s, 3H), 3.92 (s, 2H), 2.74 (q, 2H), 1.17 (t, 3H)

Example 318: Preparation of N-(2-chloro-6-methoxypyridin-3-yl)-3-(pyrrolidin-1-ylmethyl)-1-((3-(trifluoromethyl)phenyl)sulfonyl)-1H-indol-6-amine

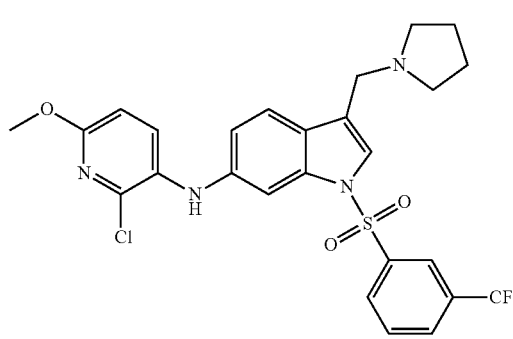

The compound was prepared in the same manner as in Example 317 except that pyrrolidine was used instead of 2 M ethylamine-tetrahydrofuran solution to obtain 27 mg of a title compound (yield: 49%).

$^1$H NMR (500 MHz, CD$_3$OD): 8.16 (d, 1H), 8.13 (s, 1H), 7.99 (d, 1H), 7.79 (t, 1H), 7.68 (s, 1H), 7.64 (d, 1H), 7.53 (d, 1H), 7.39 (d, 1H), 6.92 (dd, 1H), 6.81 (s, 1H), 4.12 (s, 2H), 3.95 (s, 3H), 2.98 (s, 4H), 1.95 (s, 4H)

Example 319: Preparation of N-(2-chloro-6-methoxypyridin-3-yl)-3-((dimethylamino)methyl)-1-((3-(trifluoromethyl)phenyl)sulfonyl)-1H-indol-6-amine

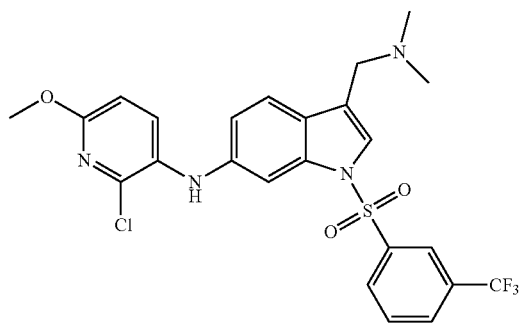 [SMILES: COc1ccc(Nc2ccc3c(CN(C)C)cn(S(=O)(=O)c4cccc(C(F)(F)F)c4)c3c2)c(Cl)n1]

The compound was prepared in the same manner as in Example 317 except that 2 M dimethylamine-tetrahydrofuran was used instead of 2 M ethylamine-tetrahydrofuran solution to obtain 25 mg of a title compound (yield: 47.3%).

$^1$H NMR (500 MHz, CD$_3$OD): 8.17 (s, 1H), 8.11 (s, 1H), 7.89 (d, 1H), 7.78 (s, 1H), 7.68 (t, 1H), 7.56 (d, 1H), 7.41 (d, 1H), 7.34 (d, 1H), 6.86 (dd, 1H), 6.78 (d, 1H), 4.13 (s, 2H), 3.96 (s, 3H), 3.15 (s, 6H)

Example 320: Preparation of 6-((2-chloro-6-methoxypyridin-3-yl)amino)-N-methyl-1-((3-(trifluoromethyl)phenyl)sulfonyl)-1H-indol-3-carboxamide The compound was prepared as shown in Reaction Scheme 13 below.

[Reaction Scheme 13]

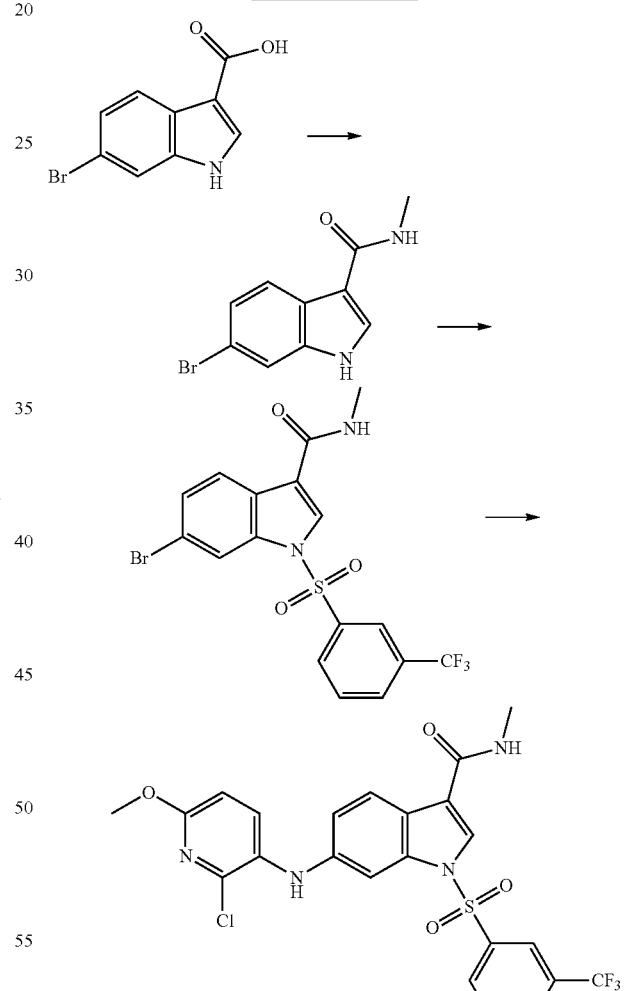

Step 1: Preparation of 6-bromo-N-methyl-1H-indol-3-carboxamide 6-bromo-1H-indol-3-carboxylic acid (240 mg, 1.0 mmol), (O-(benzotriazol-1-yl)-N,N,N',N'-tetramethyluronium tetrafluoroborate) (481 mg, 1.5 mmole), and N,N-diisopropylethylamine (276 µl, 1.5 mmole) were dissolved in 10 ml of N,N-dimethylformamide solution, stirred at room temperature for 10 minutes, added with 1 M methylamine-tetrahydrofuran solution (1.5 ml, 1.5 mmole) and stirred at room temperature for 1 hour. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 180 mg of a title compound (yield: 71%).

$^1$H NMR (500 MHz, CDCl$_3$): 7.89 (d, 1H), 7.70 (d, 1H), 7.55 (s, 1H), 7.30 (d, 1H), 2.79 (s, 3H)

Step 2: Preparation of 6-bromo-N-methyl-1-((3-(trifluoromethyl)phenyl)sulfonyl)-1H-indol-3-carboxamide 6-bromo-N-methyl-1H-indol-3-carboxamide (50 mg, 0.2 mmol) prepared in Step 1 was dissolved in 3 ml of N,N-dimethylformamide solution, cooled to 0° C., and dropwisely added with sodium hydride (60% in oil) (12 mg, 0.3 mmol). The reaction mixture was stirred at 0° C. for 30 minutes, added with 3-(trifluoromethyl)benzenesulfonyl chloride (72 mg, 0.3 mmol), and stirred at room temperature for 3 hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 30 mg of a title compound (yield: 33%).

$^1$H NMR (500 MHz, CD$_3$OD): 8.11 (s, 1H), 8.06 (s, 1H), 7.89 (s, 1H), 7.78 (d, 1H), 7.64 (d, 1H), 7.53 (t, 1H), 7.41 (d, 1H), 7.18 (d, 1H), 2.92 (s, 3H)

Step 3: Preparation of 6-((2-chloro-6-methoxypyridin-3-yl)amino)-N-methyl-1-((3-(trifluoromethyl)phenyl)sulfonyl)-1H-indol-3-carboxamide 6-bromo-N-methyl-1-((3-(trifluoromethyl)phenyl)sulfonyl)-1H-indol-3-carboxamide (23 mg, 0.05 mmol) prepared in Step 2; Bis(dibenzylideneacetone)palladium(0) (2.9 mg, 0.005 mmole); tri-tert-butylphosphine, 50% solution in toluene (3.6 μl, 0.008 mmole); 4,5-Bis(diphenylphosphino)-9,9-dimethylxanthene (4.3 mg, 0.008 mmole), cesium carbonate (26 mg, 0.075 mmole), and 2-chloro-6-methoxypyridin-3-amine (11 mg, 0.075 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 15 mg of a title compound (yield: 56%).

$^1$H NMR (500 MHz, CD$_3$OD): 8.17 (s, 1H), 8.15 (s, 1H), 8.07 (s, 1H), 8.02 (d, 1H), 7.89 (d, 1H), 7.81 (t, 1H), 7.65 (d, 1H), 7.33 (d, 1H), 6.92 (dd, 1H), 6.81 (s, 1H), 3.95 (s, 3H), 2.92 (s, 3H)

In Examples 321 through 332 below, compounds were prepared in the same manner as in Example 320 except that reactants were appropriately changed as necessary depending on the structures of the compounds to be prepared and in consideration of Reaction Scheme 13.

Example 321: Preparation of 6-((2-chloro-6-methoxypyridin-3-yl)amino)-N,N-dimethyl-1-((3-(trifluoromethyl)phenyl)sulfonyl)-1H-indol-3-carboxamide

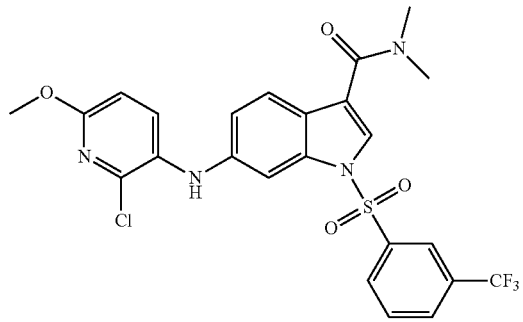 [SMILES: COc1ccc(Nc2ccc3c(C(=O)N(C)C)cn(S(=O)(=O)c4cccc(C(F)(F)F)c4)c3c2)c(Cl)n1]

$^1$H NMR (500 MHz, CD$_3$OD): 8.19 (s, 1H), 8.18 (s, 1H), 8.01 (d, 1H), 7.84 (s, 1H), 7.80 (t, 1H), 7.66 (d, 1H), 7.43 (d, 1H), 7.37 (d, 1H), 6.91 (dd, 1H), 6.82 (d, 1H), 3.95 (s, 3H), 3.13 (s, 6H)

Example 322: Preparation of 6-((2-fluoro-4-methylphenyl)amino)-N,N-dimethyl-1-(pyridin-3-ylsulfonyl)-1H-indol-3-carboxamide

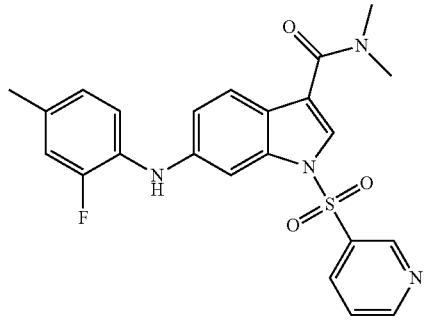 [SMILES: Cc1ccc(Nc2ccc3c(C(=O)N(C)C)cn(S(=O)(=O)c4cccnc4)c3c2)c(F)c1]

$^1$H NMR (500 MHz, CDCl$_3$): 9.12 (d, 1H), 8.81 (dd, 1H), 8.09 (td, 1H), 7.61 (d, 1H), 7.59 (s, 1H), 7.55 (d, 1H), 7.42 (q, 1H), 7.16 (t, 1H), 6.91-7.01 (m, 3H), 5.81 (s, 1H), 3.13 (s, 6H), 2.34 (s, 3H)

Example 323: Preparation of 6-((2-chloro-4-methyl-phenyl)amino)-N,N-dimethyl-1-(pyridin-3-ylsulfonyl)-1H-indol-3-carboxamide

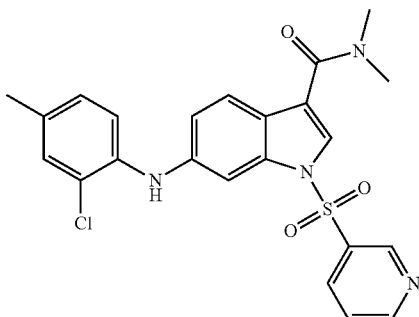

¹H NMR (500 MHz, CDCl₃): 9.11 (d, 1H), 8.79 (dd, 1H), 8.05 (td, 1H), 7.65 (d, 1H), 7.59 (s, 1H), 7.52 (d, 1H), 7.42 (q, 1H), 7.16 (t, 1H), 6.89-6.98 (m, 3H), 5.78 (s, 1H), 3.15 (s, 6H), 2.32 (s, 3H)

Example 324: Preparation of 6-((2-fluoro-4-methoxyphenyl)amino)-N,N-dimethyl-1-(pyridin-3-ylsulfonyl)-1H-indol-3-carboxamide

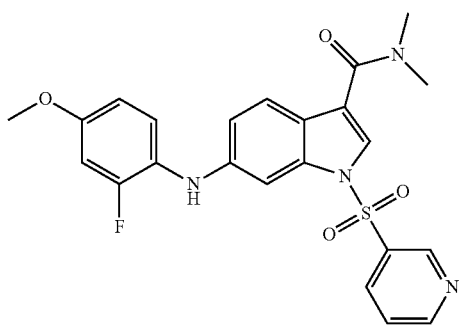

¹H NMR (500 MHz, CDCl₃): 9.12 (d, 1H), 8.79 (dd, 1H), 8.06 (td, 1H), 7.58 (d, 1H), 7.50 (s, 1H), 7.48 (d, 1H), 7.42 (q, 1H), 7.16 (t, 1H), 6.91-7.01 (m, 3H), 5.81 (s, 1H), 3.89 (s, 3H), 3.11 (s, 6H)

Example 325: Preparation of 6-((2-chloro-4-(trifluoromethyl)phenyl)amino)-N,N-dimethyl-1-(pyridin-3-ylsulfonyl)-1H-indol-3-carboxamide

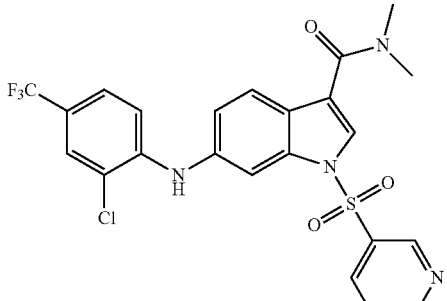

¹H NMR (500 MHz, CD₃OD): 9.10 (d, 1H), 8.82 (dd, 1H), 8.05 (td, 1H), 7.58 (d, 1H), 7.51 (s, 1H), 7.48 (d, 1H), 7.38 (q, 1H), 7.17 (t, 1H), 6.95-7.03 (m, 3H), 3.11 (s, 6H)

Example 326: Preparation of N,N-dimethyl-6-((2-methyl-4-(trifluoromethoxy)phenyl)amino)-1-(pyridin-3-ylsulfonyl)-1H-indol-3-carboxamide

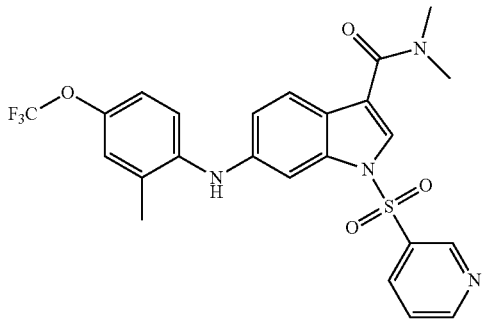 [SMILES: Cc1cc(OC(F)(F)F)ccc1Nc1ccc2c(C(=O)N(C)C)cn(S(=O)(=O)c3cccnc3)c2c1]

¹H NMR (500 MHz, CD₃OD): 9.10 (d, 1H), 8.85 (dd, 1H), 8.11 (td, 1H), 7.75 (d, 1H), 7.63 (s, 1H), 7.53 (d, 1H), 7.41 (q, 1H), 7.18 (t, 1H), 6.92-7.03 (m, 3H), 3.15 (s, 6H), 2.32 (s, 3H)

Example 327: Preparation of 6-((2-chloro-4-(trifluoromethoxy)phenyl)amino)-N,N-dimethyl-1-(pyridin-3-ylsulfonyl)-1H-indol-3-carboxamide

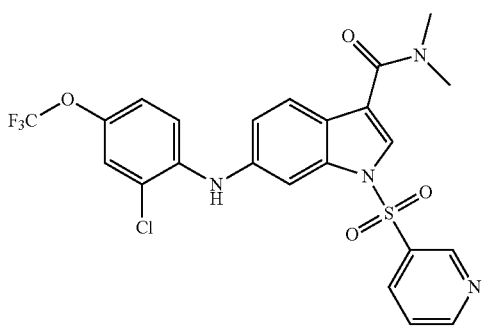 [SMILES: CN(C)C(=O)c1cn(S(=O)(=O)c2cccnc2)c2cc(Nc3ccc(OC(F)(F)F)cc3Cl)ccc12]

¹H NMR (500 MHz, CD₃OD): 9.09 (d, 1H), 8.84 (dd, 1H), 8.08 (td, 1H), 7.73 (d, 1H), 7.60 (s, 1H), 7.51 (d, 1H), 7.38 (q, 1H), 7.15 (t, 1H), 6.88-6.98 (m, 3H), 3.12 (s, 6H)

Example 328: Preparation of 6-((2-methoxy-4-(trifluoromethoxy)phenyl)amino)-N,N-dimethyl-1-(pyridin-3-ylsulfonyl)-1H-indol-3-carboxamide

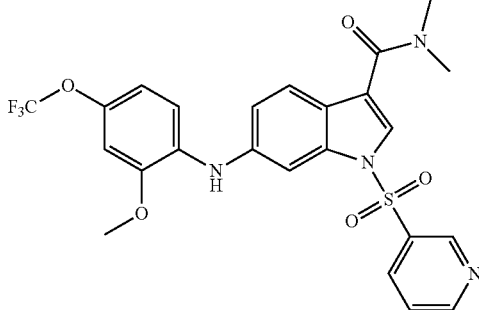 [SMILES: COc1cc(OC(F)(F)F)ccc1Nc1ccc2c(C(=O)N(C)C)cn(S(=O)(=O)c3cccnc3)c2c1]

¹H NMR (500 MHz, CD₃OD): 9.14 (d, 1H), 8.83 (dd, 1H), 8.35 (td, 1H), 7.86 (s, 1H), 7.70 (d, 1H), 7.60-7.64 (m, 1H), 7.48 (d, 1H), 7.24 (d, 1H), 7.12 (dd, 1H), 6.97 (d, 1H), 6.88 (d, 1H), 3.94 (s, 3H), 3.14 (s, 6H)

Example 329: Preparation of 6-((2,3-difluoro-4-methylphenyl)amino)-N,N-dimethyl-1-(pyridin-3-ylsulfonyl)-1H-indol-3-carboxamide

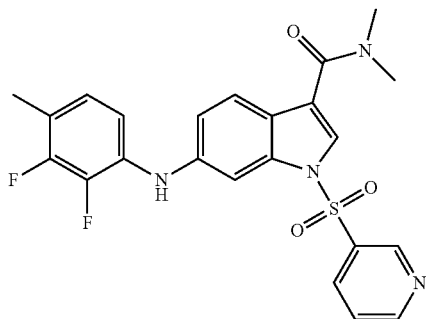 [SMILES: Cc1ccc(Nc2ccc3c(C(=O)N(C)C)cn(S(=O)(=O)c4cccnc4)c3c2)c(F)c1F]

¹H NMR (500 MHz, CD₃OD): 9.11 (d, 1H), 8.80 (dd, 1H), 8.31 (td, 1H), 7.82 (s, 1H), 7.65 (d, 1H), 7.44 (d, 1H), 7.21 (d, 1H), 7.10 (dd, 1H), 6.95 (d, 1H), 6.84 (d, 1H), 3.11 (s, 6H), 2.35 (s, 3H)

Example 330: Preparation of 6-((2-chloro-6-methylpyridin-3-yl)amino)-N,N-dimethyl-1-(pyridin-3-ylsulfonyl)-1H-indol-3-carboxamide

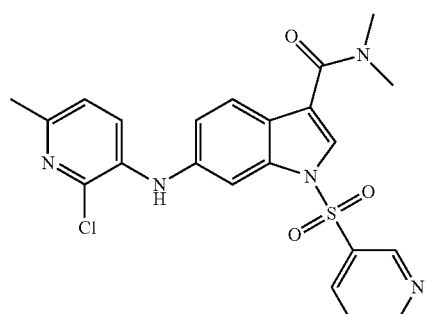

¹H NMR (500 MHz, CD₃OD): 8.19 (s, 1H), 8.15 (s, 1H), 8.01 (d, 1H), 7.84 (s, 1H), 7.79 (t, 1H), 7.66 (d, 1H), 7.43 (d, 1H), 7.37 (d, 1H), 6.91 (dd, 1H), 6.82 (d, 1H), 3.93 (s, 3H), 3.11 (s, 6H)

Example 331: Preparation of 6-((2,6-dichloropyridin-3-yl)amino)-N,N-dimethyl-1-(pyridin-3-ylsulfonyl)-1H-indol-3-carboxamide

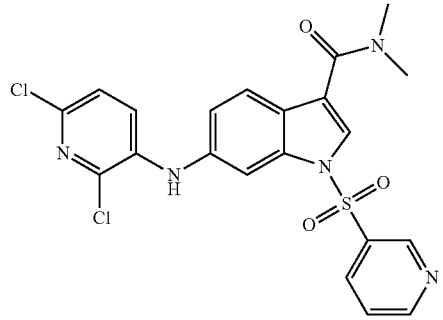 [SMILES: CN(C)C(=O)c1cn(S(=O)(=O)c2cccnc2)c2cc(Nc3ccc(Cl)nc3Cl)ccc12]

¹H NMR (500 MHz, CD₃OD): 8.21 (s, 1H), 8.15 (s, 1H), 8.03 (d, 1H), 7.85 (s, 1H), 7.76 (t, 1H), 7.61 (d, 1H), 7.45 (d, 1H), 7.31 (d, 1H), 6.88 (dd, 1H), 6.78 (d, 1H), 3.13 (s, 6H)

Example 332: Preparation of 6-((2-chloro-6-methoxypyridin-3-yl)amino)-N,N-dimethyl-1-(pyridin-3-ylsulfonyl)-1H-indol-3-carboxamide

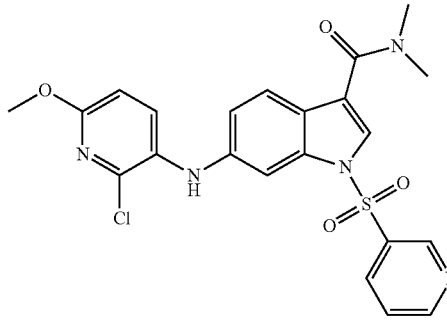

¹H NMR (500 MHz, CD₃OD): 8.17 (s, 1H), 8.14 (s, 1H), 7.99 (d, 1H), 7.81 (s, 1H), 7.75 (t, 1H), 7.61 (d, 1H), 7.42 (d, 1H), 7.34 (d, 1H), 6.87 (dd, 1H), 6.76 (d, 1H), 3.98 (s, 3H), 3.13 (s, 6H)

Example 333: Preparation of N6-(2-fluoro-4-methylphenyl)-N3-methyl-1-(pyridin-3ylsulfonyl)-1H-indol-3,6-diamine hydrochloride The compound was prepared as shown in Reaction Scheme 14 below.

[Reaction Scheme 14]

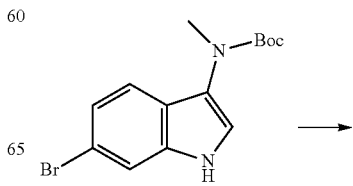

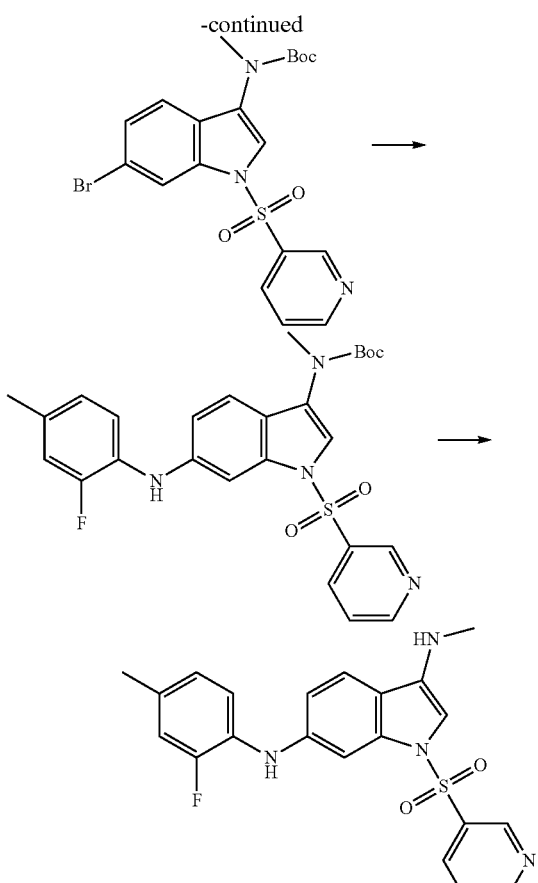

Step 1: Preparation of tert-butyl (6-bromo-1-(pyridin-3-ylsulfonyl)-1H-indol-3-yl)(methyl)carbamate Tert-butyl (6-bromo-1H-indol-3-yl)(methyl)carbamate (100 mg, 0.3 mmol) was dissolved in 3 ml of tetrahydrofuran solution, cooled to 0° C., and dropwisely added with sodium hydride (60% in oil) (18 mg, 0.4 mmol). The reaction mixture was stirred at 0° C. for 30 minutes, added with pyridin-3-sulfonyl chloride (82 mg, 0.4 mmol) prepared in Step 1 of Example 1, and stirred at room temperature for 5 h hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:1 (v/v)) to obtain 100 mg of a title compound (yield: 70%).

$^1$H NMR (300 MHz, CDCl$_3$): 9.10 (d, 1H), 8.80 (dd, 1H), 8.15-8.19 (m, 2H), 7.39-7.48 (m, 4H), 4.38 (s, 3H), 1.46 (s, 9H)

Step 2: Preparation of tert-butyl (6-((2-fluoro-4-methylphenyl)amino)-1-(pyridin-3-ylsulfonyl)-1H-indol-3-yl)(methyl)carbamate Tert-butyl (6-bromo-1-(pyridin-3-ylsulfonyl)-1H-indol-3-yl)(methyl)carbamate (100 mg, 0.2 mmol) prepared in Step 1; Bis(dibenzylideneacetone)palladium(0) (12 mg, 0.02 mmole); tri-tert-butylphosphine, 50% solution in toluene (7.7 μl, 0.03 mmole); 4,5-Bis(diphenylphosphino)-9,9-dimethylxanthene (18 mg, 0.03 mmole); cesium carbonate (113 mg, 0.3 mmole); and 2-fluoro-4-methylaniline (36 μl, 0.3 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:1 (v/v)) to obtain 81 mg of a title compound (yield: 74.3%).

$^1$H NMR (300 MHz, CDCl$_3$): 9.11 (d, 1H), 8.82 (dd, 1H), 8.16-8.20 (m, 2H), 7.65 (d, 1H), 7.44 (d, 2H), 7.41-7.48 (m, 3H), 6.88 (s, 1H), 4.38 (s, 3H), 2.31 (s, 3H), 1.46 (s, 9H)

Step 3: Preparation of N6-(2-fluoro-4-methylphenyl)-N3-methyl-1-(pyridin-3ylsulfonyl)-1H-indol-3,6-diamine hydrochloride Tert-butyl (6-((2-fluoro-4-methylphenyl)amino)-1-(pyridin-3-ylsulfonyl)-1H-indol-3-yl)(methyl)carbamate (50 mg, 0.1 mmol) prepared in Step 2 was added with 3 ml of 1.25 M HCl-methanol solution, and stirred at room temperature for 3 hours. The reaction mixture was concentrated under reduced pressure, and the resulting residue was recrystallized with dichloromethane to obtain 30 mg of a title compound (yield: 59%).

$^1$H NMR (300 MHz, CD$_3$OD): 9.04 (d, 1H), 8.78 (dd, 1H), 8.28 (d, 1H), 7.68 (s, 1H), 7.58-7.61 (m, 1H), 7.46 (s, 2H), 7.25 (s, 1H), 7.11-7.17 (m, 2H), 7.01 (dd, 1H), 4.81 (s, 3H), 2.31 (s, 3H)

Example 334: Preparation of N6-(2-chloro-4-methylphenyl)-N3-methyl-1-(pyridin-3ylsulfonyl)-1H-indol-3,6-diamine hydrochloride

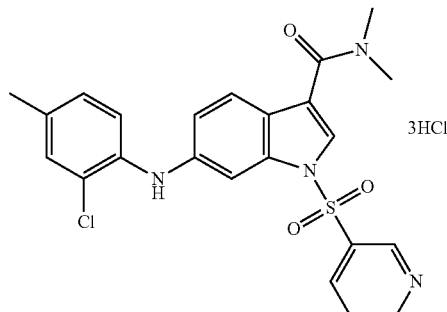

The compound was prepared in the same manner as in Example 333 except that 2-chloro-4-methylaniline was used instead of 2-fluoro-4-methylaniline to obtain 33 mg of a title compound (yield: 65%).

$^1$H NMR (300 MHz, CD$_3$OD): 9.06 (d, 1H), 8.81 (dd, 1H), 8.32 (d, 1H), 7.71 (s, 1H), 7.62-7.64 (m, 1H), 7.52 (s, 2H), 7.30 (s, 1H), 7.12-7.18 (m, 2H), 7.03 (dd, 1H), 4.85 (s, 3H), 2.33 (s, 3H)

Example 335: Preparation of methyl 6-(4-methoxyphenyl)-1-(pyridin-3-ylsulfonyl)-1H-indol-3-carboxylate The compound was prepared as shown in Reaction Scheme 15 below.

[Reaction Scheme 15]

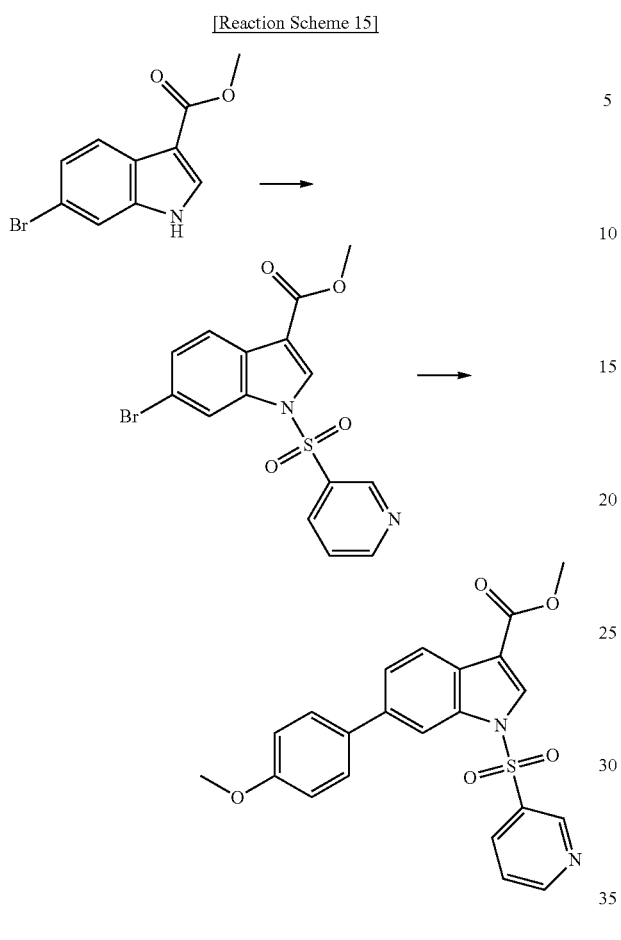

Step 1: Preparation of methyl 6-bromo-1-(pyridin-3-ylsulfonyl)-1H-indol-3-carboxylate Methyl 6-bromo-1H-indol-3-carboxylate (200 mg, 0.8 mmol) was dissolved in 2 ml of tetrahydrofuran solution, cooled to 0° C., and dropwisely added with sodium hydride (60% in oil) (44 mg, 1.1 mmol). The reaction mixture was stirred at 0° C. for 30 minutes, added with pyridin-3-sulfonyl chloride (232 mg, 1.1 mmol) prepared in Step 1 of Example 1, and stirred at room temperature for 12 hours. The resulting reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:2 (v/v)) to obtain 250 mg of a title compound (yield: 80%).

$^1$H NMR (300 MHz, CDCl$_3$): 8.88 (d, 1H), 8.57 (s, 1H), 8.27 (dd, 1H), 8.03 (dd, 1H), 7.54 (d, 1H), 7.49 (d, 1H), 7.25 (s, 1H), 7.21 (d, 1H), 3.97 (s, 9H)

Step 2: Preparation of methyl 6-(4-methoxyphenyl)-1-(pyridin-3-ylsulfonyl)-1H-indol-3-carboxylate Methyl 6-bromo-1-(pyridin-3-ylsulfonyl)-1H-indol-3-carboxylate (20 mg, 0.05 mmol) prepared in Step 1, (4-methoxyphenyl)boronic acid (11 mg, 0.07 mmol), Tetrakis (triphenylphosphine)palladium(0) (11 mg, 0.01 mmol), and potassium carbonate (14 mg, 0.1 mmol) were suspended in 1 ml of toluene, and reacted in a microwave reactor maintained at 170° C. for 30 minutes. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 7 mg of a title compound (yield: 33.3%).

$^1$H NMR (300 MHz, CDCl$_3$): 9.20 (s, 1H), 8.80 (dd, 1H), 8.24 (s, 1H), 8.13-8.21 (m, 3H), 7.55-7.59 (m, 3H), 7.41-7.45 (m, 1H), 7.02 (d, 2H), 3.95 (s, 3H), 3.88 (s, 3H)

In Examples 336 through 338 below, compounds were prepared in the same manner as in Example 335 except that reactants were appropriately changed as necessary depending on the structures of the compounds to be prepared and in consideration of Reaction Scheme 15.

Example 336: Preparation of methyl 6-(6-fluoropyridin-3-yl)-1-(pyridin-3-ylsulfonyl)-1H-indol-3-carboxylate

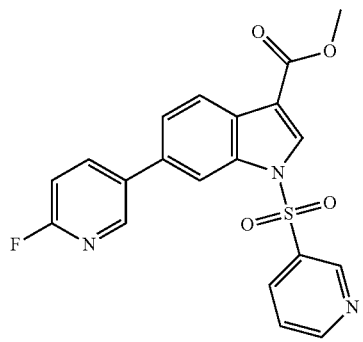 [SMILES: COC(=O)c1cn(S(=O)(=O)c2cccnc2)c2cc(-c3ccc(F)nc3)ccc12]

$^1$H NMR (500 MHz, CD$_3$OD): 9.30 (d, 1H), 8.92 (d, 1H), 8.63 (td, 1H), 7.50 (dd, 1H), 8.45 (s, 1H), 8.22 (d, 1H), 8.12 (d, 1H), 8.01 (d, 1H), 7.95 (s, 1H), 7.54 (dd, 1H), 7.16 (dd, 1H), 3.97 (s, 3H)

Example 337: Preparation of methyl 1-((6-chloropyridin-3-yl)sulfonyl)-6-(6-fluoropyridin-3-yl)-1H-indol-3-carboxylate

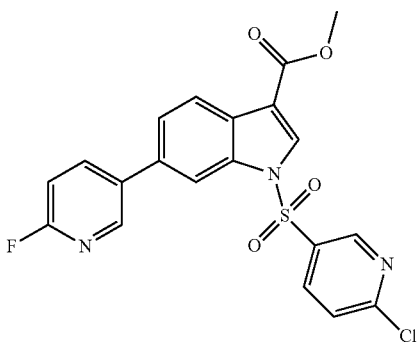 [SMILES: COC(=O)c1cn(S(=O)(=O)c2ccc(Cl)nc2)c2cc(-c3ccc(F)nc3)ccc12]

$^1$H NMR (500 MHz, CD$_3$OD): 9.32 (d, 1H), 8.94 (d, 1H), 8.66 (td, 1H), 7.53 (dd, 1H), 8.49 (s, 1H), 8.26 (d, 1H), 8.16 (d, 1H), 8.06 (d, 1H), 7.98 (s, 1H), 7.57 (dd, 1H), 7.21 (dd, 1H), 3.95 (s, 3H)

Example 338: Preparation of methyl 6-(6-methoxy-pyridin-3-yl)-1-(pyridin-3-ylsulfonyl)-1H-indol-3-carboxylate

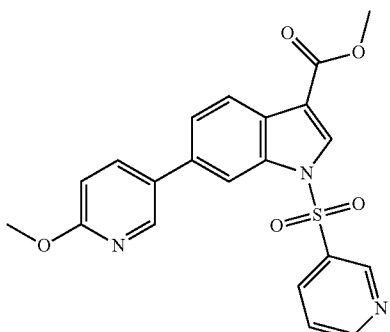

¹H NMR (300 MHz, CDCl₃): 9.19 (s, 1H), 8.81 (d, 1H), 8.42 (d, 1H), 8.27 (s, 1H), 8.18-8.22 (m, 2H), 8.11 (s, 1H), 7.83 (dd, 1H), 7.53 (dd, 1H), 7.45 (q, 1H), 3.86 (d, 1H), 4.02 (s, 3H), 3.99 (s, 3H)

Example 339: Preparation of N-(2-fluoro-4-methyl-phenyl)-1-((3-fluorophenyl)sulfonyl)-3-((methyl-amino)methyl)-1H-pyrrolo[3,2-b]pyridin-6-amine hydrochloride The compound was prepared as shown in Reaction Scheme 16 below.

[Reaction Scheme 16]

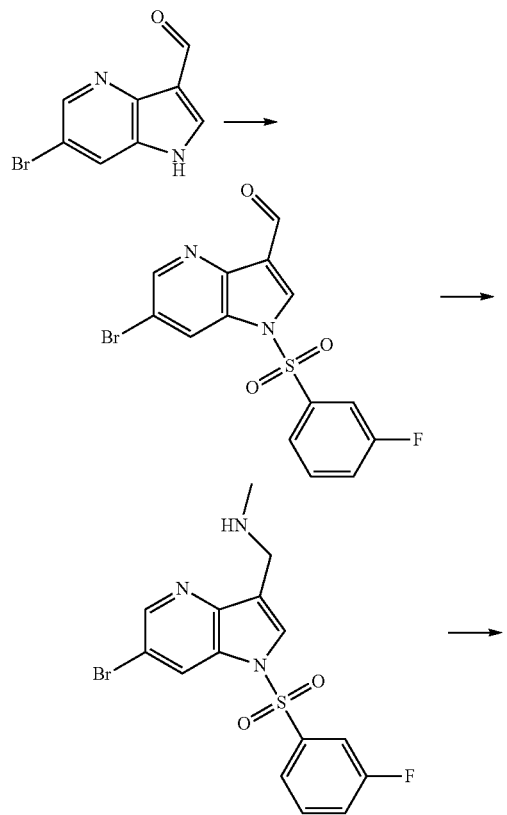

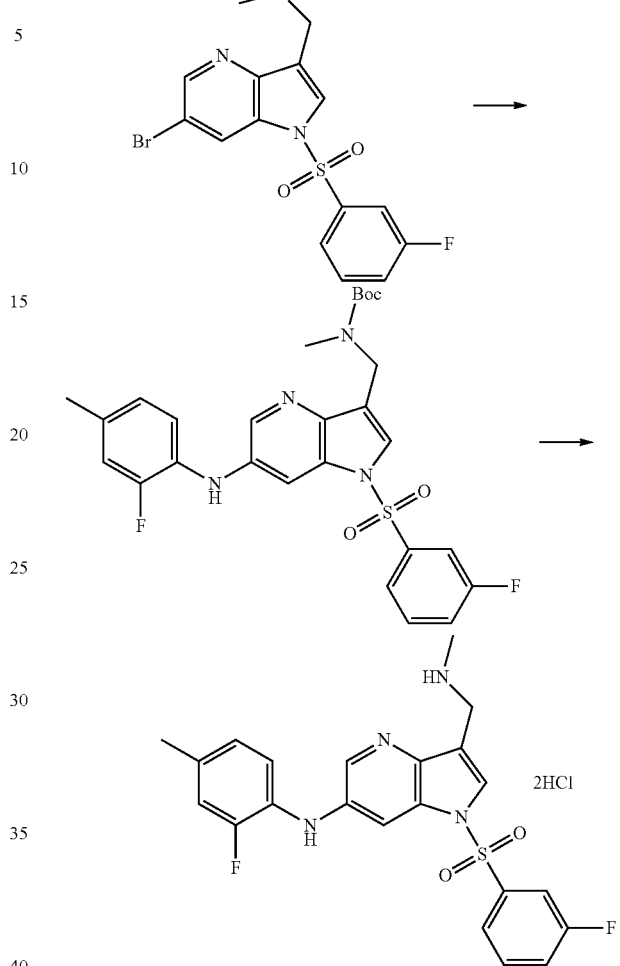

Step 1: Preparation of 6-bromo-1-((3-fluorophenyl)sulfonyl)-1H-pyrrolo[3,2-b]pyridin-3-carbaldehyde 6-bromo-1H-pyrrolo[3,2-b]pyridin-3-carbaldehyde (1 g, 4.4 mmol) was dissolved in 40 ml of N,N-dimethylformamide solution, cooled to 0° C., and dropwisely added with sodium hydride (60% in oil) (213 mg, 5.3 mmol). The reaction mixture was stirred at 0° C. for 30 minutes, added with 3-fluorobenzenesulfonyl chloride (887 μl, 6.6 mmol), and stirred at room temperature for 5 hours. The resulting reaction mixture was recrystallized with water to obtain 1 g of a title compound (yield: 57.8%).

¹H NMR (500 MHz, CDCl₃): 9.26 (s, 1H), 8.76 (s, 1H), 8.46 (s, 1H), 7.36 (s, 1H), 7.77 (d, 1H), 7.65-7.67 (m, 1H), 7.57-7.61 (m, 1H), 7.39-7.42 (m, 1H)

Step 2: Preparation of 1-(6-bromo-1-((3-fluorophenyl)sulfonyl)-1H-pyrrolo[3,2-b]pyridin-3-yl)-N-methylmethanamine 6-bromo-1-((3-fluorophenyl)sulfonyl)-1H-pyrrolo[3,2-b]pyridin-3-carbaldehyde (1 g, 2.6 mmol) prepared in Step 1, dissolved in 30 ml of methanol, was added with sodium cyanoborohydride (817 mg, 13 mmole) and 2 M methylamine-tetrahydrofuran solution (2.6 ml, 5.2 mmole), and stirred at room temperature for 12 hours. The reaction mixture was added with a saturated sodium bicarbonate solution and extracted with ethyl acetate. The resulting extract was washed with saturated brine, dried on anhydrous magnesium sulfate, and concentrated under reduced pressure. The resulting residue was purified by silica gel column chromatography (dichloromethane:methanol=10:1 (v/v)) to obtain 600 mg of a title compound (yield: 57.7%).

$^1$H NMR (500 MHz, CD$_3$OD): 8.61 (d, 1H), 8.55 (d, 1H), 8.04 (s, 1H), 7.84-7.87 (m, 2H), 7.60-7.64 (m, 1H), 7.46 (td, 1H), 3.89 (s, 2H), 2.32 (s, 3H)

Step 3: Preparation of tert-butyl ((6-bromo-1-((3-fluorophenyl)sulfonyl)-1H-pyrrolo[3,2-b]pyridin-3-yl)methyl)(methyl)carbamate 1-(6-bromo-1-((3-fluorophenyl)sulfonyl)-1H-pyrrolo[3,2-b]pyridin-3-yl)-N-methylmethanamine (100 mg, 0.2 mmol) prepared in Step 2 was dissolved in 10 ml of dichloromethane solution, added with triethylamine (52 μl, 0.4 mmole), di-tert-butyl dicarbonate (109 mg, 0.5 mmole), and stirred at room temperature for 3 hours. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:4 (v/v)) to obtain 100 mg of a title compound (yield: 80%).

$^1$H NMR (500 MHz, CDCl$_3$): 8.59 (d, 1H), 8.41 (s, 1H), 7.72 (br, 1H), 7.66 (d, 1H), 7.49-7.57 (m, 2H), 7.31 (br, 1H), 4.53 (s, 2H), 2.94 (d, 3H), 1.46 (s, 9H)

Step 4: Preparation of tert-butyl ((6-((2-fluoro-4-methylphenyl)amino)-1-((3-fluorophenyl)sulfonyl)-1H-pyrrolo[3,2-b]pyridin-3-yl)methyl)(methyl)carbamate Tert-butyl ((6-bromo-1-((3-fluorophenyl)sulfonyl)-1H-pyrrolo[3,2-b]pyridin-3-yl)methyl)(methyl)carbamate (20 mg, 0.04 mmol) prepared in Step 3; Bis(dibenzylideneacetone)palladium(0) (2.3 mg, 0.004 mmole); tri-tert-butylphosphine, 50% solution in toluene (2.9 μl, 0.006 mmole); 4,5-Bis(diphenylphosphino)-9,9-dimethylxanthene (3.5 mg, 0.006 mmole); cesium carbonate (21 mg, 0.06 mmole), and 2-fluoro-4-methylaniline (7.5 mg, 0.06 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate: n-hexane=1:2 (v/v)) to obtain 13 mg of a title compound (yield: 60%).

$^1$H NMR (300 MHz, CDCl$_3$): 8.61 (d, 2H), 8.55 (dd, 1H), 8.43-8.48 (m, 2H), 8.26-8.31 (m, 2H), 8.16 (t, 1H), 7.88-7.97 (m, 2H), 4.45 (s, 2H), 2.75 (m, 3H), 2.32 (s, 3H), 1.45 (s, 9H)

Step 5: Preparation of N-(2-fluoro-4-methylphenyl)-1-((3-fluorophenyl)sulfonyl)-3-((methylamino)methyl)-1H-pyrrolo[3,2-b]pyridin-6-amine hydrochloride Tert-butyl ((6-((2-fluoro-4-methylphenyl)amino)-1-((3-fluorophenyl)sulfonyl)-1H-pyrrolo[3,2-b]pyridin-3-yl)methyl)(methyl)carbamate (13 mg, 0.02 mmol) prepared in Step 4 was added with 1 ml of 1.25 M HCl-methanol solution, and stirred at room temperature for 3 hours. The reaction mixture was concentrated under reduced pressure and recrystallized with dichloromethane to obtain 8 mg of a title compound (yield: 65%).

$^1$H NMR (500 MHz, CDCl$_3$): 8.29 (d, 1H), 8.10 (s, 1H), 7.82 (s, 1H), 7.79 (d, 1H), 7.73 (td, 1H), 7.64-7.68 (m, 1H), 7.52 (td, 1H), 7.21 (t, 1H), 7.12 (d, 1H), 7.06 (d, 1H), 4.39 (s, 1H), 2.76 (s, 3H), 2.39 (s, 3H)

In Examples 340 through 352 below, compounds were prepared in the same manner as in Example 339 except that reactants were appropriately changed as necessary depending on the structures of the compounds to be prepared and in consideration of Reaction Scheme 16

Example 340: Preparation of 1-((3-fluorophenyl)sulfonyl)-N-(4-methyl-2-(trifluoromethoxy)phenyl)-3-((methylamino)methyl)-1H-pyrrolo[3,2-b]pyridin-6-amine hydrochloride

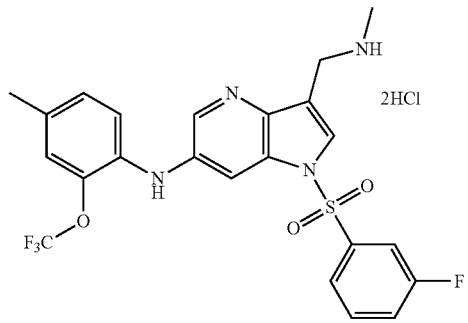 [SMILES: CNCc1cn(S(=O)(=O)c2cccc(F)c2)c2cc(Nc3ccc(C)cc3OC(F)(F)F)cnc12]

$^1$H NMR (500 MHz, CD$_3$OD): 8.31 (d, 1H), 8.12 (s, 1H), 7.78-7.79 (m, 2H), 7.72 (td, 1H), 7.66-7.69 (m, 1H), 7.54 (td, 1H), 7.29 (s, 1H), 7.27 (s, 1H), 7.18 (d, 1H), 4.41 (s, 2H), 2.78 (s, 3H), 2.29 (s, 3H)

Example 341: Preparation of N-(4-chloro-2-methylphenyl)-1-((3-fluorophenyl)sulfonyl)-3-((methylamino)methyl)-1H-pyrrolo[3,2-b]pyridin-6-amine hydrochloride

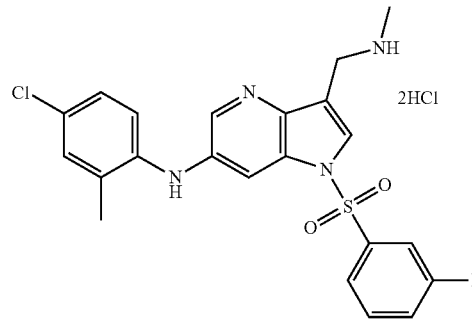

$^1$H NMR (500 MHz, CD$_3$OD): 8.26 (d, 1H), 8.16 (s, 1H), 7.84 (s, 1H), 7.79 (d, 1H), 7.73 (d, 1H), 7.65-7.69 (m, 1H), 7.53 (td, 1H), 7.37 (d, 1H), 7.26 (d, 1H), 7.19 (d, 1H), 4.41 (s, 2H), 2.77 (s, 3H), 2.24 (s, 3H)

Example 342: Preparation of N-(2,4-dichlorophenyl)-1-((3-fluorophenyl)sulfonyl)-3-((methylamino)methyl)-1H-pyrrolo[3,2-b]pyridin-6-amine hydrochloride

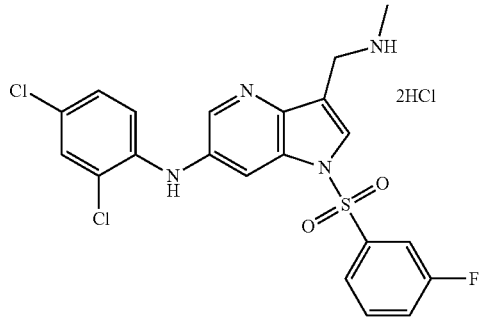 [SMILES: CNCc1cn(S(=O)(=O)c2cccc(F)c2)c2cc(Nc3ccc(Cl)cc3Cl)cnc12]

¹H NMR (500 MHz, CD₃OD): 8.43 (d, 1H), 8.13 (s, 1H), 7.96 (d, 1H), 7.85 (d, 1H), 7.79 (td, 1H), 7.65-7.70 (m, 1H), 7.58 (d, 1H), 7.53 (td, 1H), 7.33 (d, 1H), 7.26 (d, 1H), 4.41 (s, 2H), 2.78 (s, 3H)

Example 343: Preparation of 1-((3-fluorophenyl)sulfonyl)-N-(2-methoxy-4-(trifluoromethoxy)phenyl)-3-((methylamino)methyl)-1H-pyrrolo[3,2-b]pyridin-6-amine hydrochloride

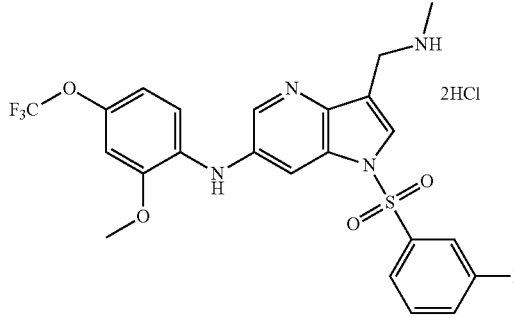

¹H NMR (500 MHz, CD₃OD): 8.40 (d, 1H), 8.09 (s, 1H), 7.93 (d, 1H), 7.82 (d, 1H), 7.77 (td, 1H), 7.64-7.68 (m, 1H), 7.52 (td, 1H), 7.26 (d, 1H), 7.04 (d, 1H), 6.91 (d, 1H), 4.40 (s, 2H), 3.92 (s, 3H), 2.78 (s, 3H)

Example 344: Preparation of N-(6-chloro-2-methylpyridin-3-yl)-1-((3-fluorophenyl)sulfonyl)-3-((methylamino)methyl)-1H-pyrrolo[3,2-b]pyridin-6-amine hydrochloride

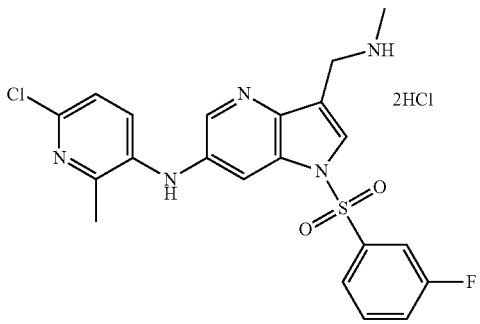 [SMILES: CNCc1cn(S(=O)(=O)c2cccc(F)c2)c2cc(Nc3ccc(Cl)nc3C)cnc12]

¹H NMR (500 MHz, CD₃OD): 8.39 (d, 1H), 8.16 (s, 1H), 7.93 (d, 1H), 7.84 (d, 1H), 7.79 (td, 1H), 7.66-7.70 (m, 1H), 7.64 (d, 1H), 7.53 (td, 1H), 7.34 (d, 1H), 4.44 (s, 2H), 2.78 (s, 3H), 2.50 (s, 3H)

Example 345: Preparation of N-(2-chloro-4-methylphenyl)-3-((methylamino)methyl)-1-(pyridin-3-ylsulfonyl)-1H-pyrrolo[3,2-b]pyridin-6-amine hydrochloride

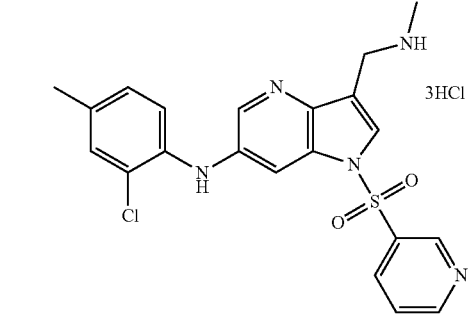 [SMILES: CNCc1cn(S(=O)(=O)c2cccnc2)c2cc(Nc3ccc(C)cc3Cl)cnc12]

¹H NMR (500 MHz, CD₃OD): 9.10 (d, 1H), 8.87 (dd, 1H), 8.32-8.35 (m, 2H), 8.03 (s, 1H), 7.75 (d, 1H), 7.65 (q, 1H), 7.39 (s, 1H), 7.19-7.23 (m, 2H), 4.38 (s, 2H), 2.76 (s, 3H), 2.39 (s, 3H)

Example 346: Preparation of N-(4-fluoro-2-methyl-phenyl)-3-((methylamino)methyl)-1-(pyridin-3-yl-sulfonyl)-1H-pyrrolo[3,2-b]pyridin-6-amine hydrochloride

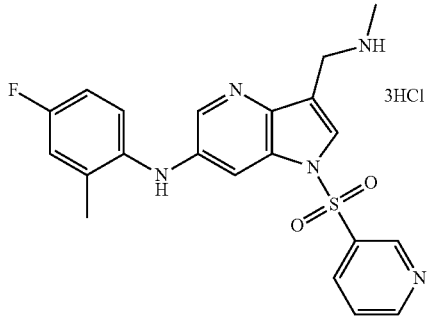 [SMILES: CNCc1cn(S(=O)(=O)c2cccnc2)c2cc(Nc3ccc(F)cc3C)cnc12]

¹H NMR (500 MHz, CD₃OD): 9.07 (d, 1H), 8.88 (dd, 1H), 8.32 (td, 1H), 8.20 (d, 1H), 8.09 (s, 1H), 7.67 (q, 1H), 7.63 (d, 1H), 7.23 (q, 1H), 7.16 (dd, 1H), 7.06 (td, 1H), 4.39 (s, 2H), 2.78 (s, 3H), 2.24 (s, 3H)

Example 347: Preparation of N-(2-chloro-4-fluoro-phenyl)-3-((methylamino)methyl)-1-(pyridin-3-yl-sulfonyl)-1H-pyrrolo[3,2-b]pyridin-6-amine hydrochloride

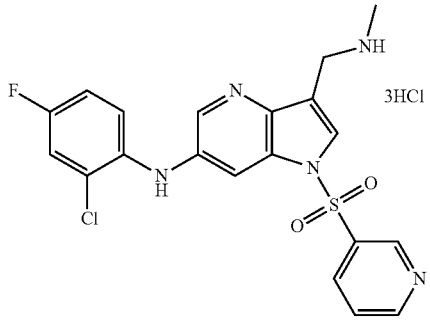 [SMILES: CNCc1cn(S(=O)(=O)c2cccnc2)c2cc(Nc3ccc(F)cc3Cl)cnc12]

¹H NMR (500 MHz, CD₃OD): 9.11 (d, 1H), 8.86 (dd, 1H), 8.35 (td, 1H), 8.33 (d, 1H), 8.06 (s, 1H), 7.75 (d, 1H), 7.65 (q, 1H), 7.42 (dd, 1H), 7.35 (q, 1H), 7.18 (td, 1H), 4.39 (s, 2H), 2.77 (s, 3H)

Example 348: Preparation of N-(4-chloro-2-methyl-phenyl)-3-((methylamino)methyl)-1-(pyridin-3-yl-sulfonyl)-1H-pyrrolo[3,2-b]pyridin-6-amine hydrochloride

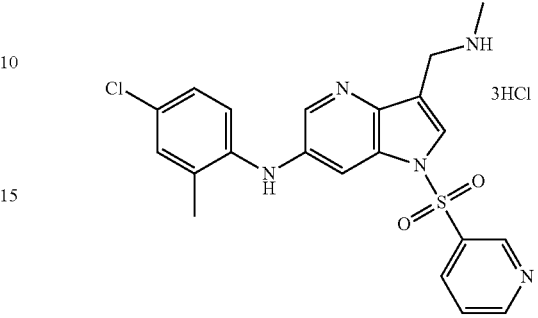

¹H NMR (500 MHz, CD₃OD): 9.13 (d, 1H), 8.90 (d, 1H), 8.39 (td, 1H), 8.29 (d, 1H), 8.20 (s, 1H), 7.89 (d, 1H), 7.68 (q, 1H), 7.39 (d, 1H), 7.29 (dd, 1H), 7.22 (d, 1H), 4.43 (s, 2H), 2.79 (s, 3H), 2.26 (s, 3H)

Example 349: Preparation of N-(2,4-dichlorophe-nyl)-3-((methylamino)methyl)-1-(pyridin-3-ylsulfo-nyl)-1H-pyrrolo[3,2-b]pyridin-6-amine hydrochloride

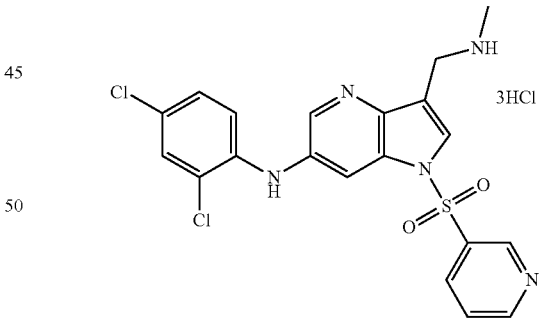

¹H NMR (500 MHz, CD₃OD): 9.19 (d, 1H), 8.89 (dd, 1H), 8.43-8.45 (m, 2H), 8.21 (s, 1H), 8.05 (d, 1H), 7.69 (q, 1H), 7.59 (d, 1H), 7.36 (dd, 1H), 7.30 (d, 1H), 4.43 (s, 2H), 2.79 (s, 3H)

Example 350: Preparation of N-(2-chloro-4-methyl-phenyl)-1-((5-fluoropyridin-3-yl)sulfonyl)-3-((methylamino)methyl)-1H-pyrrolo[3,2-b]pyridin-6-amine hydrochloride

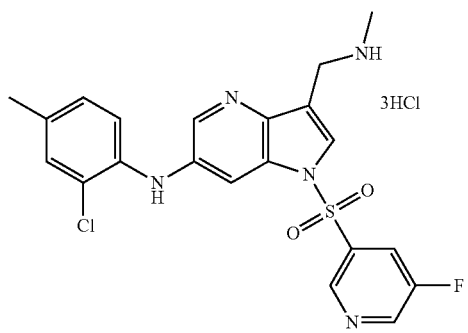 [SMILES: CNCc1cn(S(=O)(=O)c2cncc(F)c2)c2cc(Nc3ccc(C)cc3Cl)cnc12]

$^1$H NMR (500 MHz, CD$_3$OD): 8.97 (s, 1H), 8.83 (d, 1H), 8.34 (d, 1H), 8.23 (td, 1H), 8.08 (s, 1H), 7.75 (d, 1H), 7.39 (s, 1H), 7.19-7.24 (m, 2H), 4.40 (s, 2H), 2.78 (s, 3H), 2.39 (s, 3H)

Example 351: Preparation of N-(4-fluoro-2-methyl-phenyl)-1-((5-fluoropyridin-3-yl)sulfonyl)-3-((methylamino)methyl)-1H-pyrrolo[3,2-b]pyridin-6-amine hydrochloride

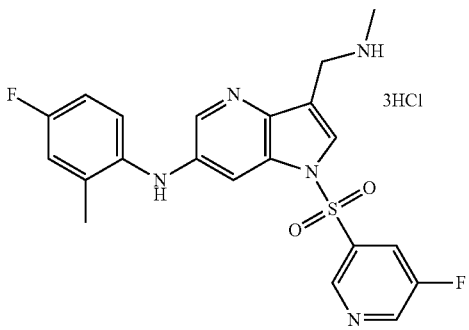 [SMILES: CNCc1cn(S(=O)(=O)c2cncc(F)c2)c2cc(Nc3ccc(F)cc3C)cnc12]

$^1$H NMR (500 MHz, CD$_3$OD): 8.93 (s, 1H), 8.84 (d, 1H), 8.17-8.20 (m, 2H), 8.14 (s, 1H), 7.71 (s, 1H), 7.24 (q, 1H), 7.15 (dd, 1H), 7.05 (td, 1H), 4.40 (s, 2H), 2.77 (s, 3H), 2.24 (s, 3H)

Example 352: Preparation of N-(2-chloro-4-fluoro-phenyl)-1-((5-fluoropyridin-3-yl)sulfonyl)-3-((methylamino)methyl)-1H-pyrrolo[3,2-b]pyridin-6-amine hydrochloride

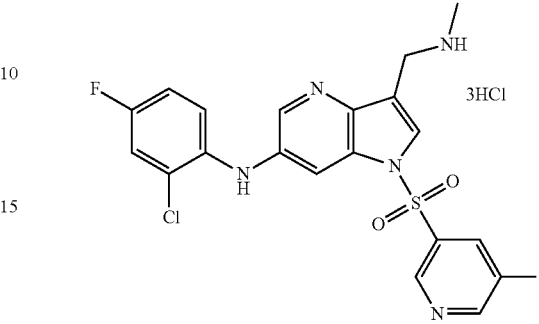

$^1$H NMR (500 MHz, CD$_3$OD): 8.97 (s, 1H), 8.83 (d, 1H), 8.34 (d, 1H), 8.23 (td, 1H), 8.07 (s, 1H), 7.74 (d, 1H), 7.41 (dd, 1H), 7.36 (q, 1H), 7.18 (td, 1H), 4.39 (s, 2H), 2.78 (s, 3H)

Example 353: Preparation of N-(2-chloro-4-methyl-phenyl)-1-((3-fluorophenyl)sulfonyl)-3-((methylamino)methyl)-1H-pyrrolo[3,2-c]pyridin-6-amine hydrochloride The compound was prepared as shown in Reaction Scheme 17 below.

[Reaction Scheme 17]

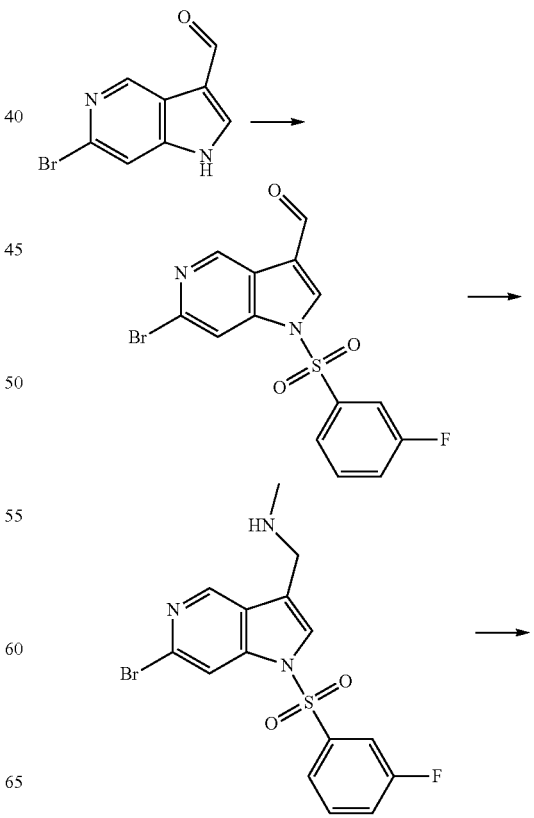

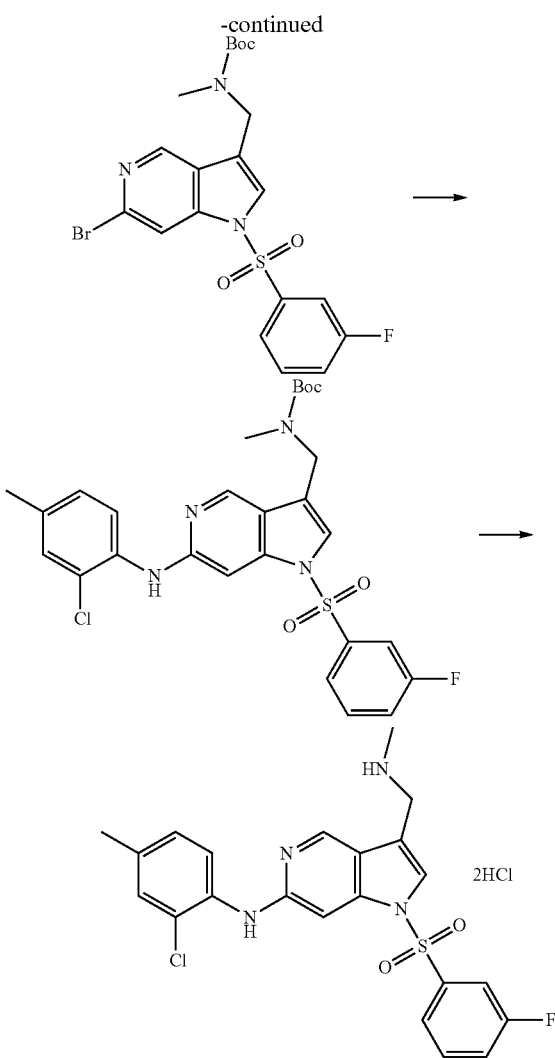

Step 1: Preparation of 6-bromo-1-((3-fluorophenyl)sulfonyl)-1H-pyrrolo[3,2-c]pyridin-3-carbaldehyde 6-bromo-1H-pyrrolo[3,2-c]pyridin-3-carbaldehyde (50 mg, 0.2 mmol) was dissolved in 1 ml of N,N-dimethylformamide solution, cooled to 0° C., and dropwisely added with sodium hydride (60% in oil) (10 mg, 0.3 mmol). The reaction mixture was stirred at 0° C. for 30 minutes, added with 3-fluorobenzenesulfonyl chloride (44 μl, 0.3 mmol), and stirred at room temperature for 3 hours. The resulting reaction mixture was recrystallized with water to obtain 60 mg of a title compound (yield: 70.5%).

$^1$H NMR (500 MHz, CDCl$_3$): 9.27 (s, 1H), 8.17 (s, 1H), 8.07 (s, 1H), 7.80 (d, 1H), 7.68 (td, 1H), 7.59-7.63 (m, 1H), 7.42 (td, 1H), 4.52 (s, 2H), 2.86 (s, 3H), 1.47 (s, 9H)

Step 2: Preparation of 1-(6-bromo-1-((3-fluorophenyl)sulfonyl)-1H-pyrrolo[3,2-c]pyridin-3-yl)-N-methylmethanamine 6-bromo-1-((3-fluorophenyl)sulfonyl)-1H-pyrrolo[3,2-c]pyridin-3-carbaldehyde (30 mg, 0.07 mmol) prepared in Step 1, dissolved in 1 ml of methanol, was added with sodium cyanoborohydride (24 mg, 0.4 mmole) and 2 M methylamine-tetrahydrofuran solution (0.2 ml, 0.4 mmole), and stirred at room temperature for 8 hours. The reaction mixture was added with a saturated sodium bicarbonate solution and extracted with ethyl acetate. The resulting extract was washed with saturated brine, dried on anhydrous magnesium sulfate, and concentrated under reduced pressure. The resulting residue was purified by silica gel column chromatography (dichloromethane:methanol=10:1 (v/v)) to obtain 15 mg of a title compound (yield: 48.2%).

$^1$H NMR (500 MHz, CD$_3$OD): 8.82 (s, 1H), 8.18 (s, 1H), 8.01 (s, 1H), 7.92 (d, 1H), 7.89 (d, 1H), 7.60-7.69 (m, 2H), 7.48-7.52 (m, 1H), 4.30 (s, 2H), 2.69 (s, 3H)

Step 3: Preparation of tert-butyl ((6-bromo-1-((3-fluorophenyl)sulfonyl)-1H-pyrrolo[3,2-c]pyridin-3-yl)methyl)(methyl)carbamate 1-(6-bromo-1-((3-fluorophenyl)sulfonyl)-1H-pyrrolo[3,2-c]pyridin-3-yl)-N-methylmethanamine (15 mg, 0.04 mmol) prepared in Step 2 was dissolved in 1 ml of dichloromethane solution, added with triethylamine (8 μl, 0.06 mmole) and di-tert-butyl dicarbonate (16 mg, 0.07 mmole), and stirred at room temperature for 5 hours. The reaction mixture was added with water and extracted with ethyl acetate. The resulting separated organic layer was washed with saturated brine, dried on anhydrous magnesium sulfate, and concentrated under reduced pressure. The resulting residue was purified by silica gel column chromatography (ethyl acetate:n-hexane=1:4 (v/v)) to obtain 15 mg of a title compound (yield: 80%).

$^1$H NMR (500 MHz, CDCl$_3$): 8.72 (br, 1H), 8.06 (s, 1H), 7.70 (d, 1H), 7.58 (d, 1H), 7.50-7.55 (m, 1H), 7.41 (s, 1H), 7.34 (td, 1H), 4.52 (s, 2H), 2.86 (s, 3H), 1.47 (s, 9H)

Step 4: Preparation of tert-butyl ((6-((2-chloro-4-methylphenyl)amino)-1-((3-fluorophenyl)sulfonyl)-1H-pyrrolo[3,2-c]pyridin-3-yl)methyl)(methyl)carbamate Tert-butyl ((6-bromo-1-((3-fluorophenyl)sulfonyl)-1H-pyrrolo[3,2-c]pyridin-3-yl)methyl)(methyl)carbamate (15 mg, 0.03 mmol) prepared in Step 3; Bis(dibenzylideneacetone)palladium(0) (1.7 mg, 0.003 mmole); tri-tert-butylphosphine, 50% solution in toluene (2.3 μl, 0.004 mmole); 4,5-Bis(diphenylphosphino)-9,9-dimethylxanthene (2.6 mg, 0.004 mmole); cesium carbonate (16 mg, 0.04 mmole); and 2-chloro-4-methylaniline (6.4 mg, 0.04 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:2 (v/v)) to obtain 10 mg of a title compound (yield: 59.5%).

$^1$H NMR (300 MHz, CDCl$_3$): 8.63 (d, 2H), 8.54 (dd, 1H), 8.38-8.42 (m, 2H), 8.24-8.29 (m, 2H), 8.13 (t, 1H), 7.81-7.90 (m, 2H), 4.41 (s, 2H), 2.73 (m, 3H), 2.33 (s, 3H), 1.46 (s, 9H)

Step 5: Preparation of N-(2-chloro-4-methylphenyl)-1-((3-fluorophenyl)sulfonyl)-3-((methylamino)methyl)-1H-pyrrolo[3,2-c]pyridin-6-amine hydrochloride Tert-butyl ((6-((2-chloro-4-methylphenyl)amino)-1-((3-fluorophenyl)sulfonyl)-1H-pyrrolo[3,2-c]pyridin-3-yl)

methyl)(methyl)carbamate (10 mg, 0.02 mmol) prepared in Step 4 was dissolved in 1 ml of 1.25 M HCl-methanol solution, and stirred at room temperature for 3 hours. The reaction mixture was concentrated under reduced pressure, and then recrystallized with dichloromethane to obtain 5 mg of a title compound (yield: 52.6%).

$^1$H NMR (500 MHz, CD$_3$OD): 8.74 (s, 1H), 8.14 (s, 1H), 7.90 (d, 1H), 7.83 (td, 1H), 7.72-7.77 (m, 1H), 7.62 (td, 1H), 7.54 (s, 1H), 7.44-7.45 (m, 2H), 7.35 (dd, 1H), 4.40 (s, 2H), 2.79 (s, 3H), 2.46 (s, 3H)

In Examples 354 through 358 below, compounds were prepared in the same manner as in Example 351 except that reactants were appropriately changed as necessary depending on the structures of the compounds to be prepared and in consideration of Reaction Scheme 17.

Example 354: Preparation of N-(4-fluoro-2-methylphenyl)-1-((3-fluorophenyl)sulfonyl)-3-((methylamino)methyl)-1H-pyrrolo[3,2-c]pyridin-6-amine hydrochloride

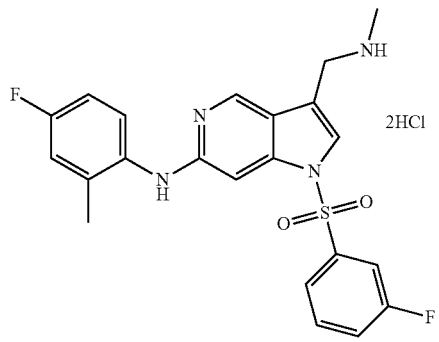

$^1$H NMR (500 MHz, CD$_3$OD): 8.64 (s, 1H), 8.10 (s, 1H), 7.88 (d, 1H), 7.82 (d, 1H), 7.72-7.77 (m, 1H), 7.62 (td, 1H), 7.36-7.39 (m, 2H), 7.26 (dd, 1H), 7.15 (td, 1H), 4.38 (s, 2H), 2.79 (s, 3H), 2.28 (s, 3H)

Example 355: Preparation of N-(2-chloro-4-fluorophenyl)-1-((3-fluorophenyl)sulfonyl)-3-((methylamino)methyl)-1H-pyrrolo[3,2-c]pyridin-6-amine hydrochloride

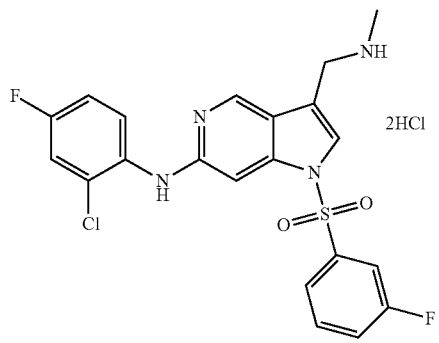

$^1$H NMR (500 MHz, CD$_3$OD): 8.76 (s, 1H), 8.15 (s, 1H), 7.92 (dd, 1H), 7.86 (td, 1H), 7.73-7.77 (m, 1H), 7.59-7.65 (m, 2H), 7.56 (dd, 1H), 7.49 (s, 1H), 7.33 (td, 1H), 4.40 (s, 2H), 2.79 (s, 3H)

Example 356: Preparation of 1-((3-fluorophenyl)sulfonyl)-N-(2-methoxy-4-(trifluoromethoxy)phenyl)-3-((methylamino)methyl)-1H-pyrrolo[3,2-c]pyridin-6-amine hydrochloride

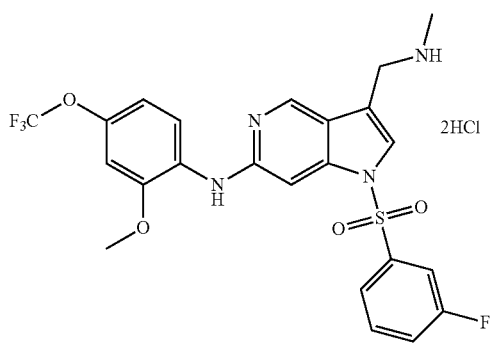 [SMILES: CNCc1cn(S(=O)(=O)c2cccc(F)c2)c2cc(Nc3ccc(OC(F)(F)F)cc3OC)ncc12]

$^1$H NMR (500 MHz, CD$_3$OD): 8.86 (s, 1H), 8.21 (s, 1H), 7.98 (dd, 1H), 7.89 (td, 1H), 7.75-7.82 (m, 1H), 7.54-7.62 (m, 2H), 7.48 (dd, 1H), 7.41 (s, 1H), 7.28 (td, 1H), 4.42 (s, 2H), 3.98 (s, 3H), 2.75 (s, 3H)

Example 357: Preparation of N-(2,6-dichloropyridin-3-yl)-1-((3-fluorophenyl)sulfonyl)-3-((methylamino)methyl)-1H-pyrrolo[3,2-c]pyridin-6-amine hydrochloride

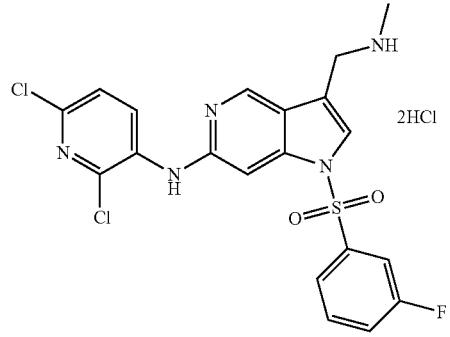 [SMILES: CNCc1cn(S(=O)(=O)c2cccc(F)c2)c2cc(Nc3ccc(Cl)nc3Cl)ncc12]

$^1$H NMR (500 MHz, CD$_3$OD): 8.75 (s, 1H), 8.39 (d, 1H), 8.04 (s, 1H), 7.96 (d, 1H), 7.91 (td, 1H), 7.69-7.74 (m, 2H), 7.57 (td, 1H), 7.48 (d, 1H), 4.41 (s, 2H), 2.79 (s, 3H)

Example 358: Preparation of N-(2-chloro-6-methyl-pyridin-3-yl)-1-((3-fluorophenyl)sulfonyl)-3-((methylamino)methyl)-1H-pyrrolo[3,2-c]pyridin-6-amine hydrochloride

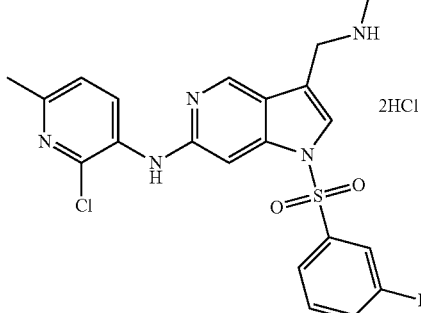

¹H NMR (500 MHz, CD₃OD): 8.75 (s, 1H), 8.11 (s, 1H), 8.04 (d, 1H), 7.94 (dd, 1H), 7.90 (td, 1H), 7.72-7.76 (m, 1H), 7.58-7.62 (m, 2H), 7.41 (d, 1H), 4.40 (s, 2H), 2.79 (s, 3H), 2.59 (s, 3H)

Example 359: Preparation of N-(2-chloro-4-methyl-phenyl)-1-((3-fluorophenyl)sulfonyl)-3-((methylamino)methyl)-1H-pyrrolo[3,2-c]pyridin-6-amine hydrochloride The compound was prepared as shown in Reaction Scheme 18 below.

[Reaction Scheme 18]

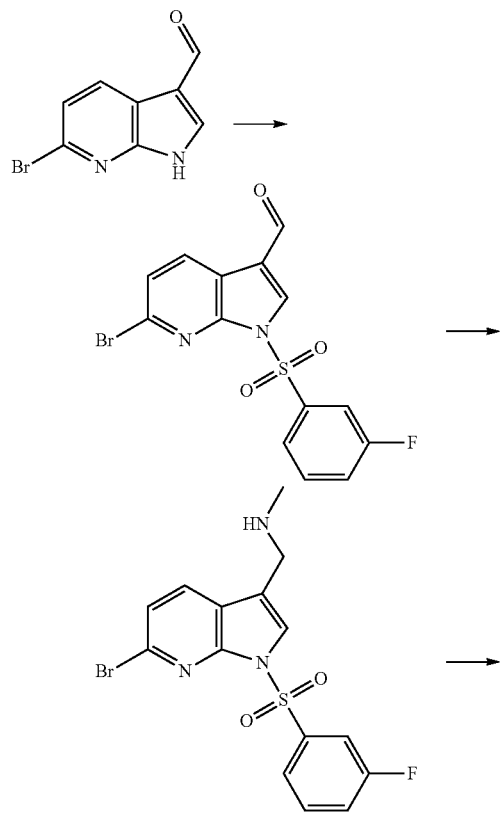

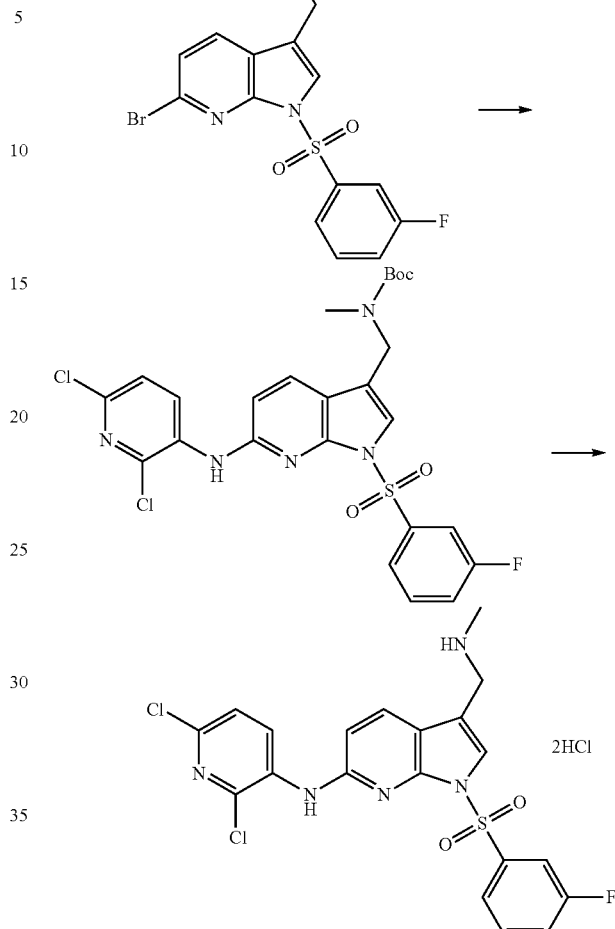

Step 1: Preparation of 6-bromo-1-((3-fluorophenyl)sulfonyl)-1H-pyrrolo[2,3-b]pyridin-3-carbaldehyde 6-bromo-1H-pyrrolo[2,3-b]pyridin-3-carbaldehyde (300 mg, 1.3 mmol) was dissolved in 5 ml of N,N-dimethylformamide solution, cooled to 0° C., and dropwisely added with sodium hydride (60% in oil) (64 mg, 1.6 mmol). The reaction mixture was stirred at 0° C. for 30 minutes, added with 3-fluorobenzenesulfonyl chloride (267 μl, 2.0 mmol), and stirred at room temperature for 5 hours. The resulting reaction mixture was recrystallized with water to obtain 400 mg of a title compound (yield: 78.4%).

¹H NMR (500 MHz, CDCl₃): 10.01 (s, 1H), 8.37 (d, 1H), 8.32 (s, 1H), 8.13 (d, 1H), 8.05 (td, 1H), 7.56-7.61 (m, 1H), 7.49 (d, 1H), 7.39 (td, 1H)

Step 2: Preparation of 1-(6-bromo-1-((3-fluorophenyl)sulfonyl)-1H-pyrrolo[2,3-b]pyridin-3-yl)-N-methylmethanamine 6-bromo-1-((3-fluorophenyl)sulfonyl)-1H-pyrrolo[2,3-b]pyridin-3-carbaldehyde (400 mg, 1.0 mmol) prepared in Step 1, dissolved in 10 ml of methanol, was added with sodium cyanoborohydride (328 mg, 5.22 mmole) and 2 M methylamine-tetrahydrofuran solution (1 ml, 2.0 mmole), and stirred at room temperature for 12 hours. The reaction mixture was added with a saturated sodium bicarbonate solution, and extracted with ethyl acetate. The resulting extract was washed with saturated brine, dried on anhydrous magnesium sulfate, and concentrated under reduced pressure. The resulting residue was purified by silica gel column chromatography (dichloromethane:methanol=10:1 (v/v)) to obtain 150 mg of a title compound (yield: 36.1%).

$^1$H NMR (300 MHz, CD$_3$OD): 9.13 (s, 1H), 8.82 (d, 1H), 8.41 (dd, 1H), 8.23 (s, 1H), 8.01 (s, 1H), 7.68 (d, 1H), 7.54-7.63 (m, 1H), 4.31 (s, 2H), 2.72 (s, 3H)

Step 3: Preparation of tert-butyl ((6-bromo-1-((3-fluorophenyl)sulfonyl)-1H-pyrrolo[2,3-b]pyridin-3-yl)methyl)(methyl)carbamate 1-(6-bromo-1-((3-fluorophenyl)sulfonyl)-1H-pyrrolo[2,3-b]pyridin-3-yl)-N-methylmethanamine (120 mg, 0.3 mmol) prepared in Step 2 was dissolved in 5 ml of dichloromethane solution, added with triethylamine (63 μl, 0.4 mmole) and di-tert-butyl dicarbonate (131 mg, 0.6 mmole), and stirred at room temperature for 3 hours. The reaction mixture was added with water and extracted with dichloromethane. The resulting separated organic layer was washed with saturated brine, dried on anhydrous magnesium sulfate, and concentrated under reduced pressure. The resulting residue was purified by silica gel column chromatography (ethyl acetate:n-hexane=1:1 (v/v)) to obtain 120 mg of a title compound (yield: 80%).

$^1$H NMR (500 MHz, CDCl$_3$): 8.05 (d, 1H), 7.96 (td, 1H), 7.92 (br, 1H), 7.57 (s, 1H), 7.50-7.54 (m, 1H), 7.30-7.35 (m, 2H), 4.47 (s, 2H), 2.73 (s, 3H), 1.47 (s, 9H)

Step 4: Preparation of tert-butyl ((6-((2,6-dichloropyridin-3-yl)amino)-1-((3-fluorophenyl)sulfonyl)-1H-pyrrolo[2,3-b]pyridin-3-yl)methyl)(methyl)carbamate Tert-butyl ((6-bromo-1-((3-fluorophenyl)sulfonyl)-1H-pyrrolo[2,3-b]pyridin-3-yl)methyl)(methyl)carbamate (20 mg, 0.04 mmol) prepared in Step 3; Bis(dibenzylideneacetone)palladium(0) (2.3 mg, 0.004 mmole); tri-tert-butylphosphine, 50% solution in toluene (3 μl, 0.006 mmole); 4,5-Bis(diphenylphosphino)-9,9-dimethylxanthene (3.5 mg, 0.006 mmole); cesium carbonate (21 mg, 0.06 mmole); and 2,6-dichloropyridin-3-amine (10 mg, 0.06 mmole) were suspended in 1 ml of toluene, and stirred at 110° C. for 15 hours. The reaction mixture was filtered with celite, and the resulting filtrate was added with water and extracted with ethyl acetate. The resulting extract was washed with saturated brine, dried on anhydrous magnesium sulfate, and concentrated under reduced pressure. The resulting residue was purified by silica gel column chromatography (ethyl acetate:n-hexane=1:3 (v/v)) to obtain 12 mg of a title compound (yield: 51.7%).

$^1$H NMR (300 MHz, CDCl$_3$): 9.08 (d, 2H), 8.98 (dd, 1H), 8.78-8.88 (m, 2H), 8.61-8.68 (m, 1H), 8.42 (t, 1H), 8.02-8.10 (m, 2H), 4.43 (s, 2H), 2.75 (m, 3H), 1.44 (s, 9H)

Step 5: Preparation of N-(2-chloro-4-methylphenyl)-1-((3-fluorophenyl)sulfonyl)-3-((methylamino)methyl)-1H-pyrrolo[3,2-c]pyridin-6-amine hydrochloride Tert-butyl ((6-((2-chloro-4-methylphenyl)amino)-1-((3-fluorophenyl)sulfonyl)-1H-pyrrolo[3,2-c]pyridin-3-yl)methyl)(methyl)carbamate (10 mg, 0.02 mmol) prepared in Step 4 was added with 1 ml of 1.25 M HCl-methanol solution, and stirred at room temperature for 3 hours. The reaction mixture was concentrated under reduced pressure, and recrystallzed with dichloromethane to obtain 5 mg of a title compound (yield: 52.6%).

$^1$H NMR (500 MHz, CD$_3$OD): 9.12 (d, 1H), 8.05 (d, 1H), 7.87 (s, 1H), 7.81 (d, 1H), 7.76 (td, 1H), 7.56 (d, 1H), 7.50-7.54 (m, 1H), 7.42 (td, 1H), 7.13 (d, 1H), 4.35 (s, 2H), 2.78 (s, 3H)

Experimental Example

1) Preparation of Gastric Vesicles

Gastric vesicles were prepared from hog stomach via centrifugal separation (Edd C. Rabon et al., Preparation of Gastric H$^+$,K$^+$-ATPase, Methods in enzymology, vol. 157 Academic Press Inc., (1988), pp. 649-654). The protein contents of the thus prepared gastric vesicles were quantitated by Bicinchoninic Acid (BCA) kit.

2) Measurement of Inhibitory Effects on Proton Pump (H$^+$/K$^+$-ATPase) Activities The inhibitory effects of the compounds of the present invention against proton pump activities were measured using a 96-well plate. In this assay, the K$^+$-specific H$^+$/K$^+$-ATPase activities were calculated based on the difference between the H$^+$/K$^+$-ATPase activity in the presence of K$^+$ and that in the absence of K. In the 96-well plate, 0.5% dimethyl sulfoxide (DMSO) in buffer was added to the negative and positive control groups, and the diluted compounds of the present invention were added to the test groups. All assays were performed in a reaction volume of 100 μl at room temperature. The reaction buffer solution (60 mmol/l Tris-HCl buffer, pH 7.4) including the hog gastric vesicles was added with DMSO and the compounds at various concentrations, and then further added with 10 μl of 10 mmol/l adenosine triphosphate Tris buffer solution (60 mmol/l Tris-HCl buffer, pH 7.4) to initiate an enzyme reaction. The enzyme reaction was performed at 37° C. for 40 minutes, terminated by adding 50 μl of malachite green solution (a mixture containing 0.12% malachite green solution, 5.8% ammonium molybdate and 11% Tween 20 in a mixed ratio of 100:67:2 in 6.2 N sulfuric acid), and added with 50 μl of 15.1% sodium citrate. The amount of monophosphate (Pi) in the reaction was measured at 570 nm using a micro plate reader (FLUOstar Omega, BMG LABTECH). The inhibition rates (%) were determined from the activity values of control groups and those of test compounds at various concentrations, and the 1050 values of the test compounds were calculated based on the respective inhibition value (%) using the Logistic 4-parameter function of Sigmaplot 8.0 program. The results are shown in Tables 1 through 8 below.

TABLE 1

| Example No. | IC$_{50}$(uM) |
|---|---|
| Example 1 | 0.18 |
| Example 2 | 1.15 |
| Example 3 | 0.25 |
| Example 4 | 0.06 |
| Example 5 | 0.80 |
| Example 6 | 1.18 |
| Example 7 | 0.59 |
| Example 8 | 0.17 |
| Example 9 | 1.05 |
| Example 10 | 0.20 |
| Example 11 | 1.02 |
| Example 12 | 0.42 |
| Example 13 | 1.08 |
| Example 14 | 1.50 |

TABLE 1-continued

| Example No. | IC$_{50}$(uM) |
|---|---|
| Example 15 | 1.85 |
| Example 16 | 0.78 |
| Example 17 | 2.25 |
| Example 18 | 1.30 |
| Example 19 | 1.91 |
| Example 20 | 0.38 |
| Example 21 | 0.21 |
| Example 22 | 0.21 |
| Example 23 | 0.22 |
| Example 24 | 0.56 |
| Example 25 | 0.16 |
| Example 26 | 0.18 |
| Example 27 | 0.42 |
| Example 28 | 0.74 |
| Example 29 | 0.13 |
| Example 30 | 1.14 |
| Example 31 | 0.92 |
| Example 32 | 0.81 |
| Example 33 | 1.36 |
| Example 34 | 0.39 |
| Example 35 | 1.63 |
| Example 36 | 0.34 |
| Example 37 | 0.50 |
| Example 38 | 2.19 |
| Example 39 | 0.13 |
| Example 40 | 1.83 |
| Example 41 | 0.48 |
| Example 42 | 0.34 |
| Example 43 | 3.02 |
| Example 44 | 0.27 |
| Example 45 | 1.20 |

TABLE 2

| Example No. | IC$_{50}$(uM) |
|---|---|
| Example 46 | 2.35 |
| Example 47 | 0.84 |
| Example 48 | 0.26 |
| Example 49 | 0.32 |
| Example 50 | 1.37 |
| Example 51 | 1.20 |
| Example 52 | 0.29 |
| Example 53 | 0.49 |
| Example 54 | 1.05 |
| Example 55 | 0.42 |
| Example 56 | 0.46 |
| Example 57 | 0.43 |
| Example 58 | 0.41 |
| Example 59 | 0.35 |
| Example 60 | 2.46 |
| Example 61 | 0.29 |
| Example 62 | 0.93 |
| Example 63 | 1.31 |
| Example 64 | 1.84 |
| Example 65 | 0.31 |
| Example 66 | 0.27 |
| Example 67 | 0.38 |
| Example 68 | 2.39 |
| Example 69 | 2.35 |
| Example 70 | 0.30 |
| Example 71 | 0.43 |
| Example 72 | 0.61 |
| Example 73 | 0.16 |
| Example 74 | 0.45 |
| Example 75 | 0.29 |
| Example 76 | 0.35 |
| Example 77 | 0.35 |
| Example 78 | 2.26 |
| Example 79 | 1.38 |
| Example 80 | 0.17 |
| Example 81 | 0.31 |
| Example 82 | 0.45 |
| Example 83 | 1.03 |
| Example 84 | 0.53 |

TABLE 2-continued

| Example No. | IC$_{50}$(uM) |
|---|---|
| Example 85 | 0.37 |
| Example 86 | 0.65 |
| Example 87 | 0.40 |
| Example 88 | 0.43 |
| Example 89 | 0.87 |
| Example 90 | 0.71 |

TABLE 3

| Example No. | IC$_{50}$(uM) |
|---|---|
| Example 91 | 0.87 |
| Example 92 | 1.51 |
| Example 93 | 2.22 |
| Example 94 | 0.78 |
| Example 95 | 0.48 |
| Example 96 | 1.73 |
| Example 97 | 0.67 |
| Example 98 | 1.92 |
| Example 99 | 1.38 |
| Example 100 | 0.80 |
| Example 101 | 2.20 |
| Example 102 | 2.52 |
| Example 103 | 40.00 |
| Example 104 | 40.00 |
| Example 105 | 0.88 |
| Example 106 | 3.38 |
| Example 107 | 0.48 |
| Example 108 | 1.59 |
| Example 109 | 1.98 |
| Example 110 | 5.04 |
| Example 111 | 3.21 |
| Example 112 | 0.95 |
| Example 113 | 0.34 |
| Example 114 | 40.00 |
| Example 115 | 1.30 |
| Example 116 | 1.57 |
| Example 117 | 40.00 |
| Example 118 | 0.48 |
| Example 119 | 0.48 |
| Example 120 | 0.42 |
| Example 121 | 0.44 |
| Example 122 | 40.00 |
| Example 123 | 0.35 |
| Example 124 | 0.58 |
| Example 125 | 1.06 |
| Example 126 | 0.51 |
| Example 127 | 0.64 |
| Example 128 | 1.22 |
| Example 129 | 10.23 |
| Example 130 | 20.00 |
| Example 131 | 0.78 |
| Example 132 | 0.73 |
| Example 133 | 0.77 |
| Example 134 | 2.05 |
| Example 135 | 3.00 |

TABLE 4

| Example No. | IC$_{50}$(uM) |
|---|---|
| Example 136 | 0.71 |
| Example 137 | 0.06 |
| Example 138 | 0.12 |
| Example 139 | 0.18 |
| Example 140 | 0.19 |
| Example 141 | 0.39 |
| Example 142 | 0.12 |
| Example 143 | 0.29 |
| Example 144 | 0.38 |
| Example 145 | 0.17 |
| Example 146 | 0.15 |
| Example 147 | 0.09 |

TABLE 4-continued

| Example No. | IC$_{50}$(uM) |
|---|---|
| Example 148 | 0.01 |
| Example 149 | 0.01 |
| Example 150 | 0.57 |
| Example 151 | 0.51 |
| Example 152 | 0.35 |
| Example 153 | 0.26 |
| Example 154 | 0.48 |
| Example 155 | 0.44 |
| Example 156 | 0.38 |
| Example 157 | 0.38 |
| Example 158 | 0.41 |
| Example 159 | 0.34 |
| Example 160 | 0.29 |
| Example 161 | 0.46 |
| Example 162 | 0.02 |
| Example 163 | 0.14 |
| Example 164 | 7.06 |
| Example 165 | 0.08 |
| Example 166 | 0.34 |
| Example 167 | 0.61 |
| Example 168 | 0.79 |
| Example 169 | 0.08 |
| Example 170 | 0.26 |
| Example 171 | 0.63 |
| Example 172 | 1.50 |
| Example 173 | 1.19 |
| Example 174 | 0.02 |
| Example 175 | 0.15 |
| Example 176 | 0.37 |
| Example 177 | 1.41 |
| Example 178 | 0.61 |
| Example 179 | 0.33 |
| Example 180 | 0.27 |

TABLE 5

| Example No. | IC$_{50}$(uM) |
|---|---|
| Example 181 | 1.28 |
| Example 182 | 0.39 |
| Example 183 | 0.59 |
| Example 184 | 0.36 |
| Example 185 | 1 |
| Example 186 | 0.41 |
| Example 187 | 0.98 |
| Example 188 | 0.4 |
| Example 189 | 0.65 |
| Example 190 | 0.44 |
| Example 191 | 0.07 |
| Example 192 | 0.06 |
| Example 193 | 0.58 |
| Example 194 | 0.01 |
| Example 195 | 1.27 |
| Example 196 | 0.39 |
| Example 197 | 0.85 |
| Example 198 | 0.16 |
| Example 199 | 0.34 |
| Example 200 | 0.9 |
| Example 201 | 0.66 |
| Example 202 | 0.58 |
| Example 203 | 0.45 |
| Example 204 | 0.5 |
| Example 205 | 1.75 |
| Example 206 | 2.55 |
| Example 207 | 0.55 |
| Example 208 | 0.55 |
| Example 209 | 1.06 |
| Example 210 | 0.37 |
| Example 211 | 0.09 |
| Example 212 | 0.18 |
| Example 213 | 0.16 |
| Example 214 | 1.69 |
| Example 215 | 0.82 |
| Example 216 | 1.5 |
| Example 217 | 0.54 |

TABLE 5-continued

| Example No. | IC$_{50}$(uM) |
|---|---|
| Example 218 | 2.92 |
| Example 219 | 0.27 |
| Example 220 | 0.29 |
| Example 221 | 1.58 |
| Example 222 | 1.84 |
| Example 223 | 1.29 |
| Example 224 | 3.3 |
| Example 225 | 2.06 |

TABLE 6

| Example No. | IC$_{50}$(uM) |
|---|---|
| Example 226 | 1.16 |
| Example 227 | 6.49 |
| Example 228 | 0.90 |
| Example 229 | 1.11 |
| Example 230 | 0.91 |
| Example 231 | 2.62 |
| Example 232 | 2.15 |
| Example 233 | 2.85 |
| Example 234 | 1.47 |
| Example 235 | 2.89 |
| Example 236 | 2.04 |
| Example 237 | 0.99 |
| Example 238 | 2.56 |
| Example 239 | 1.75 |
| Example 240 | 1.67 |
| Example 241 | 2.19 |
| Example 242 | 3.85 |
| Example 243 | 7.14 |
| Example 244 | 2.44 |
| Example 245 | 12.89 |
| Example 246 | 0.53 |
| Example 247 | 4.15 |
| Example 248 | 20.00 |
| Example 249 | 50.00 |
| Example 250 | 40.00 |
| Example 251 | 2.60 |
| Example 252 | 1.00 |
| Example 253 | 0.49 |
| Example 254 | 9.15 |
| Example 255 | 11.66 |
| Example 256 | 20.00 |
| Example 257 | 14.17 |
| Example 258 | 20.00 |
| Example 259 | 40.00 |
| Example 260 | 0.38 |
| Example 261 | 9.24 |
| Example 262 | 8.44 |
| Example 263 | 60.00 |
| Example 264 | 20.00 |
| Example 265 | 40.00 |
| Example 266 | 45.00 |
| Example 267 | 0.23 |
| Example 268 | 0.76 |
| Example 269 | 0.77 |
| Example 270 | 0.79 |

TABLE 7

| Example No. | IC$_{50}$(uM) |
|---|---|
| Example 271 | 3.95 |
| Example 272 | 0.50 |
| Example 273 | 0.37 |
| Example 274 | 1.17 |
| Example 275 | 1.76 |
| Example 276 | 0.67 |
| Example 277 | 0.76 |
| Example 278 | 1.97 |
| Example 279 | 2.19 |
| Example 280 | 0.86 |

TABLE 7-continued

| Example No. | IC$_{50}$(uM) |
|---|---|
| Example 281 | 1.87 |
| Example 282 | 2.92 |
| Example 283 | 2.63 |
| Example 284 | 1.01 |
| Example 285 | 0.65 |
| Example 286 | 0.39 |
| Example 287 | 1.67 |
| Example 288 | 1.45 |
| Example 289 | 0.78 |
| Example 290 | 0.93 |
| Example 291 | 0.66 |
| Example 292 | 0.64 |
| Example 293 | 0.55 |
| Example 294 | 0.63 |
| Example 295 | 0.92 |
| Example 296 | 0.93 |
| Example 297 | 1.19 |
| Example 298 | 3.60 |
| Example 299 | 0.27 |
| Example 300 | 1.53 |
| Example 301 | 0.79 |
| Example 302 | 0.32 |
| Example 303 | 0.47 |
| Example 304 | 0.60 |
| Example 305 | 0.61 |
| Example 306 | 0.68 |
| Example 307 | 1.21 |
| Example 308 | 1.34 |
| Example 309 | 2.13 |
| Example 310 | 0.33 |
| Example 311 | 4.17 |
| Example 312 | 0.66 |
| Example 313 | 25.00 |
| Example 314 | 19.43 |
| Example 315 | 2.95 |

TABLE 8

| Example No. | IC$_{50}$(uM) |
|---|---|
| Example 316 | 8.30 |
| Example 317 | 1.92 |
| Example 318 | 4.25 |
| Example 319 | 1.24 |
| Example 320 | 20.00 |
| Example 321 | 3.35 |
| Example 322 | 24.00 |
| Example 323 | 20.00 |
| Example 324 | 20.00 |
| Example 325 | 68.00 |
| Example 326 | 37.00 |
| Example 327 | 40.00 |
| Example 328 | 5.00 |
| Example 329 | 42.00 |
| Example 330 | 22.00 |
| Example 331 | 70.00 |
| Example 332 | 60.00 |
| Example 333 | 5.84 |
| Example 334 | 1.47 |
| Example 335 | 1.34 |
| Example 336 | 2.70 |
| Example 337 | 3.15 |
| Example 338 | 3.50 |
| Example 339 | 0.37 |
| Example 340 | 0.57 |
| Example 341 | 0.38 |
| Example 342 | 0.40 |
| Example 343 | 1.92 |
| Example 344 | 0.97 |
| Example 345 | 0.12 |
| Example 346 | 0.23 |
| Example 347 | 0.18 |
| Example 348 | 0.20 |
| Example 349 | 0.28 |
| Example 350 | 0.26 |
| Example 351 | 0.35 |
| Example 352 | 0.25 |
| Example 353 | 0.83 |
| Example 354 | 0.80 |
| Example 355 | 0.48 |
| Example 356 | 2.00 |
| Example 357 | 0.95 |
| Example 358 | 1.27 |
| Example 359 | 18.27 |

3) Inhibitory Effect on the Basal Gastric Acid Secretion in Pylorus-Ligated Rats Assays for determining inhibitory effect of the compounds of the present invention on the basal gastric acid secretion was performed according to Shay's rat model (Shay, H., et al., 1945, gastroenterology, 5, p. 43-61). Male Sprague Dawley (SD) rats with a body weight in the range of 180~220 g were divided into test (n=5) and control groups (n=5), and fasted for 18 hours with free access to water. Under isoflurane anesthesia, the abdomens of the rats were incised and then the pylorus was ligated. After the ligation, the control groups were administered with only 10% ethanol, 20% polyethylene glycol (PEG) 400, and 10% aqueous Cremophor solution through the duodenum, and the other groups were administered with test compounds suspended in 10% ethanol, 20% PEG 400, and 10% aqueous Cremophor solution at a concentration of 3 mg/kg/2 ml into the duodenum. Five hours after the ligation, the experimental animals were euthanized and their stomach contents were collected. The thus obtained contents were centrifuged at 4,000×g for 10 minutes, and the supernatant was recovered to obtain gastric juice therefrom. The amount of the gastric juice and its pH were measured. The acidity of the gastric juice was determined by 0.1 N-NaOH volume (ueq/mL) for automatic titration of gastric acid to pH 7.0. The total acid output was obtained by multiplying the gastric acidity by the amount of gastric juice. The inhibitory activities (%) of the representative compounds are shown in Table 9 below.

Inhibition Activity (%) of Test Compounds=(total gastric acid secretion in control group−total gastric acid secretion in groups treated with test compounds)/total gastric acid secretion in control group×100

TABLE 9

| Example No. | Inhibitory Activity (%) |
|---|---|
| Example 1 | 58% |
| Example 22 | 48% |
| Example 28 | 44% |
| Example 29 | 44% |
| Example 31 | 41% |
| Example 34 | 45% |
| Example 50 | 67% |
| Example 52 | 70% |
| Example 53 | 45% |
| Example 55 | 55% |
| Example 56 | 82% |
| Example 65 | 42% |
| Example 72 | 49% |
| Example 108 | 49% |
| Example 120 | 46% |
| Example 123 | 40% |
| Example 125 | 45% |
| Example 133 | 40% |
| Example 138 | 55% |

TABLE 9-continued

| Example No. | Inhibitory Activity (%) |
|---|---|
| Example 139 | 40% |
| Example 141 | 51% |
| Example 142 | 42% |
| Example 143 | 53% |
| Example 144 | 53% |
| Example 145 | 45% |
| Example 148 | 45% |
| Example 153 | 42% |
| Example 160 | 57% |
| Example 182 | 44% |
| Example 194 | 42% |
| Example 210 | 43% |
| Example 211 | 43% |
| Example 212 | 56% |
| Example 213 | 50% |
| Example 214 | 75% |
| Example 216 | 69% |
| Example 217 | 44% |
| Example 218 | 49% |
| Example 226 | 44% |
| Example 267 | 44% |
| Example 270 | 38% |
| Example 272 | 41% |
| Example 273 | 32% |
| Example 286 | 35% |
| Example 315 | 45% |
| Example 342 | 41% |
| Example 356 | 63% |

The invention claimed is:

1. A compound represented by Chemical Formula 1 below or a pharmaceutically acceptable salt thereof:

[Chemical Formula 1]

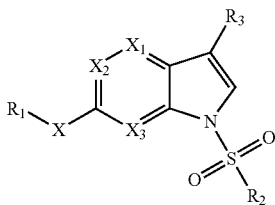

wherein,

X is a bond, —$CH_2$—, —O—, —NH—, —N($CH_3$)—, or —N(CHO)—, $X_1$, $X_2$ and $X_3$ are each independently CH or N, $R_1$ is phenyl, pyrazolyl, pyridinyl, pyrimidinyl, quinolinyl, or phenyl fused with a 6-membered-heterocycloalkyl including one or two nitrogen or oxygen atoms, wherein the $R_1$ is unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), $R_2$ is naphthyl, phenyl, or pyridinyl, wherein the $R_2$ is unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl, $R_3$ is —$CH_2NR_4R_5$, —$CONR_4R_5$, —$COOR_4$ or —$NR_4R_5$, wherein the $R_4$ and $R_5$ are each independently hydrogen or $C_{1-4}$ alkyl, or the $R_4$ and $R_5$ together with the nitrogen atom to which the $R_4$ and $R_5$ are attached form a 5-membered or 6-membered nitrogen-containing heterocyclyl.

2. The compound of claim 1, wherein $R_1$ is phenyl, said phenyl being unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), or a pharmaceutically acceptable salt thereof.

3. The compound of claim 1, wherein $R_1$ is pyridinyl, said pyridinyl being unsubstituted or substituted with one to three substituents independently selected from the group consisting of $C_{1-6}$ alkyl, $C_{1-4}$ alkoxy, $C_{1-4}$ haloalkyl and halogen, or a pharmaceutically acceptable salt thereof.

4. The compound of claim 1, wherein $R_1$ is pyrimidinyl, said pyrimidinyl being unsubstituted or substituted with a $C_{1-4}$ alkoxy or halogen, or a pharmaceutically acceptable salt thereof.

5. The compound of claim 1, wherein $R_2$ is phenyl, said phenyl being unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl, or a pharmaceutically acceptable salt thereof.

6. The compound of claim 1, wherein $R_2$ is pyridinyl, said pyridinyl being unsubstituted or substituted with a $C_{1-4}$ alkoxy or halogen, or a pharmaceutically acceptable salt thereof.

7. The compound of claim 1, wherein $R_3$ is —$CH_2NHCH_3$, —$CH_2NHCH_2CH_3$, —$CH_2N(CH_3)_2$, —$CH_2$(pyrrolidin-1-yl), —$CONHCH_3$, —$CON(CH_3)_2$, —$COOCH_3$ or —$NHCH_3$, or a pharmaceutically acceptable salt thereof.

8. The compound of claim 1, wherein $R_1$ is phenyl, said phenyl being unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO(C1-4 alkyl), and $R_2$ is phenyl, said phenyl being unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl, or a pharmaceutically acceptable salt thereof.

9. The compound of claim 1, wherein $R_1$ is phenyl, said phenyl being unsubstituted or substituted with one to five substituents independently selected from the group consisting of $C_{1-6}$ alkyl, $C_{1-4}$ alkoxy, $C_{1-4}$ haloalkyl, $C_{1-4}$ haloalkoxy, hydroxy, nitro, cyano, halogen, amino, phenyl, phenoxy, halogen-substituted phenoxy, —COO($C_{1-4}$ alkyl) and —NHCO($C_{1-4}$ alkyl), and $R_2$ is pyridinyl, said pyridinyl being unsubstituted or substituted with one $C_{1-4}$ alkoxy or halogen, or a pharmaceutically acceptable salt thereof.

10. The compound of claim 1, wherein $R_1$ is pyridinyl, said pyridinyl being unsubstituted or substituted with a $C_{1-4}$ alkoxy or halogen, and $R_2$ is phenyl, said phenyl being unsubstituted or substituted with one to three substituents independently selected from the group consisting of $C_{1-6}$ alkyl, $C_{1-4}$ alkoxy, $C_{1-4}$ haloalkyl, $C_{1-4}$ haloalkoxy, cyano, halogen and phenyl, or a pharmaceutically acceptable salt thereof.

11. The compound of claim 1, wherein $R_1$ is pyridinyl, said pyridinyl being unsubstituted or substituted with a $C_{1-4}$ alkoxy or halogen, and $R_2$ is pyridinyl, said pyridinyl being unsubstituted or substituted with a $C_{1-4}$ alkoxy or halogen, or a pharmaceutically acceptable salt thereof.

12. The compound of claim 1, wherein the phenyl fused with a 6-membered-hetercocycloalkyl containing one or two nitrogen or oxygen is 1,2,3,4-tetrahydroquinolinyl or 2,3-dihydrobenzo[b][1,4]dioxynyl, or a pharmaceutically acceptable salt thereof.

13. The compound of claim 1, wherein $X_1$, $X_2$ and $X_3$ are all CH, or a pharmaceutically acceptable salt thereof.

14. The compound of claim 1, wherein one of $X_1$, $X_2$ and $X_3$ is N, and the others are both CH, or a pharmaceutically acceptable salt thereof.

15. The compound of claim 1, wherein the compound or a pharmaceutically acceptable salt thereof is one selected from the group consisting of:

1) N-(2-fluoro-4-methylphenyl)-3-((methylamino)methyl)-1-(pyridin-3-ylsulfonyl)-1H-indol-6-amine hydrochloride,
2) 3-((methylamino)methyl)-N-phenyl-1-(pyridin-3-ylsulfonyl)-1H-indol-6-amine hydrochloride,
3) N-(2-fluorophenyl)-3-((methylamino)methyl)-1-(pyridin-3-ylsulfonyl)-1H-indol-6-amine hydrochloride,
4) N-(2-chlorophenyl)-3-((methylamino)methyl)-1-(pyridin-3-ylsulfonyl)-1H-indol-6-amine hydrochloride,
5) N-(3-bromophenyl)-3-((methylamino)methyl)-1-(pyridin-3-ylsulfonyl)-1H-indol-6-amine hydrochloride,
6) N-(3-fluorophenyl)-3-((methylamino)methyl)-1-(pyridin-3-ylsulfonyl)-1H-indol-6-amine hydrochloride,
7) N-(3-chlorophenyl)-3-((methylamino)methyl)-1-(pyridin-3-ylsulfonyl)-1H-indol-6-amine hydrochloride,
8) N-(3-ethylphenyl)-3-((methylamino)methyl)-1-(pyridin-3-ylsulfonyl)-1H-indol-6-amine hydrochloride,
9) N-(4-fluorophenyl)-3-((methylamino)methyl)-1-(pyridin-3-ylsulfonyl)-1H-indol-6-amine hydrochloride,
10) 3-((methylamino)methyl)-1-(pyridin-3-ylsulfonyl)-N-(p-tolyl)-1H-indol-6-amine hydrochloride,
11) N-(4-chlorophenyl)-3-((methylamino)methyl)-1-(pyridin-3-ylsulfonyl)-1H-indol-6-amine hydrochloride,
12) N-(4-methoxyphenyl)-3-((methylamino)methyl)-1-(pyridin-3-ylsulfonyl)-1H-indol-6-amine hydrochloride,
13) 3-((methylamino)methyl)-1-(pyridin-3-ylsulfonyl)-N-(4-(trifluoromethyl)phenyl)-1H-indol-6-amine hydrochloride,
14) N-(4-(tert-butyl)phenyl)-3-((methylamino)methyl)-1-(pyridin-3-ylsulfonyl)-1H-indol-6-amine hydrochloride,
15) N-(3'-methoxy-[1,1'-biphenyl]-4-yl)-3-((methylamino)methyl)-1-(pyridin-3-ylsulfonyl)-1H-indol-6-amine hydrochloride,
16) N-(4-methyl-[1,1'-biphenyl]-3-yl)-3-((methylamino)methyl)-1-(pyridin-3-ylsulfonyl)-1H-indol-6-amine hydrochloride,
17) 3-((methylamino)methyl)-N-(4-phenoxyphenyl)-1-(pyridin-3-ylsulfonyl)-1H-indol-6-amine hydrochloride,
18) N-(4-(4-fluorophenoxy)phenyl)-3-((methylamino)methyl)-1-(pyridin-3-ylsulfonyl)-1H-indol-6-amine hydrochloride,
19) N-(4-(4-chlorophenoxy)phenyl)-3-((methylamino)methyl)-1-(pyridin-3-ylsulfonyl)-1H-indol-6-amine hydrochloride,
20) N-(2-fluoro-3-methylphenyl)-3-((methylamino)methyl)-1-(pyridin-3-ylsulfonyl)-1H-indol-6-amine hydrochloride,
21) N-(2,4-dimethylphenyl)-3-((methylamino)methyl)-1-(pyridin-3-ylsulfonyl)-1H-indol-6-amine hydrochloride,
22) N-(2-chloro-4-methylphenyl)-3-((methylamino)methyl)-1-(pyridin-3-ylsulfonyl)-1H-indol-6-amine,
23) N-(4-fluoro-2-methylphenyl)-3-((methylamino)methyl)-1-(pyridin-3-ylsulfonyl)-1H-indol-6-amine hydrochloride,
24) N-(2,4-difluorophenyl)-3-((methylamino)methyl)-1-(pyridin-3-ylsulfonyl)-1H-indol-6-amine hydrochloride,
25) N-(2-chloro-4-fluorophenyl)-3-((methylamino)methyl)-1-(pyridin-3-ylsulfonyl)-1H-indol-6-amine hydrochloride,
26) N-(4-fluoro-2-(trifluoromethyl)phenyl)-3-((methylamino)methyl)-1-(pyridin-3-ylsulfonyl)-1H-indol-6-amine hydrochloride,
27) N-(4-chloro-2-methylphenyl)-3-((methylamino)methyl)-1-(pyridin-3-ylsulfonyl)-1H-indol-6-amine hydrochloride,
28) N-(4-chloro-2-fluorophenyl)-3-((methylamino)methyl)-1-(pyridin-3-ylsulfonyl)-1H-indol-6-amine hydrochloride,
29) N-(2,4-dichlorophenyl)-3-((methylamino)methyl)-1-(pyridin-3-ylsulfonyl)-1H-indol-6-amine hydrochloride,
30) 5-chloro-2-((3-((methylamino)methyl)-1-(pyridin-3-ylsulfonyl)-1H-indol-6-yl)amino)benzonitrile hydrochloride,
31) N-(4-chloro-2-(trifluoromethyl)phenyl)-3-((methylamino)methyl)-1-(pyridin-3-ylsulfonyl)-1H-indol-6-amine hydrochloride,
32) N-(2-methyl-4-(trifluoromethyl)phenyl)-3-((methylamino)methyl)-1-(pyridin-3-ylsulfonyl)-1H-indol-6-amine hydrochloride,
33) N-(2-fluoro-4-(trifluoromethyl)phenyl)-3-((methylamino)methyl)-1-(pyridin-3-ylsulfonyl)-1H-indol-6-amine hydrochloride,
34) N-(2-chloro-4-(trifluoromethyl)phenyl)-3-((methylamino)methyl)-1-(pyridin-3-ylsulfonyl)-1H-indol-6-amine hydrochloride,
35) N-(2,4-Bis(trifluoromethyl)phenyl)-3-((methylamino)methyl)-1-(pyridin-3-ylsulfonyl)-1H-indol-6-amine hydrochloride,
36) 3-methyl-4-((3-((methylamino)methyl)-1-(pyridin-3-ylsulfonyl)-1H-indol-6-yl)amino)benzonitrile hydrochloride,
37) 3-ethyl-4-((3-((methylamino)methyl)-1-(pyridin-3-ylsulfonyl)-1H-indol-6-yl)amino)benzonitrile hydrochloride,
38) 3-fluoro-4-((3-((methylamino)methyl)-1-(pyridin-3-ylsulfonyl)-1H-indol-6-yl)amino)benzonitrile hydrochloride,
39) 3-chloro-4-((3-((methylamino)methyl)-1-(pyridin-3-ylsulfonyl)-1H-indol-6-yl)amino)benzonitrile hydrochloride,
40) 4-((3-((methylamino)methyl)-1-(pyridin-3-ylsulfonyl)-1H-indol-6-yl)amino)-3-(trifluoromethyl)benzonitrile hydrochloride, 41) N-(2-chloro-4-nitrophenyl)-3-((methylamino)methyl)-1-(pyridin-3-ylsulfonyl)-1H-indol-6-amine hydrochloride,
42) N-(2-methyl-4-nitrophenyl)-3-((methylamino)methyl)-1-(pyridin-3-ylsulfonyl)-1H-indol-6-amine hydrochloride,
43) N-(4-bromo-2-ethylphenyl)-3-((methylamino)methyl)-1-(pyridin-3-ylsulfonyl)-1H-indol-6-amine hydrochloride,
44) N-(4-bromo-2-chlorophenyl)-3-((methylamino)methyl)-1-(pyridin-3-ylsulfonyl)-1H-indol-6-amine hydrochloride,
45) N-(4-bromo-2-(trifluoromethyl)phenyl)-3-((methylamino)methyl)-1-(pyridin-3-ylsulfonyl)-1H-indol-6-amine hydrochloride,
46) N-(4-bromo-2-(trifluoromethoxy)phenyl)-3-((methylamino)methyl)-1-(pyridin-3-ylsulfonyl)-1H-indol-6-amine hydrochloride,
47) 3-methyl-4-((3-((methylamino)methyl)-1-(pyridin-3-ylsulfonyl)-1H-indol-6-yl)amino)phenol hydrochloride,
48) N-(4-methoxy-2-methylphenyl)-3-((methylamino)methyl)-1-(pyridin-3-ylsulfonyl)-1H-indol-6-amine hydrochloride,
49) N-(2-fluoro-4-methoxyphenyl)-3-((methylamino)methyl)-1-(pyridin-3-ylsulfonyl)-1H-indol-6-amine hydrochloride,
50) N-(4-methoxy-2-(trifluoromethoxy)phenyl)-3-((methylamino)methyl)-1-(pyridin-3-ylsulfonyl)-1H-indol-6-amine hydrochloride,
51) N-(4-methoxy-2-(trifluoromethyl)phenyl)-3-((methylamino)methyl)-1-(pyridin-3-ylsulfonyl)-1H-indol-6-amine hydrochloride,
52) N-(4-methoxy-2-nitrophenyl)-3-((methylamino)methyl)-1-(pyridin-3-ylsulfonyl)-1H-indol-6-amine hydrochloride,
53) N-(2-methyl-4-(trifluoromethoxy)phenyl)-3-((methylamino)methyl)-1-(pyridin-3-ylsulfonyl)-1H-indol-6-amine hydrochloride,
54) N-(2-fluoro-4-(trifluoromethoxy)phenyl)-3-((methylamino)methyl)-1-(pyridin-3-ylsulfonyl)-1H-indol-6-amine hydrochloride,
55) N-(2-chloro-4-(trifluoromethoxy)phenyl)-3-((methylamino)methyl)-1-(pyridin-3-ylsulfonyl)-1H-indol-6-amine hydrochloride,
56) N-(2-methoxy-4-(trifluoromethoxy)phenyl)-3-((methylamino)methyl)-1-(pyridin-3-ylsulfonyl)-1H-indol-6-amine hydrochloride,
57) methyl 3-chloro-4-((3-((methylamino)methyl)-1-(pyridin-3-ylsulfonyl)-1H-indol-6-yl)amino)benzoate hydrochloride,
58) N-(2,5-difluorophenyl)-3-((methylamino)methyl)-1-(pyridin-3-ylsulfonyl)-1H-indol-6-amine hydrochloride,
59) N-(2-fluoro-5-methylphenyl)-3-((methylamino)methyl)-1-(pyridin-3-ylsulfonyl)-1H-indol-6-amine hydrochloride,
60) N-(2,6-difluorophenyl)-3-((methylamino)methyl)-1-(pyridin-3-ylsulfonyl)-1H-indol-6-amine hydrochloride,
61) N-(2-chloro-6-methylphenyl)-3-((methylamino)methyl)-1-(pyridin-3-ylsulfonyl)-1H-indol-6-amine hydrochloride,
62) N-(3,4-difluorophenyl)-3-((methylamino)methyl)-1-(pyridin-3-ylsulfonyl)-1H-indol-6-amine hydrochloride,
63) N-(3,5-dimethoxyphenyl)-3-((methylamino)methyl)-1-(pyridin-3-ylsulfonyl)-1H-indol-6-amine hydrochloride,
64) N-(3,5-dichlorophenyl)-3-((methylamino)methyl)-1-(pyridin-3-ylsulfonyl)-1H-indol-6-amine hydrochloride,
65) N-(2,3-difluoro-4-methylphenyl)-3-((methylamino)methyl)-1-(pyridin-3-ylsulfonyl)-1H-indol-6-amine hydrochloride,
66) N-(4-fluoro-2,3-dimethylphenyl)-3-((methylamino)methyl)-1-(pyridin-3-ylsulfonyl)-1H-indol-6-amine hydrochloride,
67) 3-((methylamino)methyl)-1-(pyridin-3-ylsulfonyl)-N-(2,3,4-trifluorophenyl)-1H-indol-6-amine hydrochloride,
68) N-(2,4-difluoro-3-methoxyphenyl)-3-((methylamino)methyl)-1-(pyridin-3-ylsulfonyl)-1H-indol-6-amine hydrochloride,
69) N-(3-ethoxy-2,4-difluorophenyl)-3-((methylamino)methyl)-1-(pyridin-3-ylsulfonyl)-1H-indol-6-amine hydrochloride,
70) N-(2,3-difluoro-4-methoxyphenyl)-3-((methylamino)methyl)-1-(pyridin-3-ylsulfonyl)-1H-indol-6-amine hydrochloride,
71) N-(4-ethoxy-2,3-difluorophenyl)-3-((methylamino)methyl)-1-(pyridin-3-ylsulfonyl)-1H-indol-6-amine hydrochloride,
72) N-(2,5-difluoro-4-methylphenyl)-3-((methylamino)methyl)-1-(pyridin-3-ylsulfonyl)-1H-indol-6-amine hydrochloride,
73) N-(4,5-difluoro-2-methylphenyl)-3-((methylamino)methyl)-1-(pyridin-3-ylsulfonyl)-1H-indol-6-amine hydrochloride,
74) 3-((methylamino)methyl)-1-(pyridin-3-ylsulfonyl)-N-(2,4,5-trifluorophenyl)-1H-indol-6-amine hydrochloride,
75) N-(4-chloro-2,5-dimethylphenyl)-3-((methylamino)methyl)-1-(pyridin-3-ylsulfonyl)-1H-indol-6-amine hydrochloride,
76) 3-((methylamino)methyl)-1-(pyridin-3-ylsulfonyl)-N-(2,4,5-trichlorophenyl)-1H-indol-6-amine hydrochloride,
77) N-(2,4-dichloro-5-methoxyphenyl)-3-((methylamino)methyl)-1-(pyridin-3-ylsulfonyl)-1H-indol-6-amine hydrochloride,
78) N-(2,5-difluoro-4-(trifluoromethyl)phenyl)-3-((methylamino)methyl)-1-(pyridin-3-ylsulfonyl)-1H-indol-6-amine hydrochloride,
79) N-(4-bromo-2,5-difluorophenyl)-3-((methylamino)methyl)-1-(pyridin-3-ylsulfonyl)-1H-indol-6-amine hydrochloride,
80) N-mesityl-3-((methylamino)methyl)-1-(pyridin-3-ylsulfonyl)-1H-indol-6-amine hydrochloride,
81) N-(4-fluoro-2,6-dimethylphenyl)-3-((methylamino)methyl)-1-(pyridin-3-ylsulfonyl)-1H-indol-6-amine hydrochloride,
82) 3-((methylamino)methyl)-1-(pyridin-3-ylsulfonyl)-N-(2,4,6-trifluorophenyl)-1H-indol-6-amine hydrochloride,
83) N-(2-chloro-4,6-difluorophenyl)-3-((methylamino)methyl)-1-(pyridin-3-ylsulfonyl)-1H-indol-6-amine hydrochloride,
84) N-(2,6-dichloro-4-fluorophenyl)-3-((methylamino)methyl)-1-(pyridin-3-ylsulfonyl)-1H-indol-6-amine hydrochloride, 85) N-(4-chloro-2,6-dimethylphenyl)-3-((methylamino)methyl)-1-(pyridin-3-ylsulfonyl)-1H-indol-6-amine hydrochloride,
86) N-(4-chloro-2,6-difluorophenyl)-3-((methylamino)methyl)-1-(pyridin-3-ylsulfonyl)-1H-indol-6-amine hydrochloride,
87) 3-((methylamino)methyl)-1-(pyridin-3-ylsulfonyl)-N-(2,4,6-trichlorophenyl)-1H-indol-6-amine hydrochloride,
88) N-(2,6-difluoro-4-methoxyphenyl)-3-((methylamino)methyl)-1-(pyridin-3-ylsulfonyl)-1H-indol-6-amine hydrochloride,
89) N-(4-ethoxy-2,6-difluorophenyl)-3-((methylamino)methyl)-1-(pyridin-3-ylsulfonyl)-1H-indol-6-amine hydrochloride,
90) N-(4-bromo-2,6-dimethylphenyl)-3-((methylamino)methyl)-1-(pyridin-3-ylsulfonyl)-1H-indol-6-amine hydrochloride,
91) N-(2-bromo-4,6-difluorophenyl)-3-((methylamino)methyl)-1-(pyridin-3-ylsulfonyl)-1H-indol-6-amine hydrochloride,
92) N-(4-bromo-2,6-difluorophenyl)-3-((methylamino)methyl)-1-(pyridin-3-ylsulfonyl)-1H-indol-6-amine hydrochloride,
93) N-(2,4-dibromo-6-fluorophenyl)-3-((methylamino)methyl)-1-(pyridin-3-ylsulfonyl)-1H-indol-6-amine hydrochloride,
94) N-(4-chloro-2-methyl-6-nitrophenyl)-3-((methylamino)methyl)-1-(pyridin-3-ylsulfonyl)-1H-indol-6-amine hydrochloride,
95) 3-((methylamino)methyl)-1-(pyridin-3-ylsulfonyl)-N-(2,3,5,6-tetrafluorophenyl)-1H-indol-6-amine hydrochloride,
96) 3-((methylamino)methyl)-1-(pyridin-3-ylsulfonyl)-N-(2,3,5,6-tetrafluoro-4-(trifluoromethyl)phenyl)-1H-indol-6-amine hydrochloride,
97) N-(2,3-dihydrobenzo[b][1,4]dioxin-6-yl)-3-((methylamino)methyl)-1-(pyridin-3-ylsulfonyl)-1H-indol-6-amine hydrochloride,
98) 3-((methylamino)methyl)-N-(3-methylpyridin-2-yl)-1-(pyridin-3-ylsulfonyl)-1H-indol-6-amine hydrochloride,
99) N-(3-fluoropyridin-2-yl)-3-((methylamino)methyl)-1-(pyridin-3-ylsulfonyl)-1H-indol-6-amine hydrochloride,
100) N-(3-chloropyridin-2-yl)-3-((methylamino)methyl)-1-(pyridin-3-ylsulfonyl)-1H-indol-6-amine hydrochloride,
101) 3-((methylamino)methyl)-1-(pyridin-3-ylsulfonyl)-N-(3-(trifluoromethyl)pyridin-2-yl)-1H-indol-6-amine hydrochloride,
102) N-(3-bromopyridin-2-yl)-3-((methylamino)methyl)-1-(pyridin-3-ylsulfonyl)-1H-indol-6-amine hydrochloride,
103) N-(5-chloro-4-methylpyridin-2-yl)-3-((methylamino)methyl)-1-(pyridin-3-ylsulfonyl)-1H-indol-6-amine hydrochloride,
104) N-(5-chloro-6-methylpyridin-2-yl)-3-((methylamino)methyl)-1-(pyridin-3-ylsulfonyl)-1H-indol-6-amine hydrochloride,
105) 3-((methylamino)methyl)-N-(2-methylpyridin-3-yl)-1-(pyridin-3-ylsulfonyl)-1H-indol-6-amine hydrochloride,
106) N-(2-fluoropyridin-3-yl)-3-((methylamino)methyl)-1-(pyridin-3-ylsulfonyl)-1H-indol-6-amine hydrochloride,
107) N-(2-chloropyridin-3-yl)-3-((methylamino)methyl)-1-(pyridin-3-ylsulfonyl)-1H-indol-6-amine hydrochloride,
108) N-(2-methoxypyridin-3-yl)-3-((methylamino)methyl)-1-(pyridin-3-ylsulfonyl)-1H-indol-6-amine hydrochloride,
109) 3-((methylamino)methyl)-1-(pyridin-3-ylsulfonyl)-N-(2-(trifluoromethyl)pyridin-3-yl)-1H-indol-6-amine hydrochloride,
110) N-(5-bromopyridin-3-yl)-3-((methylamino)methyl)-1-(pyridin-3-ylsulfonyl)-1H-indol-6-amine hydrochloride,
111) N-(2,6-dimethylpyridin-3-yl)-3-((methylamino)methyl)-1-(pyridin-3-ylsulfonyl)-1H-indol-6-amine hydrochloride,
112) N-(2-fluoro-6-methylpyridin-3-yl)-3-((methylamino)methyl)-1-(pyridin-3-ylsulfonyl)-1H-indol-6-amine hydrochloride,
113) N-(2-chloro-6-methylpyridin-3-yl)-3-((methylamino)methyl)-1-(pyridin-3-ylsulfonyl)-1H-indol-6-amine hydrochloride,
114) N-(2-methoxy-6-methylpyridin-3-yl)-3-((methylamino)methyl)-1-(pyridin-3-ylsulfonyl)-1H-indol-6-amine hydrochloride,
115) N-(6-methyl-2-(trifluoromethyl)pyridin-3-yl)-3-((methylamino)methyl)-1-(pyridin-3-ylsulfonyl)-1H-indol-6-amine hydrochloride,
116) N-(6-fluoro-2-methylpyridin-3-yl)-3-((methylamino)methyl)-1-(pyridin-3-ylsulfonyl)-1H-indol-6-amine hydrochloride,
117) N-(2-bromo-6-fluoropyridin-3-yl)-3-((methylamino)methyl)-1-(pyridin-3-ylsulfonyl)-1H-indol-6-amine hydrochloride,
118) N-(6-chloro-2-methylpyridin-3-yl)-3-((methylamino)methyl)-1-(pyridin-3-ylsulfonyl)-1H-indol-6-amine hydrochloride,
119) N-(2,6-dichloropyridin-3-yl)-3-((methylamino)methyl)-1-(pyridin-3-ylsulfonyl)-1H-indol-6-amine hydrochloride,
120) N-(6-chloro-2-methoxypyridin-3-yl)-3-((methylamino)methyl)-1-(pyridin-3-ylsulfonyl)-1H-indol-6-amine hydrochloride,
121) N-(6-chloro-2-(trifluoromethyl)pyridin-3-yl)-3-((methylamino)methyl)-1-(pyridin-3-ylsulfonyl)-1H-indol-6-amine hydrochloride,
122) N-(6-methoxy-2-methylpyridin-3-yl)-3-((methylamino)methyl)-1-(pyridin-3-ylsulfonyl)-1H-indol-6-amine hydrochloride,
123) N-(2-chloro-6-methoxypyridin-3-yl)-3-((methylamino)methyl)-1-(pyridin-3-ylsulfonyl)-1H-indol-6-amine hydrochloride,
124) N-(2-methyl-6-(trifluoromethyl)pyridin-3-yl)-3-((methylamino)methyl)-1-(pyridin-3-ylsulfonyl)-1H-indol-6-amine hydrochloride,
125) N-(2-chloro-6-(trifluoromethyl)pyridin-3-yl)-3-((methylamino)methyl)-1-(pyridin-3-ylsulfonyl)-1H-indol-6-amine hydrochloride,
126) N-(5-chloro-2-methylpyridin-3-yl)-3-((methylamino)methyl)-1-(pyridin-3-ylsulfonyl)-1H-indol-6-amine hydrochloride,
127) N-(2-chloro-4-methylpyridin-3-yl)-3-((methylamino)methyl)-1-(pyridin-3-ylsulfonyl)-1H-indol-6-amine hydrochloride,
128) N-(3-chloropyridin-4-yl)-3-((methylamino)methyl)-1-(pyridin-3-ylsulfonyl)-1H-indol-6-amine hydrochloride, 129) 3-((methylamino)methyl)-1-(pyridin-3-ylsulfonyl)-N-(3-(trifluoromethyl)pyridin-4-yl)-1H-indol-6-amine hydrochloride,
130) N-(3-chloro-2-methoxypyridin-4-yl)-3-((methylamino)methyl)-1-(pyridin-3-ylsulfonyl)-1H-indol-6-amine hydrochloride,
131) N-(3-bromo-2-methoxypyridin-4-yl)-3-((methylamino)methyl)-1-(pyridin-3-ylsulfonyl)-1H-indol-6-amine hydrochloride,
132) N-(2,3-dichloropyridin-4-yl)-3-((methylamino)methyl)-1-(pyridin-3-ylsulfonyl)-1H-indol-6-amine hydrochloride,
133) N-(3-bromo-2-chloropyridin-4-yl)-3-((methylamino)methyl)-1-(pyridin-3-ylsulfonyl)-1H-indol-6-amine hydrochloride,
134) 3-((methylamino)methyl)-1-(pyridin-3-ylsulfonyl)-N-(2,3,5-trifluoropyridin-4-yl)-1H-indol-6-amine hydrochloride,
135) N-3-((methylamino)methyl)-1-(pyridin-3-ylsulfonyl)-1H-indol-6-yl)quinolin-6-amine hydrochloride,
136) N-(2-fluoro-4-methylphenyl)-1-((3-fluorophenyl)sulfonyl)-3-((methylamino)methyl)-1H-indol-6-amine hydrochloride,
137) N-(2-chloro-4-methylphenyl)-1-((3-fluorophenyl)sulfonyl)-3-((methylamino)methyl)-1H-indol-6-amine hydrochloride,
138) N-(4-fluoro-2-methylphenyl)-1-((3-fluorophenyl)sulfonyl)-3-((methylamino)methyl)-1H-indol-6-amine hydrochloride,
139) N-(2-fluoro-4-methoxyphenyl)-1-((3-fluorophenyl)sulfonyl)-3-((methylamino)methyl)-1H-indol-6-amine hydrochloride,
140) 1-((3-fluorophenyl)sulfonyl)-N-(2-methyl-4-(trifluoromethoxy)phenyl)-3-((methylamino)methyl)-1H-indol-6-amine hydrochloride,
141) N-(6-chloro-2-methoxypyridin-3-yl)-1-((3-fluorophenyl)sulfonyl)-3-((methylamino)methyl)-1H-indol-6-amine hydrochloride,
142) N-(2,6-dichloropyridin-3-yl)-1-((3-fluorophenyl)sulfonyl)-3-((methylamino)methyl)-1H-indol-6-amine hydrochloride,
143) N-(6-chloro-2-(trifluoromethyl)pyridin-3-yl)-1-((3-fluorophenyl)sulfonyl)-3-((methylamino)methyl)-1H-indol-6-amine hydrochloride,
144) N-(2-chloro-6-methoxypyridin-3-yl)-1-((3-fluorophenyl)sulfonyl)-3-((methylamino)methyl)-1H-indol-6-amine hydrochloride,
145) N-(2-chloro-6-(trifluoromethyl)pyridin-3-yl)-1-((3-fluorophenyl)sulfonyl)-3-((methylamino)methyl)-1H-indol-6-amine hydrochloride,
146) 1-((3-chlorophenyl)sulfonyl)-N-(2-fluoro-4-methylphenyl)-3-((methylamino)methyl)-1H-indol-6-amine hydrochloride,
147) N-(2-chloro-4-methylphenyl)-1-((3-chlorophenyl)sulfonyl)-3-((methylamino)methyl)-1H-indol-6-amine hydrochloride,
148) 1-((3-chlorophenyl)sulfonyl)-N-(4-methyl-2-(trifluoromethoxy)phenyl)-3-((methylamino)methyl)-1H-indol-6-amine hydrochloride,
149) N-(2-chloro-4-fluorophenyl)-1-((3-chlorophenyl)sulfonyl)-3-((methylamino)methyl)-1H-indol-6-amine hydrochloride,
150) N-(4-chloro-2-fluorophenyl)-1-((3-chlorophenyl)sulfonyl)-3-((methylamino)methyl)-1H-indol-6-amine hydrochloride,
151) N-(4-chloro-2-(trifluoromethyl)phenyl)-1-((3-chlorophenyl)sulfonyl)-3-((methylamino)methyl)-1H-indol-6-amine hydrochloride,
152) N-(2-chloro-4-(trifluoromethyl)phenyl)-1-((3-chlorophenyl)sulfonyl)-3-((methylamino)methyl)-1H-indol-6-amine hydrochloride,
153) 1-((3-chlorophenyl)sulfonyl)-N-(2-fluoro-4-methoxyphenyl)-3-((methylamino)methyl)-1H-indol-6-amine hydrochloride,
154) 1-((3-chlorophenyl)sulfonyl)-N-(2-methyl-4-(trifluoromethoxy)phenyl)-3-((methylamino)methyl)-1H-indol-6-amine hydrochloride,
155) 1-((3-chlorophenyl)sulfonyl)-N-(2-fluoro-4-(trifluoromethoxy)phenyl)-3-((methylamino)methyl)-1H-indol-6-amine hydrochloride,
156) 1-((3-chlorophenyl)sulfonyl)-N-(2,3-difluoro-4-methylphenyl)-3-((methylamino)methyl)-1H-indol-6-amine hydrochloride,
157) 1-((3-chlorophenyl)sulfonyl)-N-(2-methoxypyridin-3-yl)-3-((methylamino)methyl)-1H-indol-6-amine hydrochloride,
158) 1-((3-chlorophenyl)sulfonyl)-N-(2-fluoro-6-methylpyridin-3-yl)-3-((methylamino)methyl)-1H-indol-6-amine hydrochloride,
159) 1-((3-chlorophenyl)sulfonyl)-N-(2,6-dichloropyridin-3-yl)-3-((methylamino)methyl)-1H-indol-6-amine hydrochloride,
160) N-(2-chloro-6-methoxypyridin-3-yl)-1-((3-chlorophenyl)sulfonyl)-3-((methylamino)methyl)-1H-indol-6-amine hydrochloride,
161) N-(2-chloro-6-(trifluoromethyl)pyridin-3-yl)-1-((3-chlorophenyl)sulfonyl)-3-((methylamino)methyl)-1H-indol-6-amine hydrochloride,
162) N-(2-fluoro-4-methylphenyl)-1-((3-methoxyphenyl)sulfonyl)-3-((methylamino)methyl)-1H-indol-6-amine hydrochloride,
163) N-(2-chloro-4-methylphenyl)-1-((3-methoxyphenyl)sulfonyl)-3-((methylamino)methyl)-1H-indol-6-amine hydrochloride,
164) N-(4-chloro-2-fluorophenyl)-1-((3-methoxyphenyl)sulfonyl)-3-((methylamino)methyl)-1H-indol-6-amine hydrochloride,
165) N-(4-chloro-2-(trifluoromethyl)phenyl)-1-((3-methoxyphenyl)sulfonyl)-3-((methylamino)methyl)-1H-indol-6-amine hydrochloride,
166) N-(2-chloro-4-(trifluoromethyl)phenyl)-1-((3-methoxyphenyl)sulfonyl)-3-((methylamino)methyl)-1H-indol-6-amine hydrochloride,
167) N-(2-fluoro-4-methoxyphenyl)-1-((3-methoxyphenyl)sulfonyl)-3-((methylamino)methyl)-1H-indol-6-amine hydrochloride,
168) 1-((3-methoxyphenyl)sulfonyl)-N-(2-methyl-4-(trifluoromethoxy)phenyl)-3-((methylamino)methyl)-1H-indol-6-amine hydrochloride,
169) N-(2-chloro-4-(trifluoromethoxy)phenyl)-1-((3-methoxyphenyl)sulfonyl)-3-((methylamino)methyl)-1H-indol-6-amine hydrochloride,
170) N-(2,3-difluoro-4-methylphenyl)-1-((3-methoxyphenyl)sulfonyl)-3-((methylamino)methyl)-1H-indol-6-amine hydrochloride,
171) N-(2-fluoro-6-methylpyridin-3-yl)-1-((3-methoxyphenyl)sulfonyl)-3-((methylamino)methyl)-1H-indol-6-amine hydrochloride,
172) N-(2-chloro-6-methylpyridin-3-yl)-1-((3-methoxyphenyl)sulfonyl)-3-((methylamino)methyl)-1H-indol-6-amine hydrochloride, 173) N-(2-chloro-6-methoxypyridin-3-yl)-1-((3-methoxyphenyl)sulfonyl)-3-((methylamino)methyl)-1H-indol-6-amine hydrochloride,
174) 1-((3-(difluoromethoxy)phenyl)sulfonyl)-N-(2-fluoro-4-methylphenyl)-3-((methylamino)methyl)-1H-indol-6-amine hydrochloride,
175) N-(2-chloro-4-methylphenyl)-1-((3-(difluoromethoxy)phenyl)sulfonyl)-3-((methylamino)methyl)-1H-indol-6-amine hydrochloride,
176) N-(4-chloro-2-fluorophenyl)-1-((3-(difluoromethoxy)phenyl)sulfonyl)-3-((methylamino)methyl)-1H-indol-6-amine hydrochloride,
177) N-(4-chloro-2-(trifluoromethyl)phenyl)-1-((3-(difluoromethoxy)phenyl)sulfonyl)-3-((methylamino)methyl)-1H-indol-6-amine hydrochloride,
178) 1-((3-(difluoromethoxy)phenyl)sulfonyl)-N-(2-fluoro-4-methoxyphenyl)-3-((methylamino)methyl)-1H-indol-6-amine hydrochloride,
179) 1-((3-(difluoromethoxy)phenyl)sulfonyl)-N-(2-methyl-4-(trifluoromethoxy)phenyl)-3-((methylamino)methyl)-1H-indol-6-amine hydrochloride,
180) N-(2,3-difluoro-4-methylphenyl)-1-((3-(difluoromethoxy)phenyl)sulfonyl)-3-((methylamino)methyl)-1H-indol-6-amine hydrochloride,
181) 1-((3-(difluoromethoxy)phenyl)sulfonyl)-N-(2-fluoro-6-methylpyridin-3-yl)-3-((methylamino)methyl)-1H-indol-6-amine hydrochloride,
182) N-(2-chloro-6-methoxypyridin-3-yl)-1-((3-(difluoromethoxy)phenyl)sulfonyl)-3-((methylamino)methyl)-1H-indol-6-amine hydrochloride,
183) N-(2-fluoro-4-methylphenyl)-3-((methylamino)methyl)-1-((3-(trifluoromethyl)phenyl)sulfonyl)-1H-indol-6-amine hydrochloride,
184) N-(2-chloro-4-methylphenyl)-3-((methylamino)methyl)-1-((3-(trifluoromethyl)phenyl)sulfonyl)-1H-indol-6-amine hydrochloride,
185) N-(4-chloro-2-fluorophenyl)-3-((methylamino)methyl)-1-((3-(trifluoromethyl)phenyl)sulfonyl)-1H-indol-6-amine hydrochloride,
186) N-(4-chloro-2-(trifluoromethyl)phenyl)-3-((methylamino)methyl)-1-((3-(trifluoromethyl)phenyl)sulfonyl)-1H-indol-6-amine hydrochloride,
187) N-(2-chloro-4-(trifluoromethyl)phenyl)-3-((methylamino)methyl)-1-((3-(trifluoromethyl)phenyl)sulfonyl)-1H-indol-6-amine hydrochloride,
188) N-(2-fluoro-4-methoxyphenyl)-3-((methylamino)methyl)-1-((3-(trifluoromethyl)phenyl)sulfonyl)-1H-indol-6-amine hydrochloride,
189) N-(2-methyl-4-(trifluoromethoxy)phenyl)-3-((methylamino)methyl)-1-((3-(trifluoromethyl)phenyl)sulfonyl)-1H-indol-6-amine hydrochloride,
190) N-(2-methoxy-4-(trifluoromethoxy)phenyl)-3-((methylamino)methyl)-1-((3-(trifluoromethyl)phenyl)sulfonyl)-1H-indol-6-amine hydrochloride,
191) N-(2,3-difluoro-4-methylphenyl)-3-((methylamino)methyl)-1-((3-(trifluoromethyl)phenyl)sulfonyl)-1H-indol-6-amine hydrochloride,
192) N-(2-chloro-6-methylpyridin-3-yl)-3-((methylamino)methyl)-1-((3-(trifluoromethyl)phenyl)sulfonyl)-1H-indol-6-amine hydrochloride,
193) N-(2,6-dichloropyridin-3-yl)-3-((methylamino)methyl)-1-((3-(trifluoromethyl)phenyl)sulfonyl)-1H-indol-6-amine hydrochloride,
194) N-(2-chloro-6-methoxypyridin-3-yl)-3-((methylamino)methyl)-1-((3-(trifluoromethyl)phenyl)sulfonyl)-1H-indol-6-amine hydrochloride,
195) N-(2-chloro-6-(trifluoromethyl)pyridin-3-yl)-3-((methylamino)methyl)-1-((3-(trifluoromethyl)phenyl)sulfonyl)-1H-indol-6-amine hydrochloride,
196) N-(2-chloro-4-methylphenyl)-3-((methylamino)methyl)-1-((3-(trifluoromethoxy)phenyl)sulfonyl)-1H-indol-6-amine hydrochloride,
197) N-(4-chloro-2-fluorophenyl)-3-((methylamino)methyl)-1-((3-(trifluoromethoxy)phenyl)sulfonyl)-1H-indol-6-amine hydrochloride,
198) N-(2-chloro-4-(trifluoromethyl)phenyl)-3-((methylamino)methyl)-1-((3-(trifluoromethoxy)phenyl)sulfonyl)-1H-indol-6-amine hydrochloride,
199) N-(2-fluoro-4-methoxyphenyl)-3-(methylamino)methyl)-1-((3-(trifluoromethoxy)phenyl)sulfonyl)-1H-indol-6-amine hydrochloride,
200) N-(2-methyl-4-(trifluoromethoxy)phenyl)-3-((methylamino)methyl)-1-((3-(trifluoromethoxy)phenyl)sulfonyl)-1H-indol-6-amine hydrochloride,
201) N-(2-chloro-4-(trifluoromethoxy)phenyl)-3-((methylamino)methyl)-1-((3-(trifluoromethoxy)phenyl)sulfonyl)-1H-indol-6-amine hydrochloride,
202) N-(2-methoxy-4-(trifluoromethoxy)phenyl)-3-((methylamino)methyl)-1-((3-(trifluoromethoxy)phenyl)sulfonyl)-1H-indol-6-amine hydrochloride,
203) N-(2,3-difluoro-4-methylphenyl)-3-((methylamino)methyl)-1-((3-(trifluoromethoxy)phenyl)sulfonyl)-1H-indol-6-amine hydrochloride,
204) N-(2-fluoro-6-methylpyridin-3-yl)-3-((methylamino)methyl)-1-((3-(trifluoromethoxy)phenyl)sulfonyl)-1H-indol-6-amine hydrochloride,
205) N-(2-chloro-6-methylpyridin-3-yl)-3-((methylamino)methyl)-1-((3-(trifluoromethoxy)phenyl)sulfonyl)-1H-indol-6-amine hydrochloride,
206) N-(2-fluoro-4-methylphenyl)-3-((methylamino)methyl)-1-((4-(trifluoromethoxy)phenyl)sulfonyl)-1H-indol-6-amine hydrochloride,
207) N-(2-chloro-4-methylphenyl)-3-((methylamino)methyl)-1-((4-(trifluoromethoxy)phenyl)sulfonyl)-1H-indol-6-amine hydrochloride,
208) N-(2-chloro-4-(trifluoromethyl)phenyl)-3-((methylamino)methyl)-1-((4-(trifluoromethoxy)phenyl)sulfonyl)-1H-indol-6-amine hydrochloride,
209) N-(2-methyl-4-(trifluoromethoxy)phenyl)-3-((methylamino)methyl)-1-((4-(trifluoromethoxy)phenyl)sulfonyl)-1H-indol-6-amine hydrochloride,
210) N-(2-fluoro-4-methylphenyl)-1-((5-fluoropyridin-3-yl)sulfonyl)-3-((methylamino)methyl)-1H-indol-6-amine hydrochloride,
211) N-(2-chloro-4-methylphenyl)-1-((5-fluoropyridin-3-yl)sulfonyl)-3-((methylamino)methyl)-1H-indol-6-amine hydrochloride,
212) N-(4-fluoro-2-methylphenyl)-1-((5-fluoropyridin-3-yl)sulfonyl)-3-((methylamino)methyl)-1H-indol-6-amine hydrochloride,
213) N-(2-chloro-4-fluorophenyl)-1-((5-fluoropyridin-3-yl)sulfonyl)-3-((methylamino)methyl)-1H-indol-6-amine hydrochloride,
214) 1-((5-fluoropyridin-3-yl)sulfonyl)-N-(4-methoxy-2-(trifluoromethoxy)phenyl)-3-((methylamino)methyl)-1H-indol-6-amine hydrochloride,
215) N-(2-chloro-4-(trifluoromethoxy)phenyl)-1-((5-fluoropyridin-3-yl)sulfonyl)-3-((methylamino)methyl)-1H-indol-6-amine hydrochloride,
216) 1-((5-fluoropyridin-3-yl)sulfonyl)-N-(2-methoxy-4-(trifluoromethoxy)phenyl)-3-((methylamino)methyl)-1H-indol-6-amine hydrochloride, 217) N-(2-chloro-6-methoxypyridin-3-yl)-1-((5-fluoropyridin-3-yl)sulfonyl)-3-((methylamino)methyl)-1H-indol-6-amine hydrochloride,
218) N-(2-chloro-6-(trifluoromethyl)pyridin-3-yl)-1-((5-fluoropyridin-3-yl)sulfonyl)-3-((methylamino)methyl)-1H-indol-6-amine hydrochloride,
219) N-(2-chloro-4-methylphenyl)-1-((4-methoxyphenyl)sulfonyl)-3-((methylamino)methyl)-1H-indol-6-amine hydrochloride,
220) N-(2-chloro-4-methylphenyl)-1-((4-(difluoromethoxy)phenyl)sulfonyl)-3-((methylamino)methyl)-1H-indol-6-amine hydrochloride,
221) N-(2-chloro-4-methylphenyl)-3-((methylamino)methyl)-1-((4-(trifluoromethyl)phenyl)sulfonyl)-1H-indol-6-amine hydrochloride,
222) N-(2-fluoro-4-methylphenyl)-3-((methylamino)methyl)-1-(phenylsulfonyl)-1H-indol-6-amine hydrochloride,
223) N-(2-fluoro-4-methylphenyl)-3-((methylamino)methyl)-1-(o-tolylsulfonyl)-1H-indol-6-amine hydrochloride,
224) N-(2-fluoro-4-methylphenyl)-1-((2-fluorophenyl)sulfonyl)-3-((methylamino)methyl)-1H-indol-6-amine hydrochloride,
225) 1-((2-chlorophenyl)sulfonyl)-N-(2-fluoro-4-methylphenyl)-3-((methylamino)methyl)-1H-indol-6-amine hydrochloride,
226) N-(2-fluoro-4-methylphenyl)-3-((methylamino)methyl)-1-(m-tolylsulfonyl)-1H-indol-6-amine hydrochloride,
227) 3-((6-((2-fluoro-4-methylphenyl)amino)-3-((methylamino)methyl)-1H-indol-1-yl)sulfonyl)benzonitrile hydrochloride,
228) 1-((3-bromophenyl)sulfonyl)-N-(2-fluoro-4-methylphenyl)-3-((methylamino)methyl)-1H-indol-6-amine hydrochloride,
229) N-(2-fluoro-4-methylphenyl)-3-((methylamino)methyl)-1-tosyl-1H-indol-6-amine hydrochloride,
230) 1-((4-chlorophenyl)sulfonyl)-N-(2-fluoro-4-methylphenyl)-3-((methylamino)methyl)-1H-indol-6-amine hydrochloride,
231) 1-((4-(tert-butyl)phenyl)sulfonyl)-N-(2-fluoro-4-methylphenyl)-3-((methylamino)methyl)-1H-indol-6-amine hydrochloride,
232) 1-([1,1'-biphenyl]-4-ylsulfonyl)-N-(2-fluoro-4-methylphenyl)-3-((methylamino)methyl)-1H-indol-6-amine hydrochloride,
233) N-(2-fluoro-4-methylphenyl)-3-((methylamino)methyl)-1-(naphthalen-1-ylsulfonyl)-1H-indol-6-amine hydrochloride,
234) 1-((2,3-dichlorophenyl)sulfonyl)-N-(2-fluoro-4-methylphenyl)-3-((methylamino)methyl)-1H-indol-6-amine hydrochloride,
235) 1-((2,4-dichlorophenyl)sulfonyl)-N-(2-fluoro-4-methylphenyl)-3-((methylamino)methyl)-1H-indol-6-amine hydrochloride,
236) 1-((2,5-dimethylphenyl)sulfonyl)-N-(2-fluoro-4-methylphenyl)-3-((methylamino)methyl)-1H-indol-6-amine hydrochloride,
237) 1-((3,4-difluorophenyl)sulfonyl)-N-(2-fluoro-4-methylphenyl)-3-((methylamino)methyl)-1H-indol-6-amine hydrochloride,
238) 1-((3,4-dichlorophenyl)sulfonyl)-N-(2-fluoro-4-methylphenyl)-3-((methylamino)methyl)-1H-indol-6-amine hydrochloride,
239) 1-((3,5-dimethylphenyl)sulfonyl)-N-(2-fluoro-4-methylphenyl)-3-((methylamino)methyl)-1H-indol-6-amine hydrochloride,
240) N-(2-fluoro-4-methylphenyl)-3-((methylamino)methyl)-1-((2,3,4-trichlorophenyl)sulfonyl)-1H-indol-6-amine hydrochloride,
241) 1-((5-bromopyridin-3-yl)sulfonyl)-N-(2-fluoro-4-methylphenyl)-3-((methylamino)methyl)-1H-indol-6-amine hydrochloride,
242) N-(2-fluoro-4-methylphenyl)-1-((6-methoxypyridin-3-yl)sulfonyl)-3-((methylamino)methyl)-1H-indol-6-amine hydrochloride,
243) N-methyl-1-(6-phenyl-1-(pyridin-3-ylsulfonyl)-1H-indol-3-yl)-methanamine,
244) 1-(6-(3-chlorophenyl)-1-(pyridin-3-ylsulfonyl)-1H-indol-3-yl)-N-methylmethanamine,
245) N-(3-(3-((methylamino)methyl)-1-(pyridin-3-ylsulfonyl)-1H-indol-6-yl)phenyl)acetamide,
246) 4-(3-((methylamino)methyl)-1-(pyridin-3-ylsulfonyl)-1H-indol-6-yl)aniline,
247) 1-(6-([1,1'-biphenyl]-4-yl)-1-(pyridin-3-ylsulfonyl)-1H-indol-3-yl)-N-methylmethanamine,
248) 1-(6-(6-methoxypyridin-3-yl)-1-(pyridin-3-ylsulfonyl)-1H-indol-3-yl)-N-methylmethanamine,
249) N-methyl-1-(6-(1-methyl-1H-pyrazol-4-yl)-1-(pyridin-3-ylsulfonyl)-1H-indol-3-yl)methanamine,
250) N-methyl-1-(6-(1-methyl-1H-pyrazol-5-yl)-1-(pyridin-3-ylsulfonyl)-1H-indol-3-yl)methanamine,
251) 1-(6-(4-methoxyphenyl)-1-(pyridin-3-ylsulfonyl)-1H-indol-3-yl)-N-methylmethanamine hydrochloride,
252) 1-(6-(2-fluoro-4-methylphenyl)-1-(pyridin-3-ylsulfonyl)-1H-indol-3-yl)-N-methylmethanamine hydrochloride,
253) 1-(6-(2-chloro-4-methylphenyl)-1-(pyridin-3-ylsulfonyl)-1H-indol-3-yl)-N-methylmethanamine hydrochloride,
254) N-methyl-1-(1-(pyridin-3-ylsulfonyl)-6-(2-(trifluoromethyl)pyridin-3-yl)-1H-indol-3-yl)methanamine hydrochloride,
255) 1-(6-(6-fluoropyridin-3-yl)-1-(pyridin-3-ylsulfonyl)-1H-indol-3-yl)-N-methylmethanamine hydrochloride,
256) 1-(6-(2-fluoropyridin-4-yl)-1-(pyridin-3-ylsulfonyl)-1H-indol-3-yl)-N-methylmethanamine hydrochloride,
257) 1-(6-(6-fluoro-5-methylpyridin-3-yl)-1-(pyridin-3-ylsulfonyl)-1H-indol-3-yl)-N-methylmethanamine hydrochloride,
258) N-methyl-1-(1-(pyridin-3-ylsulfonyl))-6-(pyrimidin-5-yl)-1H-indol-3-yl)methanamine hydrochloride,
259) 1-(6-(2-methoxypyrimidin-5-yl)-1-(pyridin-3-ylsulfonyl)-1H-indol-3-yl)-N-methylmethanamine hydrochloride,
260) N-methyl-1-(6-(6-methyl-3,4-dihydroquinolin-1(2H)-yl)-1-(pyridin-3-ylsulfonyl)-1H-indol-3-yl)methanamine hydrochloride,
261) 1-(1-((3-(difluoromethoxy)phenyl)sulfonyl)-6-(2-(trifluoromethyl)pyridin-3-yl)-1H-indol-3-yl)-N-methylmethanamine hydrochloride,
262) 1-(1-((3-(difluoromethoxy)phenyl)sulfonyl)-6-(2-fluoropyridin-4-yl)-1H-indol-3-yl)-N-methylmethanamine hydrochloride,
263) 1-(1-((3-(difluoromethoxy)phenyl)sulfonyl)-6-(6-fluoro-5-methylpyridin-3-yl)-1H-indol-3-yl)-N-methylmethanamine hydrochloride, 264) 1-(1-((3-(difluoromethoxy)phenyl)sulfonyl)-6-(pyrimidin-5-yl)-1H-indol-3-yl)-N-methylmethanamine hydrochloride,
265) 1-(1-((4-(difluoromethoxy)phenyl)sulfonyl)-6-(pyrimidin-5-yl)-1H-indol-3-yl)-N-methylmethanamine hydrochloride,
266) 1-(1-((3-(difluoromethoxy)phenyl)sulfonyl)-6-(2-methoxypyrimidin-5-yl)-1H-indol-3-yl)-N-methylmethanamine hydrochloride,
267) 1-(6-(2-chloro-4-methylbenzyl)-1-(pyridin-3-ylsulfonyl)-1H-indol-3-yl)-N-methylmethanamine hydrochloride,
268) 1-(6-benzyl-1-(pyridin-3-ylsulfonyl)-1H-indol-3-yl)-N-methylmethanamine hydrochloride,
269) 1-(6-(2-fluorobenzyl)-1-(pyridin-3-ylsulfonyl)-1H-indol-3-yl)-N-methylmethanamine hydrochloride,
270) N-methyl-1-(6-(4-methylbenzyl)-1-(pyridin-3-ylsulfonyl)-1H-indol-3-yl)methanamine hydrochloride,
271) N-methyl-1-(1-(pyridin-3-ylsulfonyl)-6-(4-(trifluoromethoxy)benzyl)-1H-indol-3-yl)methanamine hydrochloride,
272) 1-(6-(2-fluoro-4-methylbenzyl)-1-(pyridin-3-ylsulfonyl)-1H-indol-3-yl)-N-methylmethanamine hydrochloride,
273) 1-(6-(2-chloro-4-fluorobenzyl)-1-(pyridin-3-ylsulfonyl)-1H-indol-3-yl)-N-methylmethanamine hydrochloride,
274) 1-(6-(4-chloro-2-fluorobenzyl)-1-(pyridin-3-ylsulfonyl)-1H-indol-3-yl)-N-methylmethanamine hydrochloride,
275) 1-(6-(4-chloro-2-(trifluoromethyl)benzyl)-1-(pyridin-3-ylsulfonyl)-1H-indol-3-yl)-N-methylmethanamine hydrochloride,
276) 1-(6-(2-chloro-4-(trifluoromethyl)benzyl)-1-(pyridin-3-ylsulfonyl)-1H-indol-3-yl)-N-methylmethanamine hydrochloride,
277) 1-(6-(2-fluoro-4-methoxybenzyl)-1-(pyridin-3-ylsulfonyl)-1H-indol-3-yl)-N-methylmethanamine hydrochloride,
278) N-methyl-1-(6-(2-methyl-4-(trifluoromethoxy)benzyl)-1-(pyridin-3-ylsulfonyl)-1H-indol-3-yl)methanamine hydrochloride,
279) 1-(6-(2-fluoro-4-(trifluoromethoxy)benzyl)-1-(pyridin-3-ylsulfonyl)-1H-indol-3-yl)-N-methylmethanamine hydrochloride,
280) 1-(6-(2-chloro-4-(trifluoromethoxy)benzyl)-1-(pyridin-3-ylsulfonyl)-1H-indol-3-yl)-N-methylmethanamine hydrochloride,
281) 1-(6-(2-methoxy-4-(trifluoromethoxy)benzyl)-1-(pyridin-3-ylsulfonyl)-1H-indol-3-yl)-N-methylmethanamine hydrochloride,
282) 1-(6-((2-methoxypyridin-3-yl)methyl)-1-(pyridin-3-ylsulfonyl)-1H-indol-3-yl)-N-methylmethanamine hydrochloride,
283) 1-(6-((2-fluoro-6-methylpyridin-3-yl)methyl)-1-(pyridin-3-ylsulfonyl)-1H-indol-3-yl)-N-methylmethanamine hydrochloride,
284) 1-(6-((2-chloro-6-methylpyridin-3-yl)methyl)-1-(pyridin-3-ylsulfonyl)-1H-indol-3-yl)-N-methylmethanamine hydrochloride,
285) 1-(6-((2,6-dichloropyridin-3-yl)methyl)-1-(pyridin-3-ylsulfonyl)-1H-indol-3-yl)-N-methylmethanamine hydrochloride,
286) 1-(6-(2,3-difluoro-4-methylbenzyl)-1-(pyridin-3-ylsulfonyl)-1H-indol-3-yl)-N-methylmethanamine hydrochloride,
287) 1-(6-(2,3-difluoro-4-methylbenzyl)-1-((3-fluorophenyl)sulfonyl)-1H-indol-3-yl)-N-methylmethanamine,
288) 1-(6-(2,3-difluoro-4-methylbenzyl)-1-((3-(trifluoromethyl)phenyl)sulfonyl)-1H-indol-3-yl)-N-methylmethanamine,
289) 1-(6-(2,3-difluoro-4-methylbenzyl)-1-((3-methoxyphenyl)sulfonyl)-1H-indol-3-yl)-N-methylmethanamine,
290) 1-(6-(2,3-difluoro-4-methylbenzyl)-1-((3-(difluoromethoxy)phenyl)sulfonyl)-1H-indol-3-yl)-N-methylmethanamine,
291) 1-(6-((2-chloro-6-methoxypyridin-3-yl)methyl)-1-(pyridin-3-ylsulfonyl)-1H-indol-3-yl)-N-methylmethanamine hydrochloride,
292) 1-(6-((2-chloro-6-methoxypyridin-3-yl)methyl)-1-((3-fluorophenyl)sulfonyl)-1H-indol-3-yl)-N-methylmethanamine hydrochloride,
293) 1-(6-((2-chloro-6-methoxypyridin-3-yl)methyl)-1-((3-chlorophenyl)sulfonyl)-1H-indol-3-yl)-N-methylmethanamine,
294) 1-(6-((2-chloro-6-methoxypyridin-3-yl)methyl)-1-((3-(trifluoromethyl)phenyl)sulfonyl)-1H-indol-3-yl)-N-methylmethanamine hydrochloride,
295) 1-(6-((2-chloro-6-methoxypyridin-3-yl)methyl)-1-((3-methoxyphenyl)sulfonyl)-1H-indol-3-yl)-N-methylmethanamine,
296) 1-(6-((2-chloro-6-methoxypyridin-3-yl)methyl)-1-((3-(difluoromethoxy)phenyl)sulfonyl)-1H-indol-3-yl)-N-methylmethanamine,
297) 1-(6-((2-chloro-6-methoxypyridin-3-yl)methyl)-1-((3-(trifluoromethoxy)phenyl)sulfonyl)-1H-indol-3-yl)-N-methylmethanamine,
298) 1-(6-((2-chloro-6-methoxypyridin-3-yl)methyl)-1-((4-(difluoromethoxy)phenyl)sulfonyl)-1H-indol-3-yl)-N-methylmethanamine,
299) 1-(6-(2-chloro-4-methylbenzyl)-1-((3-fluorophenyl)sulfonyl)-1H-indol-3-yl)-N-methylmethanamine,
300) 1-(6-(2-chloro-4-methylbenzyl)-1-((2-fluorophenyl)sulfonyl)-1H-indol-3-yl)-N-methylmethanamine,
301) 1-(6-(2-chloro-4-methylbenzyl)-1-((3-chlorophenyl)sulfonyl)-1H-indol-3-yl)-N-methylmethanamine,
302) 1-(6-(2-chloro-4-methylbenzyl)-1-((3-(trifluoromethyl)phenyl)sulfonyl)-1H-indol-3-yl)-N-methylmethanamine,
303) 1-(6-(2-chloro-4-methylbenzyl)-1-((3-methoxyphenyl)sulfonyl)-1H-indol-3-yl)-N-methylmethanamine,
304) 1-(6-(2-chloro-4-methylbenzyl)-1-((3-(difluoromethoxy)phenyl)sulfonyl)-1H-indol-3-yl)-N-methylmethanamine,
305) 1-(6-(2-chloro-4-methylbenzyl)-1-((3-(trifluoromethoxy)phenyl)sulfonyl)-1H-indol-3-yl)-N-methylmethanamine,
306) 1-(6-(2-chloro-4-methylbenzyl))-1-((4-fluorophenyl)sulfonyl)-1H-indol-3-yl)-N-methylmethanamine,
307) 1-(6-(2-chloro-4-methylbenzyl)-1-((4-methoxyphenyl)sulfonyl)-1H-indol-3-yl)-N-methylmethanamine,
308) 1-(6-(2-chloro-4-methylbenzyl)-1-((4-(difluoromethoxy)phenyl)sulfonyl)-1H-indol-3-yl)-N-methylmethanamine,
309) 1-(6-(5-chloro-nitrophenoxy)-1-(pyridin-3-ylsulfonyl)-1H-indol-3-yl)-N-methylmethanamine hydrochloride,
310) N-methyl-1-(6-(2-nitrophenoxy)-1-(pyridin-3-ylsulfonyl)-1H-indol-3-yl)methanamine hydrochloride,
311) 1-(6-(2-chloro-4-(trifluoromethyl)phenoxy)-1-(pyridin-3-ylsulfonyl)-1H-indol-3-yl)-N-methylmethanamine hydrochloride, 312) 1-(6-((3-chloro-5-(trifluoromethyl)pyridin-2-yl)oxy)-1-(pyridin-3-ylsulfonyl)-1H-indol-3-yl)-N-methylmethanamine hydrochloride,
313) 1-(6-((5-fluoropyrimidin-2-yl)oxy)-1-(pyridin-3-ylsulfonyl)-1H-indol-3-yl)-N-methylmethanamine hydrochloride,
314) 1-(6-((6-chloropyrimidin-4-yl)oxy)-1-(pyridin-3-ylsulfonyl)-1H-indol-3-yl)-N-methylmethanamine hydrochloride,
315) N-(2-chloro-6-methoxypyridin-3-yl)-N-methyl-3-((methylamino)methyl)-1-((3-(trifluoromethyl)phenyl)sulfonyl)-1H-indol-6-amine hydrochloride,
316) N-(2-methoxy-4-(trifluoromethoxy)phenyl)-N-(3-((methylamino)methyl)-1-(pyridin-3-ylsulfonyl)-1H-indol-6-yl)formamide,
317) N-(2-chloro-6-methoxypyridin-3-yl)-3-((ethylamino)methyl)-1-((3-(trifluoromethyl)phenyl)sulfonyl)-1H-indol-6-amine,
318) N-(2-chloro-6-methoxypyridin-3-yl)-3-(pyrrolidin-1-ylmethyl)-1-((3-(trifluoromethyl)phenyl)sulfonyl)-1H-indol-6-amine,
319) N-(2-chloro-6-methoxypyridin-3-yl)-3-((dimethylamino)methyl)-1-((3-(trifluoromethyl)phenyl)sulfonyl)-1H-indol-6-amine,
320) 6-((2-chloro-6-methoxypyridin-3-yl)amino)-N-methyl-1-((3-(trifluoromethyl)phenyl)sulfonyl)-1H-indol-3-carboxamide,
321) 6-((2-chloro-6-methoxypyridin-3-yl)amino)-N,N-dimethyl-1-((3-(trifluoromethyl)phenyl)sulfonyl)-1H-indol-3-carboxamide,
322) 6-((2-fluoro-4-methylphenyl)amino)-N,N-dimethyl-1-(pyridin-3-ylsulfonyl)-1H-indol-3-carboxamide,
323) 6-((2-chloro-4-methylphenyl)amino)-N,N-dimethyl-1-(pyridin-3-ylsulfonyl)-1H-indol-3-carboxamide,
324) 6-((2-fluoro-4-methoxyphenyl)amino)-N,N-dimethyl-1-(pyridin-3-ylsulfonyl)-1H-indol-3-carboxamide,
325) 6-((2-chloro-4-(trifluoromethyl)phenyl)amino)-N,N-dimethyl-1-(pyridin-3-ylsulfonyl)-1H-indol-3-carboxamide,
326) N,N-dimethyl-6-((2-methyl-4-(trifluoromethoxy)phenyl)amino)-1-(pyridin-3-ylsulfonyl)-1H-indol-3-carboxamide,
327) 6-((2-chloro-4-(trifluoromethoxy)phenyl)amino)-N,N-dimethyl-1-(pyridin-3-ylsulfonyl)-1H-indol-3-carboxamide,
328) 6-((2-methoxy-4-(trifluoromethoxy)phenyl)amino)-N,N-dimethyl-1-(pyridin-3-ylsulfonyl)-1H-indol-3-carboxamide,
329) 6-((2,3-difluoro-4-methylphenyl)amino)-N,N-dimethyl-1-(pyridin-3-ylsulfonyl)-1H-indol-3-carboxamide,
330) 6-((2-chloro-6-methylpyridin-3-yl)amino)-N,N-dimethyl-1-(pyridin-3-ylsulfonyl)-1H-indol-3-carboxamide,
331) 6-((2,6-dichloropyridin-3-yl)amino)-N,N-dimethyl-1-(pyridin-3-ylsulfonyl)-1H-indol-3-carboxamide,
332) 6-((2-chloro-6-methoxypyridin-3-yl)amino)-N,N-dimethyl-1-(pyridin-3-ylsulfonyl)-1H-indol-3-carboxamide,
333) N6-(2-fluoro-4-methylphenyl)-N3-methyl-1-(pyridin-3ylsulfonyl)-1H-indol-3,6-diamine hydrochloride,
334) N6-(2-chloro-4-methylphenyl)-N3-methyl-1-(pyridin-3ylsulfonyl)-1H-indol-3,6-diamine hydrochloride,
335) methyl 6-(4-methoxyphenyl)-1-(pyridin-3-ylsulfonyl)-1H-indol-3-carboxylate,
336) methyl 6-(6-fluoropyridin-3-yl)-1-(pyridin-3-ylsulfonyl)-1H-indol-3-carboxylate,
337) methyl 1-((6-chloropyridin-3-yl)sulfonyl)-6-(6-fluoropyridin-3-yl)-1H-indol-3-carboxylate,
338) methyl 6-(6-methoxypyridin-3-yl)-1-(pyridin-3-ylsulfonyl)-1H-indol-3-carboxylate,
339) N-(2-fluoro-4-methylphenyl)-1-((3-fluorophenyl)sulfonyl)-3-((methylamino)methyl)-1H-pyrrolo[3,2-b]pyridin-6-amine hydrochloride,
340) 1-((3-fluorophenyl)sulfonyl)-N-(4-methyl-2-(trifluoromethoxy)phenyl)-3-((methylamino)methyl)-1H-pyrrolo[3,2-b]pyridin-6-amine hydrochloride,
341) N-(4-chloro-2-methylphenyl)-1-((3-fluorophenyl)sulfonyl)-3-((methylamino)methyl)-1H-pyrrolo[3,2-b]pyridin-6-amine hydrochloride,
342) N-(2,4-dichlorophenyl)-1-((3-fluorophenyl)sulfonyl)-3-((methylamino)methyl)-1H-pyrrolo[3,2-b]pyridin-6-amine hydrochloride,
343) 1-((3-fluorophenyl)sulfonyl)-N-(2-methoxy-4-(trifluoromethoxy)phenyl)-3-((methylamino)methyl)-1H-pyrrolo[3,2-b]pyridin-6-amine hydrochloride,
344) N-(6-chloro-2-methylpyridin-3-yl)-1-((3-fluorophenyl)sulfonyl)-3-((methylamino)methyl)-1H-pyrrolo[3,2-b]pyridin-6-amine hydrochloride,
345) N-(2-chloro-4-methylphenyl)-3-((methylamino)methyl)-1-(pyridin-3-ylsulfonyl)-1H-pyrrolo[3,2-b]pyridin-6-amine hydrochloride,
346) N-(4-fluoro-2-methylphenyl)-3-((methylamino)methyl)-1-(pyridin-3-ylsulfonyl)-1H-pyrrolo[3,2-b]pyridin-6-amine hydrochloride,
347) N-(2-chloro-4-fluorophenyl)-3-((methylamino)methyl)-1-(pyridin-3-ylsulfonyl)-1H-pyrrolo[3,2-b]pyridin-6-amine hydrochloride,
348) N-(4-chloro-2-methylphenyl)-3-((methylamino)methyl)-1-(pyridin-3-ylsulfonyl)-1H-pyrrolo[3,2-b]pyridin-6-amine hydrochloride,
349) N-(2,4-dichlorophenyl)-3-((methylamino)methyl)-1-(pyridin-3-ylsulfonyl)-1H-pyrrolo[3,2-b]pyridin-6-amine hydrochloride,
350) N-(2-chloro-4-methylphenyl)-1-((5-fluoropyridin-3-yl)sulfonyl)-3-((methylamino)methyl)-1H-pyrrolo[3,2-b]pyridin-6-amine hydrochloride,
351) N-(4-fluoro-2-methylphenyl)-1-((5-fluoropyridin-3-yl)sulfonyl)-3-((methylamino)methyl)-1H-pyrrolo[3,2-b]pyridin-6-amine hydrochloride,
352) N-(2-chloro-4-fluorophenyl)-1-((5-fluoropyridin-3-yl)sulfonyl)-3-((methylamino)methyl)-1H-pyrrolo[3,2-b]pyridin-6-amine hydrochloride,
353) N-(2-chloro-4-methylphenyl)-1-((3-fluorophenyl)sulfonyl)-3-((methylamino)methyl)-1H-pyrrolo[3,2-c]pyridin-6-amine hydrochloride,
354) N-(4-fluoro-2-methylphenyl)-1-((3-fluorophenyl)sulfonyl)-3-((methylamino)methyl)-1H-pyrrolo[3,2-c]pyridin-6-amine hydrochloride,
355) N-(2-chloro-4-fluorophenyl)-1-((3-fluorophenyl)sulfonyl)-3-((methylamino)methyl)-1H-pyrrolo[3,2-c]pyridin-6-amine hydrochloride,
356) 1-((3-fluorophenyl)sulfonyl)-N-(2-methoxy-4-(trifluoromethoxy)phenyl)-3-((methylamino)methyl)-1H-pyrrolo[3,2-c]pyridin-6-amine hydrochloride,
357) N-(2,6-dichloropyridin-3-yl)-1-((3-fluorophenyl)sulfonyl)-3-((methylamino)methyl)-1H-pyrrolo[3,2-c]pyridin-6-amine hydrochloride,
358) N-(2-chloro-6-methylpyridin-3-yl)-1-((3-fluorophenyl)sulfonyl)-3-((methylamino)methyl)-1H-pyrrolo[3,2-c]pyridin-6-amine hydrochloride, and 359) N-(2,6-dichloropyridin-3-yl)-1-((3-fluorophenyl)sulfonyl)-3-((methylamino)methyl)-1H-pyrrolo[2,3-b]pyridin-6-amine hydrochloride.

16. A pharmaceutical composition comprising a compound or a pharmaceutically acceptable salt thereof according to claim 1.

17. A pharmaceutical composition for the treatment of peptic ulcer, gastritis or reflux esophagitis, comprising a compound or a pharmaceutically acceptable salt thereof according to claim 1 as an active ingredient.

18. A method for the treatment of peptic ulcer, gastritis or reflux esophagitis in a subject in need thereof, comprising administering an effective amount of a compound or a pharmaceutically acceptable salt thereof according to claim 1 to the subject.

19. A compound selected from the group consisting of:
1) 6-bromo-1-(pyridin-3-ylsulfonyl)-1H-indol-3-carbaldehyde,
2) 1-(6-bromo-1-(pyridin-3-ylsulfonyl)-1H-indol-3-yl)-N-methylmethanamine,
3) tert-butyl ((6-bromo-1-(pyridin-3-ylsulfonyl)-1H-indol-3-yl)methyl)(methyl)carbamate,
4) tert-butyl ((6-((2-fluoro-4-methylphenyl)amino)-1-(pyridin-3-ylsulfonyl)-1H-indol-3-yl)methyl)(methyl)carbamate,
5) tert-butyl ((6-bromo-1H-indol-3-yl)methyl)(methyl)carbamate,
6) tert-butyl ((6-bromo-1-((3-fluorophenyl)sulfonyl)-1H-indol-3-yl)methyl)(methyl)carbamate,
7) tert-butyl ((6-((2-fluoro-4-methylphenyl)amino)-1-((3-fluorophenyl)sulfonyl)-1H-indol-3-yl)methyl)(methyl)carbamate,
8) tert-butyl ((6-((2-fluoro-4-methylphenyl)amino)-1H-indol-3-yl)methyl)(methyl)carbamate,
9) tert-butyl ((6-((2-fluoro-4-methylphenyl)amino)-1-(phenylsulfonyl)-1H-indol-3-yl)methyl)(methyl)carbamate,
10) tert-butyl ((6-(4-methoxyphenyl)-1-(pyridin-3-ylsulfonyl)-1H-indol-3-yl)methyl)(methyl)carbamate,
11) tert-butyl ((6-bromo-1-((3-(difluoromethoxy)phenyl)sulfonyl)-1H-indol-3-yl)methyl)(methyl)carbamate,
12) tert-butyl ((1-((3-(difluoromethoxy)phenyl)sulfonyl)-6-(2-(trifluoromethyl)pyridin-3-yl)-1H-indol-3-yl)methyl)(methyl)carbamate,
13) methyl 3-formyl-1-(pyridin-3-ylsulfonyl)-1H-indol-6-carboxylate,
14) methyl 3-((methylamino)methyl)-1-(pyridin-3-ylsulfonyl)-1H-indol-6-carboxylate,
15) methyl 3-(((tert-butoxycarbonyl)(methyl)amino)methyl)-1-(pyridin-3-ylsulfonyl)-1H-indol-6-carboxylate,
16) tert-butyl ((6-(hydroxymethyl)-1-(pyridin-3-ylsulfonyl)-1H-indol-3-yl)methyl)(methyl)carbamate,
17) tert-butyl ((6-(bromomethyl)-1-(pyridin-3-ylsulfonyl)-1H-indol-3-yl)methyl)(methyl)carbamate,
18) tert-butyl ((6-(2-chloro-4-methylbenzyl)-1-(pyridin-3-ylsulfonyl)-1H-indol-3-yl)methyl)(methyl)carbamate,
19) tert-butyl ((6-(2-chloro-4-methylbenzyl)-1H-indol-3-yl)methyl)(methyl)carbamate,
20) tert-butyl ((6-(2-chloro-4-methylbenzyl)-1-((3-fluorophenyl)sulfonyl)-1H-indol-3-yl)methyl)(methyl)carbamate,
21) tert-butyl methyl((1-(pyridin-3-ylsulfonyl)-6-(4,4,5,5-tetramethyl-1,3,2-dioxaborolan-2-yl)-1H-indol-3-yl)methyl)carbamate,
22) tert-butyl ((6-hydroxy-1-(pyridin-3-ylsulfonyl)-1H-indol-3-yl)methyl)(methyl)carbamate,
23) tert-butyl ((6-(5-chloro-2-nitrophenoxy)-1-(pyridin-3-ylsulfonyl)-1H-indol-3-yl)methyl)(methyl)carbamate,
24) tert-butyl ((6-bromo-1-((3-(trifluoromethyl)phenyl)sulfonyl)-1H-indol-3-yl)methyl)(methyl)carbamate,
25) tert-butyl ((6-((2-chloro-6-methoxypyridin-3-yl)amino)-1-((3-(trifluoromethyl)phenyl)sulfonyl)-1H-indol-3-yl)methyl)(methyl)carbamate,
26) tert-butyl ((6-((2-chloro-6-methoxypyridin-3-yl)(methyl)amino)-1-((3-(trifluoromethyl)phenyl)sulfonyl)-1H-indol-3-yl)methyl)(methyl)carbamate,
27) tert-butyl ((6-((2-methoxy-4-(trifluoromethoxy)phenyl)amino)-1-(pyridin-3-ylsulfonyl)-1H-indol-3-yl)methyl)(methyl)carbamate,
28) 6-bromo-1-((3-(trifluoromethyl)phenyl)sulfonyl)-1H-indol-3-carbaldehyde,
29) 6-((2-chloro-6-methoxypyridin-3-yl)amino)-1-((3-(trifluoromethyl)phenyl)sulfonyl)-1H-indol-3-carbaldehyde,
30) 6-bromo-N-methyl-1H-indol-3-carboxamide,
31) 6-bromo-N-methyl-1-((3-(trifluoromethyl)phenyl)sulfonyl)-1H-indol-3-carboxamide,
32) tert-butyl (6-bromo-1-(pyridin-3-ylsulfonyl)-1H-indol-3-yl)(methyl)carbamate,
33) tert-butyl (6-((2-fluoro-4-methylphenyl)amino)-1-(pyridin-3-ylsulfonyl)-1H-indol-3-yl)(methyl)carbamate,
34) methyl 6-bromo-1-(pyridin-3-ylsulfonyl)-1H-indol-3-carboxylate,
35) 6-bromo-1-((3-fluorophenyl)sulfonyl)-1H-pyrrolo[3,2-b]pyridin-3-carbaldehyde,
36) 1-(6-bromo-1-((3-fluorophenyl)sulfonyl)-1H-pyrrolo[3,2-b]pyridin-3-yl)-N-methylmethanamine,
37) tert-butyl ((6-bromo-1-((3-fluorophenyl)sulfonyl)-1H-pyrrolo[3,2-b]pyridin-3-yl)methyl)(methyl)carbamate,
38) tert-butyl ((6-((2-fluoro-4-methylphenyl)amino)-1-((3-fluorophenyl)sulfonyl)-1H-pyrrolo[3,2-b]pyridin-3-yl)methyl)(methyl)carbamate,
39) 6-bromo-1-((3-fluorophenyl)sulfonyl)-1H-pyrrolo[3,2-c]pyridin-3-carbaldehyde,
40) 1-(6-bromo-1-((3-fluorophenyl)sulfonyl)-1H-pyrrolo[3,2-c]pyridin-3-yl)-N-methylmethanamine,
41) tert-butyl ((6-bromo-1-((3-fluorophenyl)sulfonyl)-1H-pyrrolo[3,2-c]pyridin-3-yl)methyl)(methyl)carbamate,
42) tert-butyl ((6-((2-chloro-4-methylphenyl)amino)-1-((3-fluorophenyl)sulfonyl)-1H-pyrrolo[3,2-c]pyridin-3-yl)methyl)(methyl)carbamate,
43) 6-bromo-1-((3-fluorophenyl)sulfonyl)-1H-pyrrolo[2,3-b]pyridin-3-carbaldehyde,
44) 1-(6-bromo-1-((3-fluorophenyl)sulfonyl)-1H-pyrrolo[2,3-b]pyridin-3-yl)-N-methylmethanamine,
45) tert-butyl ((6-bromo-1-((3-fluorophenyl)sulfonyl)-1H-pyrrolo[2,3-b]pyridin-3-yl)methyl)(methyl)carbamate, and
46) tert-butyl ((6-((2,6-dichloropyridin-3-yl)amino)-1-((3-fluorophenyl)sulfonyl)-1H-pyrrolo[2,3-b]pyridin-3-yl)methyl)(methyl)carbamate.

* * * * *